United States Patent
Li et al.

(10) Patent No.: US 12,421,247 B2
(45) Date of Patent: Sep. 23, 2025

(54) ORGANIC ELECTROLUMINESCENT MATERIAL AND DEVICE THEREOF

(71) Applicant: BEIJING SUMMER SPROUT TECHNOLOGY CO., LTD., Beijing (CN)

(72) Inventors: Feng Li, Beijing (CN); Yang Wang, Beijing (CN); Jianfei Yao, Beijing (CN); Junfei Wang, Beijing (CN); Gang Yang, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

(*) Notice: Subject to any disclaimer, the term of this patent is extended or adjusted under 35 U.S.C. 154(b) by 835 days.

(21) Appl. No.: 17/547,793

(22) Filed: Dec. 10, 2021

(65) Prior Publication Data

US 2022/0194956 A1    Jun. 23, 2022

(30) Foreign Application Priority Data

Dec. 11, 2020  (CN) .......................... 202011438483.5
Oct. 27, 2021  (CN) .......................... 202111245328.6

(51) Int. Cl.

| | |
|---|---|
| C07D 493/00 | (2006.01) |
| C07D 498/04 | (2006.01) |
| C07F 7/08 | (2006.01) |
| C07F 7/30 | (2006.01) |
| C07F 15/00 | (2006.01) |
| H10K 85/30 | (2023.01) |
| H10K 85/40 | (2023.01) |
| H10K 85/60 | (2023.01) |
| H10K 50/11 | (2023.01) |
| H10K 50/16 | (2023.01) |
| H10K 101/10 | (2023.01) |
| H10K 101/30 | (2023.01) |
| H10K 101/40 | (2023.01) |

(52) U.S. Cl.
CPC ......... *C07D 493/00* (2013.01); *C07D 498/04* (2013.01); *C07F 7/0812* (2013.01); *C07F 7/30* (2013.01); *C07F 15/0033* (2013.01); *C07F 15/0086* (2013.01); *H10K 85/342* (2023.02); *H10K 85/346* (2023.02); *H10K 85/40* (2023.02); *H10K 85/622* (2023.02); *H10K 85/626* (2023.02); *H10K 85/653* (2023.02); *H10K 85/654* (2023.02); *H10K 85/655* (2023.02); *H10K 85/6574* (2023.02); *H10K 50/11* (2023.02); *H10K 50/16* (2023.02); *H10K 2101/10* (2023.02); *H10K 2101/30* (2023.02); *H10K 2101/40* (2023.02)

(58) Field of Classification Search
None
See application file for complete search history.

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |
| 5,844,363 A | 12/1998 | Gu et al. |
| 6,097,147 A | 8/2000 | Baldo et al. |
| 6,303,238 B1 | 10/2001 | Thompson et al. |
| 7,279,704 B2 | 10/2007 | Walters et al. |
| 7,968,146 B2 | 6/2011 | Wagner et al. |
| 11,616,202 B2 | 3/2023 | Lee et al. |
| 2003/0230980 A1 | 12/2003 | Forrest et al. |
| 2004/0174116 A1 | 9/2004 | Lu et al. |
| 2014/0158992 A1 | 6/2014 | Xia et al. |
| 2015/0207082 A1 | 7/2015 | Dyatkin et al. |
| 2015/0249221 A1 | 9/2015 | Zeng et al. |
| 2015/0349273 A1 | 12/2015 | Hung et al. |
| 2016/0028021 A1 | 1/2016 | Zeng et al. |
| 2016/0093808 A1 | 3/2016 | Adamovich et al. |
| 2016/0197285 A1 | 7/2016 | Zeng et al. |
| 2016/0233429 A1 | 8/2016 | Xia et al. |
| 2016/0233436 A1 | 8/2016 | Zeng et al. |
| 2016/0359122 A1 | 12/2016 | Boudreault et al. |
| 2017/0054087 A1 | 2/2017 | Zeng et al. |
| 2018/0301639 A1 | 10/2018 | Zeng et al. |
| 2019/0363261 A1 | 11/2019 | Lee et al. |
| 2020/0176685 A1 | 6/2020 | Kang et al. |

(Continued)

FOREIGN PATENT DOCUMENTS

| | | |
|---|---|---|
| CN | 110294703 A | 10/2019 |
| CN | 110540536 A | 12/2019 |

(Continued)

OTHER PUBLICATIONS

Tang et al., "Organic electroluminescent diodes," Appl. Phys. Lett. 51(12), pp. 913-915, DOI: 10.1063/1.98799 (1987).
Uoyama et al., "Highly efficient organic light-emitting diodes from delayed fluorescence," Nature 492, pp. 234-240, DOI:10.1038/nature11687 (Dec. 2012).
Notice of Reasons for Refusal in JP Application No. 2021-201243, dated Nov. 18, 2022 (with English machine translation), 10 pgs.
First Office Action in DE Application No. 10 2021 132 670.2, dated Jul. 4, 2022 (with English translation), 9 pgs.

(Continued)

*Primary Examiner* — Robert S Loewe

(74) *Attorney, Agent, or Firm* — ArentFox Schiff LLP; Joseph M. Maraia; Marlo Schepper Grolnic

(57) ABSTRACT

Provided are an organic electroluminescent material and device. The organic electroluminescent material is a compound having a structure of Formula 1. Those novel compounds are applicable to electroluminescent devices and can provide better device performance, such as an increased device lifetime. Further provided are an organic electroluminescent device containing the compound and a compound composition containing the compound.

21 Claims, 2 Drawing Sheets

(56) References Cited

U.S. PATENT DOCUMENTS

| | | | |
|---|---|---|---|
| 2020/0203631 A1 | 6/2020 | Gao et al. | |
| 2020/0259098 A1* | 8/2020 | Lee | H10K 85/657 |
| 2021/0257554 A1 | 8/2021 | Zeng et al. | |
| 2021/0273164 A1* | 9/2021 | Song | H10K 85/6574 |
| 2022/0102647 A1* | 3/2022 | Galan | C07D 405/14 |
| 2022/0320442 A1* | 10/2022 | Kim | H10K 85/654 |
| 2022/0340550 A1* | 10/2022 | Yang | C07D 405/04 |
| 2022/0396568 A1* | 12/2022 | Yang | C07D 211/82 |
| 2023/0172065 A1* | 6/2023 | Park | C07D 487/04 257/40 |
| 2023/0232717 A1* | 7/2023 | Lee | C07D 405/04 257/40 |
| 2023/0263054 A1* | 8/2023 | Hwang | H10K 85/633 257/40 |
| 2023/0301183 A1* | 9/2023 | Lee | C09K 11/06 257/40 |
| 2024/0172560 A1* | 5/2024 | Lee | C07D 405/14 |

FOREIGN PATENT DOCUMENTS

| | | |
|---|---|---|
| CN | 111527083 A | 8/2020 |
| CN | 111808087 A | 10/2020 |
| CN | 112759578 A | 5/2021 |
| EP | 3689867 A1 | 8/2020 |
| JP | 2017107992 A | 6/2017 |
| JP | 2020066622 A | 4/2020 |
| JP | 2020125289 A | 8/2020 |
| KR | 20200072211 A | 6/2020 |
| WO | 2019151682 A1 | 8/2019 |
| WO | 2020122460 A1 | 6/2020 |
| WO | 2020138944 A1 | 7/2020 |

OTHER PUBLICATIONS

First Office Action in Chinese Application No. 202111245328.6 dated Oct. 27, 2023 [with English translation], 15 pages.

Search Report in Chinese Application No. 202111245328.6 dated Oct. 24, 2023 [with English translation], 5 pages.

Request for the Submission of an Opinion in Korean Application No. 10-2021-0176270 dated Feb. 15, 2024 [with English translation], 19 pages.

* cited by examiner

ORGANIC ELECTROLUMINESCENT MATERIAL AND DEVICE THEREOF

CROSS-REFERENCE TO RELATED APPLICATION(S)

This application claims priority to Chinese Patent Application No. CN202011438483.5 filed on Dec. 11, 2020 and Chinese Patent Application No. CN202111245328.6 filed on Oct. 27, 2021, the disclosure of which are incorporated herein by reference in their entireties.

TECHNICAL FIELD

The present disclosure relates to compounds for organic electronic devices such as organic light-emitting devices. In particular, the present disclosure relates to a compound having a structure of Formula 1, an organic electroluminescent device containing the compound and a compound composition containing the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

WO2020138944A1 has disclosed an organic compound having the following general structural formula

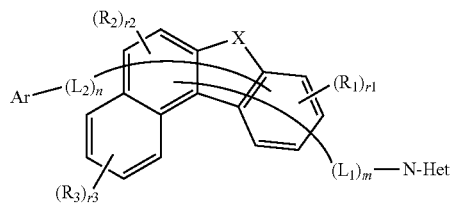

and an organic light-emitting device structural formula: containing the compound, wherein X is O, S or $NR_{21}$, and N-Het is a monocyclic or polycyclic heteroaryl group containing at least one N atom. This application has disclosed the following compounds among specific structures:

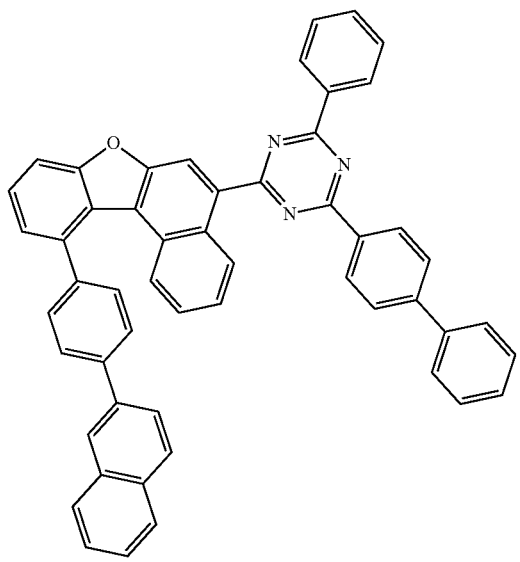

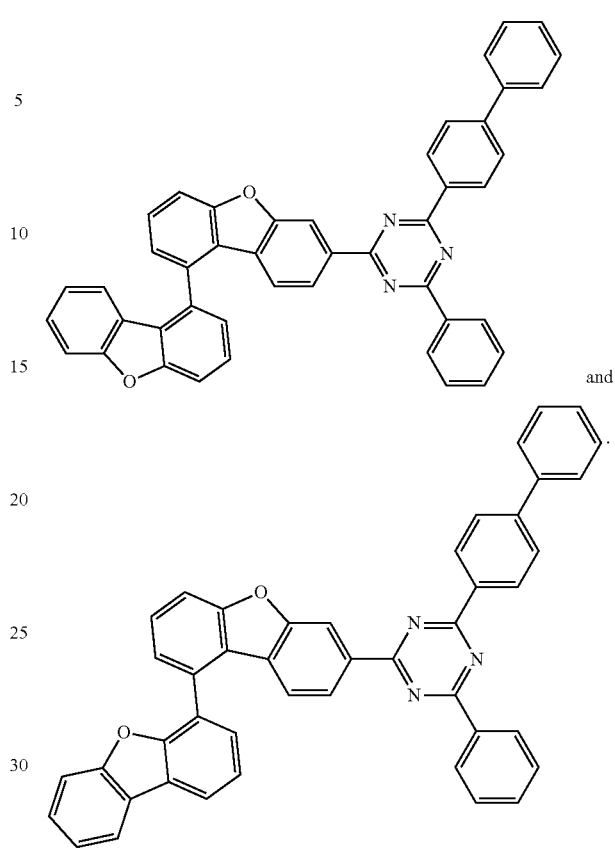

and

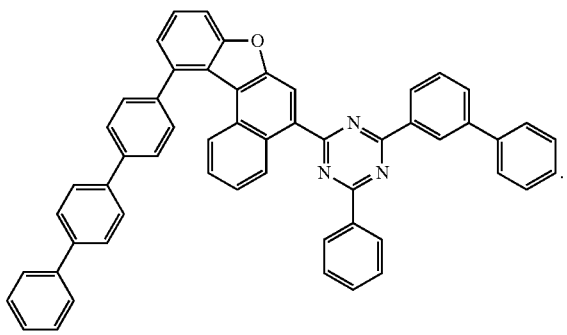

This application focuses on only compounds having a benzodibenzofuran (thiophene or carbazole) skeleton structure and has not disclosed compounds with a dibenzofuran (thiophene or carbazole) skeleton structure and an effect of such compounds on device performance.

CN111527083A has disclosed an organic compound having the following general structural formula;

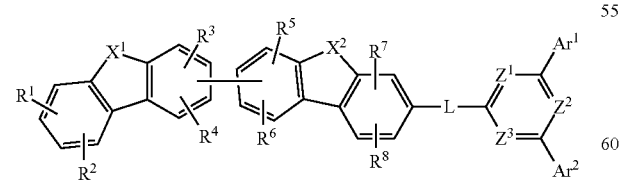

and an organic light-emitting device containing the compound, wherein $X_1$ and $X_2$ are independently O or S. This application has disclosed the following compounds among specific structures:

This application focuses on only a skeleton structure where two dibenzofuran (thiophene) are joined to azaphenyl through L and has neither disclosed nor studied compounds with only one dibenzofuran (thiophene) joined to triazine and an effect of such compounds on device performance.

US20200176685A1 has disclosed an organic optoelectronic device, the light-emitting layer of which contains an organic compound having the following general structural formula:

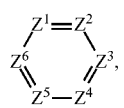

wherein $Z^1$ to $Z^6$ are each independently N or CR. The structure having the general formula can further be

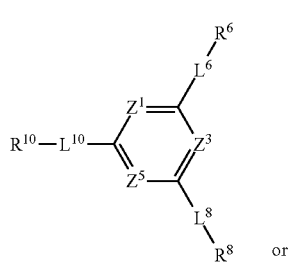

or

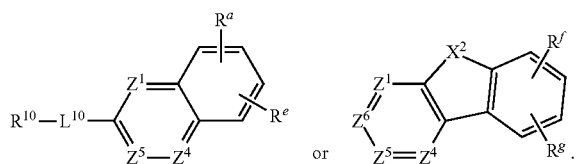

This application has disclosed the following compounds among specific structures:

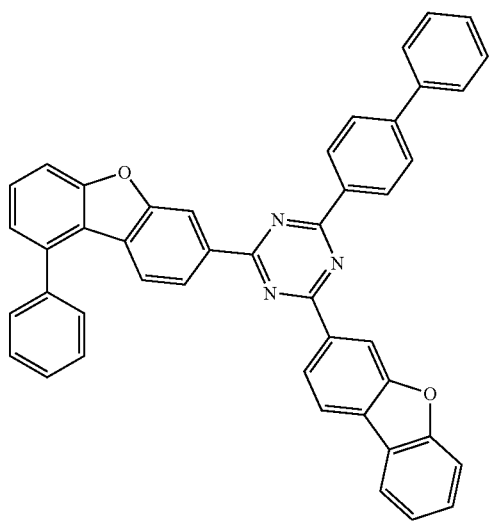

and

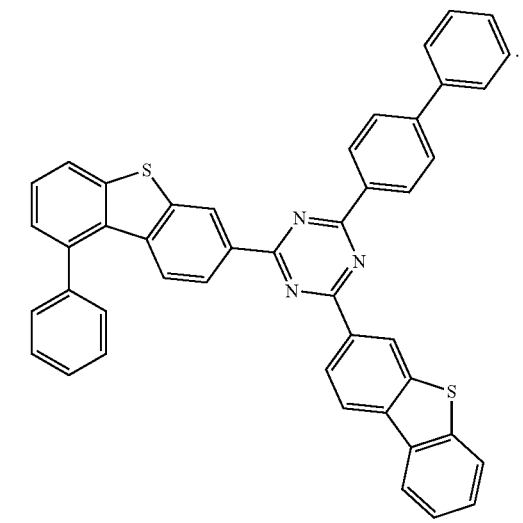

This application has neither studied nor focused on compounds where an aryl substituent exists at position 1 of dibenzofuran and triazine having two aryl substitutions is joined at position 7 of dibenzofuran and an effect of such compounds on device performance.

CN110294703A has disclosed a compound represented by a combination of Formula 1 and Formula 2;

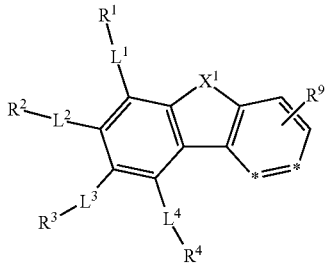

Formula 1

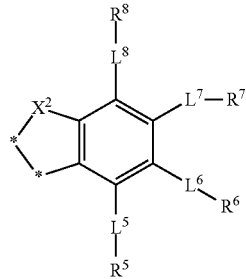

Formula 2 and an organic light-emitting device containing the compound, wherein $X^1$ and $X^2$ are independently O or S. This application has disclosed the following compounds among specific structures:

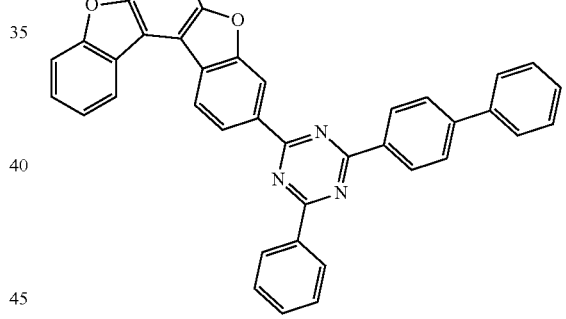

and

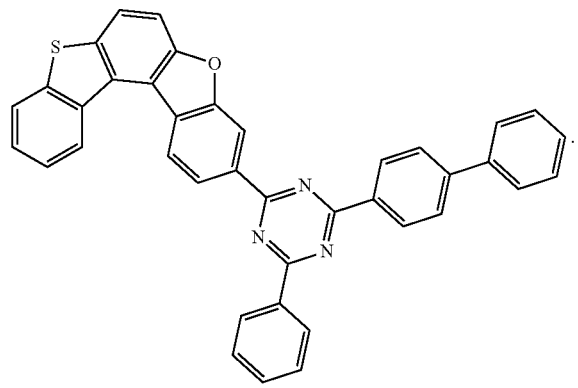

This application only focuses on compounds with a dibenzofuran (thiophene) fused ring as a skeleton and has neither studied nor focused on compounds with an unfused dibenzofuran (thiophene) skeleton and an effect of such compounds on device performance.

SUMMARY

The present disclosure aims to provide a series of compounds each having a structure of Formula 1 to solve at least part of the preceding problems. Those novel compounds are applicable to organic electroluminescent devices and can provide better device performance, especially the improvement of device lifetime.

An embodiment of the present disclosure provides a compound having a structure of Formula 1:

Formula 1

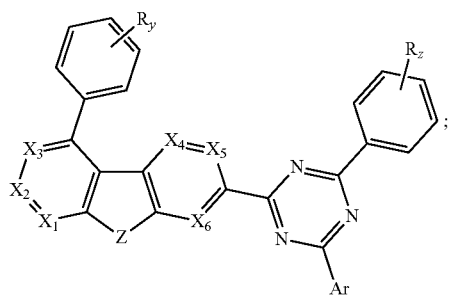

wherein
Z is selected from O, S or Se;
$X_1$ to $X_6$ are, at each occurrence identically or differently, selected from $CR_x$ or N;
$R_y$ and $R_z$ represent, at each occurrence identically or differently, mono-substitution, multiple substitutions or non-substitution;
$R_x$, $R_y$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;
at least one of $R_y$ and $R_z$ is substituted or unsubstituted aryl having 6 to 30 carbon atoms; and
Ar is, at each occurrence identically or differently, selected from substituted or unsubstituted aryl having 10 to 30 carbon atoms.

Another embodiment of the present disclosure provides an organic electroluminescent device which includes an anode, a cathode and an organic layer disposed between the anode and the cathode, wherein at least one layer of the organic layer contains the compound in the preceding embodiment.

Another embodiment of the present disclosure further provides a compound composition which contains the compound in the preceding embodiment.

The present disclosure provides a series of compounds each having a structure of Formula 1. Those novel compounds are applicable to organic electroluminescent devices and can provide better device performance, especially the improvement of device lifetime.

DETAILED DESCRIPTION

Figure 1:
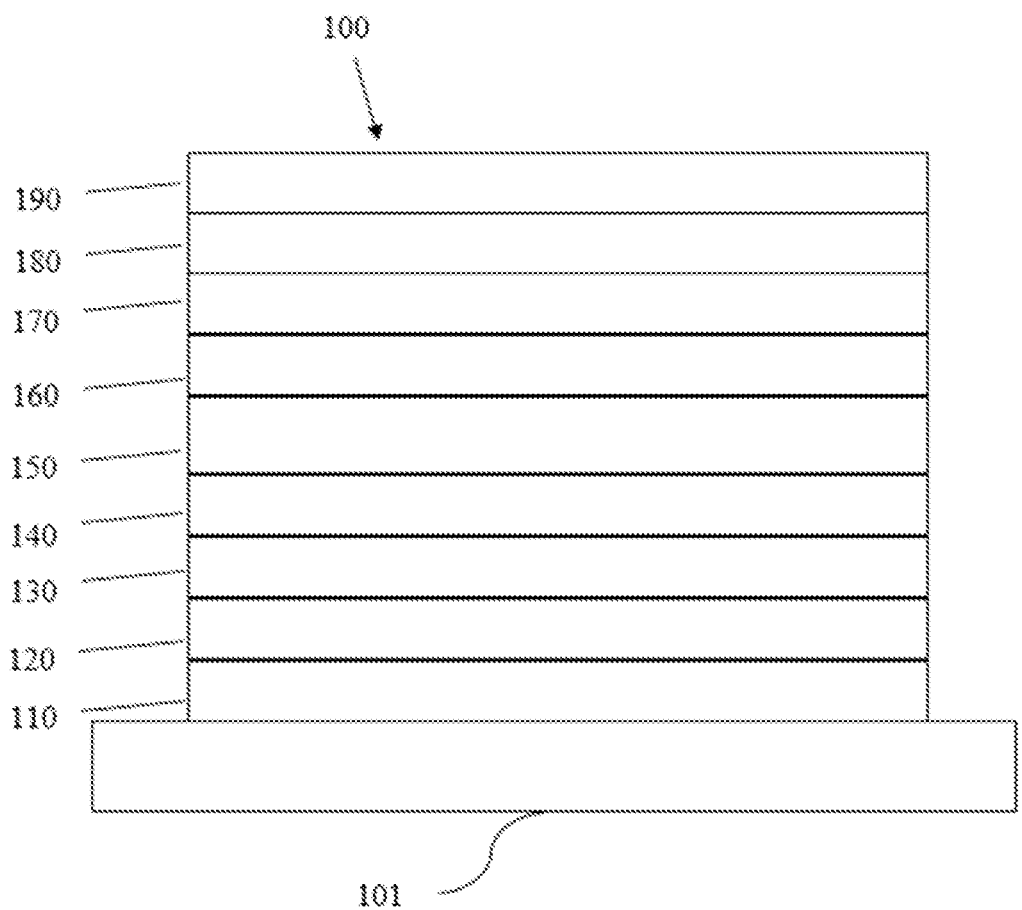
FIG. 1 is a schematic diagram of an organic light-emitting apparatus that may include a compound and a compound composition disclosed herein.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with F4-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
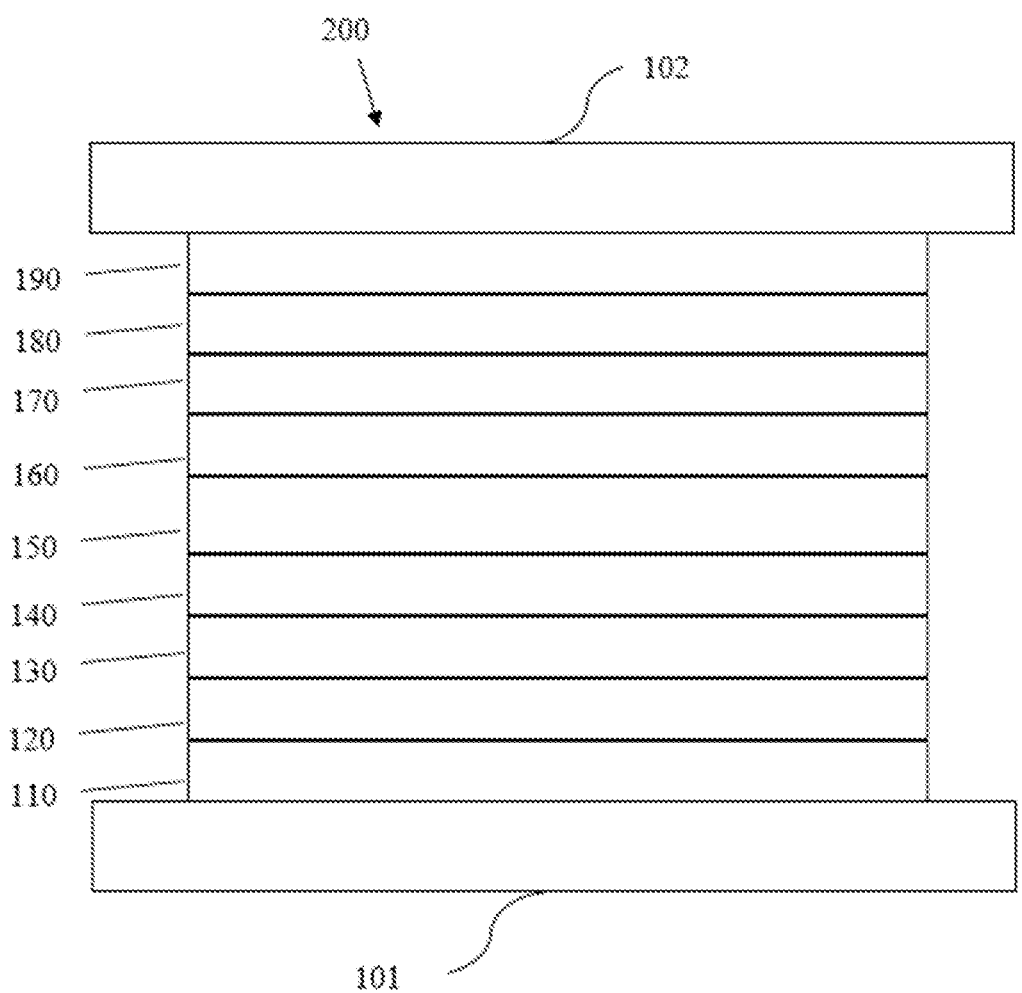
FIG. 2 is a schematic diagram of another organic light-emitting apparatus that may include a compound and a compound composition disclosed herein.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing (RISC) rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap (AES-T). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small AES-T. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms. Examples of cycloalkyl include cyclobutyl, cyclopentyl, cyclohexyl, 4-methylcyclohexyl, 4,4-dimethylcylcohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcylcohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylsilyl, dimethylethylsilyl, dimethylisopropylsilyl, t-butyldimethylsilyl, triethylsilyl, triisopropylsilyl, trimethylsilylmethyl, trimethylsilylethyl, trimethylsilylisopropyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, 1-propenyl group, 1-butenyl, 2-butenyl, 3-butenyl, 1,3-butandienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4''-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocycle—as used herein include non-aromatic cyclic groups. Non-aromatic heterocyclic groups includes saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, where at least one hetero-atom is selected from the group consisting of a nitrogen atom, an oxygen atom, a sulfur atom, a selenium atom, a silicon atom, a phosphorus atom, a germanium atom, and a boron atom. A heteroaromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthylethyl, 2-beta-naphthylethyl, 1-beta-naphthylisopropyl, 2-beta-naphthylisopropyl, p-methylbenzyl, m-methylbenzyl, O-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenylethyl, 2-phenylethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethylsilyl, tripropylsilyl, tributylsilyl, triisopropylsilyl, methyldiisopropylsilyl, dimethylisopropylsilyl, tri-t-butylsilyl, triisobutylsilyl, dimethyl t-butylsilyl, and methyldi-t-butylsilyl. Additionally, the alkylsilyl group may be optionally substituted.

Arylsilyl—as used herein, contemplates a silyl group substituted with an aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenylbutylsilyl, diphenylisobutylsilyl, diphenyl t-butylsilyl. Additionally, the arylsilyl group may be optionally substituted.

The term "aza" in azadibenzofuran, azadibenzothiophene, etc. means that one or more of C—H groups in the respective aromatic fragment are replaced by a nitrogen atom. For example, azatriphenylene encompasses dibenzo[f,h]quinoxaline, dibenzo[f,h]quinoline and other analogs with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted amino, substituted acyl, substituted carbonyl, a substituted carboxylic acid group, a substituted ester group, substituted sulfinyl, substituted sulfonyl, and substituted phosphino is used, it means that any group of alkyl, cycloalkyl, heteroalkyl, heterocyclic group, arylalkyl, alkoxy, aryloxy, alkenyl, alkynyl, aryl, heteroaryl, alkylsilyl, arylsilyl, amino, acyl, carbonyl, a carboxylic acid group, an ester group, sulfinyl, sulfonyl, and phosphino may be substituted with one or more moieties selected from the group consisting of deuterium, halogen, unsubstituted alkyl having 1 to 20 carbon atoms, unsubstituted cycloalkyl having 3 to 20 ring carbon atoms, unsubstituted heteroalkyl having 1 to 20 carbon atoms, an unsubstituted heterocyclic group having 3 to 20 ring atoms, unsubstituted arylalkyl having 7 to 30 carbon atoms, unsubstituted alkoxy having 1 to 20 carbon atoms, unsubstituted aryloxy having 6 to 30 carbon atoms, unsubstituted alkenyl having 2 to 20 carbon atoms, unsubstituted alkynyl having 2 to 20 carbon atoms, unsubstituted aryl having 6 to 30 carbon atoms, unsubstituted heteroaryl having 3 to 30 carbon atoms, unsubstituted alkylsilyl having 3 to 20 carbon atoms, unsubstituted arylsilyl group having 6 to 20 carbon atoms, unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or an attached fragment are considered to be equivalent.

In the compounds mentioned in the present disclosure, hydrogen atoms may be partially or fully replaced by deuterium. Other atoms such as carbon and nitrogen may also be replaced by their other stable isotopes. The replacement by other stable isotopes in the compounds may be preferred due to its enhancements of device efficiency and stability.

In the compounds mentioned in the present disclosure, multiple substitution refers to a range that includes a di-substitution, up to the maximum available substitution. When substitution in the compounds mentioned in the present disclosure represents multiple substitution (including di-, tri-, and tetra-substitutions etc.), that means the substituent may exist at a plurality of available substitution positions on its linking structure, the substituents present at a plurality of available substitution positions may have the same structure or different structures.

In the compounds mentioned in the present disclosure, adjacent substituents in the compounds cannot be joined to form a ring unless otherwise explicitly defined, for example, adjacent substituents can be optionally joined to form a ring. In the compounds mentioned in the present disclosure, the expression that adjacent substituents can be optionally joined to form a ring includes a case where adjacent substituents may be joined to form a ring and a case where adjacent substituents are not joined to form a ring. When adjacent substituents can be optionally joined to form a ring, the ring formed may be monocyclic or polycyclic, as well as alicyclic, heteroalicyclic, aromatic, or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

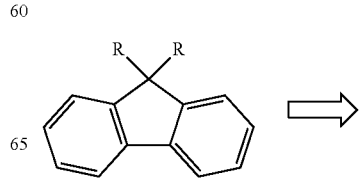

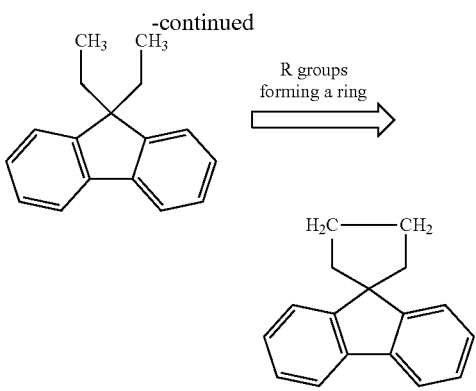

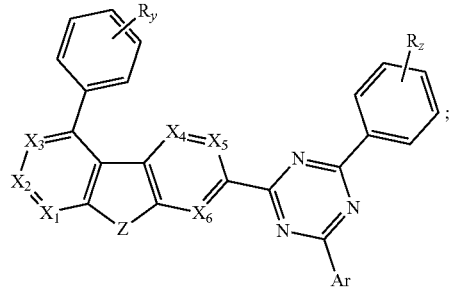

The expression that adjacent substituents can be optionally joined to form a ring is also intended to mean that two substituents bonded to carbon atoms which are directly bonded to each other are joined to each other via a chemical bond to form a ring, which can be exemplified by the following formula:

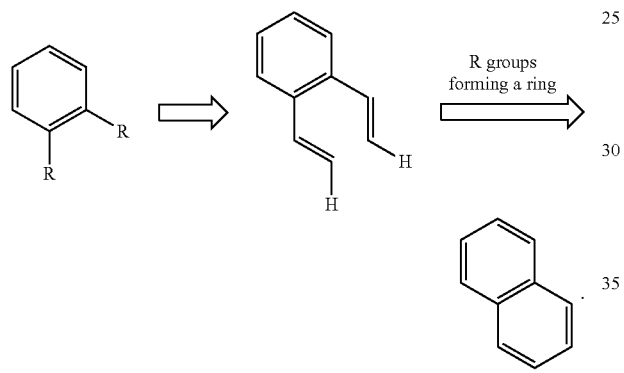

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

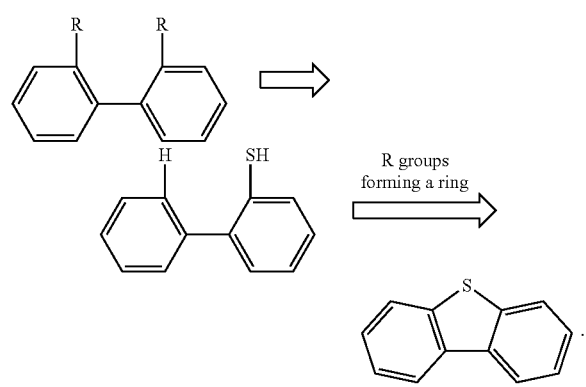

An embodiment of the present disclosure provides a compound having a structure of Formula 1:

wherein

Z is selected from O, S or Se;

$X_1$ to $X_6$ are, at each occurrence identically or differently, selected from $CR_x$ or N;

$R_y$ and $R_z$ represent, at each occurrence identically or differently, mono-substitution, multiple substitutions or non-substitution;

$R_x$, $R_y$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

at least one of $R_y$ and $R_z$ is substituted or unsubstituted aryl having 6 to 30 carbon atoms; and Ar is, at each occurrence identically or differently, selected from substituted or unsubstituted aryl having 10 to 30 carbon atoms.

According to an embodiment of the present disclosure, wherein, Z is selected from O or S.

According to an embodiment of the present disclosure, wherein, Z is selected from O.

According to an embodiment of the present disclosure, wherein, $X_1$ to $X_6$ are, at each occurrence identically or differently, selected from $CR_x$.

According to an embodiment of the present disclosure, wherein, at least one of $X_1$ to $X_6$ is selected from N.

According to an embodiment of the present disclosure, wherein, $R_x$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to an embodiment of the present disclosure, wherein, $R_x$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms and combinations thereof.

According to an embodiment of the present disclosure, wherein, $R_x$ is, at each occurrence identically or differently, selected from the group consisting of: hydrogen, deuterium, substituted or unsubstituted phenyl, substituted or unsubstituted naphthyl, substituted or unsubstituted biphenyl and combinations thereof.

According to an embodiment of the present disclosure, wherein, Ar is, at each occurrence identically or differently, selected from substituted or unsubstituted aryl having 10 to 30 carbon atoms; when Ar is selected from substituted aryl having 10 to 30 carbon atoms, the substitution is selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms and combinations thereof.

According to an embodiment of the present disclosure, wherein, Ar is, at each occurrence identically or differently, selected from substituted or unsubstituted aryl having 10 to 20 carbon atoms; when Ar is selected from substituted aryl having 10 to 20 carbon atoms, the substitution is selected from the group consisting of: deuterium, halogen, substituted or unsubstituted alkyl having 1 to 20 carbon atoms, substituted or unsubstituted cycloalkyl having 3 to 10 ring carbon atoms, substituted or unsubstituted aryl having 6 to 18 carbon atoms and combinations thereof.

According to an embodiment of the present disclosure, wherein, Ar is, at each occurrence identically or differently, selected from the group consisting of: naphthyl, biphenyl, phenanthryl, terphenyl, triphenylene and combinations thereof; optionally, the substituent can be partially or fully deuterated.

According to an embodiment of the present disclosure, wherein, at least one of $R_y$ and $R_z$ is substituted or unsubstituted aryl having 6 to 30 carbon atoms; and the rest of $R_y$ and R is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted aryl having 6 to 30 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

According to an embodiment of the present disclosure, wherein, at least one of $R_y$ and $R_z$ is substituted or unsubstituted aryl having 6 to 20 carbon atoms; and the rest of $R_y$ and $R_z$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted aryl having 6 to 20 carbon atoms and combinations thereof.

According to an embodiment of the present disclosure, wherein, at least one of $R_y$ and $R_z$ is selected from substituted or unsubstituted phenyl, substituted or unsubstituted naphthyl, substituted or unsubstituted phenanthryl, substituted or unsubstituted triphenylenyl, substituted or unsubstituted fluorenyl or a combination thereof; and the rest of $R_y$ and $R_z$ is, at each occurrence identically or differently, selected from the group consisting of: hydrogen, deuterium, substituted or unsubstituted aryl having 6 to 20 carbon atoms and combinations thereof.

According to an embodiment of the present disclosure, wherein, at least one of $R_y$ and $R_z$ is selected from phenyl, biphenyl, terphenyl, naphthyl, phenanthryl, triphenylene, dimethylfluorenyl or a combination thereof, wherein optionally, the above substituent is partially or fully deuterated; and the rest of $R_y$ and $R_z$ is, at each occurrence identically or differently, selected from the group consisting of: hydrogen, deuterium, phenyl, biphenyl, naphthyl, phenanthryl, triphenylene, terphenyl, fluorenyl, dibenzofuryl, dibenzothienyl and combinations thereof.

According to an embodiment of the present disclosure, wherein, the compound is selected from the group consisting of Compound A-1 to Compound A-552.

According to an embodiment of the present disclosure, wherein, the compound is selected from the group consisting of Compound A-1 to Compound A-577.

An embodiment of the present disclosure provides an organic electroluminescent device which includes an anode, a cathode and an organic layer disposed between the anode and the cathode, wherein the organic layer contains the compound in any one of the preceding embodiments.

According to an embodiment of the present disclosure, wherein, in the organic electroluminescent device, the organic layer is a light-emitting layer, the compound is a host compound, and the light-emitting layer contains at least a first metal complex.

According to an embodiment of the present disclosure, wherein, in the organic electroluminescent device, the organic layer is an electron transporting layer and the compound is an electron transporting compound.

According to an embodiment of the present disclosure, wherein, in the organic electroluminescent device, the first metal complex has a structure represented by Formula 2:

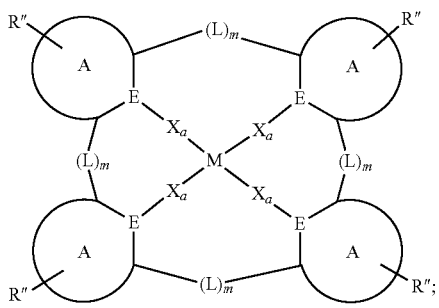

Formula 2 wherein
the metal M is, at each occurrence identically or differently, selected from the group consisting of Cu, Ag, Au, Ru, Rh, Pd, Os, Ir and Pt;
A is, at each occurrence identically or differently, selected from a substituted or unsubstituted aromatic ring having 5 to 30 ring atoms, a substituted or unsubstituted heteroaromatic ring having 5 to 30 ring atoms or a combination thereof;
L is, at each occurrence identically or differently, selected from the group consisting of: a single bond, BR', CR'R', NR', O, SiR'R', PR', S, GeR'R', Se, substituted or unsubstituted vinylene, ethynylene, substituted or unsubstituted arylene having 5 to 30 carbon atoms, substituted or unsubstituted heteroarylene having 5 to 30 carbon atoms and combinations thereof; when two R' are present at the same time, the two R' are identical or different;
m is, at each occurrence identically or differently, selected from 0 or 1; when m=0, the rings A are not joined to each other;
E is, at each occurrence identically or differently, selected from C or N;
$X_a$ is, at each occurrence identically or differently, selected from a single bond, O or S;
R" represents mono-substitution, multiple substitutions or non-substitution;
R' and R" are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof; and adjacent substituents R', R" can be optionally joined to form a ring.

In this embodiment, the expression that "adjacent substituents R', R'" can be optionally joined to form a ring" is intended to mean that any one or more of groups of adjacent substituents, such as two substituents R', two substituents R" and substituents R' and R", can be joined to form a ring. Obviously, it is possible that none of these substituents are joined to form a ring.

In this embodiment, when m is 0, it means that the corresponding L does not exist. For example, when one m is 0, Formula 2 is

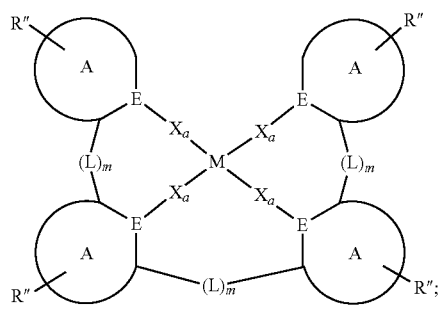

when two m are 0, Formula 2 is

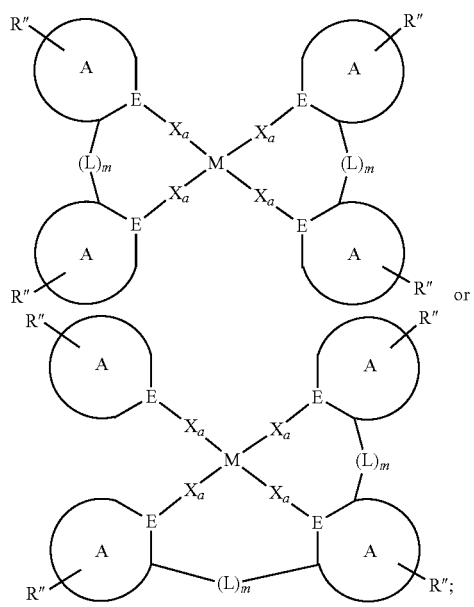

or when three m are 0, Formula 2 is

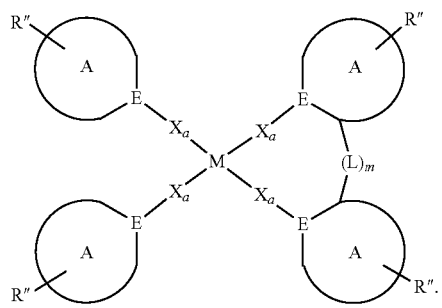

According to an embodiment of the present disclosure, wherein, in Formula 2, at least one A is selected from a substituted or unsubstituted heteroaromatic ring having 5 to 30 ring atoms.

According to an embodiment of the present disclosure, wherein, in Formula 2, at least one A is selected from substituted or unsubstituted benzimidazole, benzoxazole or benzothiazole and is coordinated to the M through a dashed line of

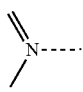

According to an embodiment of the present disclosure, wherein, in Formula 2, at least one A is selected from a substituted or unsubstituted heteroaromatic ring having 5 to 30 ring atoms.

According to an embodiment of the present disclosure, wherein, in Formula 2, at least one A is selected from substituted or unsubstituted pyridine and is coordinated to the M through the N of pyridine.

According to an embodiment of the present disclosure, wherein, in Formula 2, at least one m, at least two m or at least three m are not 0.

According to an embodiment of the present disclosure, wherein, in Formula 2, L is a single bond.

According to an embodiment of the present disclosure, wherein, in Formula 2, at least one $X_a$ is O or S.

According to an embodiment of the present disclosure, wherein, in Formula 2, at least one $X_a$ is O.

According to an embodiment of the present disclosure, wherein, the first metal complex has a general formula of $M(L_a)/(L_b)_g(L_c)_h$, wherein $L_a$ has a structure represented by Formula 3:

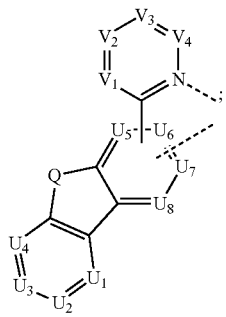

Formula 3 wherein
the metal M is, at each occurrence identically or differently, selected from the group consisting of Cu, Ag, Au, Ru, Rh, Pd, Os, Ir and Pt;
$L_a$, $L_b$ and $L_c$ are a first ligand, a second ligand and a third ligand coordinated to the metal M, respectively; $L_a$, $L_b$ and $L_c$ can be optionally joined to form a multidentate ligand; for example, any two of $L_a$, $L_b$ and $L_c$ may be joined to form a tetradentate ligand; in another example, $L_a$, $L_b$ and $L_c$ may be joined to each other to form a hexadentate ligand; in another example, none of $L_a$, $L_b$ and $L_c$ are joined so that the multidentate ligand is not formed;

f is selected from 0, 1, 2 or 3, g is selected from 0, 1, 2 or 3, and h is selected from 0, 1 or 2;
when f is 2 or 3, the plurality of $L_a$ are identical or different; when g is 2 or 3, the plurality of $L_b$ are identical or different; when h is 2, two $L_c$ are identical or different;
Q is, at each occurrence identically or differently, selected from the group consisting of O, S, Se, $NR_q$, $CR_qR_q$ and $SiR_qR_q$; when two $R_q$ are present at the same time, the two $R_q$ are identical or different;
$U_1$ to $U_8$ are, at each occurrence identically or differently, selected from C, $CR_u$ or N; at least one of $U_5$ to $U_8$ is C and joined to

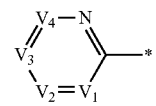

in Formula 3, wherein "*" represents a joining position;
$U_5$, $U_6$, $U_7$ or Us is joined to the metal M by a metal-carbon bond or a metal-nitrogen bond;
$V_1$ to $V_4$ are, at each occurrence identically or differently, selected from $CR_v$ or N;
$R_q$, $R_u$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;
adjacent substituents $R_q$, $R_u$ and $R_y$ can be optionally joined to form a ring;
$L_b$ and $L_c$ are, at each occurrence identically or differently, selected from a structure represented by any one of the group consisting of the following:

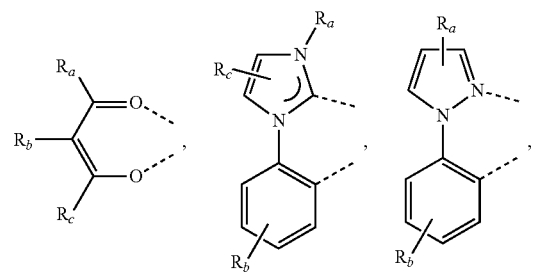

-continued

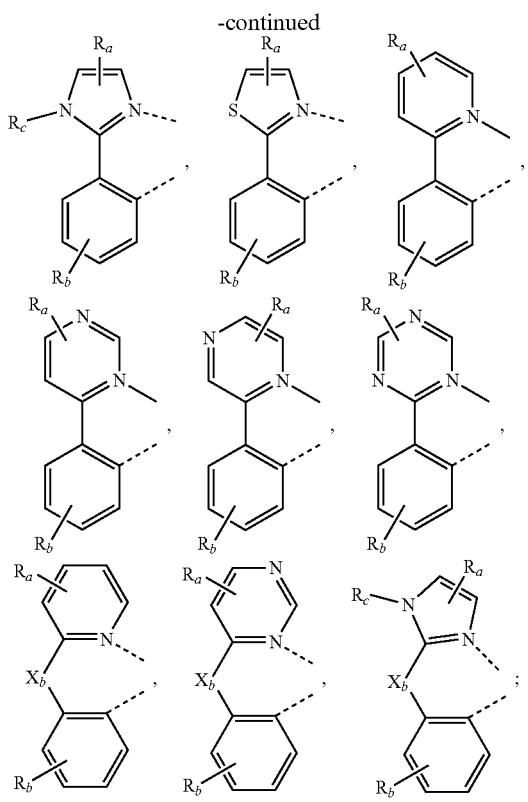

wherein
$R_a$, $R_b$ and $R_c$ represent, at each occurrence identically or differently, mono-substitution, multiple substitutions or non-substitution;
$X_b$ is, at each occurrence identically or differently, selected from the group consisting of: O, S, Se, $NR_{N1}$ and $CR_{C1}R_{C2}$;
$R_a$, $R_b$, $R_c$, $R_{N1}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof; and
adjacent substituents $R_a$, $R_b$, $R_c$, $R_{N1}$, $R_{C1}$ and $R_{C2}$ can be optionally joined to form a ring.
Herein, the expression that "adjacent substituents $R_q$, $R_u$ and $R_v$ can be optionally joined to form a ring" is intended to mean that any one or more of groups of adjacent substituents, such as two substituents $R_q$, two substituents $R_u$, two substituents $R_v$, substituents $R_u$ and R. and substituents $R_u$ and $R_q$, can be joined to form a ring. Obviously, it is possible that none of these substituents are joined to form a ring.

In this embodiment, the expression that "adjacent substituents $R_a$, $R_b$, $R_c$, $R_{x1}$, $R_{C1}$ and $R_{C2}$ can be optionally joined to form a ring" is intended to mean that any one or more of groups of adjacent substituents, such as two substituents $R_a$, two substituents $R_b$, two substituents $R_c$, substituents $R_a$ and $R_b$, substituents $R_a$ and Re, substituents $R_b$ and Re, substituents $R_a$ and $R_{N1}$, substituents $R_b$ and $R_{x1}$, substituents $R_a$ and $R_{C1}$, substituents $R_a$ and $R_{C2}$, substituents $R_b$ and $R_{C1}$, substituents $R_b$ and $R_{C2}$, and substituents $R_{C1}$ and $R_{C2}$, can be joined to form a ring. Obviously, it is possible that none of these substituents are joined to form a ring.

According to an embodiment of the present disclosure, wherein, at least one of $U_1$ to $U_8$ is N, for example, one or two of $U_1$ to Us are N.

According to an embodiment of the present disclosure, wherein, at least one of $V_1$ to $V_4$ is N, for example, one or two of $V_1$ to $V_4$ are N.

According to another embodiment of the present disclosure, wherein, the ligand $L_a$ has a structure represented by Formula 3a:

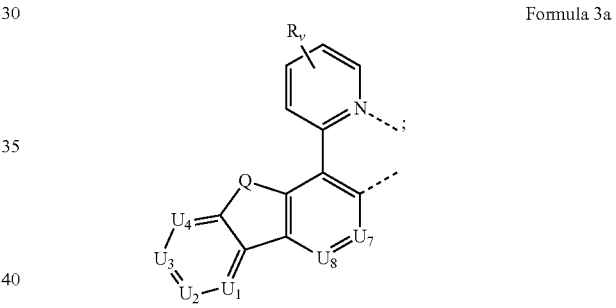

Formula 3a wherein
Q is, at each occurrence identically or differently, selected from the group consisting of O, S, Se, $NR_q$, $CR_qR_q$ and $SiR_qR_q$; when two $R_q$ are present at the same time, the two $R_q$ may be identical or different;
$U_1$ to $U_4$, $U_7$ and Us are, at each occurrence identically or differently, selected from $CR_u$ or N;
$R_v$ represents, at each occurrence identically or differently, mono-substitution, multiple substitutions or non-substitution;
$R_q$, $R_u$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and adjacent substituents $R_q$, $R_u$ and $R_v$ can be optionally joined to form a ring.

According to another embodiment of the present disclosure, wherein, the ligand $L_a$ is, at each occurrence identically or differently, selected from any one of the following structures:

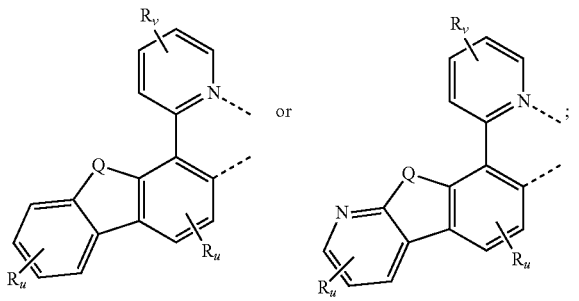

wherein

Q is, at each occurrence identically or differently, selected from the group consisting of O, S, Se, $NR_q$, $CR_qR_q$ and $SiR_qR_q$; when two $R_q$ are present at the same time, the two $R_q$ may be identical or different;

$R_u$ and $R_y$ represent, at each occurrence identically or differently, mono-substitution, multiple substitutions or non-substitution;

$R_q$, $R_u$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and adjacent substituents $R_q$, $R_u$ and $R_y$ can be optionally joined to form a ring.

According to another embodiment of the present disclosure, wherein, the first metal complex has a structure represented by Formula 4:

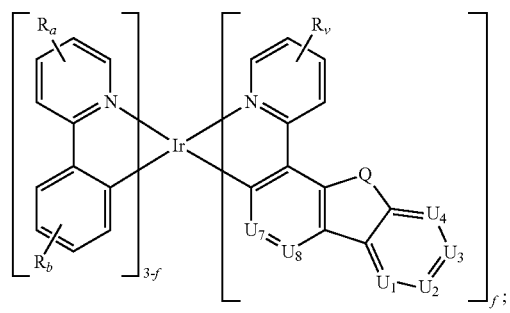

Formula 4 wherein f is 0, 1, 2 or 3; when f is 2 or 3, the plurality of $L_a$ are identical or different; when f is 0 or 1, the plurality of $L_b$ are identical or different;

$U_4$ is, at each occurrence identically or differently, selected from $CR_u$ or N;

$U_1$ to $U_3$, U and Us are, at each occurrence identically or differently, selected from $CR_u$;

$R_a$, $R_b$ and $R_y$ represent, at each occurrence identically or differently, mono-substitution, multiple substitutions or non-substitution;

$R_a$, $R_b$, $R_u$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and adjacent substituents $R_a$, $R_b$, $R_u$ and $R_y$ can be optionally joined to form a ring.

In this embodiment, the expression that "adjacent substituents $R_a$, $R_b$, $R_u$ and $R_y$ can be optionally joined to form a ring" is intended to mean that any one or more of groups of adjacent substituents, such as two substituents $R_a$, two substituents $R_b$, two substituents $R_u$, two substituents R. and substituents $R_a$ and $R_b$, can be joined to form a ring. Obviously, it is possible that none of these substituents are joined to form a ring.

According to an embodiment of the present disclosure, wherein, in Formula 3a and Formula 4, at least one of $U_1$ to Us is N, for example, one or two of $U_1$ to Us are N.

According to an embodiment of the present disclosure, wherein, in Formula 3a and Formula 4, at least one of $U_1$ to Us is selected from $CR_u$ and $R_u$ is cyano.

According to an embodiment of the present disclosure, wherein, in Formula 3a and Formula 4, at least one of U2 to $U_4$ is selected from $CR_u$ and $R_u$ is cyano.

According to an embodiment of the present disclosure, wherein, in Formula 3a and Formula 4, one of $U_3$ or $U_4$ is selected from $CR_u$ and $R_u$ is cyano.

According to an embodiment of the present disclosure, wherein, in Formula 3a and Formula 4, one of $U_2$ to $U_4$ is selected from CR, and $R_u$ is cyano; and one of $U_1$ to $U_4$ is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.

According to an embodiment of the present disclosure, wherein, in Formula 3a and Formula 4, $U_4$ is $CR_u$ and $R_u$ is substituted or unsubstituted phenyl; and $U_3$ is $CR_u$ and $R_u$ is cyano.

According to an embodiment of the present disclosure, wherein, in Formula 3a and Formula 4, $U_3$ is $CR_u$ and $R_u$ is substituted or unsubstituted phenyl; and $U_4$ is $CR_u$ and $R_u$ is cyano.

According to an embodiment of the present disclosure, wherein, in Formula 3a and Formula 4, $U_3$ is $CR_u$ and $R_u$ is substituted or unsubstituted alkyl having 1 to 10 carbon atoms; and $U_4$ is $CR_u$ and $R_u$ is cyano.

According to an embodiment of the present disclosure, wherein, in Formula 3a and Formula 4, at least one of $U_1$ to Us is selected from $CR_u$ and $R_u$ is fluorine.

According to an embodiment of the present disclosure, wherein, in Formula 3a and Formula 4, $U_3$ is selected from $CR_u$ and $R_u$ is fluorine; and $U_4$ is selected from $CR_u$ and $R_u$ is substituted or unsubstituted aryl having 6 to 30 carbon atoms or substituted or unsubstituted heteroaryl having 3 to 30 carbon atoms.

According to an embodiment of the present disclosure, wherein, $R_u$ and $R_y$ are, at each occurrence identically or differently, selected from the group consisting of: hydrogen, deuterium, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms and combinations thereof.

According to an embodiment of the present disclosure, wherein, at least one $R_u$ is selected from substituted or unsubstituted alkyl having 1 to 20 carbon atoms or substituted or unsubstituted cycloalkyl having 3 to 20 ring carbon atoms.

According to an embodiment of the present disclosure, wherein, at least one of $R_u$ is fluorine.

According to an embodiment of the present disclosure, wherein, at least one of $R_u$ is cyano.

According to an embodiment of the present disclosure, wherein, there exist at least two $R_u$, one of which is fluorine and the other one of which is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.

According to an embodiment of the present disclosure, wherein, there exist at least two $R_u$, one of which is cyano and the other one of which is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.

According to an embodiment of the present disclosure, wherein, $L_a$ is, at each occurrence identically or differently, selected from the group consisting of: $L_{a1-1}$ to $L_{a1-114}$, $L_{a2-1}$ to $L_{a2-81}$, $L_{a3-1}$ to $L_{a3-73}$ and $L_{a4-1}$ to $L_{a4-82}$.

According to an embodiment of the present disclosure, wherein, $L_b$ is, at each occurrence identically or differently, selected from the group consisting of $L_{b1}$ to $L_{b227}$.

According to an embodiment of the present disclosure, wherein, $L_c$ is, at each occurrence identically or differently, selected from the group consisting of $L_{b1}$ to $L_{b227}$.

According to an embodiment of the present disclosure, wherein, the first metal complex has a general formula of $Ir(L_b)_3$ or $Ir(L_b)_2L_c$ or $IrLb (L_c)_2$, wherein $L_b$ is, at each occurrence identically or differently, selected from the group consisting of $L_{b1}$ to $L_{b227}$ and $L_c$ is, at each occurrence identically or differently, selected from the group consisting of $L_{b1}$ to $L_{b227}$.

According to an embodiment of the present disclosure, wherein, the first metal complex has a general formula of $Ir(L_a)_2 L_b$ or $IrL_a(L_b)_2$, wherein $L_a$ is, at each occurrence identically or differently, selected from the group consisting of: $L_{a1-1}$ to $L_{a1-114}$, $L_{a2-1}$ to $L_{a2-81}$, $L_{a3-1}$ to $L_{a3-73}$ and $L_{a4-1}$ to $L_{a4-82}$ and $L_b$ is, at each occurrence identically or differently, selected from the group consisting of $L_{b1}$ to $L_{b227}$.

According to an embodiment of the present disclosure, wherein, the first metal complex is selected from the group consisting of: GD1-1 to GD1-87, GD2-1 to GD2-80, GD3-1 to GD3-75, GD4-1 to GD4-86, GD5-1 to GD5-85, GD6-1 to GD6-46 and GD7-1 to GD7-28.

According to an embodiment of the present disclosure, wherein, in the organic electroluminescent device, the light-emitting layer further contains a second host compound, wherein the second host compound comprises at least one chemical group selected from the group consisting of: benzene, pyridine, pyrimidine, triazine, carbazole, azacarbazole, indolocarbazole, dibenzothiophene, aza-dibenzothiophene, dibenzofuran, azadibenzofuran, dibenzoselenophene, triphenylene, azatriphenylene, fluorene, silafluorene, naphthalene, quinoline, isoquinoline, quinazoline, quinoxaline, phenanthrene, azaphenanthrene and combinations thereof.

According to an embodiment of the present disclosure, wherein, in the organic electroluminescent device, the light-emitting layer further contains a second host compound, wherein the second host compound comprises at least one chemical group selected from the group consisting of: benzene, carbazole, indolocarbazole, fluorene, silafluorene and combinations thereof.

According to an embodiment of the present disclosure, wherein, in the organic electroluminescent device, the second host compound has a structure represented by Formula 5:

Formula 5

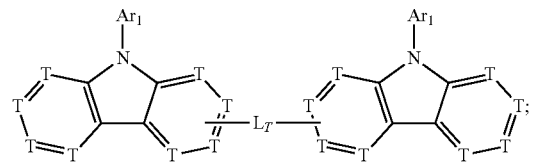

wherein
- $L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;
- T is, at each occurrence identically or differently, selected from C, $CR_t$ or N;
- $R_t$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;
- $Ar_1$ is, at each occurrence identically or differently, selected from substituted or unsubstituted aryl having 6 to 30 carbon atoms, substituted or unsubstituted heteroaryl having 3 to 30 carbon atoms or a combination thereof; and
- adjacent substituents $R_t$ can be optionally joined to form a ring.

In this present disclosure, the expression that "adjacent substituents $R_t$ can be optionally joined to form a ring" is intended to mean that any one or more of groups of two adjacent substituents $R_t$ can be joined to form a ring. Obviously, it is possible that none of these substituents are joined to form a ring.

According to an embodiment of the present disclosure, wherein, in the organic electroluminescent device, the second host compound has a structure represented by Formula 6:

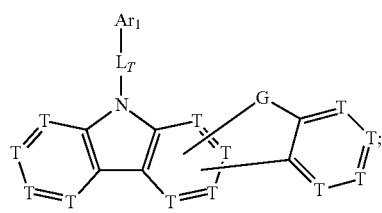

Formula 6 wherein
G is, at each occurrence identically or differently, selected from $C(R_g)_2$, $NR_g$, O or S;

T is, at each occurrence identically or differently, selected from C, $CR_t$ or N;

$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

$R_t$ and $R_g$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; $Ar_1$ is, at each occurrence identically or differently, selected from substituted or unsubstituted aryl having 6 to 30 carbon atoms, substituted or unsubstituted heteroaryl having 3 to 30 carbon atoms or a combination thereof; and adjacent substituents $R_t$, $R_g$ can be optionally joined to form a ring.

In this present disclosure the expression that "adjacent substituents $R_t$, $R_g$ can be optionally joined to form a ring" is intended to mean that any one or more of groups of two adjacent substituents $R_t$ and adjacent substituents $R_t$ and $R_g$ can be joined to form a ring. Obviously, it is possible that none of these substituents are joined to form a ring.

According to an embodiment of the present disclosure, wherein, in the organic electroluminescent device, the second host compound has a structure represented by one of Formulas 5-a to 5-j:

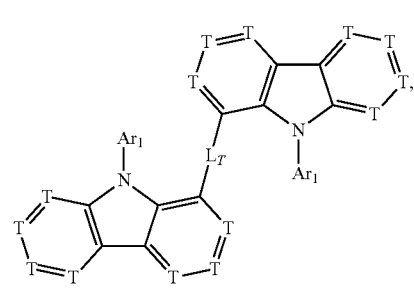

Formula 5-a

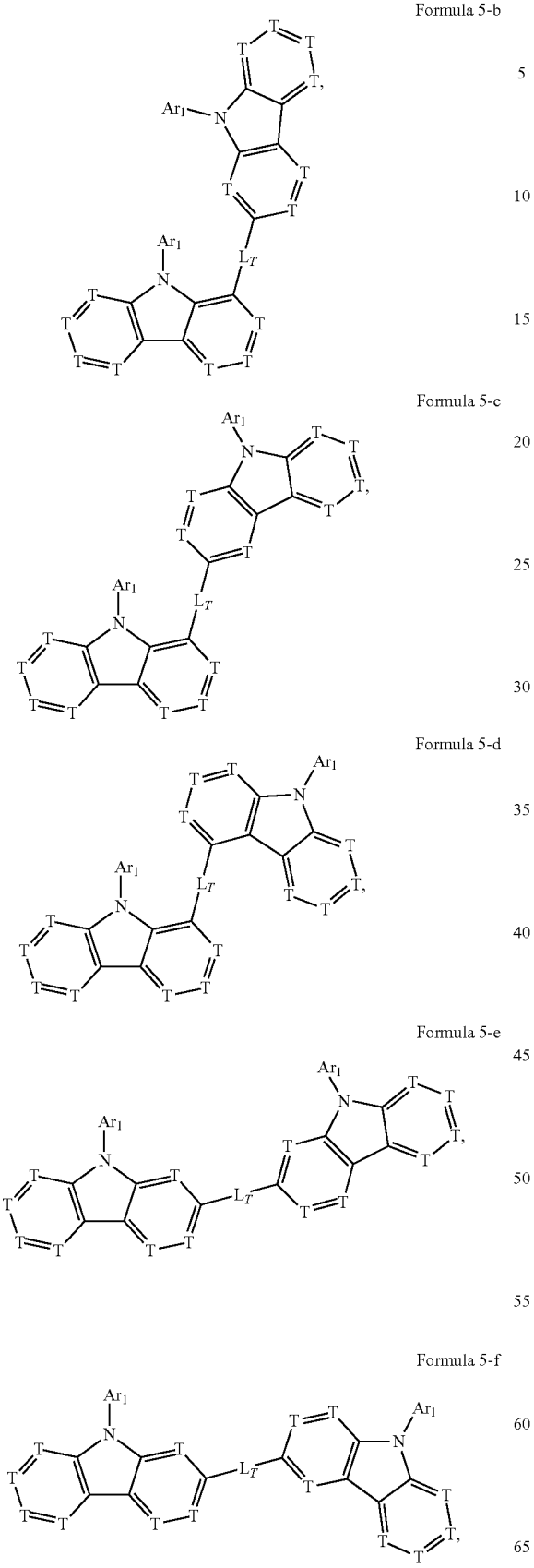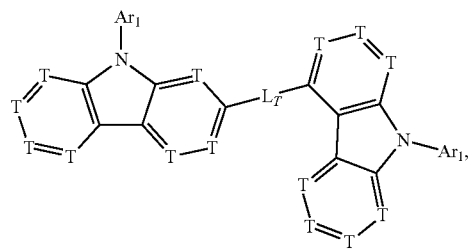
wherein
$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

T is, at each occurrence identically or differently, selected from $CR_t$ or N;

$R_t$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_1$ is, at each occurrence identically or differently, selected from substituted or unsubstituted aryl having 6 to 30 carbon atoms, substituted or unsubstituted heteroaryl having 3 to 30 carbon atoms or a combination thereof; and adjacent substituents $R_t$ can be optionally joined to form a ring.

According to an embodiment of the present disclosure, wherein, in the organic electroluminescent device, the second host compound has a structure represented by one of Formulas 6-a to 6-f:

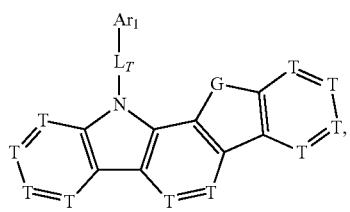

Formula 6-a

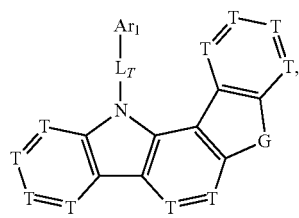

Formula 6-b

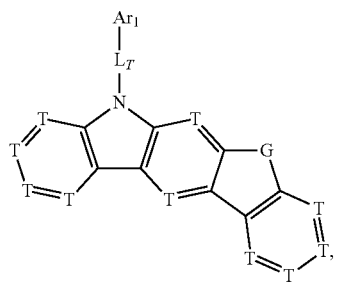

Formula 6-c

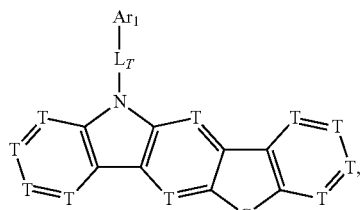

Formula 6-d

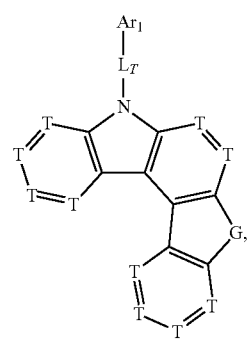

Formula 6-e

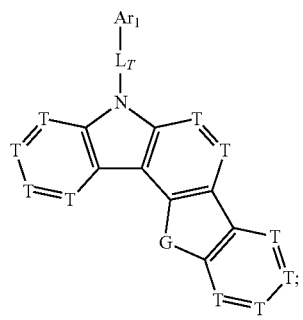

Formula 6-f wherein

G is, at each occurrence identically or differently, selected from $C(R_g)_2$, $NR_g$, O or S;

T is, at each occurrence identically or differently, selected from $CR_t$ or N;

$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

$R_t$ and $R_g$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_1$ is, at each occurrence identically or differently, selected from substituted or unsubstituted aryl having 6 to 30 carbon atoms, substituted or unsubstituted heteroaryl having 3 to 30 carbon atoms or a combination thereof; and adjacent substituents $R_f$, $R_g$ can be optionally joined to form a ring.

According to an embodiment of the present disclosure, wherein, at least one of T is selected from N, for example, one or two of T are N.

An embodiment of the present disclosure further provides a compound composition which contains the compound in any one of the preceding embodiments.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, the compound disclosed herein may be used in combination with a wide variety of hosts, emissive dopants, transporting layers, blocking layers, injection layers, electrodes and other layers that may be present. The combination of these materials is described in detail in paragraphs 0080-0101 of U.S. patent application No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

MATERIAL SYNTHESIS EXAMPLE

The method for preparing a compound in the present disclosure is not limited herein. Typically, the following compounds are used as examples without limitations, and synthesis routes and preparation methods thereof are described below.

Synthesis Example 1: Synthesis of Compound A-1

Step 1: Synthesis of Intermediate C

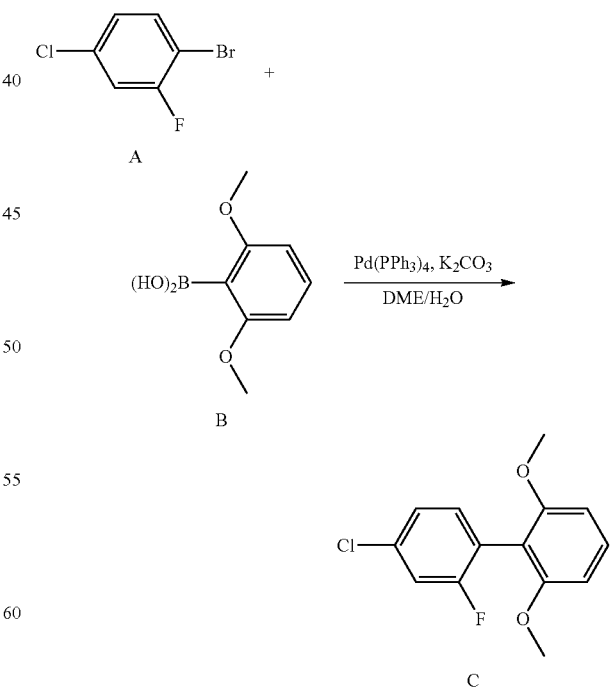

In a three-necked round-bottom flask, A (50.0 g, 238.8 mmol), B (50.0 g, 274.6 mmol), $Pd(PPh_3)_4$ (2.76 g, 2.39 mmol) and $K_2CO_3$ (50.6 g, 477.6 mmol) were added to ethylene glycol dimethyl ether (500 mL) and H₂O (250 mL) and heated to reflux overnight under nitrogen protection. Then stopped heating and the reacting system was cooled to room temperature. Organic phases were taken, the aqueous phase was added with DCM and extracted multiple times, and the organic phases were combined, dried over anhydrous Na₂SO₄, filtered and concentrated under reduced pressure. The crude product was purified through column chromatography (PE:DCM=10:1) to obtain Intermediate C(62.3 g, 233.6 mmol) as a colorless oil with a yield of 97.8%.

Step 2: Synthesis of Intermediate D

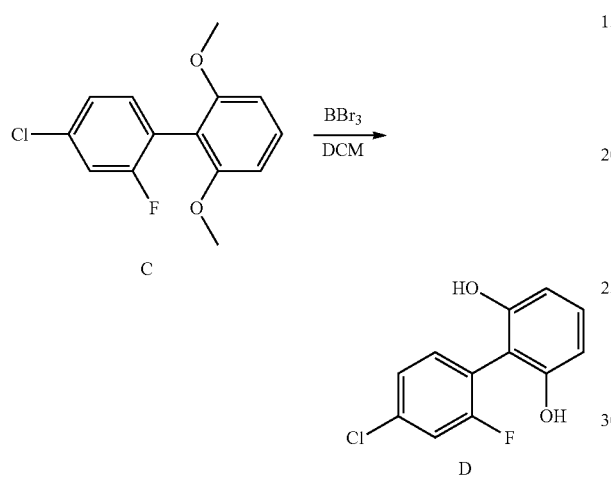

In a single-necked round-bottom flask, C(62.3 g, 233.6 mmol) was dissolved in DCM (600 mL) and BBr₃ (175.6 g, 700.8 mmol) was slowly added dropwise to the system at 0° C. After dropwise addition, the system was gradually warmed to room temperature and reacted overnight. Then the reaction solution was slowly poured into water and extracted with DCM several times. The organic phases were combined, dried over anhydrous Na₂SO₄, filtered and concentrated under reduced pressure. The crude product was purified through column chromatography (PE:EA=4:1) to obtain Intermediate D (52.0 g, 217.9 mmol) as a white solid with a yield of 93.3%.

Step 3: Synthesis of Intermediate E

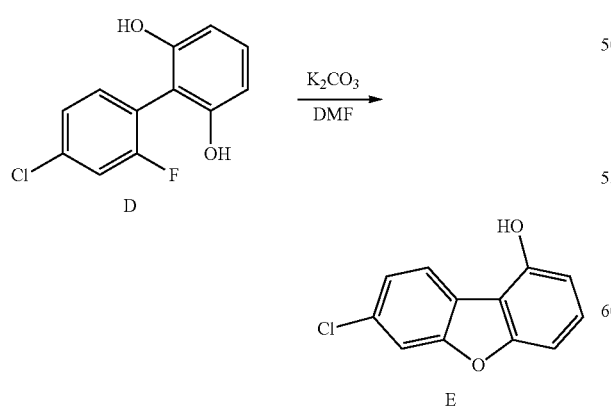

In a three-necked round-bottom flask, D (52.0 g, 217.9 mmol) and K₂CO₃ (75.3 g, 544.8 mmol) were added to DMF (500 mL) and heated to 140° C. and reacted overnight under nitrogen protection. Then stopped heating and the reacting system was cooled to room temperature, poured into a large amount of water and extracted with DCM several times. The organic phases were combined, dried over anhydrous Na₂SO₄, filtered and concentrated under reduced pressure. The crude product was purified through column chromatography (PE:EA=5:1) to obtain Intermediate E (43.9 g, 200.8 mmol) as a white solid with a yield of 92.1%.

Step 4: Synthesis of Intermediate F

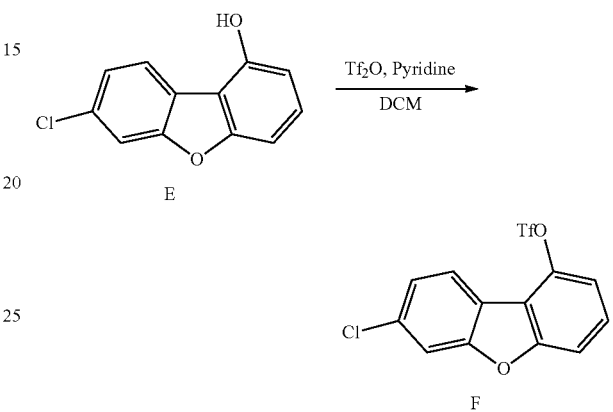

In a single-necked round-bottom flask, E (43.9 g, 200.8 mmol) and pyridine (31.8 g, 401.6 mmol) were dissolved in DCM (400 mL) and trifluoromethanesulfonic anhydride (68.0 g, 241.0 mmol) was slowly added dropwise to the system at 0° C. After dropwise addition, the system was gradually warmed to room temperature and reacted overnight. After the reaction was finished, the reaction solution was poured into water and extracted with DCM several times. The organic phases were combined, dried over anhydrous Na₂SO₄, filtered and concentrated under reduced pressure. The crude product was purified through column chromatography (PE:DCM=30:1) to obtain Intermediate F (68.2 g, 194.5 mmol) as a white solid with a yield of 96.8%.

Step 5: Synthesis of Intermediate G

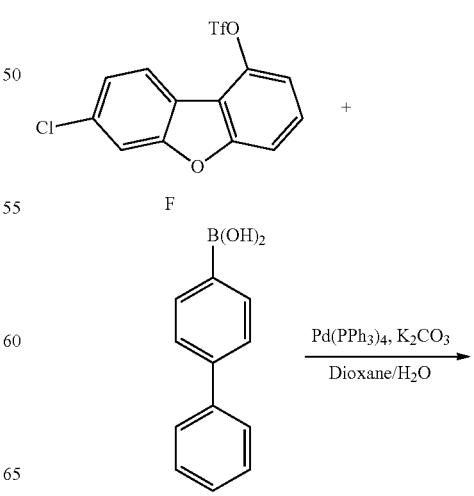

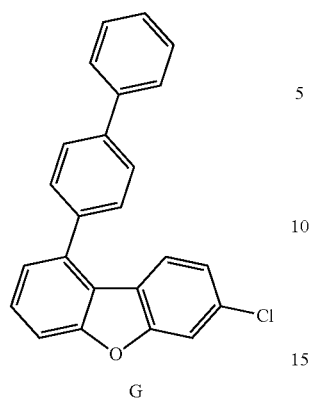

G

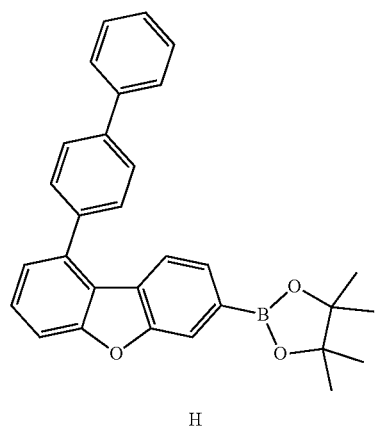

H

In a three-necked round-bottom flask, F (8.0 g, 22.9 mmol), 4-biphenylboronic acid (5.9 g, 29.7 mmol), Pd(PPh₃)₄ (1.3 g, 1.1 mmol) and K₂CO₃ (9.5 g, 68.7 mmol) were added to 1,4-dioxane (100 mL) and H₂O (25 mL) and heated to reflux overnight under nitrogen protection. Then stopped heating and the reacting system was cooled to room temperature. Organic phases were taken, the aqueous phase was added with DCM and extracted multiple times, and the organic phases were combined, dried over anhydrous Na₂SO₄, filtered and concentrated under reduced pressure. The crude product was purified through column chromatography (PE:DCM=40:1->15:1) to obtain Intermediate G (7.0 g, 19.7 mmol) as a white solid with a yield of 86.1%.

Step 6: Synthesis of Intermediate H

In a three-necked round-bottom flask, G (7.0 g, 19.7 mmol), bis(pinacolato)diboron (10.0 g, 39.4 mmol), Pd(OAc)₂ (0.2 g, 1.0 mmol), 2-dicyclohexylphosphino-2,4,6-triisopropylbiphenyl (X-Phos) (0.9 g, 2.0 mmol) and AcOK (5.8 g, 59.1 mmol) were added to 1,4-dioxane (100 mL) and heated to reflux overnight under nitrogen protection. Then stopped heating and the reacting system was cooled to room temperature. The reaction system was filtered through Celite. The filtrate was concentrated under reduced pressure. The crude product was purified through column chromatography (PE:DCM=4:1→2:1) to obtain Intermediate H (6.0 g, 13.4 mmol) as a white solid with a yield of 68.2%.

Step 7: Synthesis of Compound A-1

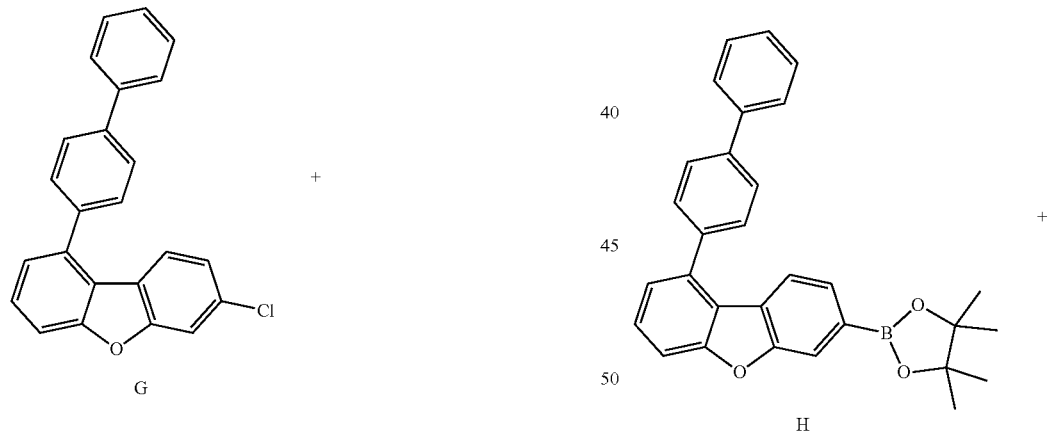

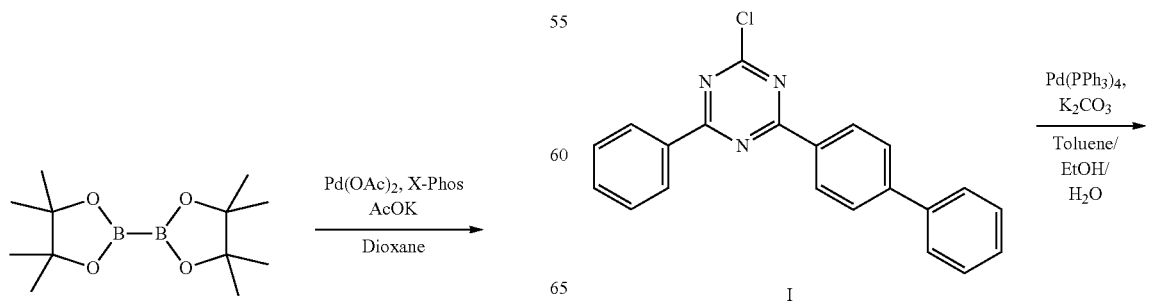

I

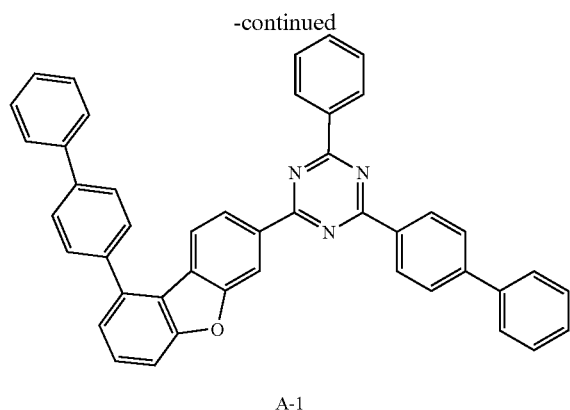

A-1

In a three-necked round-bottom flask, H (4.5 g, 10.0 mmol), I (3.4 g, 10.0 mmol), Pd(PPh₃)₄ (0.6 g, 0.5 mmol) and K₂CO₃ (4.1 g, 30.0 mmol) were added to toluene (80 mL), EtOH (20 mL) and H₂O (20 mL) and heated to reflux overnight under nitrogen protection. Then stopped heating and the reacting system was cooled to room temperature and filtered through suction under reduced pressure, and the obtained solid was washed with water and methanol in sequence. The solid was recrystallized from toluene/acetonitrile to obtain a white solid (5.7 g, 9.08 mmol) with a yield of 90.8%. The product was confirmed as the target product A-1 with a molecular weight of 627.2.

Synthesis Example 2: Synthesis of Compound A-27

Step 1: Synthesis of Intermediate J

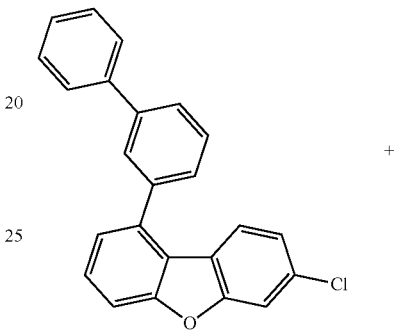

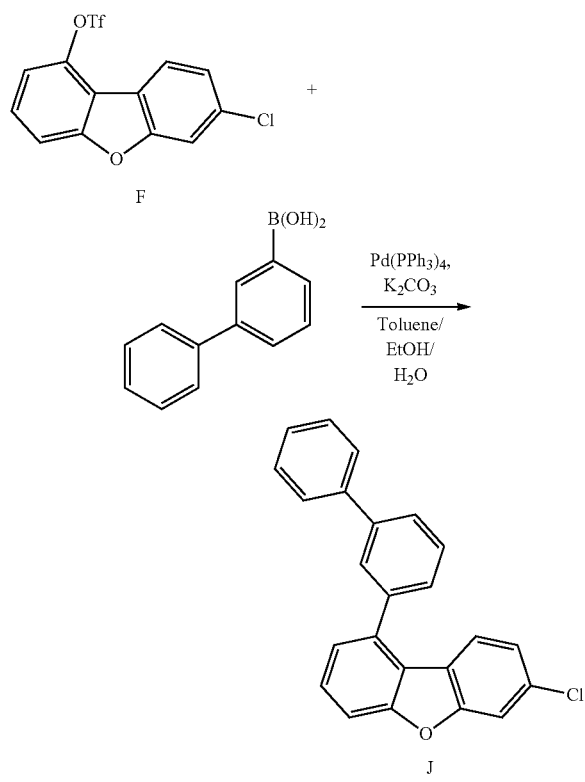

In a three-necked round-bottom flask, F (6.0 g, 17.1 mmol), 3-biphenylboronic acid (3.70 g, 18.81 mmol), Pd(PPh₃)₄ (0.59 g, 0.51 mmol) and K₂CO₃ (4.72 g, 34.2 mmol) were added to toluene (58 mL), EtOH (14 mL) and H₂O (14 mL) and heated to reflux overnight under nitrogen protection. Then stopped heating and the reacting system was cooled to room temperature. Organic phases were taken, the aqueous phase was added with DCM and extracted multiple times, and the organic phases were combined, dried over anhydrous Na₂SO₄, filtered and concentrated under reduced pressure. The crude product was purified through column chromatography (PE:DCM=50:1) to obtain Intermediate J (5.6 g, 15.8 mmol) as a colorless oil with a yield of 92.3%.

Step 2: Synthesis of Intermediate K

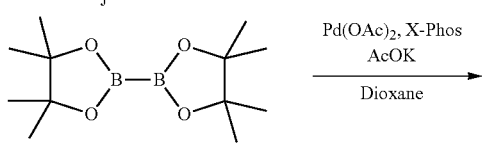

In a three-necked round-bottom flask, J (6.0 g, 17.47 mmol), bis(pinacolato)diboron (6.65 g, 26.2 mmol), Pd(OAc)₂ (0.08 g, 0.35 mmol), 2-dicyclohexylphosphino-2,4,6-triisopropylbiphenyl (X-Phos) (0.33 g, 0.67 mmol) and AcOK (3.43 g, 34.94 mmol) were added to 1,4-dioxane (87 mL) and heated to reflux overnight under nitrogen protection. Then stopped heating and the reacting system was cooled to room temperature. The reaction system was filtered through Celite. The filtrate was concentrated under reduced pressure. The crude product was purified through column chromatography (PE:DCM=4:1→2:1) to obtain Intermediate K (4.71 g, 10.55 mmol) as a white solid with a yield of 60.4%.

Step 3: Synthesis of Compound A-27

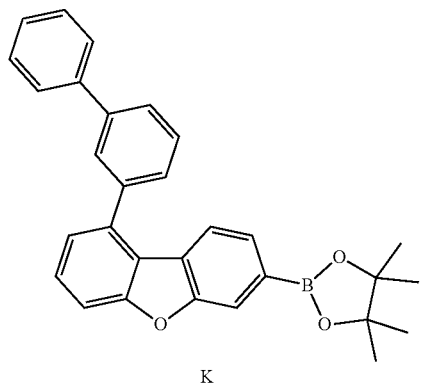

K

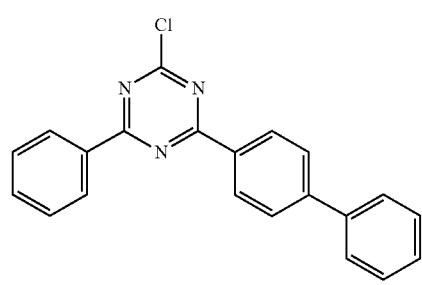

I

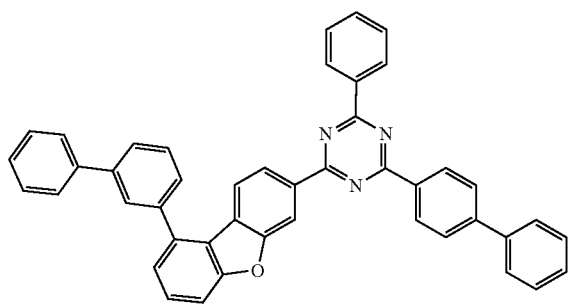

A-27

In a three-necked round-bottom flask, K (4.71 g, 10.55 mmol), I (3.63 g, 10.55 mmol), Pd(PPh$_3$)$_4$ (0.36 g, 0.32 mmol) and K$_2$CO$_3$ (2.9 g, 21.1 mmol) were added to toluene (48 mL), EtOH (12 mL) and H$_2$O (12 mL) and heated to reflux overnight under nitrogen protection. Then stopped heating and the reacting system was cooled to room temperature and filtered through suction under reduced pressure, and the obtained solid was washed with water and methanol in sequence. The solid was recrystallized from toluene to obtain a white solid (5.9 g, 9.39 mmol) with a yield of 89.0%. The product was confirmed as the target product A-27 with a molecular weight of 627.2.

Synthesis Example 3: Synthesis of Compound A-209

Step 1: Synthesis of Intermediate L

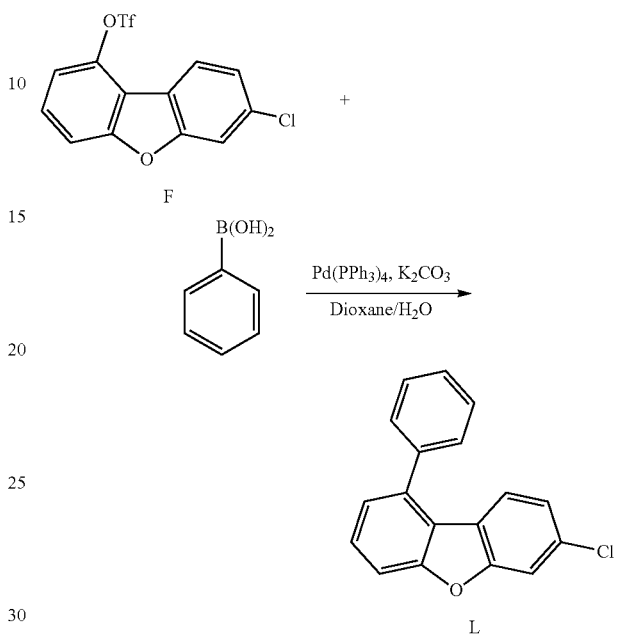

L

In a three-necked round-bottom flask, F (28.4 g, 109.7 mmol), phenylboronic acid (17.4 g, 142.6 mmol), Pd(PPh$_3$)$_4$ (2.5 g, 2.2 mmol) and K$_2$CO$_3$ (45.4 g, 329.1 mmol) were added to 1,4-dioxane (240 mL) and H$_2$O (60 mL) and heated to reflux overnight under nitrogen protection. Then stopped heating and the reacting system was cooled to room temperature. Organic phases were obtained, the aqueous phase was added with DCM and extracted multiple times, and the organic phases were combined, dried over anhydrous Na$_2$SO$_4$, filtered and concentrated under reduced pressure. The crude product was purified through column chromatography (PE:DCM=40:1) to obtain Intermediate L (20.6 g, 73.9 mmol) as a white solid with a yield of 67.4%.

Step 2: Synthesis of Intermediate M

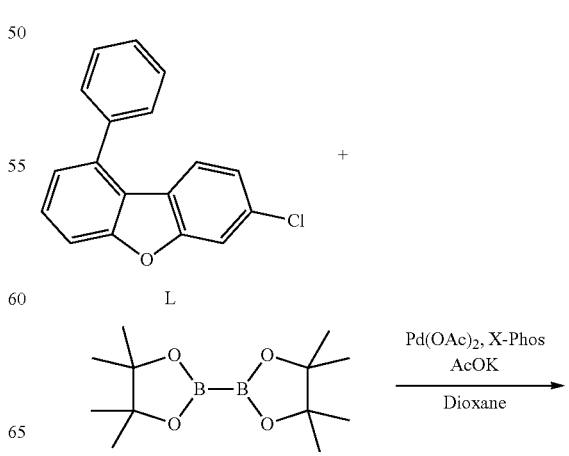

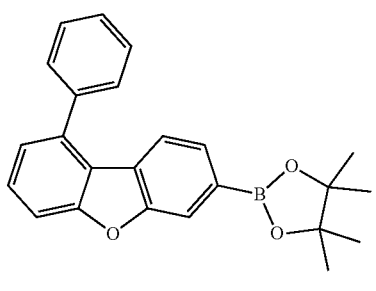

M

In a three-necked round-bottom flask, L (20.6 g, 73.9 mmol), bis(pinacolato)diboron (37.5 g, 147.8 mmol), Pd(OAc)$_2$ (0.8 g, 3.7 mmol), 2-dicyclohexylphosphino-2,4,6-triisopropylbiphenyl (X-Phos) (3.5 g, 7.4 mmol) and AcOK (21.7 g, 221.7 mmol) were added to 1,4-dioxane (200 mL) and heated to reflux overnight under nitrogen protection. Then stopped heating and the reacting system was cooled to room temperature and filtered through Celite, and the filtrate was concentrated under reduced pressure. The crude product was purified through column chromatography (PE:DCM=8:1→1:1) to obtain Intermediate M (24.0 g, 64.8 mmol) as a white solid with a yield of 87.7%.

Step 3: Synthesis of Compound A-209

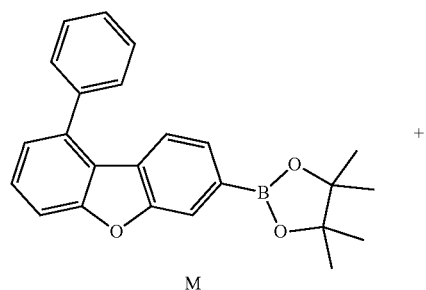

M

+

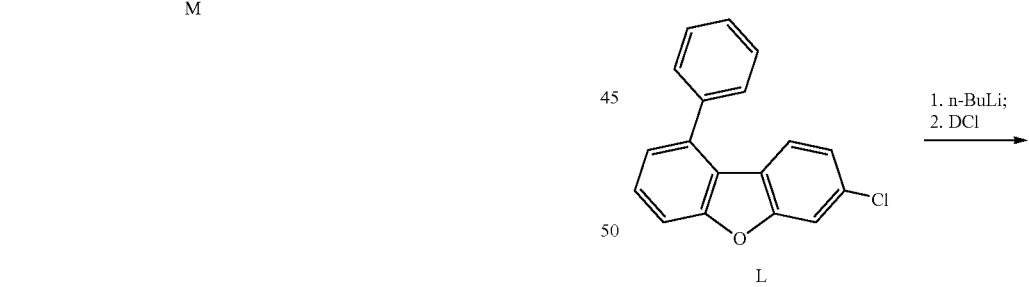

N

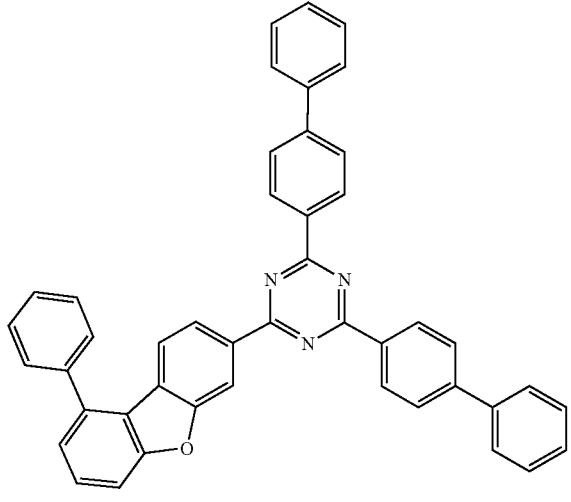

A-209

In a three-necked round-bottom flask, M (3.7 g, 10.0 mmol), N (4.2 g, 10.0 mmol), Pd(PPh$_3$)$_4$ (0.35 g, 0.3 mmol) and K$_2$CO$_3$ (2.76 g, 20.0 mmol) were added to toluene (48 mL), EtOH (12 mL) and H$_2$O (12 mL) and heated to reflux overnight under nitrogen protection. Then stopped heating and the reacting system was cooled to room temperature and filtered through suction under reduced pressure, and the obtained solid was washed with water and methanol in sequence. The solid was recrystallized from toluene to obtain a white solid (5.3 g, 8.44 mmol) with a yield of 84.4%. The product was confirmed as the target product A-209 with a molecular weight of 627.2.

Synthesis Example 4: Synthesis of Compound A-210

Step 1: Synthesis of Intermediate O

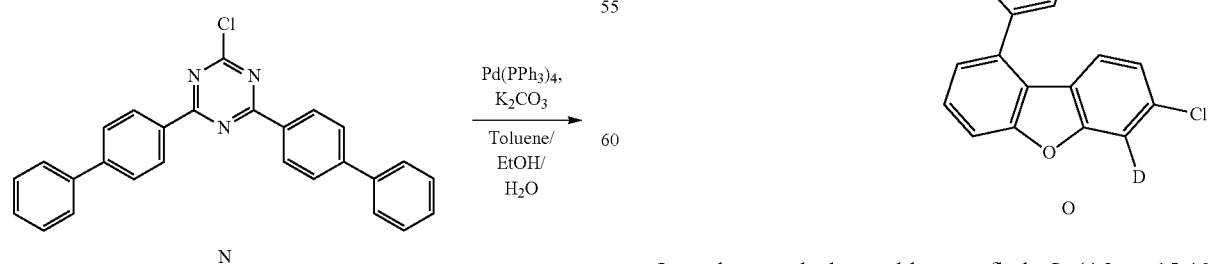

In a three-necked round-bottom flask, L (4.3 g, 15.46 mmol) was dissolved in THF (75 mL) and n-butyl lithium (2.5 M, 6.8 mL, 17 mmol) was slowly added dropwise to the system at −78° C. under nitrogen protection. Then, the system was reacted for 1 h at the temperature. Deuterated hydrochloric acid (1.16 g, 30.93 mmol) was added and the system was slowly warmed to room temperature and reacted overnight. After the reaction was finished, the solvent was removed through rotary evaporation under reduced pressure, and the solid was recrystallized from ethanol to obtain Intermediate O (3.5 g, 12.54 mmol) as a white solid with a yield of 81.1%.

Step 2: Synthesis of Intermediate P

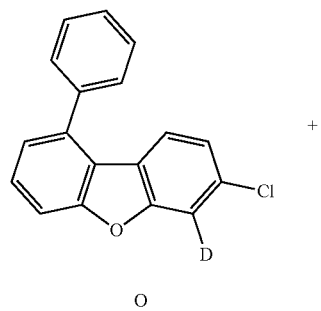

Step 3: Synthesis of Compound A-210

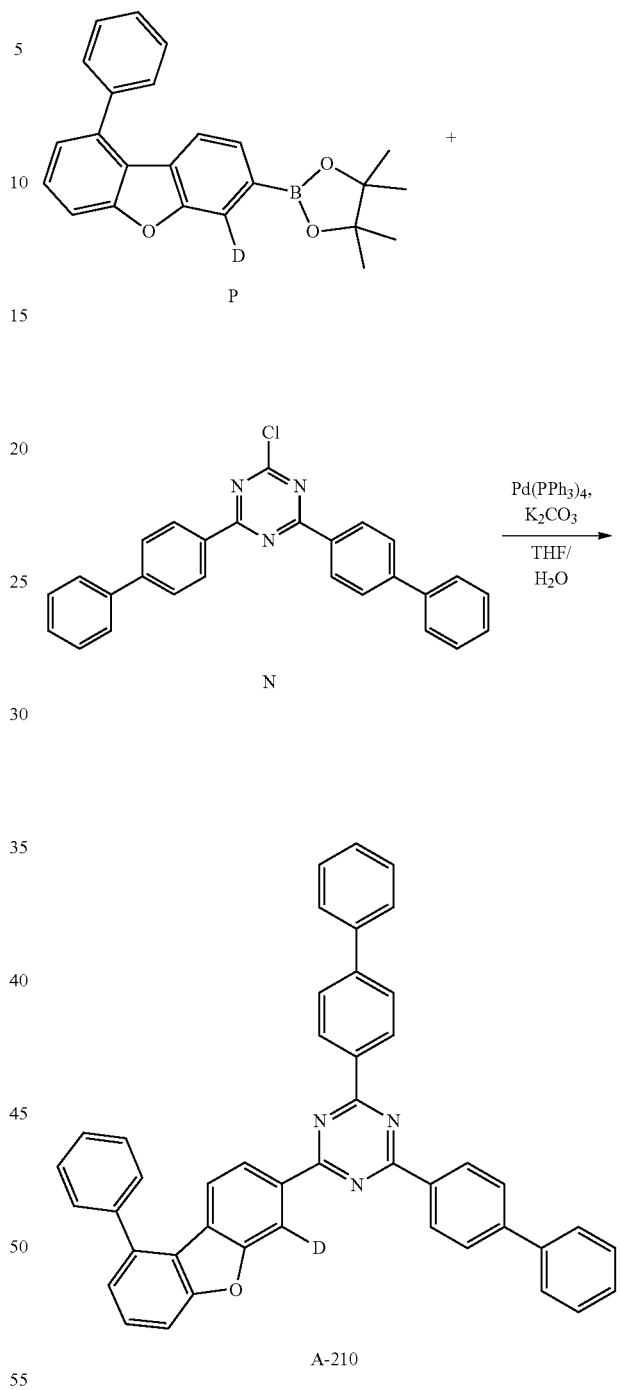

In a three-necked round-bottom flask, O (3.5 g, 12.54 mmol), bis(pinacolato)diboron (4.78 g, 18.8 mmol), Pd(OAc)₂ (56 mg, 0.25 mmol), 2-dicyclohexylphosphino-2',6'-dimethoxybiphenyl (SPhos) (0.21 g, 0.5 mmol) and AcOK (3.7 g, 37.6 mmol) were added to 1,4-dioxane (125 mL) and heated to reflux overnight under nitrogen protection. Then stopped heating and the reacting system was cooled to room temperature and filtered through Celite, and the filtrate was concentrated under reduced pressure. The crude product was purified through column chromatography (PE:DCM=2:1) to obtain Intermediate P (3.1 g, 8.35 mmol) as a white solid with a yield of 66.6%.

In a three-necked round-bottom flask, P (3.1 g, 8.35 mmol), N (3.5 g, 8.35 mmol), Pd(PPh₃)₄ (97 mg, 0.08 mmol) and K₂CO₃ (2.3 g, 16.7 mmol) were added to THF (80 mL) and H₂O (20 mL) and heated to reflux overnight under nitrogen protection. Then stopped heating and the reacting system was cooled to room temperature and filtered through suction under reduced pressure, and the obtained solid was washed with water and methanol in sequence. The solid was recrystallized from toluene to obtain a white solid (4.75 g, 7.56 mmol) with a yield of 90.5%. The product was confirmed as the target product A-210 with a molecular weight of 628.2.

49

Synthesis Example 5: Synthesis of Compound A-2

Step 1: Synthesis of Compound A-2

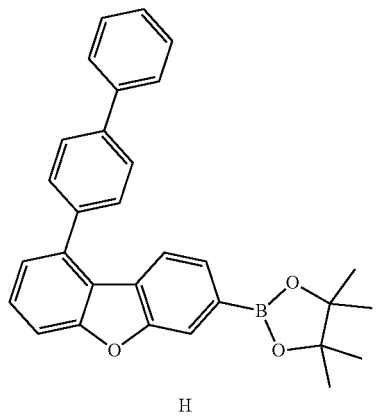

50

Synthesis Example 6: Synthesis of Compound A-4

Step 1: Synthesis of Compound A-4

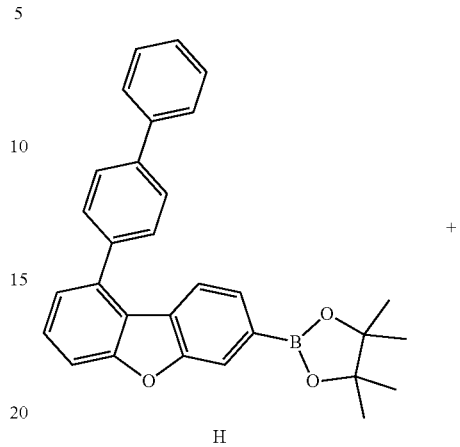

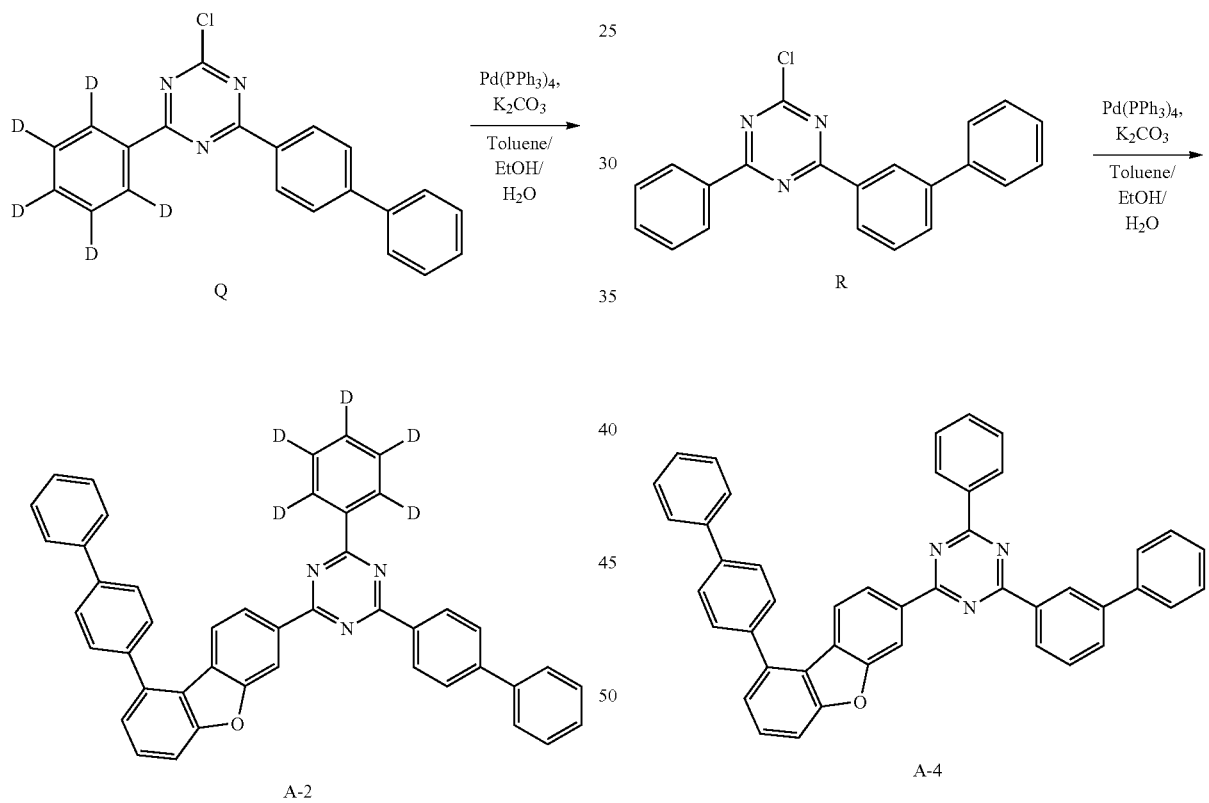

In a three-necked round-bottom flask, H (3.2 g, 7.18 mmol), Q (2.5 g, 7.18 mmol), Pd(PPh$_3$)$_4$ (0.17 g, 0.14 mmol) and K$_2$CO$_3$ (1.98 g, 14.36 mmol) were added to toluene (40 mL), EtOH (10 mL) and H$_2$O (10 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene/acetonitrile to obtain a white solid (3.5 g, 5.54 mmol) with a yield of 77.1%. The product was confirmed as the target product A-2 with a molecular weight of 632.3.

In a three-necked round-bottom flask, H (5.0 g, 11.2 mmol), R (3.84 g, 11.2 mmol), Pd(PPh$_3$)$_4$ (0.26 g, 0.22 mmol) and K$_2$CO$_3$ (3.1 g, 22.4 mmol) were added to toluene (40 mL), EtOH (10 mL) and H$_2$O (10 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene/acetonitrile to obtain a white solid (4.5 g, 7.17 mmol) with a yield of 64.1%. The product was confirmed as the target product A-4 with a molecular weight of 627.2.

Synthesis Example 7: Synthesis of Compound A-7

Step 1: Synthesis of Compound A-7

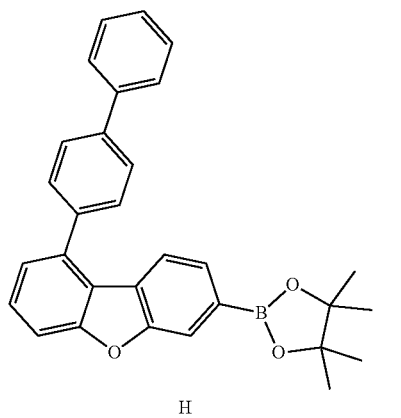

H

+

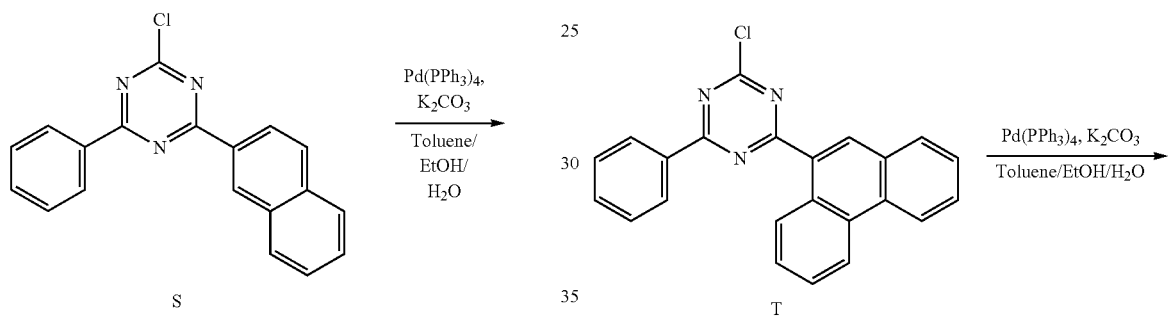

S

A-7

In a three-necked round-bottom flask, H (4.46 g, 10.0 mmol), S (3.18 g, 10.0 mmol), Pd(PPh$_3$)$_4$ (0.35 g, 0.30 mmol) and K$_2$CO$_3$ (2.76 g, 20.0 mmol) were added to toluene (48 mL), EtOH (12 mL) and H$_2$O (12 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (4.5 g, 7.48 mmol) with a yield of 74.8%. The product was confirmed as the target product A-7 with a molecular weight of 601.2.

Synthesis Example 8: Synthesis of Compound A-20

Step 1: Synthesis of Compound A-20

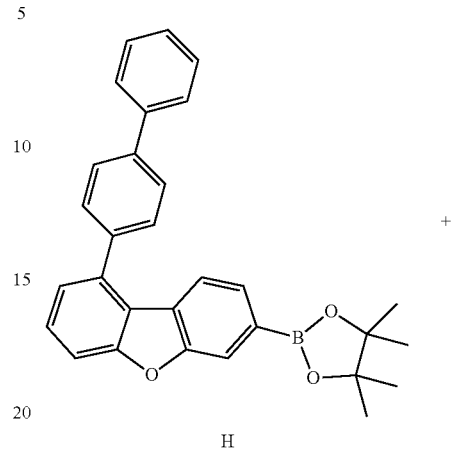

H

+

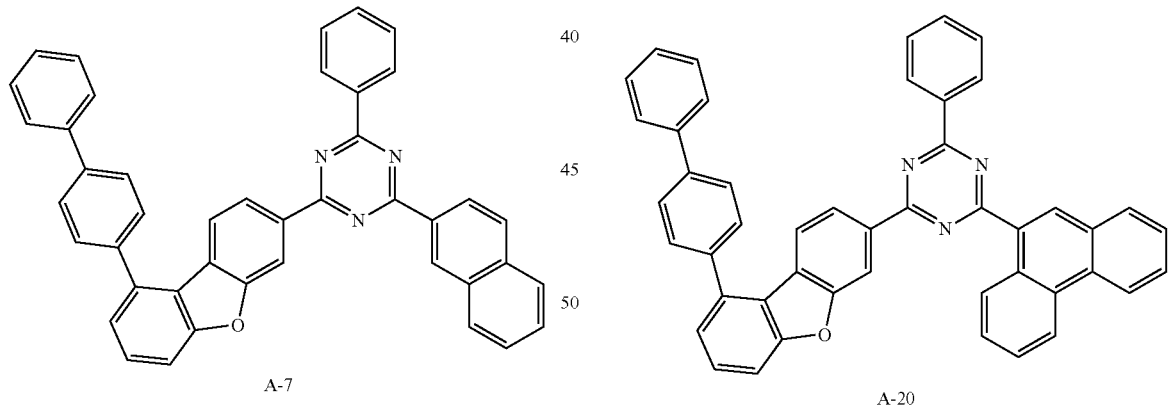

T

A-20

In a three-necked round-bottom flask, H (5.0 g, 11.2 mmol), T (3.9 g, 10.6 mmol), Pd(PPh$_3$)$_4$ (0.60 g, 0.5 mmol) and K$_2$CO$_3$ (4.4 g, 31.8 mmol) were added to toluene (80 mL), EtOH (20 mL) and H$_2$O (20 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (4.9 g, 7.52 mmol) with a yield of 70.9%. The product was confirmed as the target product A-20 with a molecular weight of 651.2.

Synthesis Example 9: Synthesis of Compound A-51

Step 1: Synthesis of Compound A-51

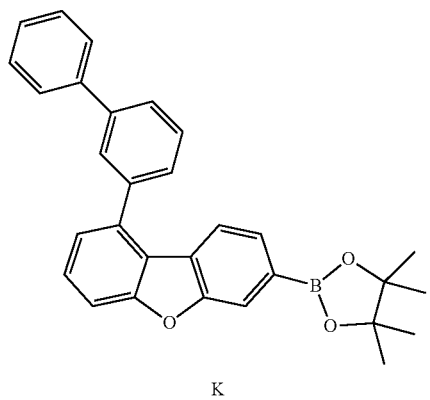

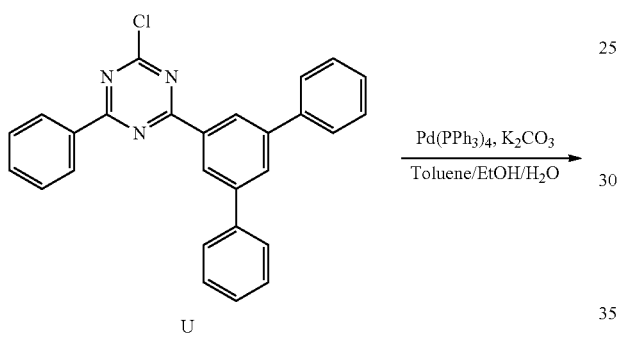

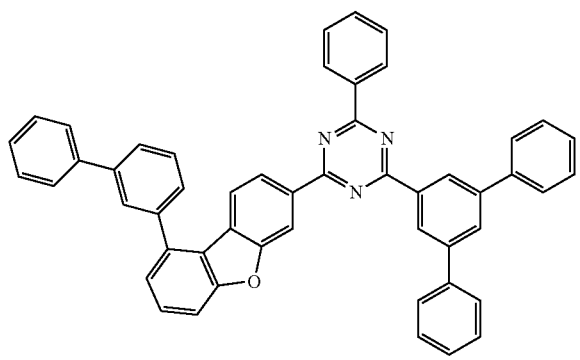

In a three-necked round-bottom flask, K (4.7 g, 10.5 mmol), U (4.2 g, 10.0 mmol), Pd(PPh$_3$)$_4$ (0.60 g, 0.52 mmol) and K$_2$CO$_3$ (4.1 g, 30.0 mmol) were added to toluene (80 mL), EtOH (20 mL) and H$_2$O (20 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (4.9 g, 6.96 mmol) with a yield of 69.6%. The product was confirmed as the target product A-51 with a molecular weight of 703.3.

Synthesis Example 10: Synthesis of Compound A-157

Step 1: Synthesis of Intermediate W

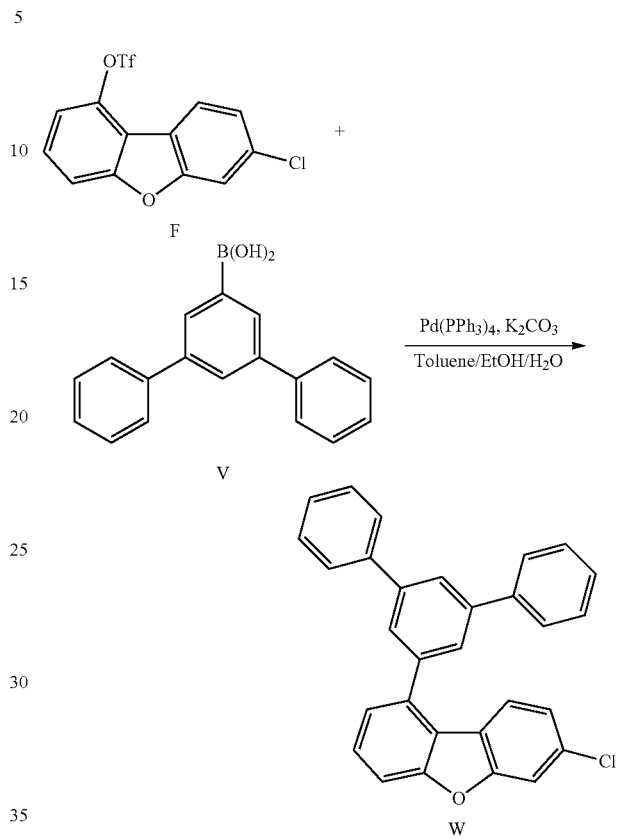

In a three-necked round-bottom flask, F (6.4 g, 18.2 mmol), V (5.0 g, 18.2 mmol), Pd(PPh$_3$)$_4$ (1.1 g, 0.9 mmol) and K$_2$CO$_3$ (7.5 g, 54.6 mmol) were added to toluene (80 mL), EtOH (20 mL) and H$_2$O (20 mL) and heated to reflux overnight under nitrogen protection. After the reaction was finished, stopped heating and the system was cooled to room temperature. Organic phases were taken, the aqueous phase was added with DCM and extracted multiple times, and the organic phases were combined, dried over anhydrous Na$_2$SO$_4$, filtered and concentrated under reduced pressure. The crude product was purified through column chromatography (PE:DCM=20:1) to obtain Intermediate W (7.0 g, 16.2 mmol) as a white solid with a yield of 89.2%.

Step 2: Synthesis of Intermediate X

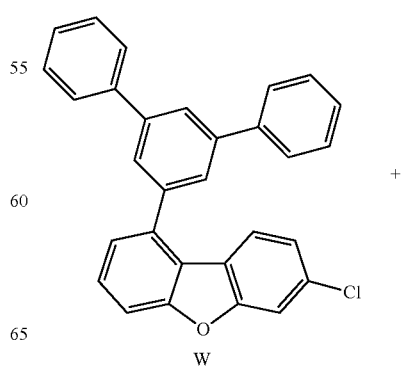

-continued

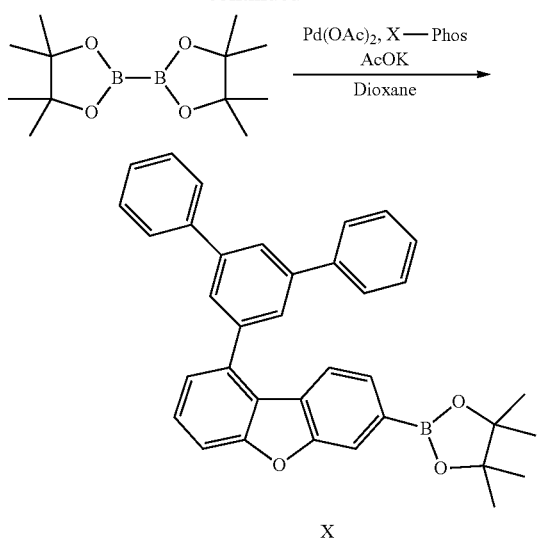

X

In a three-necked round-bottom flask, W (7.0 g, 16.2 mmol), bis(pinacolato)diboron (8.3 g, 32.6 mmol), Pd(OAc)₂ (0.20 g, 0.8 mmol), 2-dicyclohexylphosphino-2,4,6-triisopropylbiphenyl (X-Phos) (0.80 g, 1.6 mmol) and AcOK (3.2 g, 32.6 mmol) were added to 1,4-dioxane (80 mL) and heated to reflux overnight under nitrogen protection. After the reaction was finished, stopped heating and the reaction system was cooled to room temperature and filtered through Celite. The filtrate was concentrated under reduced pressure. The crude product was purified through column chromatography (PE:DCM=4:1→2:1) to obtain Intermediate X (6.5 g, 12.5 mmol) as a white solid with a yield of 77.2%.

Step 3: Synthesis of Compound A-157

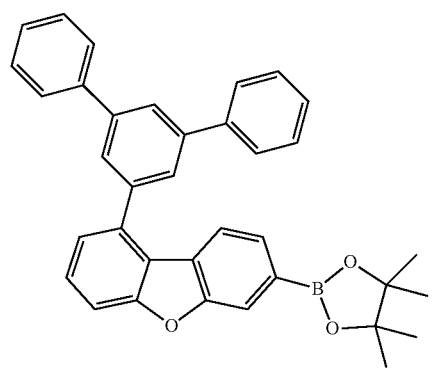

X

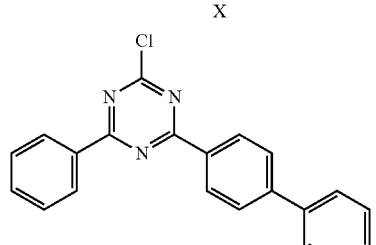

I

-continued

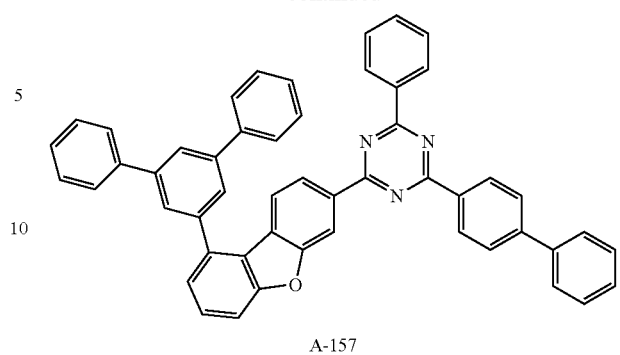

A-157

In a three-necked round-bottom flask, X (6.5 g, 12.5 mmol), I (4.2 g, 12.2 mmol), Pd(PPh₃)₄ (0.40 g, 0.35 mmol) and K₂CO₃ (5.0 g, 36.6 mmol) were added to toluene (100 mL), EtOH (25 mL) and H₂O (25 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (6.2 g, 8.81 mmol) with a yield of 72.2%. The product was confirmed as the target product A-157 with a molecular weight of 703.3.

Synthesis Example 11: Synthesis of Compound A-211

Step 1: Synthesis of Compound A-211

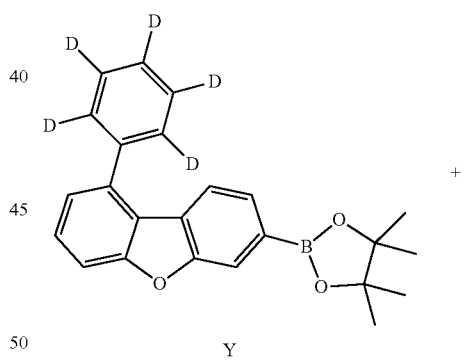

Y

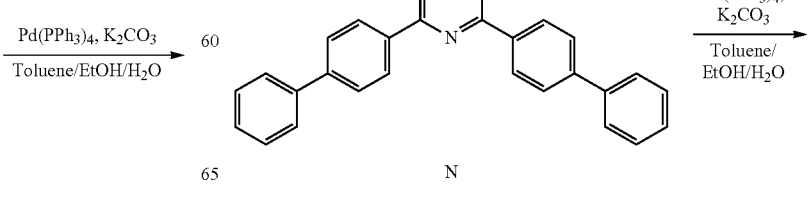

N

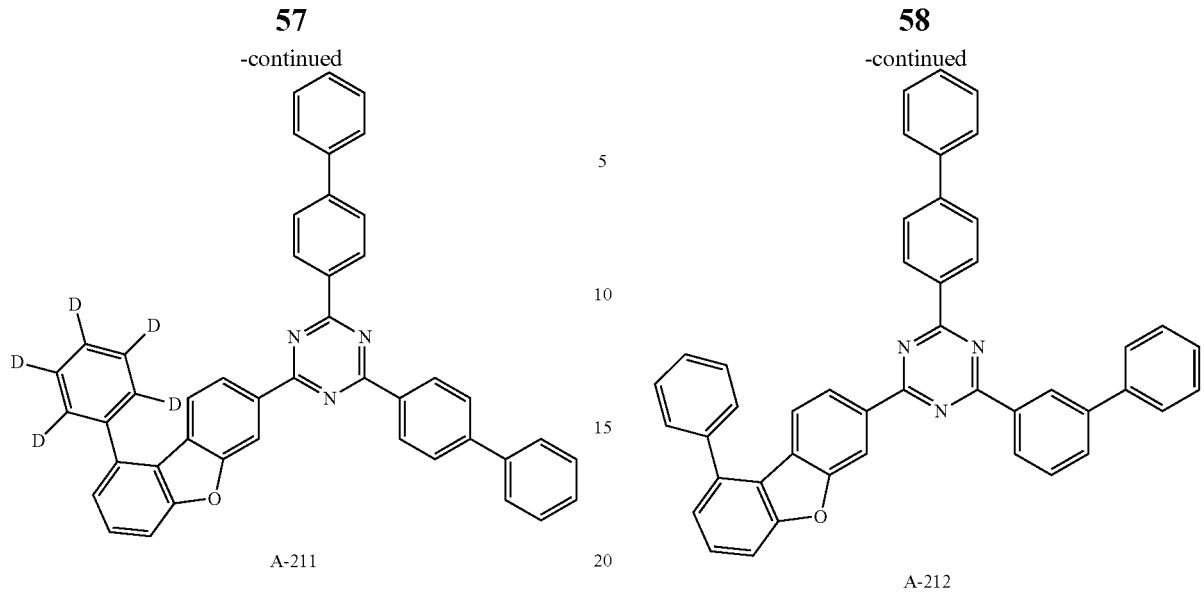

A-211

A-212

In a three-necked round-bottom flask, Y (2.41 g, 6.42 mmol), N (2.7 g, 6.42 mmol), Pd(PPh$_3$)$_4$ (0.22 g, 0.19 mmol) and K$_2$CO$_3$ (1.77 g, 12.84 mmol) were added to toluene (32 mL), EtOH (8 mL) and H$_2$O (8 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (3.3 g, 5.21 mmol) with a yield of 81.2%. The product was confirmed as the target product A-211 with a molecular weight of 632.3.

Synthesis Example 12: Synthesis of Compound A-212

Step 1: Synthesis of Compound A-212

In a three-necked round-bottom flask, M (4.4 g, 11.9 mmol), Z (5.0 g, 11.9 mmol), Pd(PPh$_3$)$_4$ (0.28 g, 0.24 mmol) and K$_2$CO$_3$ (3.3 g, 23.8 mmol) were added to toluene (40 mL), EtOH (10 mL) and H$_2$O (10 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (4.6 g, 7.3 mmol) with a yield of 61.3%. The product was confirmed as the target product A-212 with a molecular weight of 627.2.

Synthesis Example 13: Synthesis of Compound A-231

Step 1: Synthesis of Compound A-231

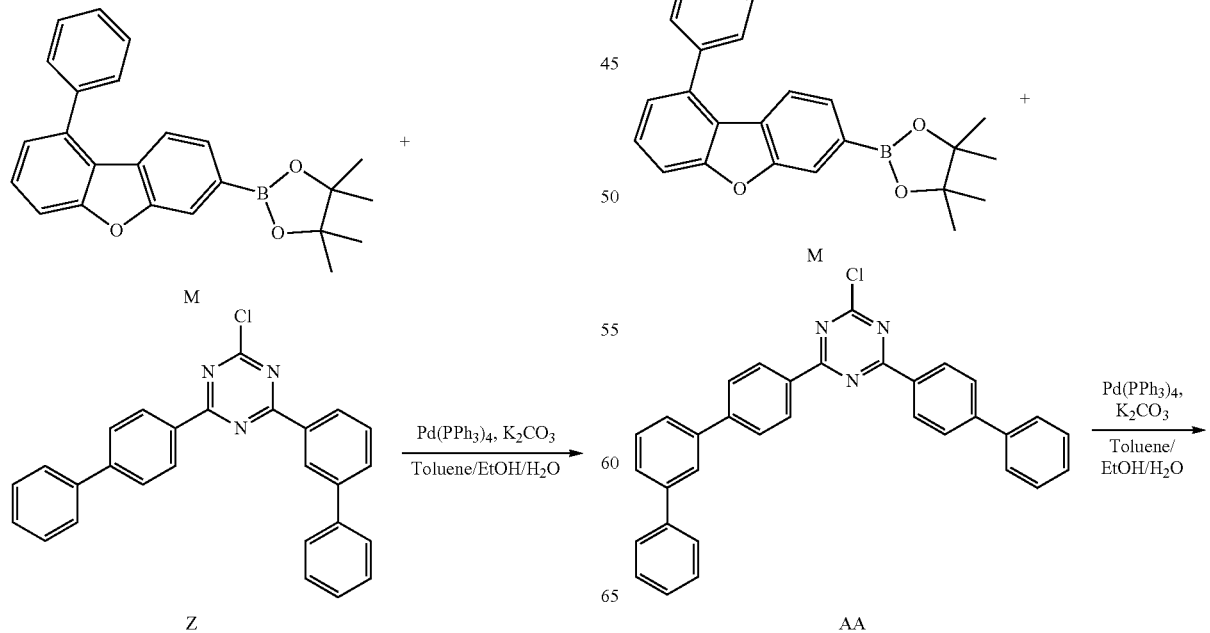

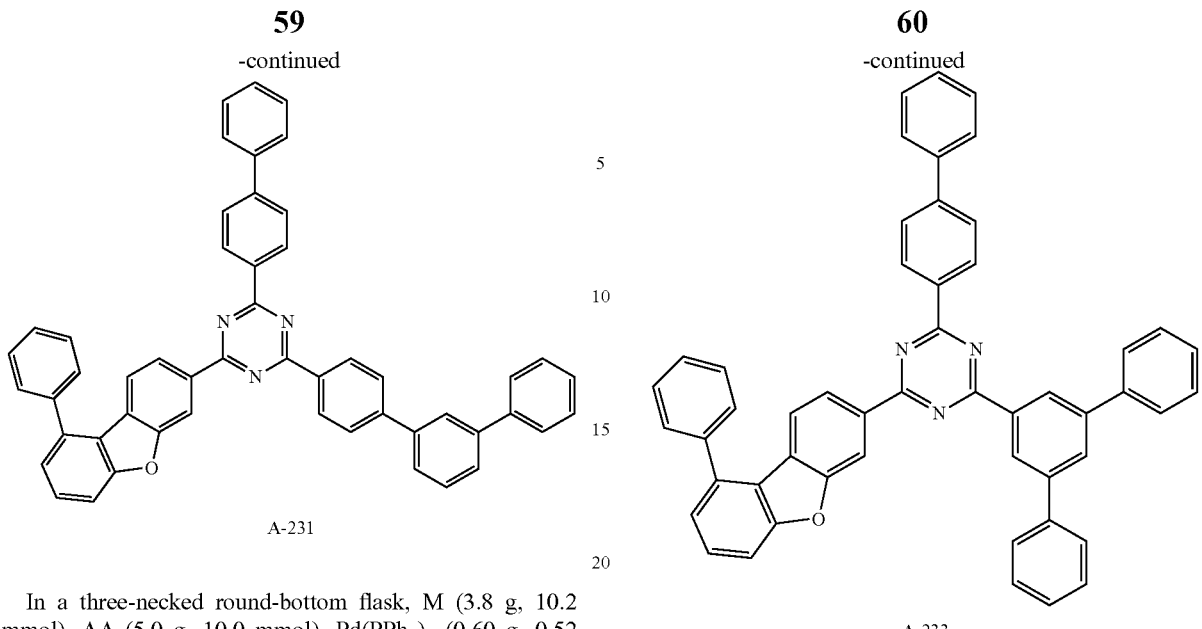

A-231

In a three-necked round-bottom flask, M (3.8 g, 10.2 mmol), AA (5.0 g, 10.0 mmol), Pd(PPh₃)₄ (0.60 g, 0.52 mmol) and K₂CO₃ (4.1 g, 30.0 mmol) were added to toluene (80 mL), EtOH (20 mL) and H₂O (20 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (5.7 g, 8.10 mmol) with a yield of 81.0%. The product was confirmed as the target product A-231 with a molecular weight of 703.3.

Synthesis Example 14: Synthesis of Compound A-233

Step 1: Synthesis of Compound A-233

A-233

In a three-necked round-bottom flask, M (3.06 g, 8.26 mmol), AB (4.1 g, 8.26 mmol), Pd(PPh₃)₄ (0.19 g, 0.17 mmol) and K₂CO₃ (2.3 g, 16.5 mmol) were added to toluene (60 mL), EtOH (15 mL) and H₂O (15 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (4.9 g, 6.96 mmol) with a yield of 84.3%. The product was confirmed as the target product A-233 with a molecular weight of 703.3.

Synthesis Example 15: Synthesis of Compound A-257

Step 1: Synthesis of Compound A-257

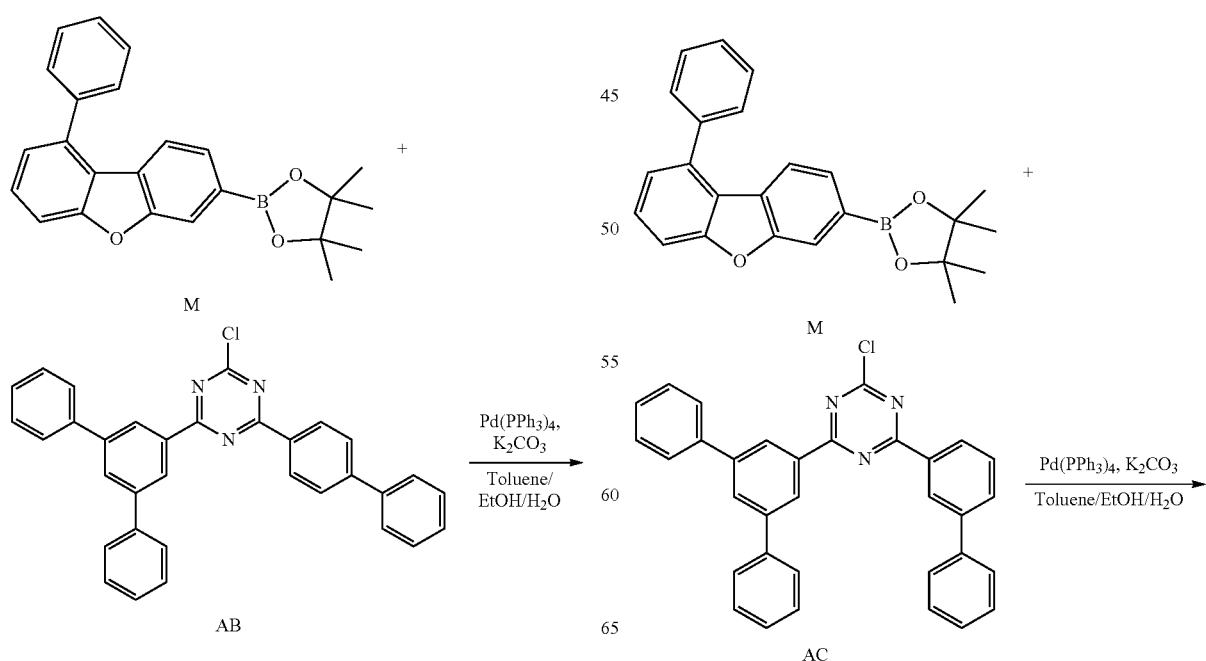

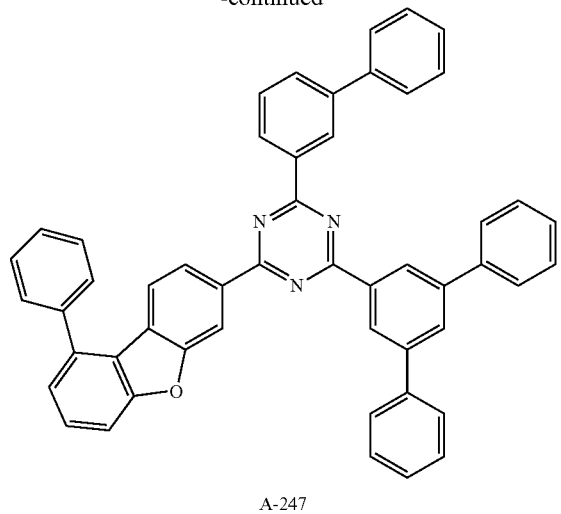

A-247

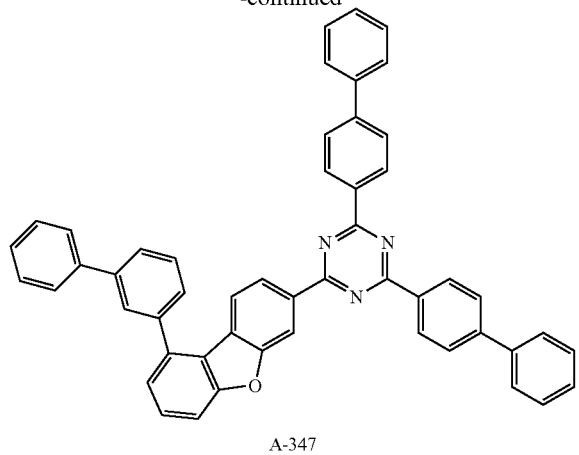

A-347

In a three-necked round-bottom flask, M (3.8 g, 10.2 mmol), AC(5.0 g, 10.0 mmol), Pd(PPh₃)₄ (0.60 g, 0.52 mmol) and K₂CO₃ (4.1 g, 30.0 mmol) were added to toluene (80 mL), EtOH (20 mL) and H₂O (20 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (5.7 g, 8.10 mmol) with a yield of 81.0%. The product was confirmed as the target product A-257 with a molecular weight of 703.3.

Synthesis Example 16: Synthesis of Compound A-347

Step 1: Synthesis of Compound A-347

In a three-necked round-bottom flask, K (3.2 g, 7.2 mmol), N (3.02 g, 7.2 mmol), Pd(PPh₃)₄ (0.17 g, 0.14 mmol) and K₂CO₃ (2.0 g, 14.4 mmol) were added to toluene (24 mL), EtOH (6 mL) and H₂O (6 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (3.4 g, 4.83 mmol) with a yield of 67.1%. The product was confirmed as the target product A-347 with a molecular weight of 703.3.

Synthesis Example 17: Synthesis of Compound A-422

Step 1: Synthesis of Compound A-422

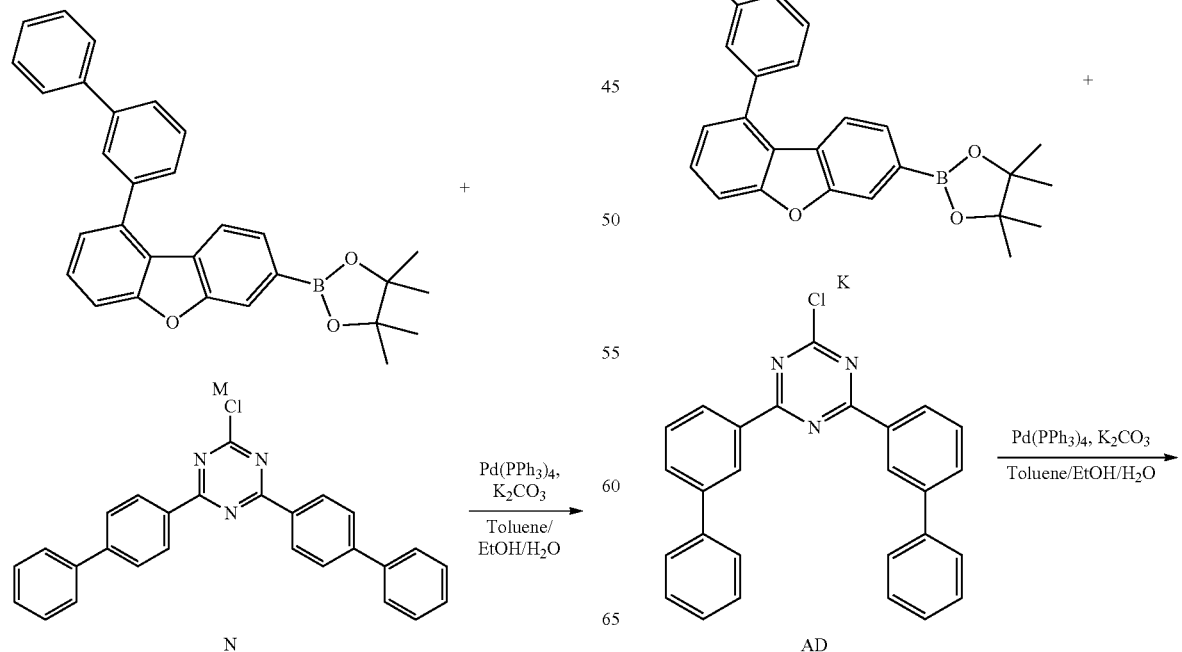

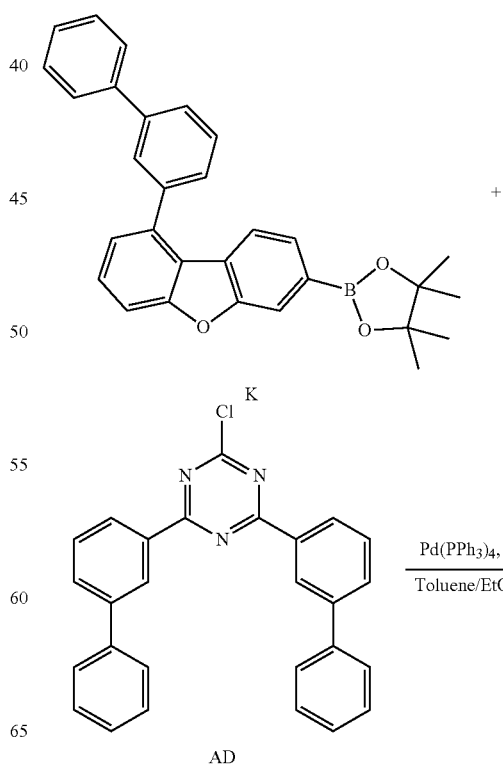

-continued

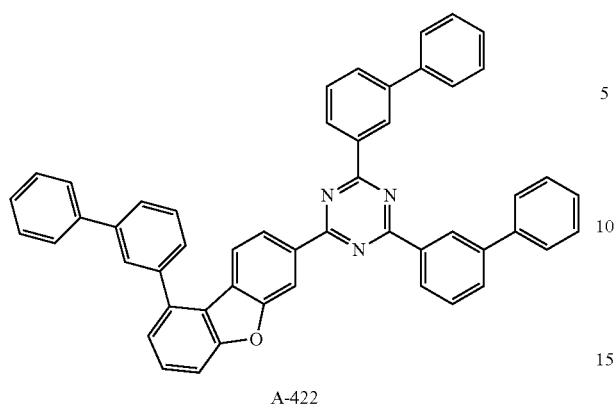

A-422

In a three-necked round-bottom flask, K (4.7 g, 10.5 mmol), AD (4.2 g, 10.0 mmol), Pd(PPh$_3$)$_4$ (0.60 g, 0.52 mmol) and K$_2$CO$_3$ (4.1 g, 30.0 mmol) were added to toluene (80 mL), EtOH (20 mL) and H$_2$O (20 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (4.9 g, 6.96 mmol) with a yield of 69.6%. The product was confirmed as the target product A-422 with a molecular weight of 703.3.

Synthesis Example 18: Synthesis of Compound A-553

Step 1: Synthesis of Compound A-553

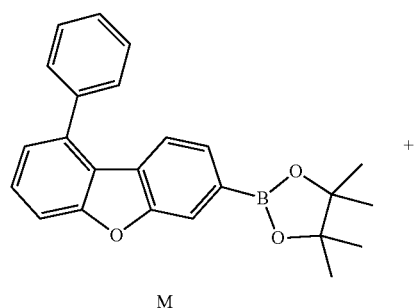

M

+

-continued

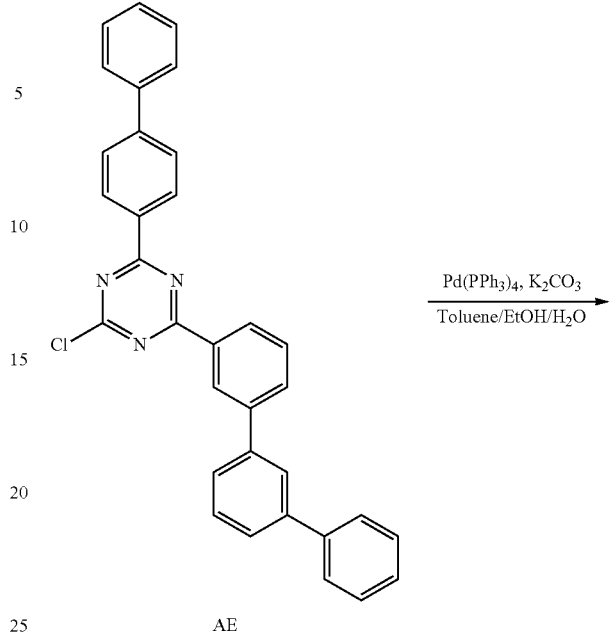

AE

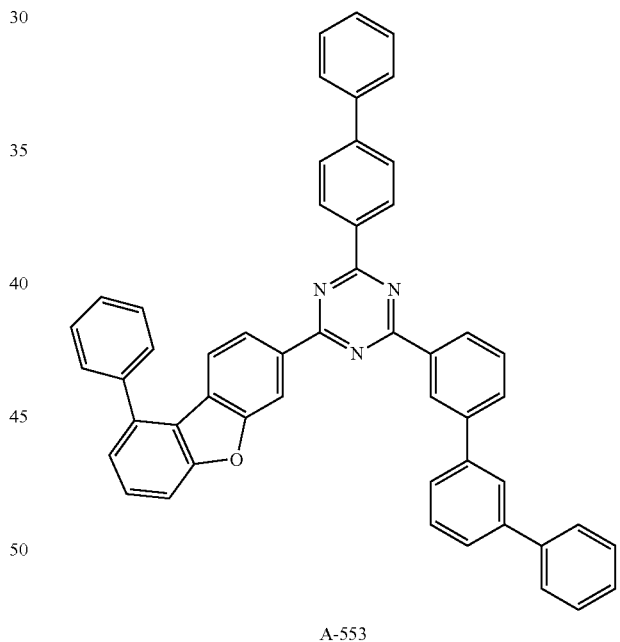

A-553

In a three-necked round-bottom flask, M (2.96 g, 8.0 mmol), AE (4.0 g, 8.0 mmol), Pd(PPh$_3$)$_4$ (0.19 g, 0.16 mmol) and K$_2$CO$_3$ (2.2 g, 16.0 mmol) were added to toluene (40 mL), EtOH (10 mL) and H$_2$O (10 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (3.9 g, 5.5 mmol) with a yield of 68.8%. The product was confirmed as the target product A-553 with a molecular weight of 703.3.

Synthesis Example 19: Synthesis of Compound A-160

Step 1: Synthesis of Compound A-160

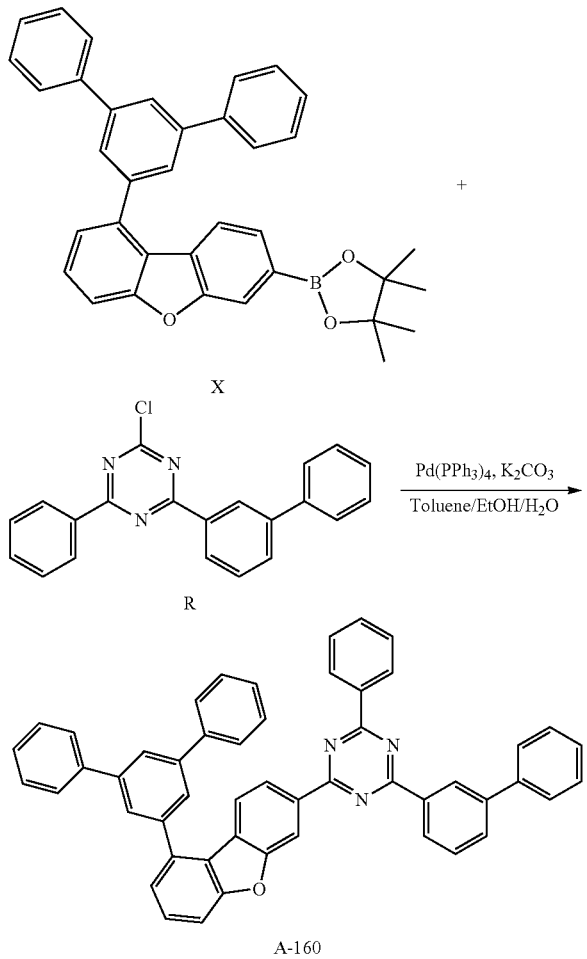

In a three-necked round-bottom flask, X (3.9 g, 7.5 mmol), R (2.6 g, 7.5 mmol), Pd(PPh₃)+ (0.40 g, 0.35 mmol) and K₂CO₃ (3.1 g, 22.4 mmol) were added to toluene (80 mL), EtOH (20 mL) and H₂O (20 mL) and heated to reflux overnight under nitrogen protection. After the reaction was finished, stopped heating, the system was cooled to room temperature and filtered through suction under reduced pressure, and the obtained solid was washed with water and methanol in sequence. The solid was recrystallized from toluene to obtain a white solid (4.5 g, 6.4 mmol) with a yield of 85.3%. The product was confirmed as the target product A-160 with a molecular weight of 703.3.

Those skilled in the art will appreciate that the above preparation methods are merely exemplary. Those skilled in the art can obtain other compound structures of the present disclosure through the modifications of the preparation methods.

Device Example Device Example 1

First, a glass substrate having an indium tin oxide (ITO) anode with a thickness of 80 nm was cleaned and then treated with oxygen plasma and UV ozone. After the treatment, the substrate was dried in a glovebox to remove moisture. Then, the substrate was mounted on a substrate holder and placed in a vacuum chamber. Organic layers specified below were sequentially deposited through vacuum thermal evaporation on the ITO anode at a rate of 0.2 to 2 Angstroms per second and a vacuum degree of about $10^{-8}$ torr. Compound H1 was used as a hole injection layer (HIL). Compound HT was used as a hole transporting layer (HTL). Compound H1 was used as an electron blocking layer (EBL). Compound GD4-59 was doped in Compound H1 and Compound A-1 of the present disclosure, all of which were co-deposited for use as an emissive layer (EML). Compound H2 was used as a hole blocking layer (HBL). On the HBL, Compound ET and 8-hydroxyquinolinolato-lithium (Liq) were co-deposited for use as an electron transporting layer (ETL). Finally, 8-hydroxyquinolinolato-lithium (Liq) was deposited as an electron injection layer with a thickness of 1 nm and Al was deposited as a cathode with a thickness of 120 nm. The device was transferred back to the glovebox and encapsulated with a glass lid and a moisture getter to complete the device.

Device Example 2

Device Example 2 was prepared by the same method as Device Example 1, except that in the EML, Compound A-1 was replaced with Compound A-27.

Device Example 3

Device Example 3 was prepared by the same method as Device Example 1, except that in the EML, Compound A-1 was replaced with Compound A-209.

Device Example 4

Device Example 4 was prepared by the same method as Device Example 1, except that in the EML, Compound A-1 was replaced with Compound A-210.

Device Example 5

Device Example 5 was prepared by the same method as Device Example 1, except that in the EML, Compound A-1 was replaced with Compound A-51.

Device Example 6

Device Example 6 was prepared by the same method as Device Example 1, except that in the EML, Compound A-1 was replaced with Compound A-157.

Device Example 7

Device Example 7 was prepared by the same method as Device Example 1, except that in the EML, Compound A-1 was replaced with Compound A-212.

Device Example 8

Device Example 8 was prepared by the same method as Device Example 1, except that in the EML, Compound A-1 was replaced with Compound A-231.

Device Example 9

Device Example 9 was prepared by the same method as Device Example 1, except that in the EML, Compound A-1 was replaced with Compound A-233.

Device Example 10

Device Example 10 was prepared by the same method as Device Example 1, except that in the EML, Compound A-1 was replaced with Compound A-257.

Device Example 11

Device Example 11 was prepared by the same method as Device Example 1, except that in the EML, Compound A-1 was replaced with Compound A-347.

Device Example 12

Device Example 12 was prepared by the same method as Device Example 1, except that in the EML, Compound A-1 was replaced with Compound A-422.

Device Example 13

Device Example 13 was prepared by the same method as Device Example 1, except that in the EML, Compound A-1 was replaced with Compound A-553.

Device Example 14

Device Example 14 was prepared by the same method as Device Example 1, except that in the EML, Compound A-1 was replaced with Compound A-160.

Device Comparative Example 1

Device Comparative Example 1 was prepared by the same method as Device Example 1, except that in the EML, Compound A-1 was replaced with Compound C-1.

Device Comparative Example 2

Device Comparative Example 2 was prepared by the same method as Device Example 1, except that in the EML, Compound A-1 was replaced with Compound C-2.

Device Comparative Example 3

Device Comparative Example 3 was prepared by the same method as Device Example 1, except that in the EML, Compound A-1 was replaced with Compound C-3.

Device Comparative Example 4

Device Comparative Example 4 was prepared by the same method as Device Example 1, except that in the EML, Compound A-1 was replaced with Compound C-4.

Detailed structures and thicknesses of layers of the devices are shown in the following table. Layers using more than one material were obtained by doping different compounds at their weight ratio as recorded.

TABLE 1

| Device ID | HIL | HTL | EBL | EML | HBL | ETL |
|---|---|---|---|---|---|---|
| Example 1 | Compound HI (100 Å) | Compound HT (350 Å) | Compound H1 (50 Å) | Compound H1:Compound A-1:Compound GD4-59 (69:23:8) (400 Å) | Compound H2 (50 Å) | Compound ET:Liq (40:60) (350 Å) |
| Example 2 | Compound HI (100 Å) | Compound HT (350 Å) | Compound H1 (50 Å) | Compound H1:Compound A-27:Compound GD4-59 (69:23:8) (400 Å) | Compound H2 (50 Å) | Compound ET:Liq (40:60) (350 Å) |
| Example 3 | Compound HI (100 Å) | Compound HT (350 Å) | Compound H1 (50 Å) | Compound H1:Compound A-209:Compound GD4-59 (69:23:8) (400 Å) | Compound H2 (50 Å) | Compound ET:Liq (40:60) (350 Å) |
| Example 4 | Compound HI (100 Å) | Compound HT (350 Å) | Compound H1 (50 Å) | Compound H1:Compound A-210:Compound GD4-59 (69:23:8) (400 Å) | Compound H2 (50 Å) | Compound ET:Liq (40:60) (350 Å) |
| Example 5 | Compound HI (100 Å) | Compound HT (350 Å) | Compound H1 (50 Å) | Compound H1:Compound A-51:Compound GD4-59 (69:23:8) (400 Å) | Compound H2 (50 Å) | Compound ET:Liq (40:60) (350 Å) |
| Example 6 | Compound HI (100 Å) | Compound HT (350 Å) | Compound H1 (50 Å) | Compound H1:Compound A-157:Compound GD4-59 (69:23:8) (400 Å) | Compound H2 (50 Å) | Compound ET:Liq (40:60) (350 Å) |
| Example 7 | Compound HI (100 Å) | Compound HT (350 Å) | Compound H1 (50 Å) | Compound H1:Compound A-212:Compound GD4-59 (69:23:8) (400 Å) | Compound H2 (50 Å) | Compound ET:Liq (40:60) (350 Å) |
| Example 8 | Compound HI (100 Å) | Compound HT (350 Å) | Compound H1 (50 Å) | Compound H1:Compound A-231:Compound GD4-59 (69:23:8) (400 Å) | Compound H2 (50 Å) | Compound ET:Liq (40:60) (350 Å) |
| Example 9 | Compound HI (100 Å) | Compound HT (350 Å) | Compound H1 (50 Å) | Compound H1:Compound A-233:Compound GD4-59 (69:23:8) (400 Å) | Compound H2 (50 Å) | Compound ET:Liq (40:60) (350 Å) |
| Example 10 | Compound HI (100 Å) | Compound HT (350 Å) | Compound H1 (50 Å) | Compound H1:Compound A-257:Compound GD4-59 (69:23:8) (400 Å) | Compound H2 (50 Å) | Compound ET:Liq (40:60) (350 Å) |
| Example 11 | Compound HI (100 Å) | Compound HT (350 Å) | Compound H1 (50 Å) | Compound H1:Compound A-347:Compound GD4-59 (69:23:8) (400 Å) | Compound H2 (50 Å) | Compound ET:Liq (40:60) (350 Å) |
| Example 12 | Compound HI (100 Å) | Compound HT (350 Å) | Compound H1 (50 Å) | Compound H1:Compound A-422:Compound GD4-59 (69:23:8) (400 Å) | Compound H2 (50 Å) | Compound ET:Liq (40:60) (350 Å) |
| Example 13 | Compound HI (100 Å) | Compound HT (350 Å) | Compound H1 (50 Å) | Compound H1:Compound A-553:Compound GD4-59 (69:23:8) (400 Å) | Compound H2 (50 Å) | Compound ET:Liq (40:60) (350 Å) |
| Example 14 | Compound HI (100 Å) | Compound HT (350 Å) | Compound H1 (50 Å) | Compound H1:Compound A-160:Compound GD4-59 (69:23:8) (400 Å) | Compound H2 (50 Å) | Compound ET:Liq (40:60) (350 Å) |
| Comparative Example 1 | Compound HI (100 Å) | Compound HT (350 Å) | Compound H1 (50 Å) | Compound H1:Compound C-1:Compound GD4-59 (69:23:8) (400 Å) | Compound H2 (50 Å) | Compound ET:Liq (40:60) (350 Å) |
| Comparative Example 2 | Compound HI (100 Å) | Compound HT (350 Å) | Compound H1 (50 Å) | Compound H1:Compound C-3:Compound GD4-59 (69:23:8) (400 Å) | Compound H2 (50 Å) | Compound ET:Liq (40:60) (350 Å) |
| Comparative Example 3 | Compound HI (100 Å) | Compound HT (350 Å) | Compound H1 (50 Å) | Compound H1:Compound C-3:Compound GD4-59 (69:23:8) (400 Å) | Compound H2 (50 Å) | Compound ET:Liq (40:60) (350 Å) |
| Comparative Example 4 | Compound HI (100 Å) | Compound HT (350 Å) | Compound H1 (50 Å) | Compound H1:Compound C-4:Compound GD4-59 (69:23:8) (400 Å) | Compound H2 (50 Å) | Compound ET:Liq (40:60) (350 Å) |

The structures of the materials used in the devices are shown as follows:
HI
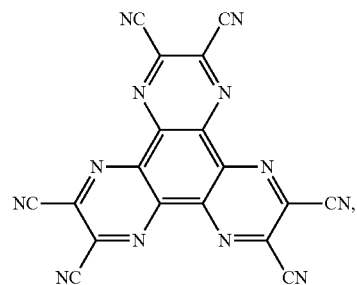
A-1
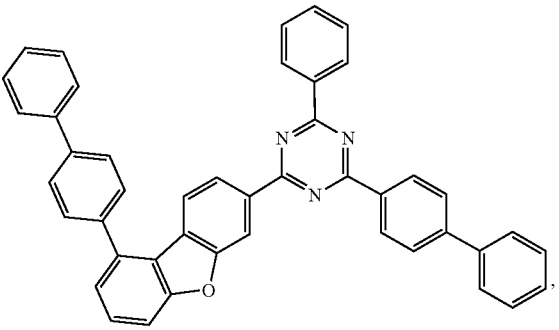
HT
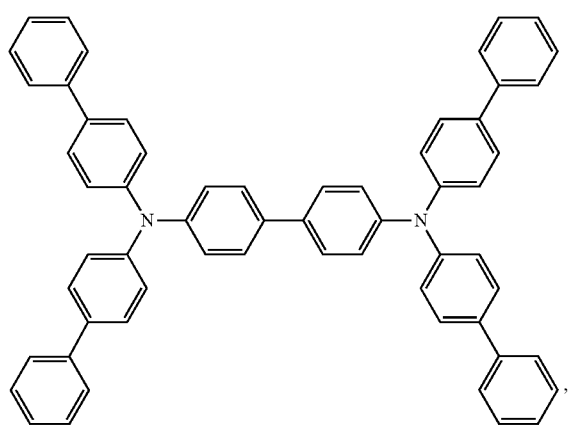
A-27
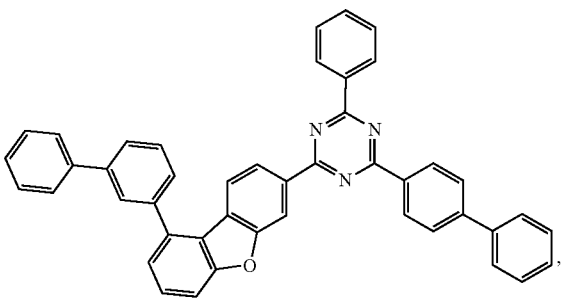
H1
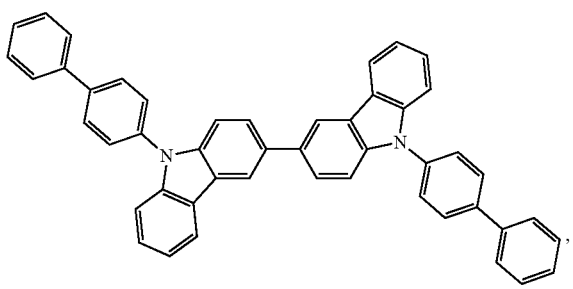
H2
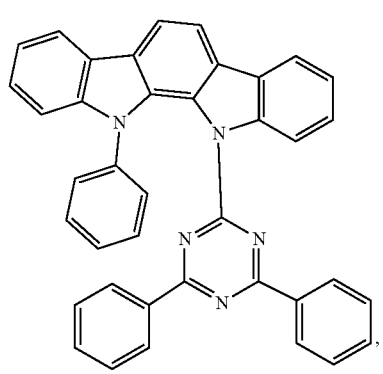
A-209
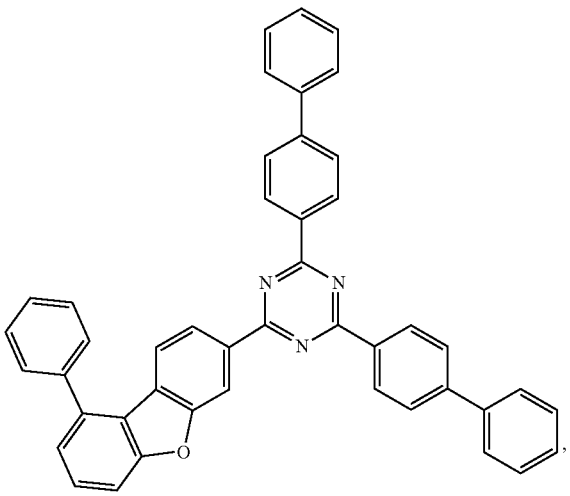

A-210

A-51

A-157

A-212

A-231

A-233

A-257
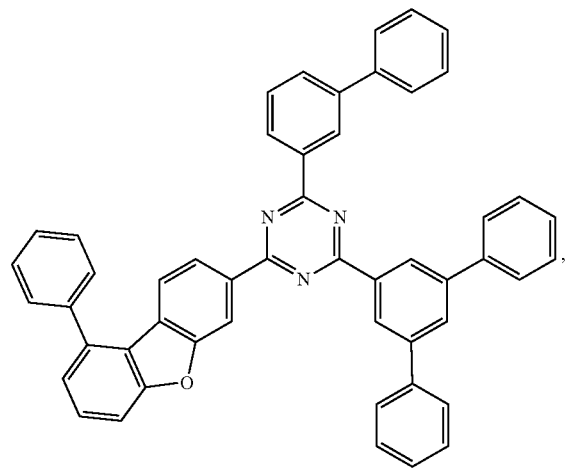
A-347
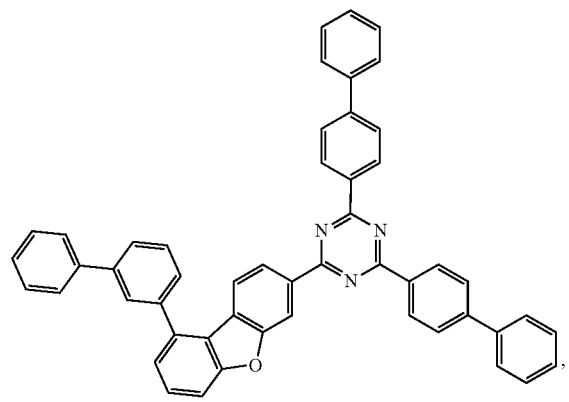
A-422
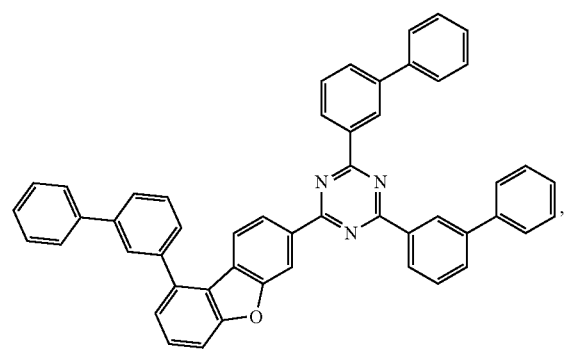
A-553
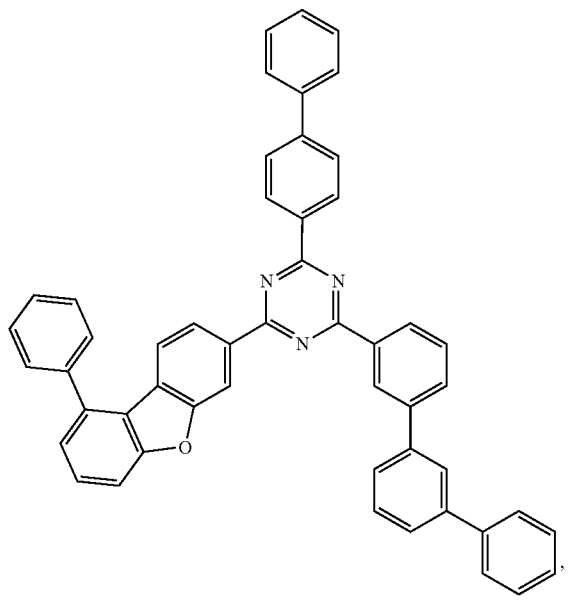
A-160
A-160
C-1
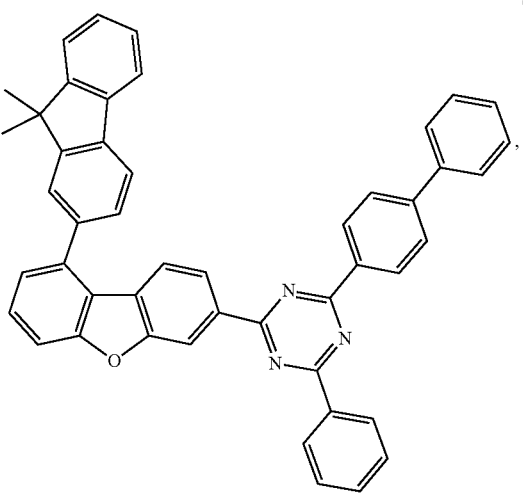

C-2
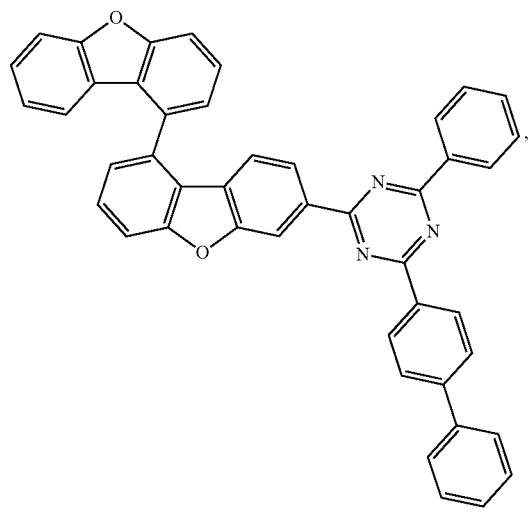
C-3
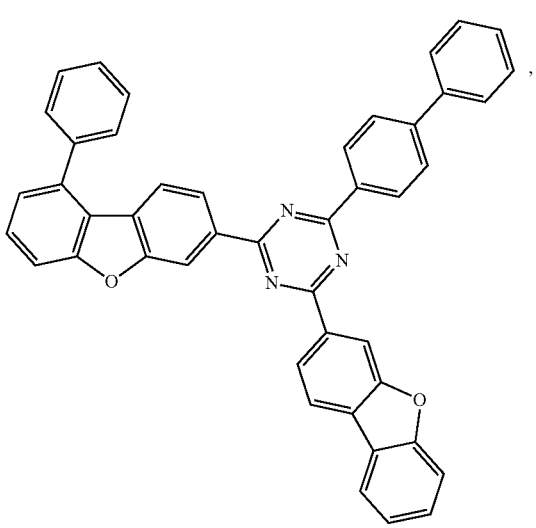
C-4
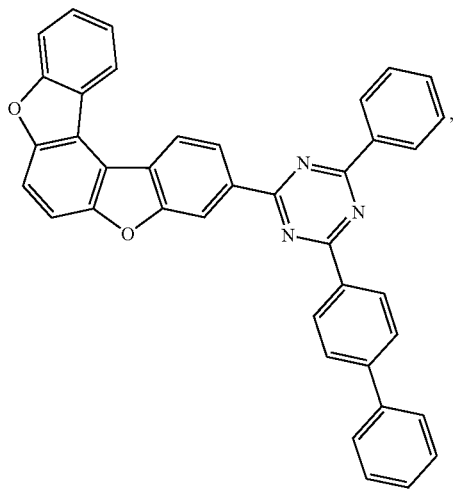
GD4-59
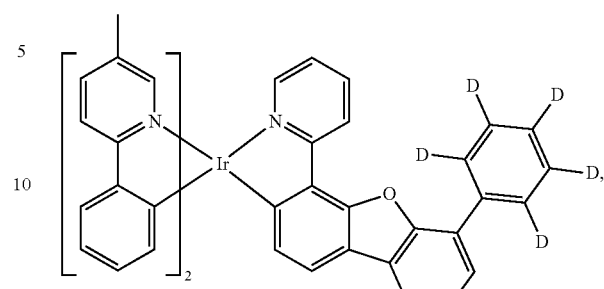
ET
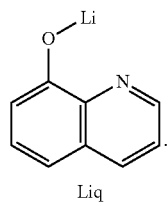
Liq
Table 2 shows CIE data and current efficiency (CE) measured at a constant current of 15 mA/cm² and a device lifetime (LT95) measured at a constant current of 80 mA/cm².

TABLE 2

Device data of Examples 1 to 14 and Comparative Examples 1 to 4

| Device ID | EML | CIE (x, y) | CE (cd/A) | Lifetime LT95 (hrs) |
|---|---|---|---|---|
| Example 1 | H1:A-1:GD4-59 (69:23:8) | (0.355, 0.620) | 85 | 70.5 |
| Example 2 | H1:A-27:GD4-59 (69:23:8) | (0.354, 0.621) | 86 | 78.3 |
| Example 3 | H1:A-209:GD4-59 (69:23:8) | (0.357, 0.619) | 84 | 70.5 |
| Example 4 | H1:A-210:GD4-59 (69:23:8) | (0.355, 0.620) | 84 | 63.0 |
| Example 5 | H1:A-51:GD4-59 (69:23:8) | (0.354, 0.621) | 86 | 63.2 |
| Example 6 | H1:A-157:GD4-59 (69:23:8) | (0.351, 0.623) | 86 | 68.9 |
| Example 7 | H1:A-212:GD4-59 (69:23:8) | (0.351, 0.623) | 86 | 74.5 |
| Example 8 | H1:A-231:GD4-59 (69:23:8) | (0.360, 0.616) | 84 | 70.6 |
| Example 9 | H1:A-233:GD4-59 (69:23:8) | (0.355, 0.620) | 84 | 71.5 |
| Example 10 | H1:A-257:GD4-59 (69:23:8) | (0.356, 0.619) | 87 | 67.3 |
| Example 11 | H1:A-347:GD4-59 (69:23:8) | (0.352, 0.623) | 85 | 72.8 |
| Example 12 | H1:A-422:GD4-59 (69:23:8) | (0.352, 0.622) | 87 | 69.5 |
| Example 13 | H1:A-553:GD4-59 (69:23:8) | (0.358, 0.618) | 87 | 82.4 |
| Example 14 | H1:A-160:GD4-59 (69:23:8) | (0.351, 0.623) | 85 | 60.0 |
| Comparative Example 1 | H1:C-1:GD4-59 (69:23:8) | (0.356, 0.620) | 84 | 40.0 |
| Comparative Example 2 | H1:C-2:GD4-59 (69:23:8) | (0.356, 0.619) | 88 | 21.2 |
| Comparative Example 3 | H1:C-3:GD4-59 (69:23:8) | (0.360, 0.616) | 82 | 36.2 |
| Comparative Example 4 | H1:C-4:GD4-59 (69:23:8) | (0.356, 0.619) | 82 | 34.8 |

DISCUSSION

In Example 1 to Example 4 and Comparative Examples 1 and 2, the phosphorescent dopant GD4-59 was doped in Compounds A-1, A-27, A-209 and A-210 of the present disclosure and Compounds C-1 and C-2 that are not provided in the present disclosure. Compared with Comparative Example 1, Example 1 to Example 4 have substantially the same or improved current efficiency and device lifetimes that are increased by 76.3%, 95.8%, 76.3% and 57.5%, respectively. Compared with Comparative Example 2, Example 1 to Example 4 have substantially the same current efficiency and device lifetimes that are increased to 3.32 times, 3.69 times, 3.32 10 times and 2.97 times, respectively. This shows that when applied to electroluminescent devices, the compound having substituted or unsubstituted phenyl at position 1 of a dibenzo five-membered heterocycle in the present disclosure has a longer device lifetime than the compound having a fused (hetero) aryl substitution at position 1.

In Example 1 to Example 4 and Comparative Example 3, the phosphorescent dopant GD4-59 was doped in Compounds A-1, A-27, A-209 and A-210 of the present disclosure and Compound C-3 that is not provided in the present disclosure. Compared with Comparative Example 3, Example 1 to Example 4 all have improved current efficiency and device lifetimes that are increased by 94.8%, 116.3%, 94.8% and 74.0%, respectively. This shows that when applied to electroluminescent devices, the compound with an aryl substitution on triazine in the present disclosure has a longer device lifetime than the compound having a fused heteroaryl substitution on triazine.

In Example 1 to Example 4 and Comparative Example 4, the phosphorescent dopant GD4-59 was doped in Compounds A-1, A-27, A-209 and A-210 of the present disclosure and Compound C-4 that is not provided in the present disclosure. Compared with Comparative Example 4, Example 1 to Example 4 all have improved current efficiency and device lifetimes that are increased by 102.6%, 125.0%, 102.6% and 81.0%, respectively. This shows that when applied to electroluminescent devices, the compound with a dibenzo five-membered heterocycle as a skeleton in the present disclosure has a longer device lifetime than the compound with a fused dibenzo five-membered heterocycle as a skeleton.

In Example 5 to Example 14 and Comparative Examples 1 and 2, the phosphorescent dopant GD4-59 was doped in a series of compounds of the present disclosure and Compounds C-1 and C-2 that are not provided in the present disclosure. Compared with Comparative Example 1, Example 5 to Example 14 have substantially the same or improved current efficiency and device lifetimes that are increased by 50.0% to 106.0%. Compared with Comparative Example 2, Example 5 to Example 14 have substantially the same current efficiency and device lifetimes that are increased by 2.83 times to 3.89 times. This shows that when applied to electroluminescent devices, the compound having substituted or unsubstituted phenyl at position 1 of a dibenzo five-membered heterocycle in the present disclosure has a longer device lifetime than the compound having a fused (hetero) aryl substitution at position 1.

In Example 5 to Example 14 and Comparative Example 3, the phosphorescent dopant GD4-59 was doped in the series of compounds of the present disclosure and Compound C-3 that is not provided in the present disclosure. Compared with Comparative Example 3, Example 5 to Example 14 all have improved current efficiency and device lifetimes that are increased by 65.7% to 127.6%. This shows that when applied to electroluminescent devices, the compound with an aryl substitution on triazine in the present disclosure has the longer device lifetime than the compound having a fused heteroaryl substitution on triazine.

In Example 5 to Example 14 and Comparative Example 4, the phosphorescent dopant GD4-59 was doped in the series of compounds of the present disclosure and Compound C-4 that is not provided in the present disclosure. Compared with Comparative Example 4, Example 5 to Example 14 all have improved current efficiency and device lifetimes that are increased by 72.4% to 136.8%. This shows that when applied to electroluminescent devices, the compound with a dibenzo five-membered heterocycle as the skeleton in the present disclosure has the longer device lifetime than the compound with a fused dibenzo five-membered heterocycle as the skeleton.

In summary, when used as host materials in a light-emitting layer, the compounds of the present disclosure improve an ability of a material to balance electron transport and hole transport. Compared with compounds that are not provided in the present disclosure and used as the host materials in the light-emitting layer, the compounds of the present disclosure improve device performance, where the devices all have substantially the same or improved current efficiency and significantly improved lifetimes compared with comparative examples. The compounds of the present disclosure are of great help to the industry.

Device Example 15

First, a glass substrate having an indium tin oxide (ITO) anode with a thickness of 80 nm was cleaned and then treated with oxygen plasma and UV ozone. After the treatment, the substrate was dried in a glovebox to remove moisture. Then, the substrate was mounted on a substrate holder and placed in a vacuum chamber. Organic layers specified below were sequentially deposited through vacuum thermal evaporation on the ITO anode at a rate of 0.2 to 2 Angstroms per second and a vacuum degree of about $10^{-8}$ torr. Compound H1 was used as a hole injection layer (HIL). Compound HT was used as a hole transporting layer (HTL). Compound EB was used as an electron blocking layer (EBL). Compound BD was doped in Compound H3, which were co-deposited for use as an emissive layer (EML). Compound HB was used as a hole blocking layer (HBL). On the HBL, Compound A-1 and 8-hydroxyquinolinolato-lithium (Liq) were co-deposited for use as an electron transporting layer (ETL). Finally, 8-hydroxyquinolinolato-lithium (Liq) was deposited as an electron injection layer with a thickness of 1 nm and Al was deposited as a cathode with a thickness of 120 nm. The device was transferred back to the glovebox and encapsulated with a glass lid and a moisture getter to complete the device.

Device Example 16

Device Example 16 was prepared by the same method as Device Example 15, except that in the ETL, Compound A-1 was replaced with Compound A-209.

Device Comparative Example 5

Device Comparative Example 5 was prepared by the same method as Device Example 15, except that in the ETL, Compound A-1 was replaced with Compound ET.

Detailed structures and thicknesses of layers of the devices are shown in the following table. A layer using more than one material is obtained by doping different compounds at their weight ratio as recorded.

TABLE 3

Device structures in Device Examples 15 and 16 and Comparative Example 5

| Device ID | HIL | HTL | EBL | EML | HBL | ETL |
|---|---|---|---|---|---|---|
| Example 15 | Compound HI (100 Å) | Compound HT (1220 Å) | Compound EB (50 Å) | Compound H3:Compound BD (98:2) (250 Å) | Compound HB (50 Å) | Compound A-1:Liq (40:60) (300 Å) |
| Example 16 | Compound HI (100 Å) | Compound HT (1220 Å) | Compound EB (50 Å) | Compound H3:Compound BD (98:2) (250 Å) | Compound HB (50 Å) | Compound A-209:Liq (40:60) (300 Å) |
| Comparative Example 5 | Compound HI (100 Å) | Compound HT (1220 Å) | Compound EB (50 Å) | Compound H3:Compound BD (98:2) (250 Å) | Compound HB (50 Å) | Compound ET:Liq (40:60) (300 Å) |

The structures of the new materials used in the devices are shown as follows:

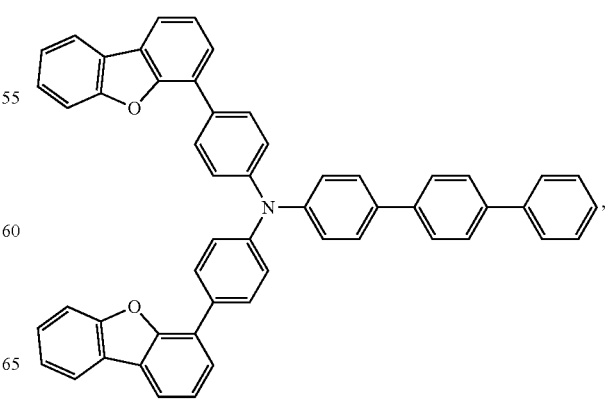

EB

-continued

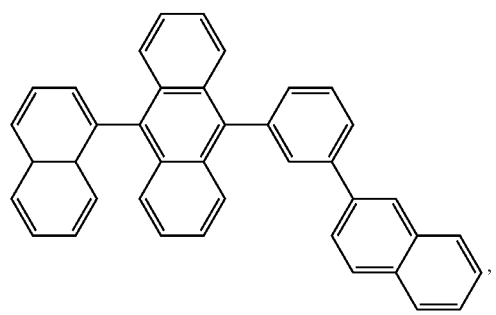

H3

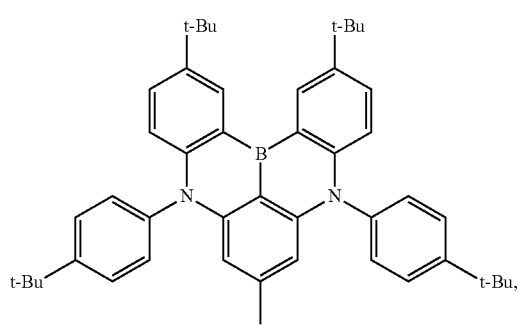

BD

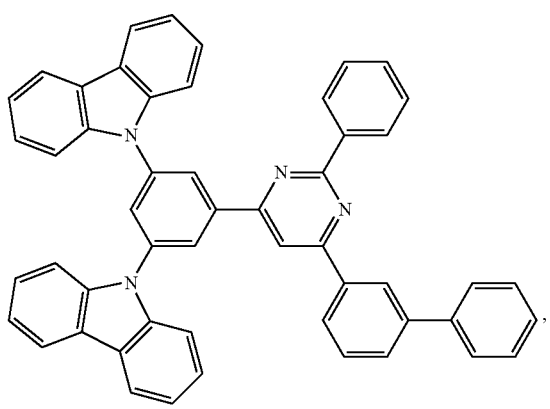

HB

Table 4 shows CIE data, driving voltage (V) and external quantum efficiency (EQE) measured at a constant current of 15 mA/cm² and a device lifetime (LT95) measured at a constant current of 80 mA/cm².

TABLE 4

Device data of Examples 15 and 16 and Comparative Example 5

| Device ID | ETL | CIE (x, y) | Driving Voltage (V) | EQE (%) | Lifetime LT95 (hrs) |
|---|---|---|---|---|---|
| Example 15 | A-1:Liq (40:60) | (0.133, 0.079) | 4.28 | 9.17 | 60.3 |
| Example 16 | A-209:Liq (40:60) | (0.132, 0.080) | 4.23 | 9.22 | 63.2 |
| Comparative Example 5 | ET:Liq (40:60) | (0.133, 0.079) | 4.51 | 8.83 | 62.7 |

DISCUSSION

10 Compounds A-1 and A-209 of the present disclosure and Compound ET that is not provided in the present disclosure are used as electron transporting materials in Examples 15 and 16 and Comparative Example 5, respectively. Compared with Comparative Example 5, Example 15 has a slightly reduced device lifetime but a 0.23 V lower driving voltage and improved EQE. Compared with Comparative Example 5, Example 16 has an increased device lifetime, improved EQE and a 0.28 V lower driving voltage. It is to be noted that Compound ET is a commercial electron transporting material at present. It can be seen that the compound of the present disclosure is also an excellent electron transporting material.

It should be understood that various embodiments described herein are merely examples and not intended to limit the scope of the present disclosure. Therefore, it is apparent to those skilled in the art that the present disclosure as claimed may include variations from specific embodiments and preferred embodiments described herein. Many of materials and structures described herein may be substituted with other materials and structures without departing from the spirit of the present disclosure. It should be understood that various theories as to why the present disclosure works are not intended to be limitative.

What is claimed is:

1. A compound having a structure of the following formula:

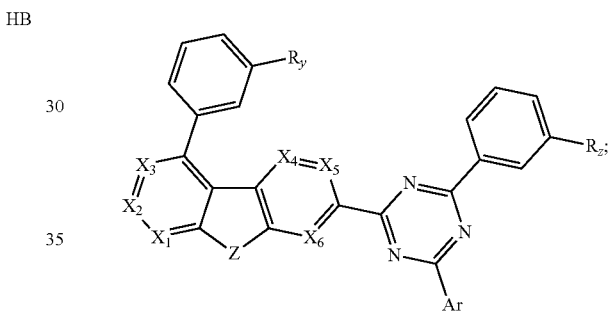

wherein

Z is selected from O, S or Se;

$X_1$ to $X_6$ are, at each occurrence identically or differently, selected from $CR_x$ or N;

$R_z$ is selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 10 to 30 carbon atoms, substituted or unsubstituted alkenyl having 2 to 20 carbon atoms, substituted or unsubstituted aryl having 10 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

$R_x$ and $R_y$ are selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

$R_y$ is a substituted or unsubstituted aryl having 6 to 30 carbon atoms, or $R_z$ is a substituted or unsubstituted aryl having 10 to 30 carbon atoms;

when $R_y$ is a substituted aryl having 6 to 30 carbon atoms, the aryl is substituted with one or more moieties selected from the group consisting of deuterium, halogen, unsubstituted alkyl having 1 to 20 carbon atoms, unsubstituted cycloalkyl having 3 to 20 ring carbon atoms, unsubstituted heteroalkyl having 1 to 20 carbon atoms, an unsubstituted heterocyclic group having 3 to 20 ring atoms, unsubstituted arylalkyl having 7 to 30 carbon atoms, unsubstituted alkoxy having 1 to 20 carbon atoms, unsubstituted aryloxy having 6 to 30 carbon atoms, unsubstituted alkenyl having 2 to 20 carbon atoms, unsubstituted alkynyl having 2 to 20 carbon atoms, unsubstituted aryl having 6 to 30 carbon atoms, unsubstituted alkylsilyl having 3 to 20 carbon atoms, unsubstituted arylsilyl group having 6 to 20 carbon atoms, unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof; and Ar is a substituted or unsubstituted aryl having 10 to 12 carbon atoms.

2. The compound according to claim 1, wherein Z is selected from O or S.

3. The compound according to claim 1, wherein $X_1$ to $X_6$ are, at each occurrence identically or differently, selected from $CR_x$.

4. The compound according to claim 1, wherein at least one of $X_1$ to $X_6$ is selected from N.

5. The compound according to claim 1, wherein $R_x$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms and combinations thereof.

6. The compound according to claim 1, wherein Ar is selected from the group consisting of: naphthyl, biphenyl, optionally, the substituent can be partially or fully deuterated.

7. The compound according to claim 1, wherein $R_y$ is substituted or unsubstituted aryl having 6 to 20 carbon atoms, or $R_z$ is substituted or unsubstituted aryl having 10 to 20 carbon atoms.

8. The compound according to claim 1, wherein the compound is selected from the group consisting of the following compounds:

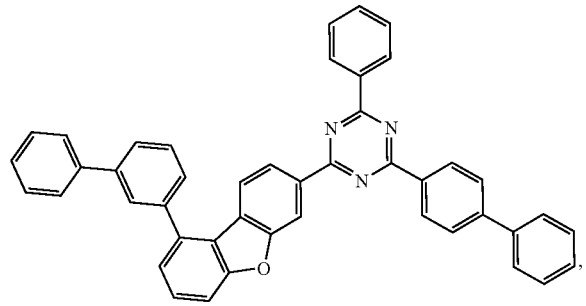

A-27

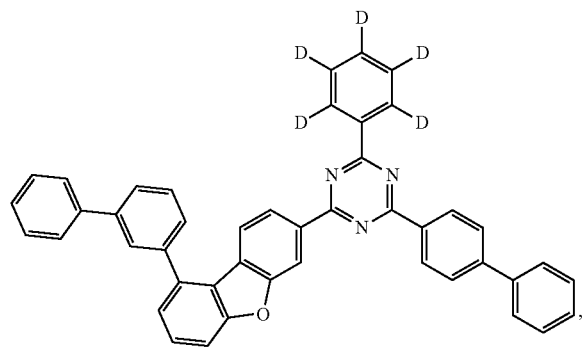

A-28

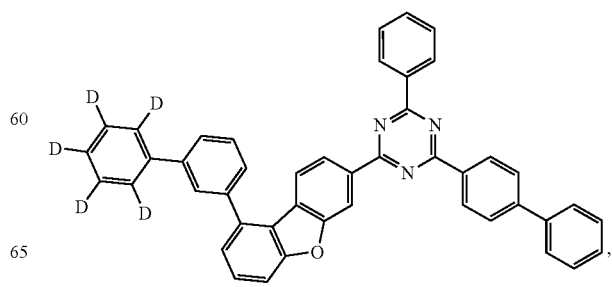

A-29

A-30
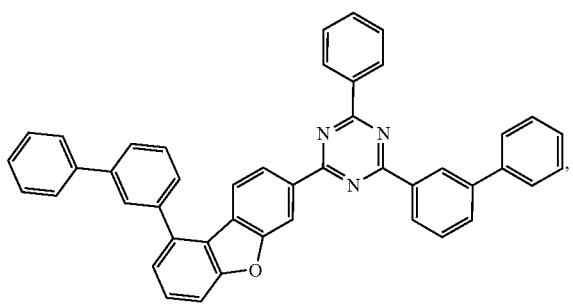
A-31
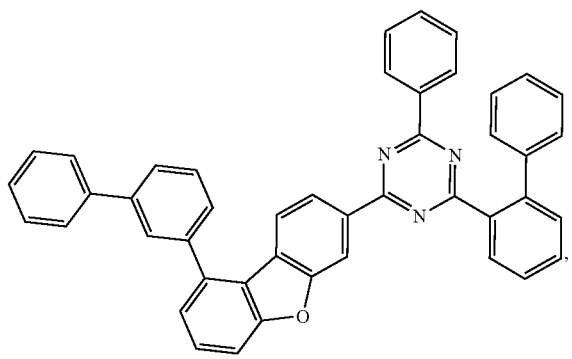
A-32
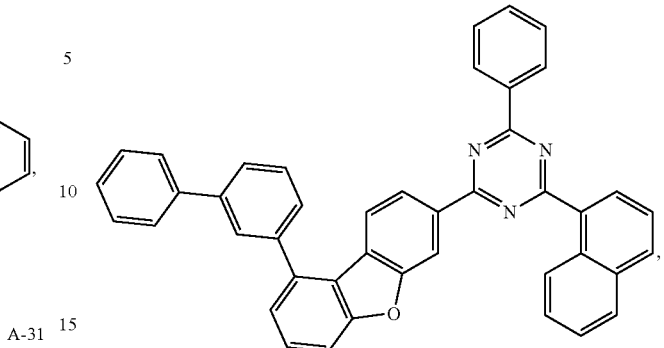
A-33
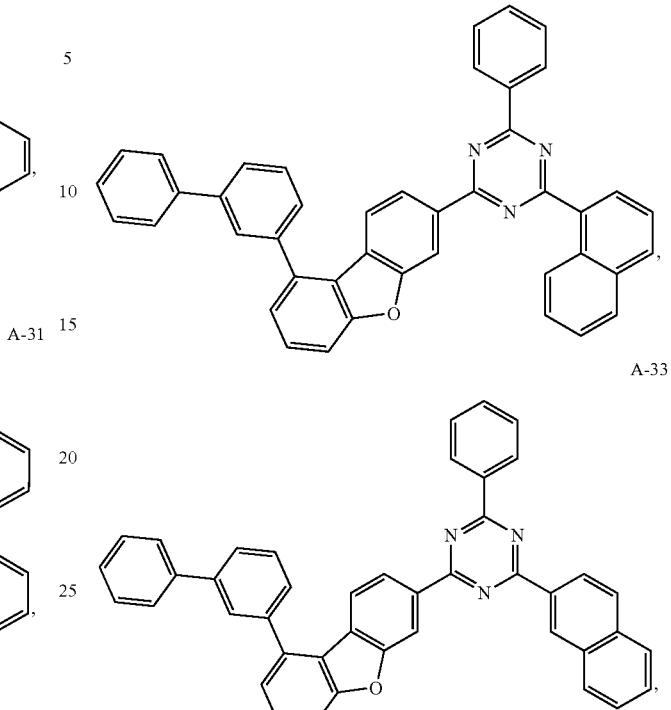
A-183
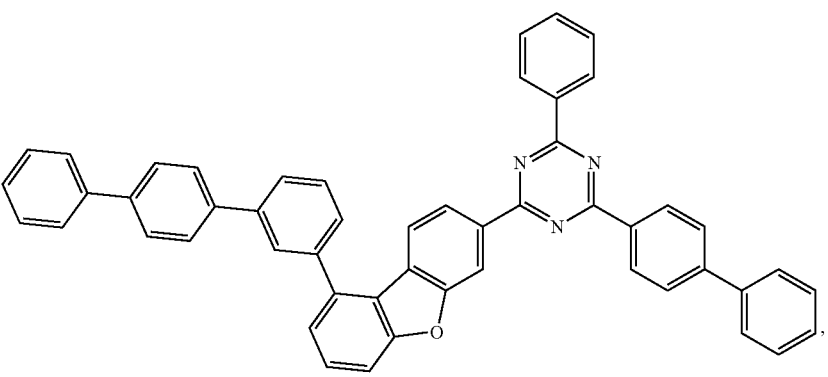
A-184
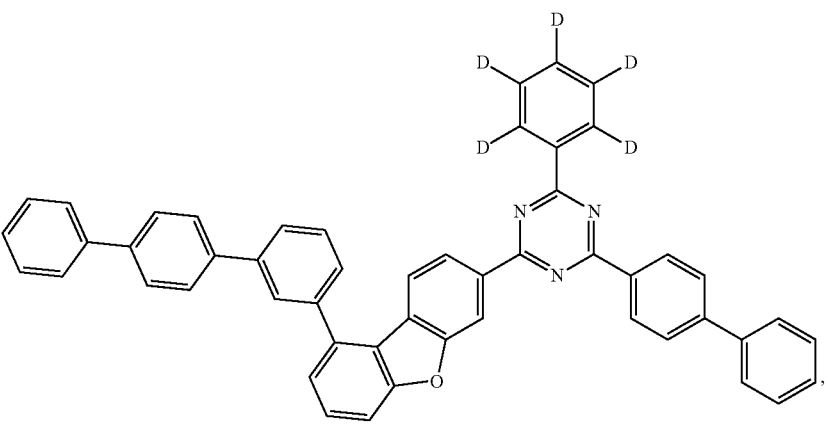

A-185
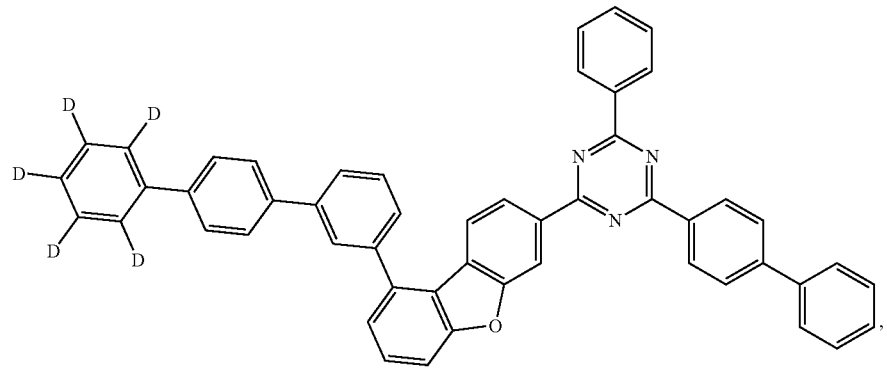
A-186
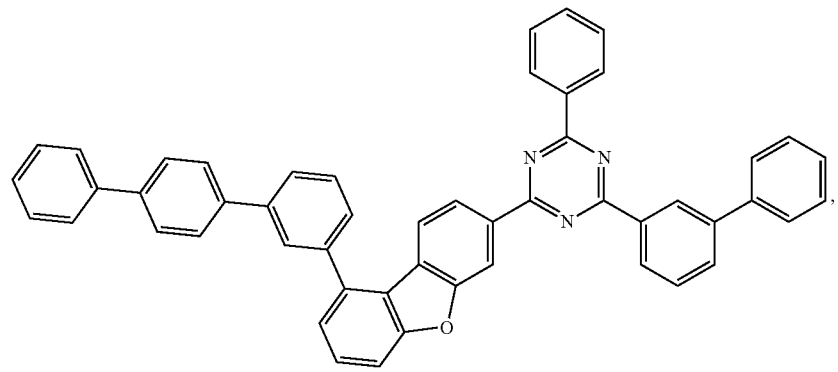
A-187 A-188
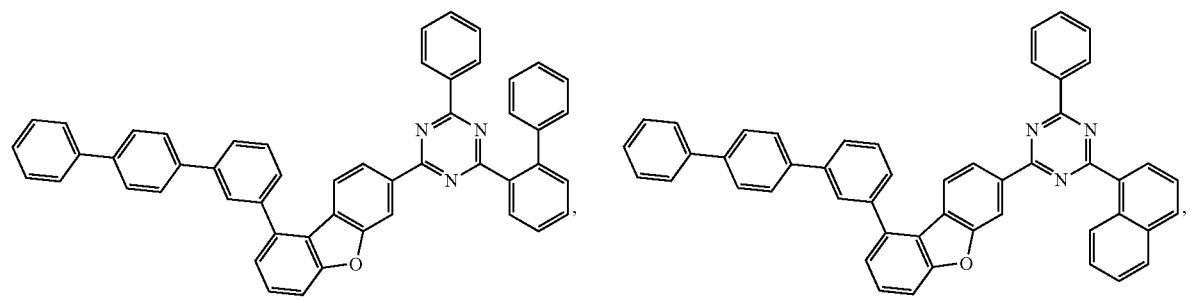
A-189
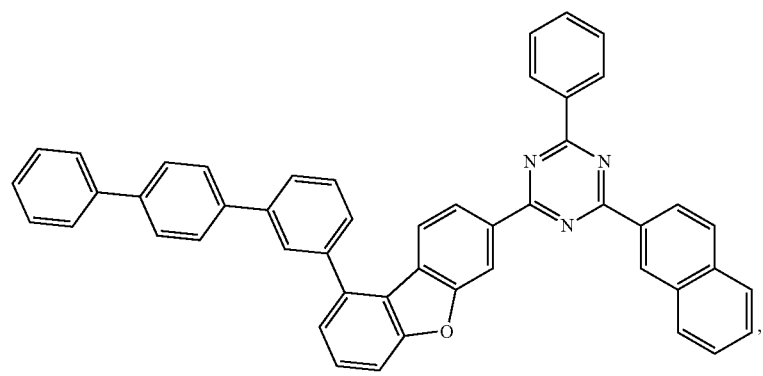

A-232
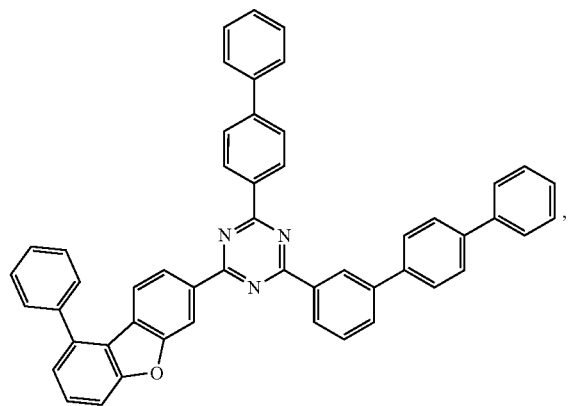
A-256
A-266
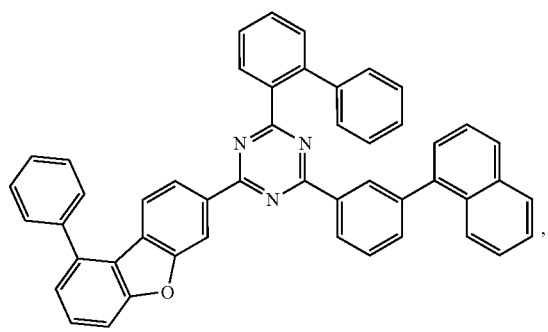
A-267
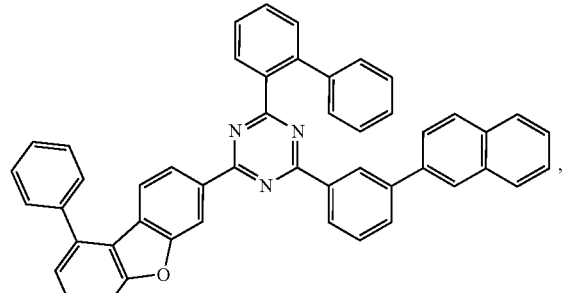
A-280
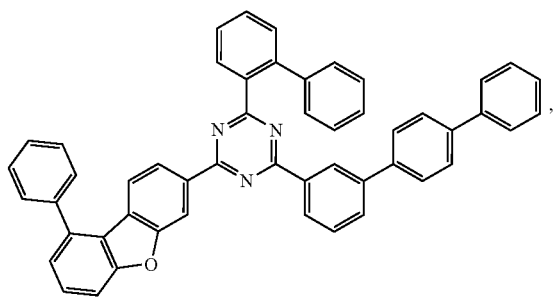
A-318

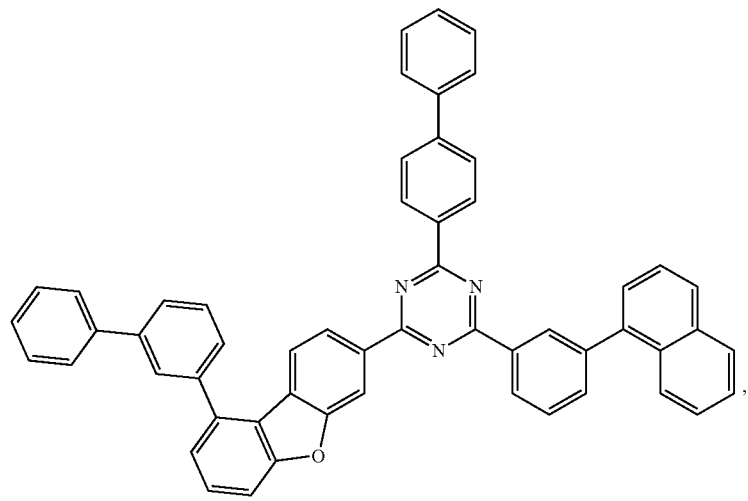
A-356
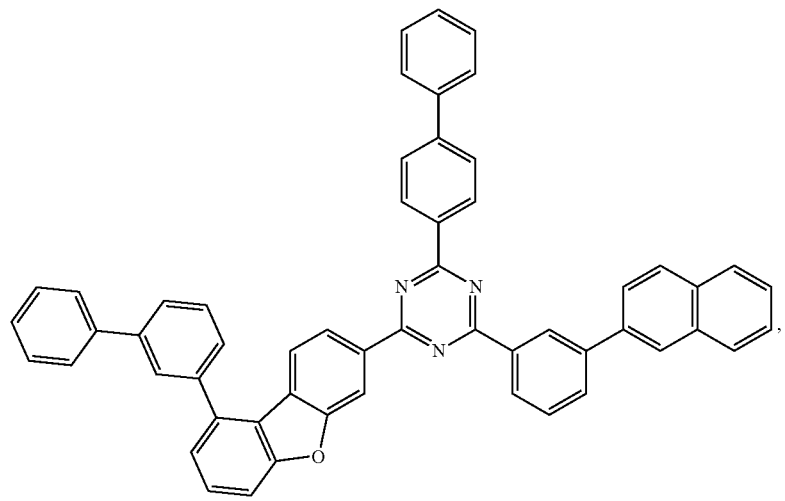
A-357
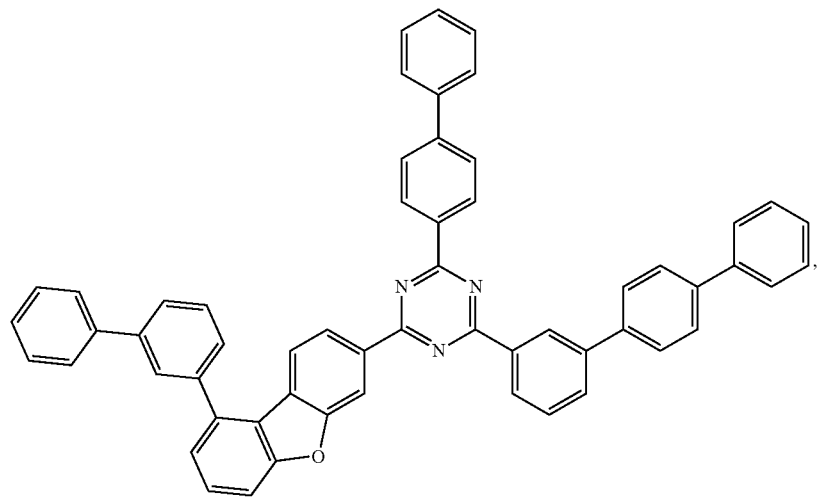
A-370

A-428

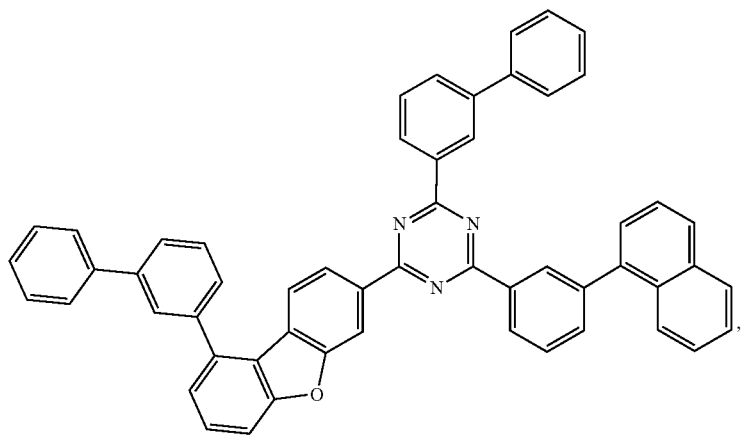

A-429

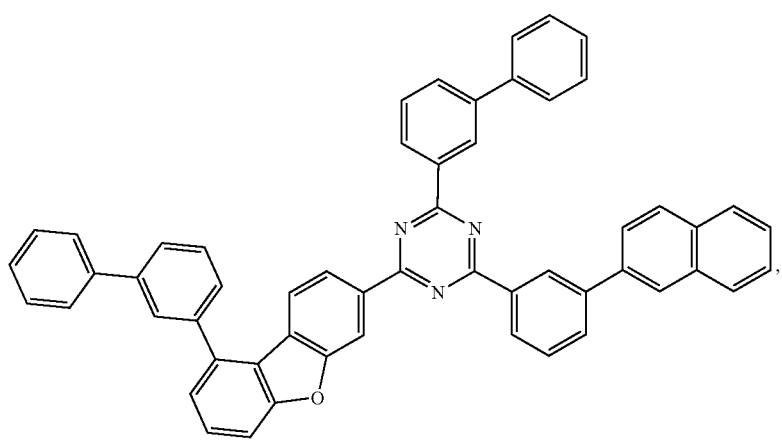

A-442

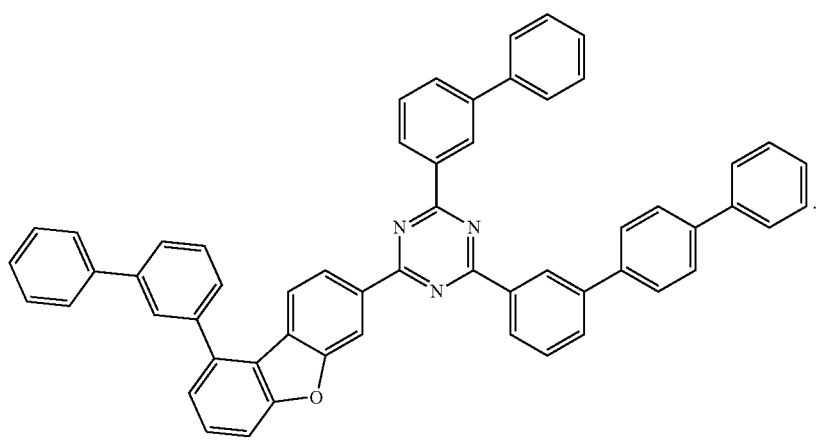

9. A composition containing the compound according to claim 1.

10. The compound according to claim 1, wherein Z is selected from O.

11. The compound according to claim 1, wherein $R_x$ is, at each occurrence identically or differently, selected from the group consisting of: hydrogen, deuterium, substituted or unsubstituted phenyl, substituted or unsubstituted naphthyl, substituted or unsubstituted biphenyl and combinations thereof.

12. An organic electroluminescent device, comprising an anode, a cathode and an organic layer disposed between the anode and the cathode, wherein the organic layer contains the compound having a structure of Formula 1:

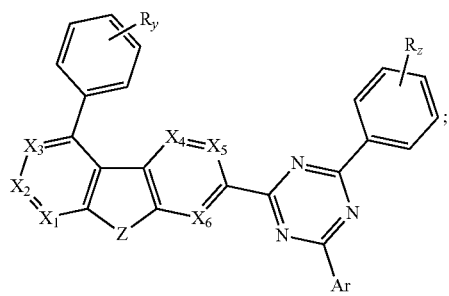

Formula 1

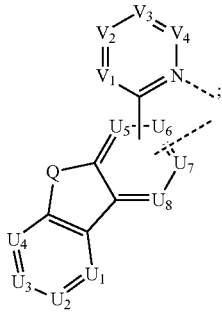

Formula 3 wherein

Z is selected from O, S or Se;

$X_1$ to $X_6$ are, at each occurrence identically or differently, selected from $CR_x$ or N;

$R_y$ and $R_z$ represent, at each occurrence identically or differently, mono-substitution, multiple substitutions or non-substitution;

$R_x$, $R_y$ and $R_z$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;

at least one of $R_y$ and $R_z$ is substituted or unsubstituted aryl having 6 to 30 carbon atoms; and Ar is a substituted or unsubstituted aryl having 10 to 30 carbon atoms;

the organic layer is a light-emitting layer, the compound is a host compound, and the light-emitting layer contains at least a first metal complex; or the organic layer is an electron transporting layer and the compound is an electron transporting compound;

the first metal complex has a general formula of $M(L_a)_f(L_b)_g(L_c)_h$, wherein $L_a$ has a structure represented by Formula 3:

wherein the metal M is, at each occurrence identically or differently, selected from the group consisting of Cu, Ag, Au, $R_u$, Rh, Pd, Os, Ir and Pt;

$L_a$, $L_b$ and $L_c$ are a first ligand, a second ligand and a third ligand coordinated to the metal M, respectively; $L_a$, $L_b$ and $L_c$ can be optionally joined to form a multidentate ligand;

f is selected from 0, 1, 2 or 3, g is selected from 0, 1, 2 or 3, and h is selected from 0, 1 or 2;

when f is 2 or 3, the plurality of $L_a$ are identical or different; when g is 2 or 3, the plurality of $L_b$ are identical or different; when h is 2, two $L_c$ are identical or different;

Q is, at each occurrence identically or differently, selected from the group consisting of O, S, Se, $NR_q$, $CR_qR_q$ and $SiR_qR_q$; when two $R_q$ are present at the same time, the two $R_q$ are identical or different;

$U_1$ to $U_8$ are, at each occurrence identically or differently, selected from C, $CR_u$ or N;

$U_5$, $U_6$, $U_7$ or $U_8$ is joined to the metal M by a metal-carbon bond or a metal-nitrogen bond;

$V_1$ to $V_4$ are, at each occurrence identically or differently, selected from CRY or N;

$R_q$, $R_u$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof; and at least one $R_u$ is fluorine or cyano;

adjacent substituents $R_q$, $R_u$ and $R_y$ can be optionally joined to form a ring;

$L_b$ and $L_c$ are, at each occurrence identically or differently, selected from a structure represented by any one of the group consisting of the following:

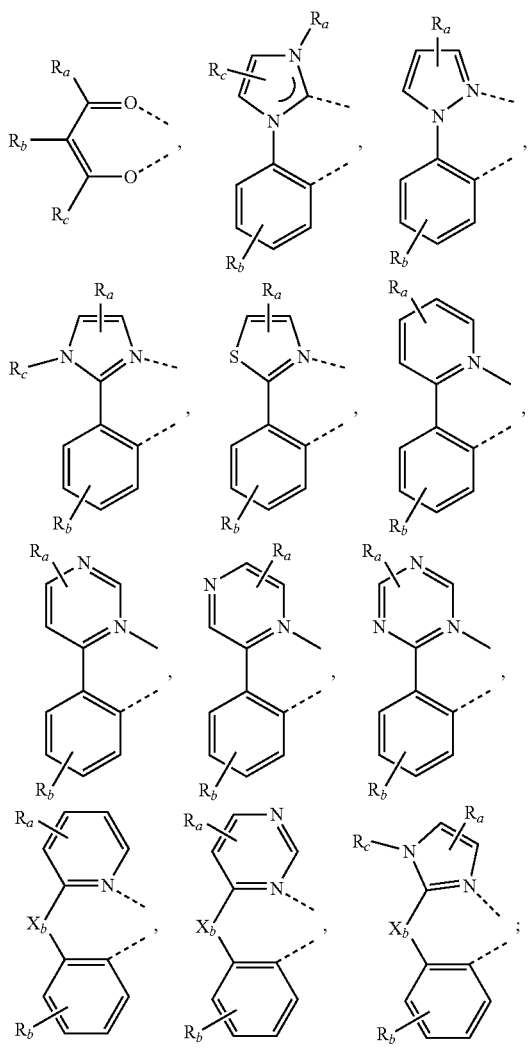

wherein
$R_a$, $R_b$ and $R_c$ represent, at each occurrence identically or differently, mono-substitution, multiple substitutions or non-substitution;
$X_b$ is, at each occurrence identically or differently, selected from the group consisting of: O, S, Se, $NR_{N1}$ and $CR_{C1}R_{C2}$;
$R_a$, $R_b$, $R_c$, $R_{N1}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof;
adjacent substituents $R_a$, $R_b$, $R_c$, $R_{N1}$, $R_{C1}$ and $R_{C2}$ can be optionally joined to form a ring.

13. The organic electroluminescent device according to claim 12, wherein the first metal complex has a structure represented by Formula 4:

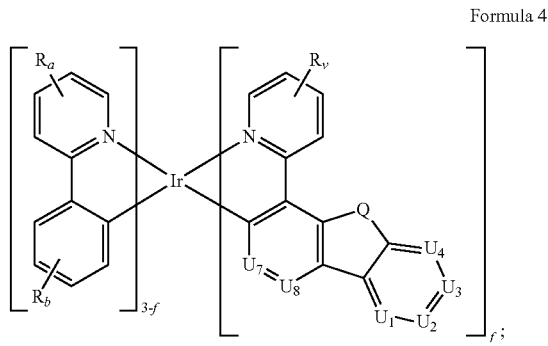

Formula 4 wherein
f is 0, 1, 2 or 3; when f is 2 or 3, the plurality of $L_a$ are identical or different; when f is 0 or 1, the plurality of $L_b$ are identical or different;
$U_4$ is, at each occurrence identically or differently, selected from $CR_u$ or N;
$U_1$ to $U_3$, $U_7$ and $U_8$ are, at each occurrence identically or differently, selected from $CR_u$;
$R_a$, $R_b$ and $R_y$ represent, at each occurrence identically or differently, mono-substitution, multiple substitutions or non-substitution;
$R_a$, $R_b$, $R_u$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof, at least one $R_u$ is fluorine or cyano; and adjacent substituents $R_a$, $R_b$, $R_u$ and $R_y$ can be optionally joined to form a ring.

14. The organic electroluminescent device according to claim 12, wherein at least one of $R_u$ is selected from substituted or unsubstituted alkyl having 1 to 20 carbon atoms or substituted or unsubstituted cycloalkyl having 3 to 20 ring carbon atoms.

15. The organic electroluminescent device according to claim 12, wherein there exist at least two $R_u$, one of which is fluorine or cyano and the other one of which is selected from substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms or substituted or unsubstituted heteroaryl having 3 to 30 carbon atoms.

16. The organic electroluminescent device according to claim 12, wherein $L_a$ is selected from the group consisting of the following:

$L_{a2-1}$ $L_{a2-2}$ $L_{a2-3}$ $L_{a2-4}$ $L_{a2-5}$
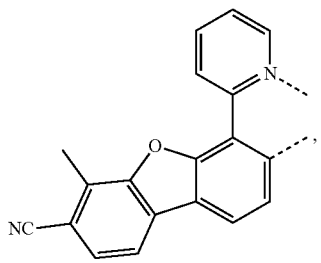

$L_{a2-6}$
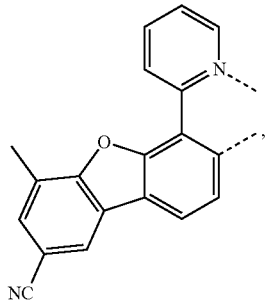

$L_{a2-7}$
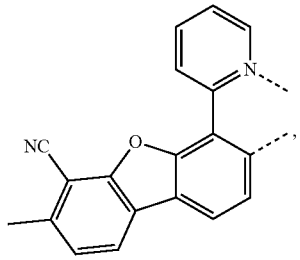

$L_{a2-8}$
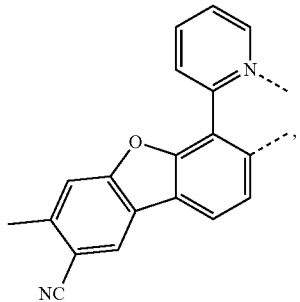

$L_{a2-9}$
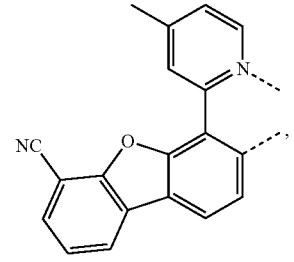

L<sub>a2-10</sub>
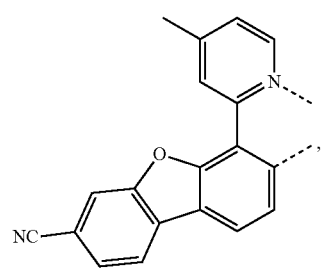
L<sub>a2-11</sub>
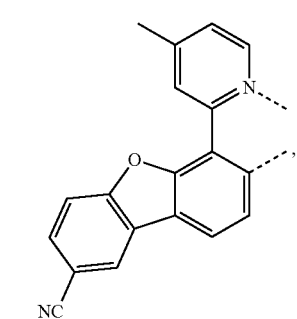
L<sub>a2-12</sub>
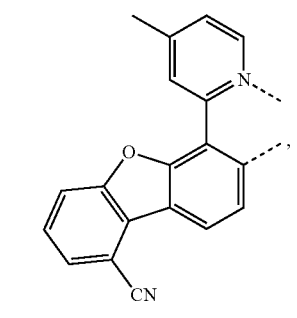
L<sub>a2-13</sub>
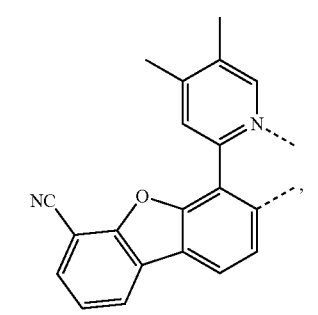
L<sub>a2-14</sub>
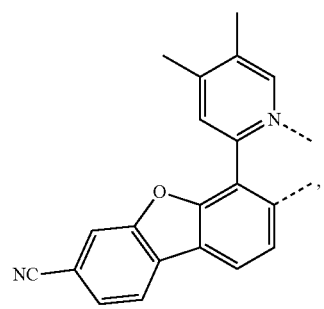
L<sub>a2-15</sub>
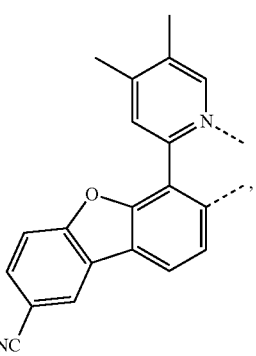
L<sub>a2-16</sub>
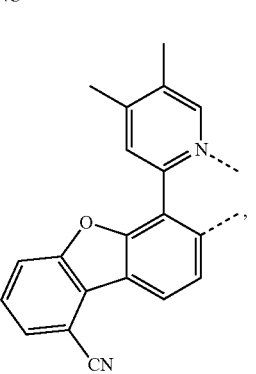
L<sub>a2-17</sub>
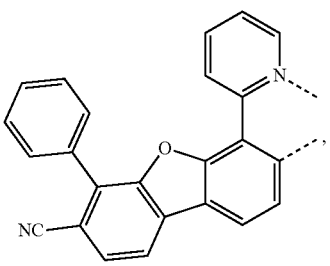
L<sub>a2-18</sub>
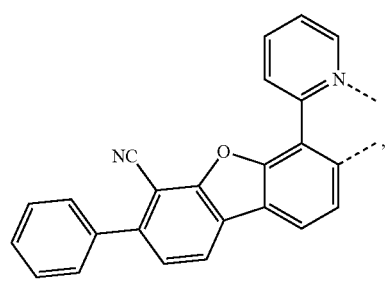
L<sub>a2-19</sub>
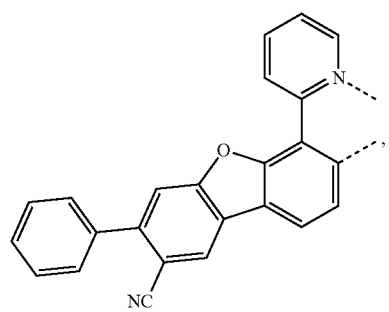

-continued
L<sub>a2-20</sub>
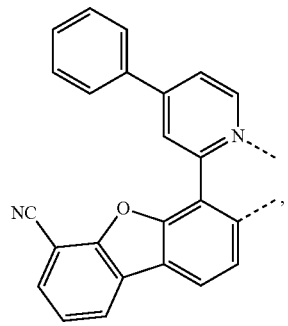
L<sub>a2-21</sub>
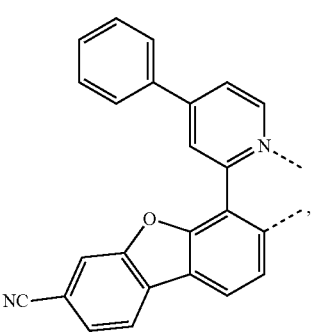
L<sub>a2-22</sub>
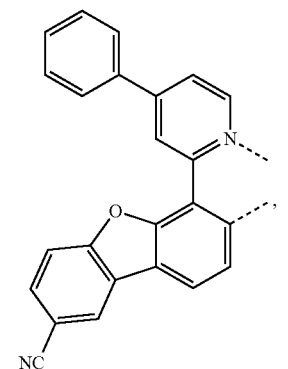
L<sub>a2-23</sub>
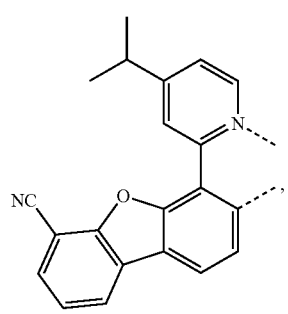
-continued
L<sub>a2-24</sub>
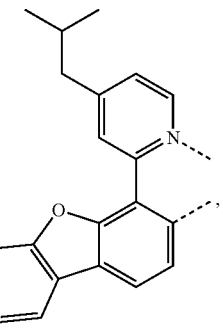
L<sub>a2-25</sub>
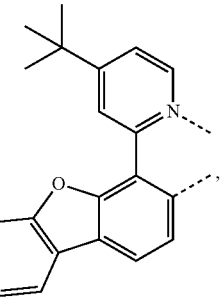
L<sub>a2-26</sub>
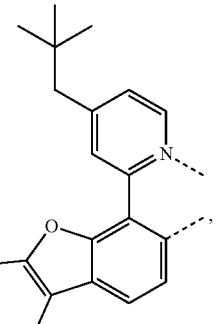
L<sub>a2-27</sub>
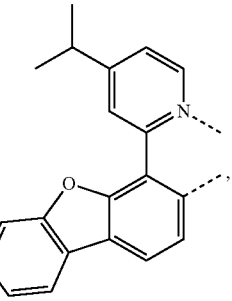
L<sub>a2-28</sub>
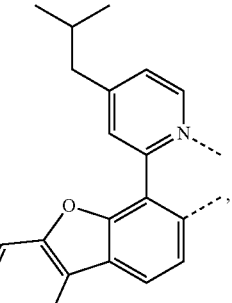

L<sub>a2-29</sub>
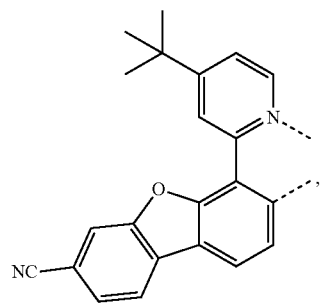
L<sub>a2-30</sub>
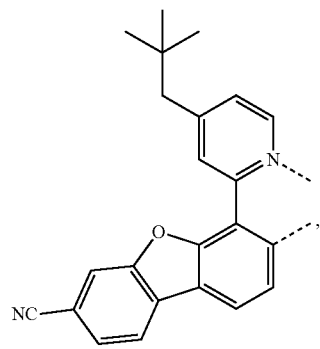
L<sub>a2-31</sub>
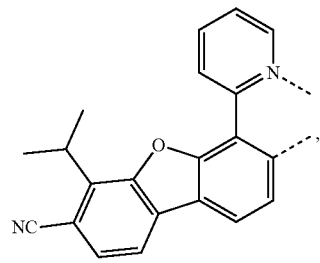
L<sub>a2-32</sub>
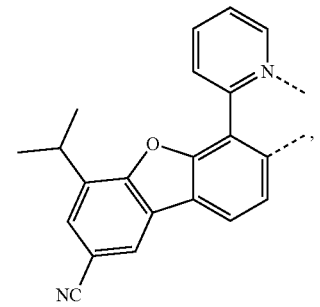
L<sub>a2-33</sub>
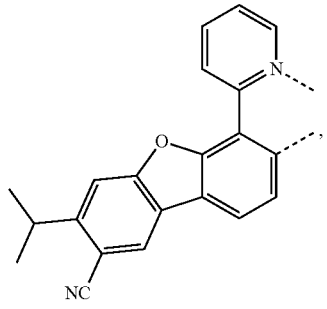
L<sub>a2-34</sub>
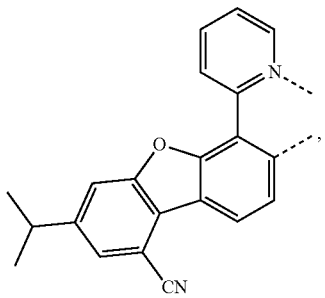
L<sub>a2-35</sub>
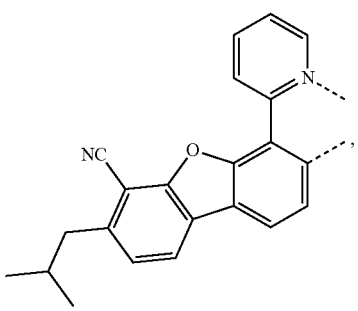
L<sub>a2-36</sub>
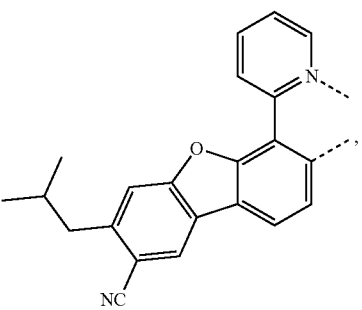
L<sub>a2-37</sub>
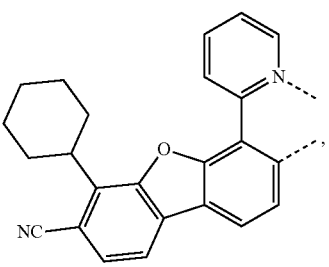
L<sub>a2-38</sub>
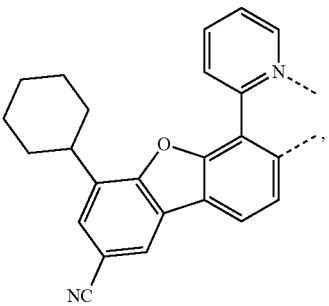

L*a2*-39 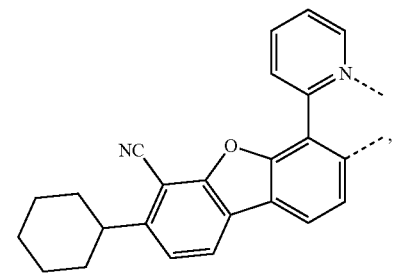
L*a2*-40 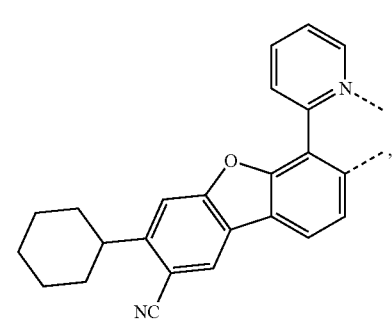
L*a2*-41 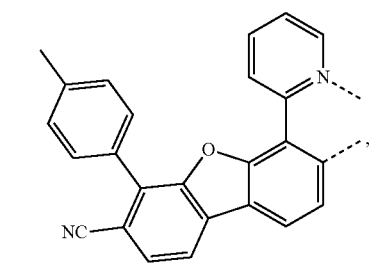
L*a2*-42 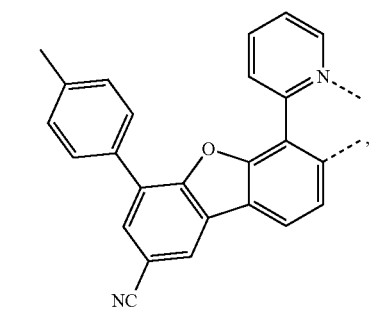
L*a2*-43 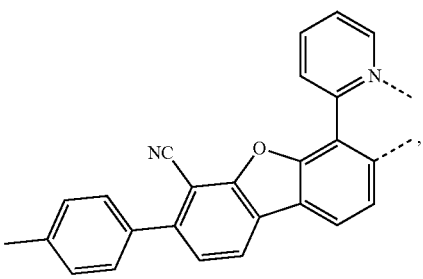
L*a2*-44 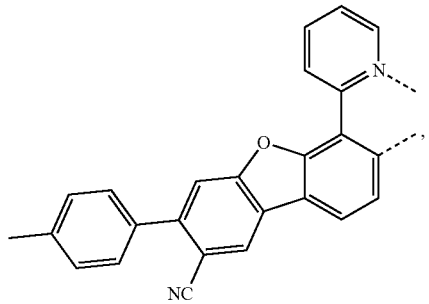
L*a2*-45 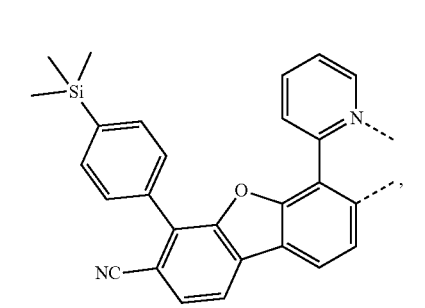
L*a2*-46 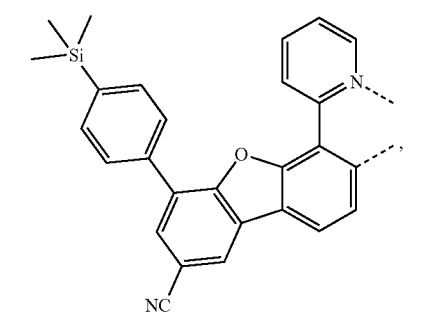
L*a2*-47 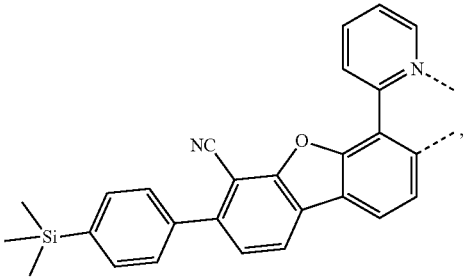
L*a2*-48 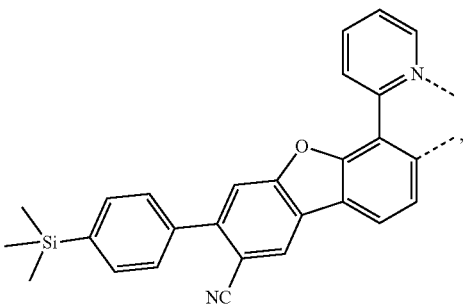

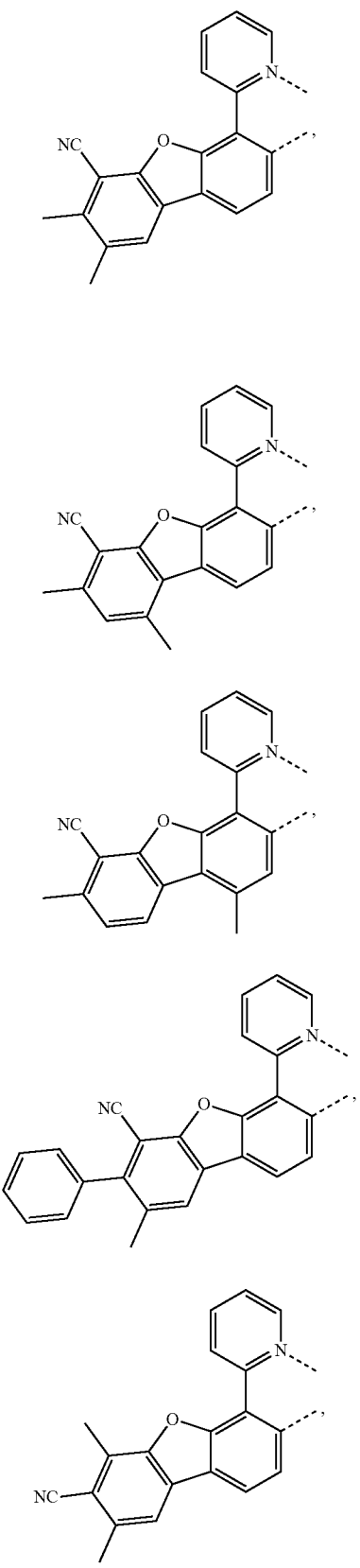
$L_{a2\text{-}49}$
$L_{a2\text{-}50}$
$L_{a2\text{-}51}$
$L_{a2\text{-}52}$
$L_{a2\text{-}53}$
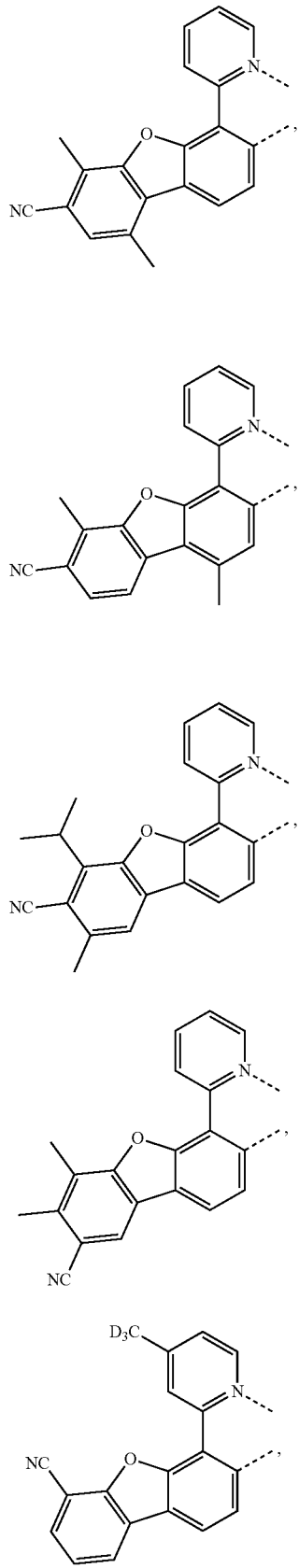
$L_{a2\text{-}54}$
$L_{a2\text{-}55}$
$L_{a2\text{-}56}$
$L_{a2\text{-}57}$
$L_{a2\text{-}58}$

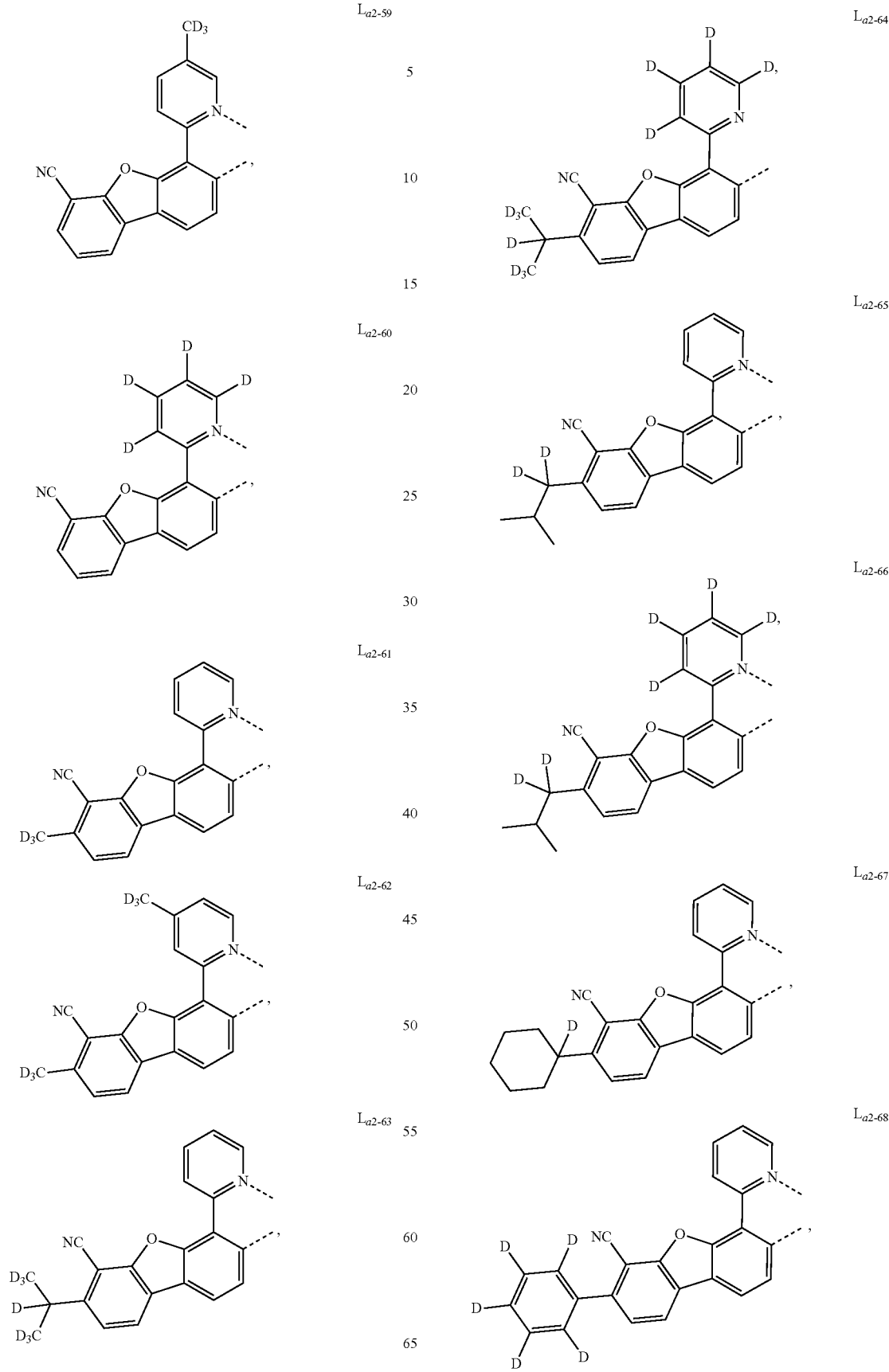

-continued
L<sub>a2-69</sub>
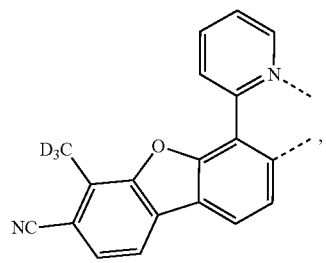
L<sub>a2-70</sub>
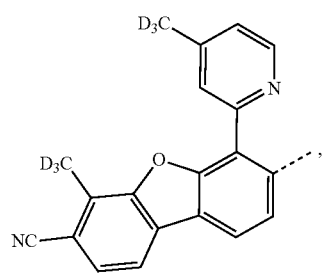
L<sub>a2-71</sub>
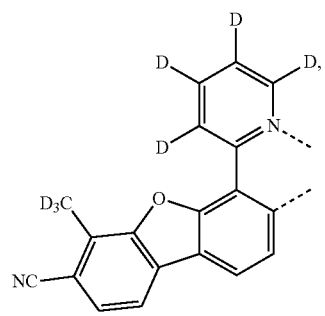
L<sub>a2-72</sub>
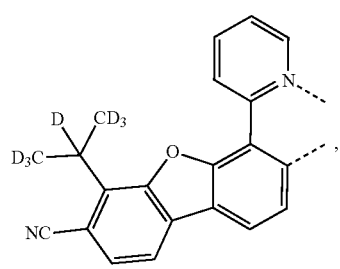
L<sub>a2-73</sub>
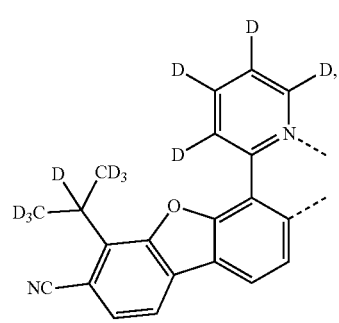
-continued
L<sub>a2-74</sub>
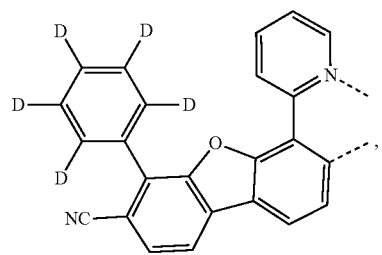
L<sub>a2-75</sub>
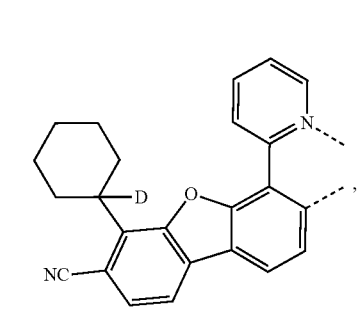
L<sub>a2-76</sub>
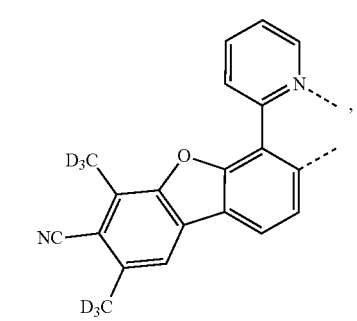
L<sub>a2-77</sub>
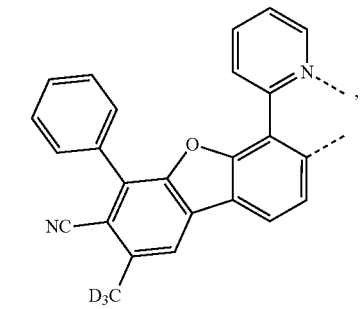
L<sub>a2-78</sub>
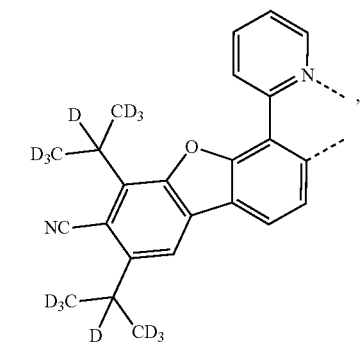

| | |
|---|---|
| 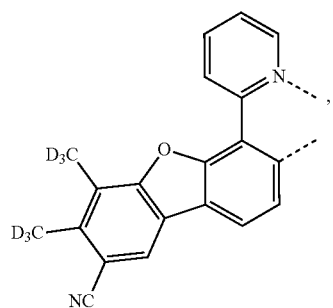 | $L_{a2-79}$ |
| 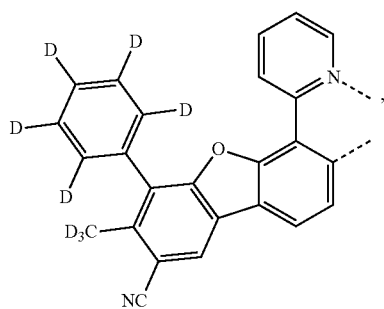 | $L_{a2-80}$ |
| 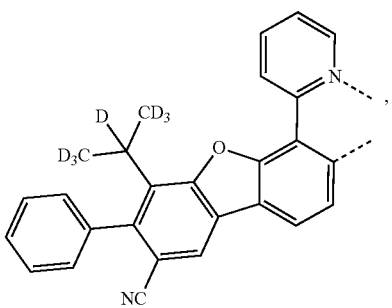 | $L_{a2-81}$ |
| 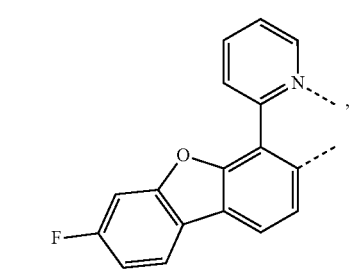 | $L_{a3-1}$ |
| 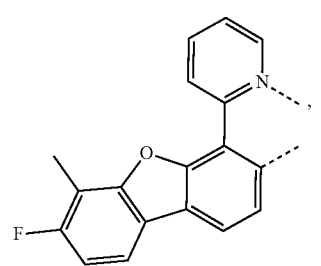 | $L_{a3-2}$ |
| 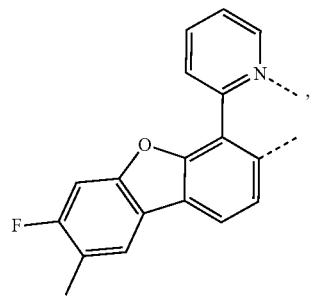 | $L_{a3-3}$ |
| 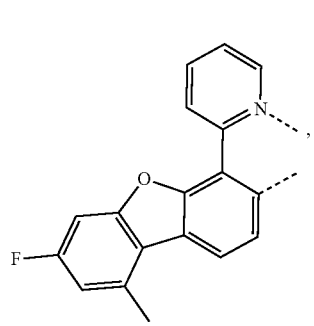 | $L_{a3-4}$ |
| 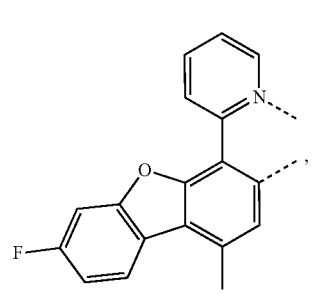 | $L_{a3-5}$ |
| 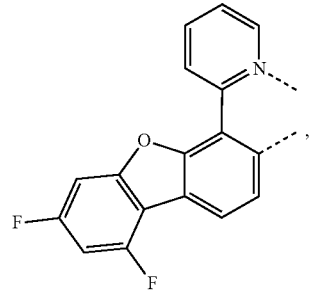 | $L_{a3-6}$ |
| 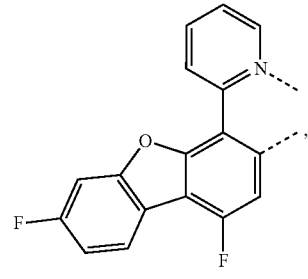 | $L_{a3-7}$ |

L_{a3-8}
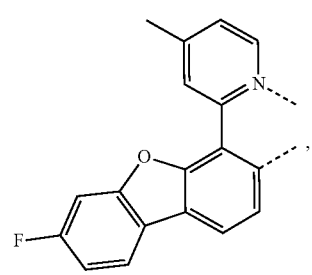
L_{a3-9}
L_{a3-10}
L_{a3-11}
L_{a3-12}
L_{a3-13}
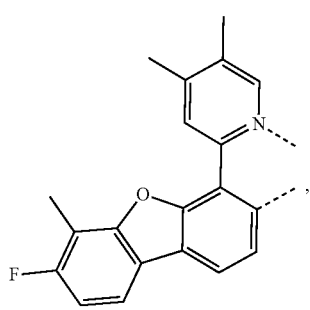
L_{a3-14}
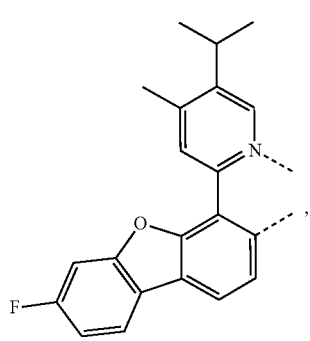
L_{a3-15}
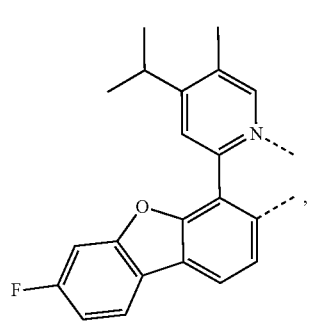
L_{a3-16}
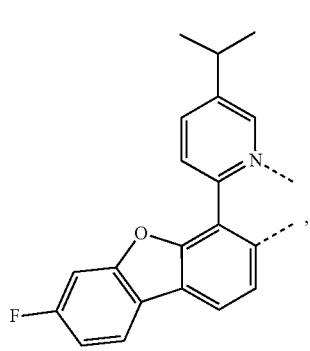
L_{a3-17}
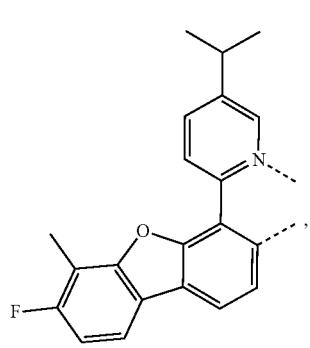

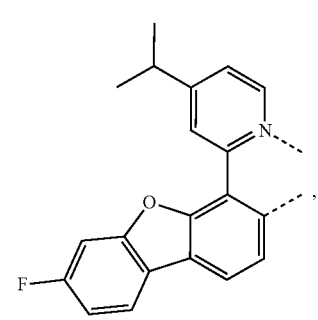
L_{a3-18}
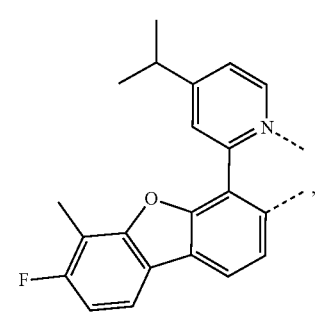
L_{a3-19}
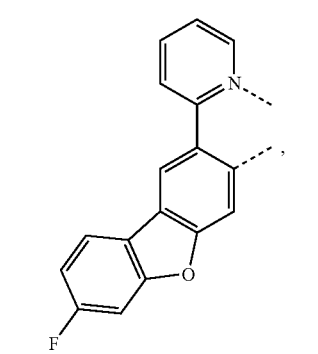
L_{a3-20}
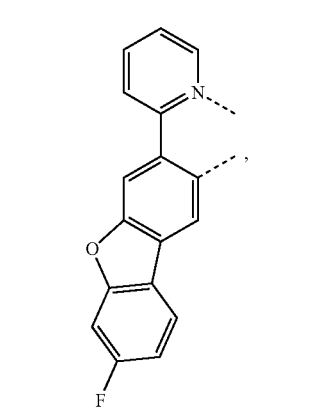
L_{a3-21}
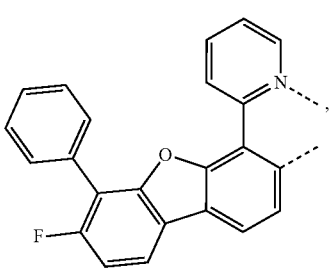
L_{a3-22}
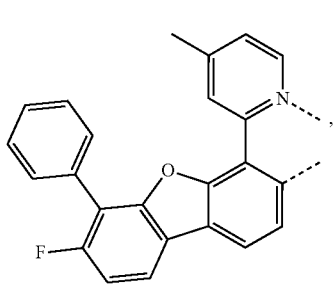
L_{a3-23}
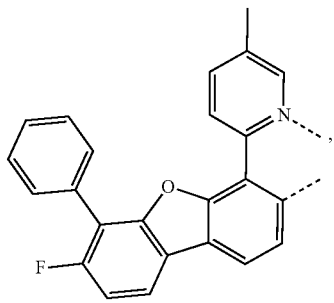
L_{a3-24}
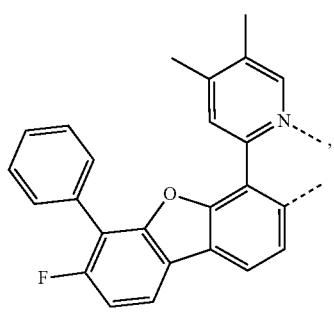
L_{a3-25}
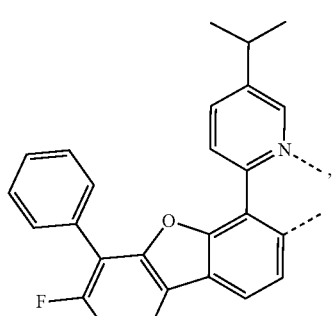
L_{a3-26}
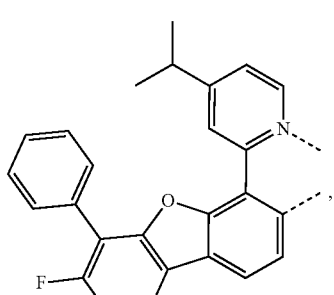
L_{a3-27}

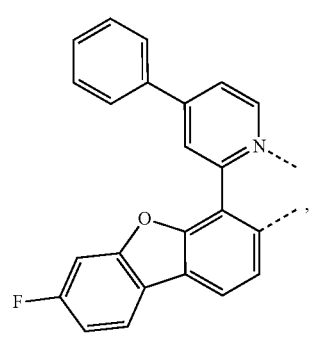
L<sub>a3-28</sub>
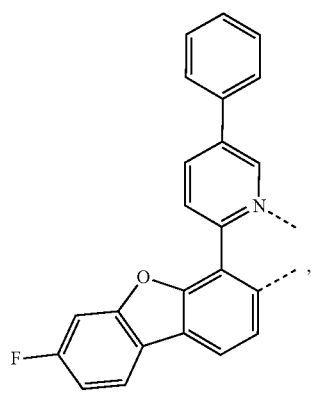
L<sub>a3-29</sub>
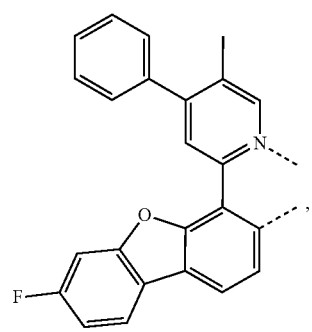
L<sub>a3-30</sub>
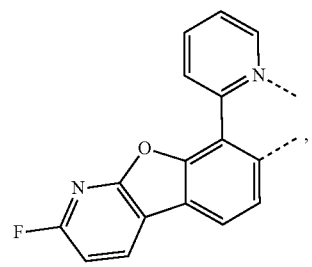
L<sub>a3-31</sub>
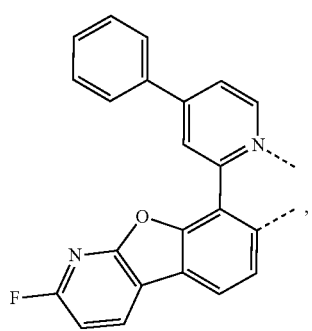
L<sub>a3-32</sub>
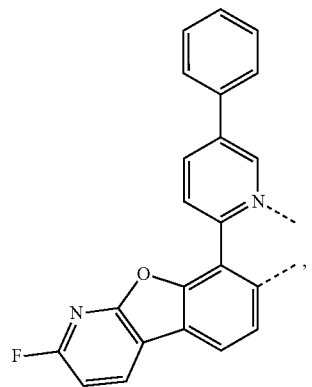
L<sub>a3-33</sub>
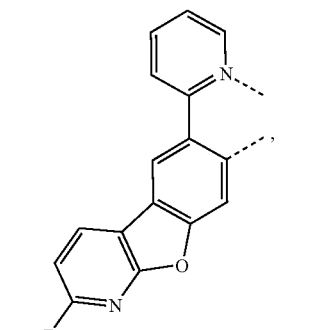
L<sub>a3-34</sub>
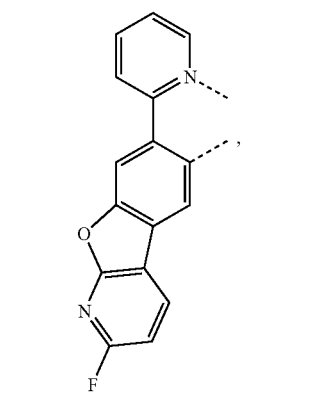
L<sub>a3-35</sub>

| | |
|---|---|
| L_{a3-36} 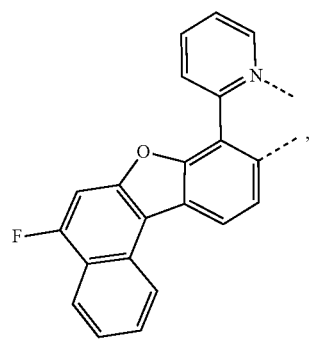 | L_{a3-40} 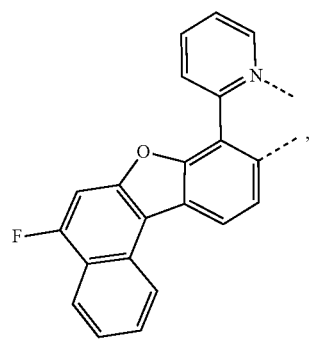 |
| L_{a3-37} 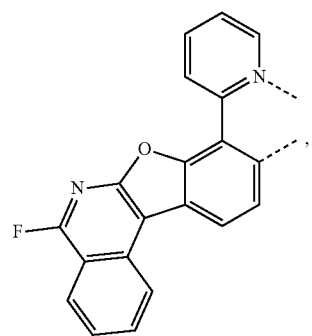 | L_{a3-41} 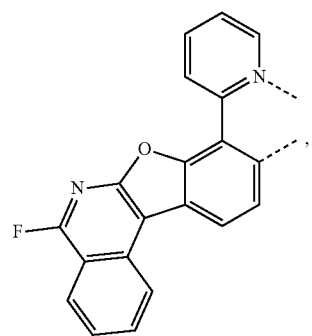 |
| L_{a3-38} 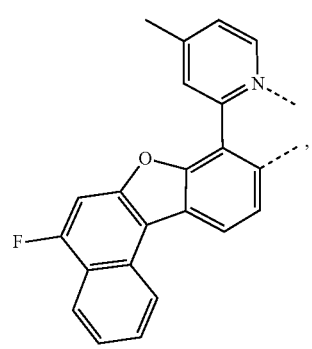 | L_{a3-42} 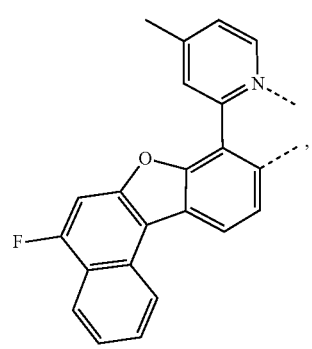 |
| | L_{a3-43} 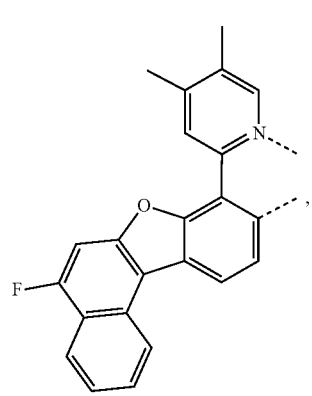 |
| L_{a3-39} 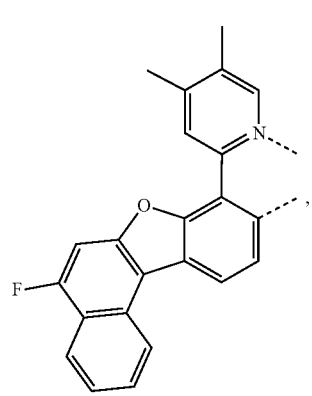 | L_{a3-44} 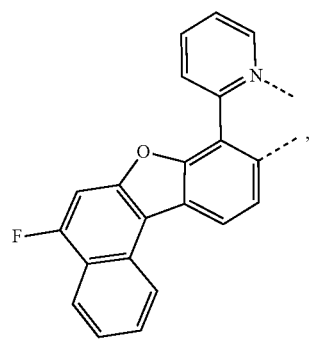 |

L<sub>a3-45</sub>
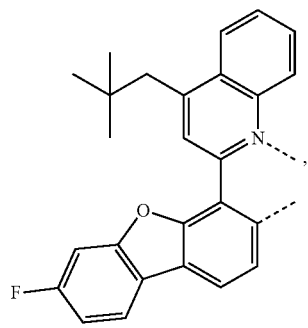
L<sub>a3-46</sub>
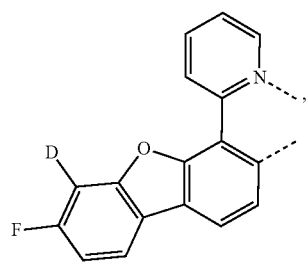
L<sub>a3-47</sub>
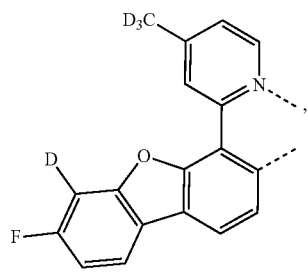
L<sub>a3-48</sub>
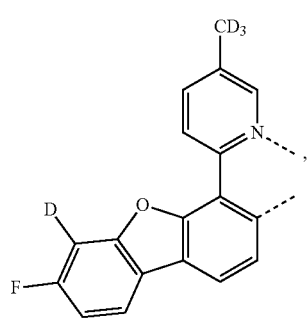
L<sub>a3-49</sub>
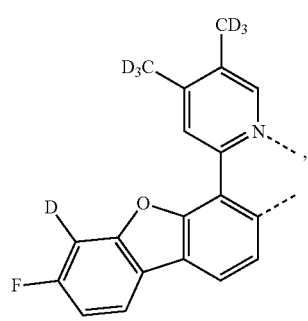
L<sub>a3-50</sub>
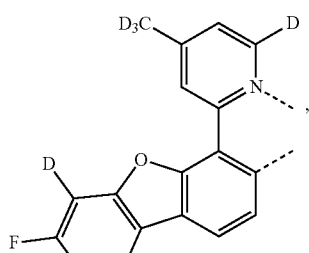
L<sub>a3-51</sub>
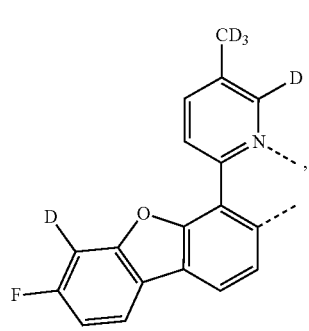
L<sub>a3-52</sub>
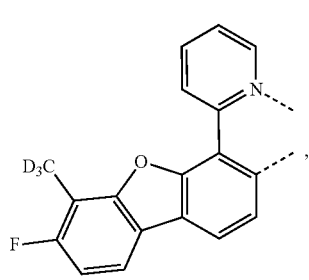
L<sub>a3-53</sub>
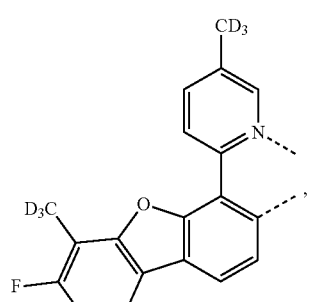
L<sub>a3-54</sub>
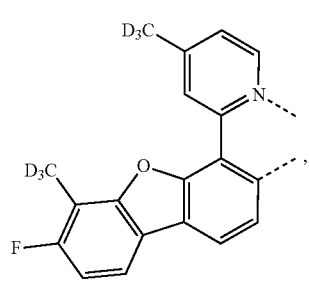

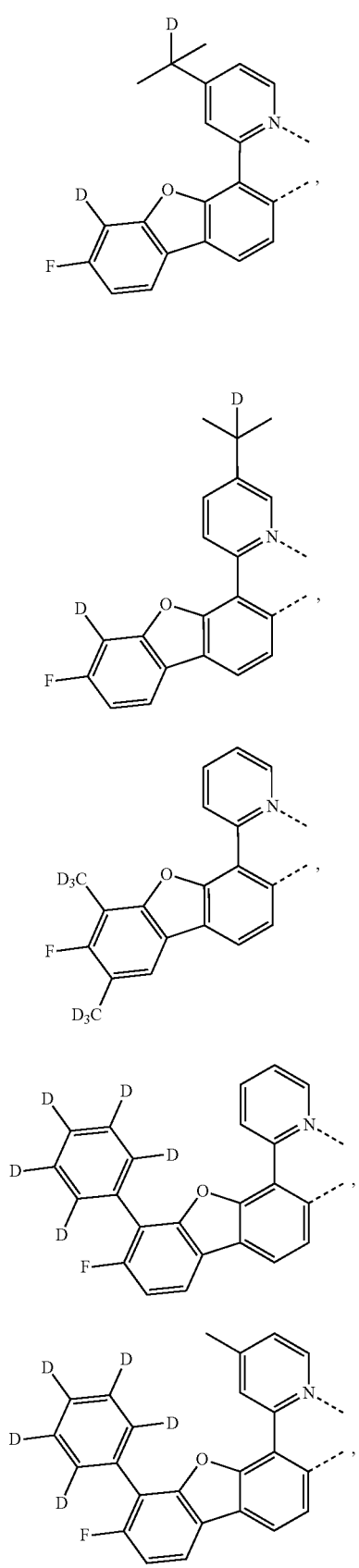
L<sub>a3-55</sub>,
L<sub>a3-56</sub>,
L<sub>a3-57</sub>,
L<sub>a3-58</sub>,
L<sub>a3-59</sub>
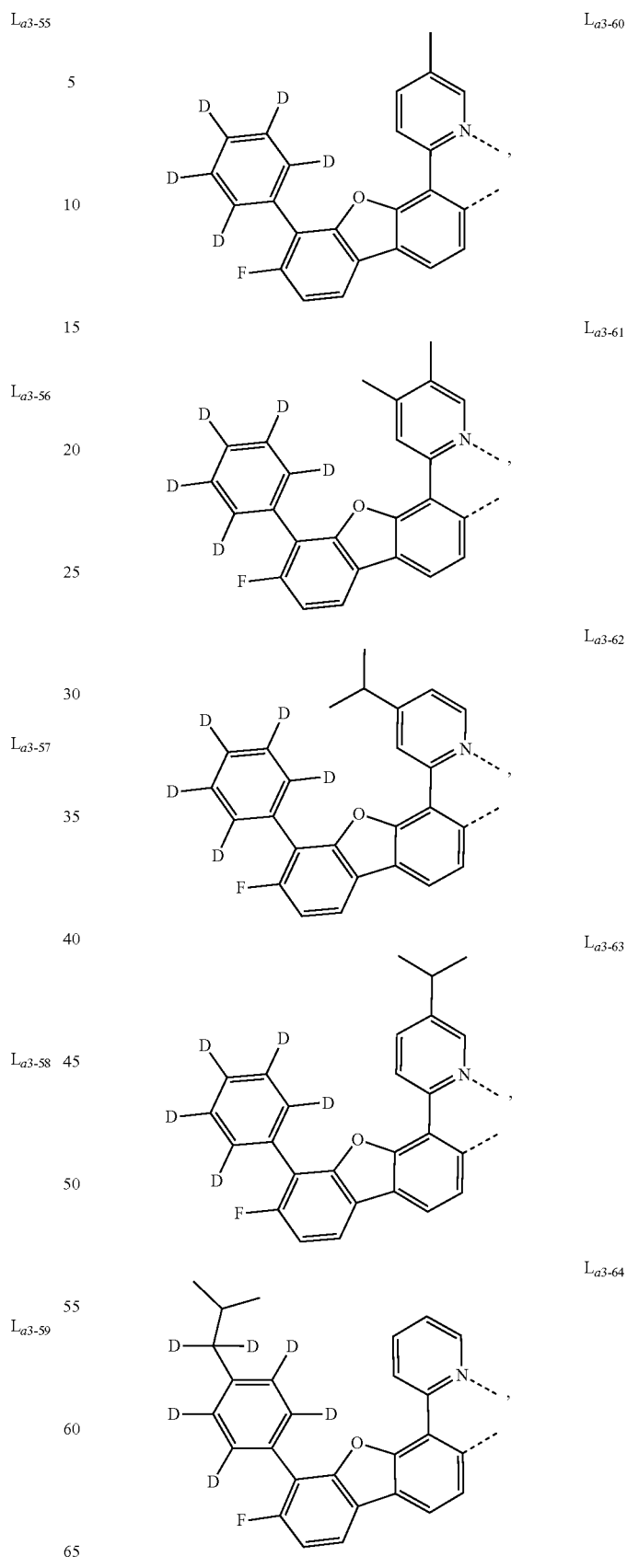
L<sub>a3-60</sub>,
L<sub>a3-61</sub>,
L<sub>a3-62</sub>,
L<sub>a3-63</sub>,
L<sub>a3-64</sub>

L<sub>a3-65</sub>
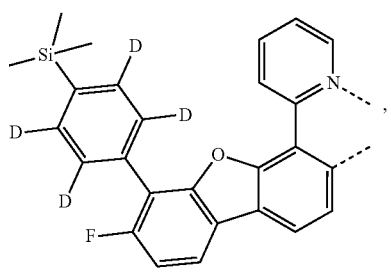
L<sub>a3-66</sub>
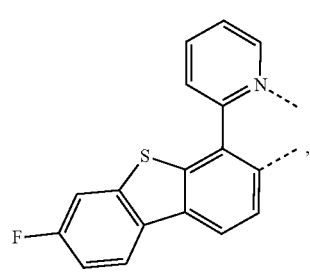
L<sub>a3-67</sub>
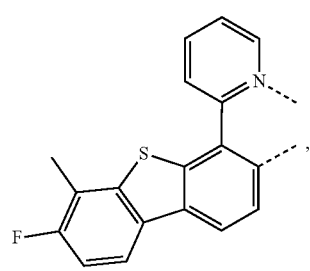
L<sub>a3-68</sub>
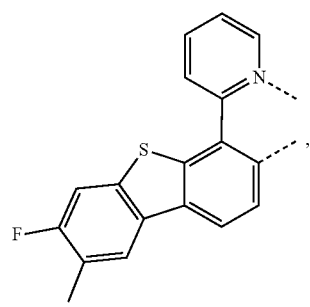
L<sub>a3-69</sub>
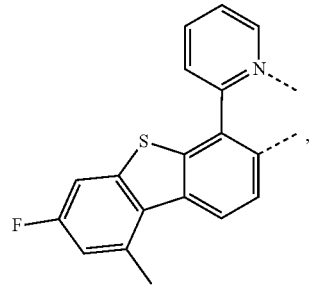
L<sub>a3-70</sub>
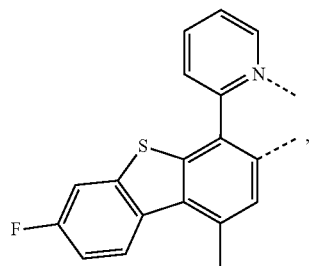
L<sub>a3-71</sub>
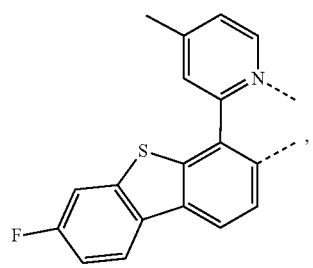
L<sub>a3-72</sub>
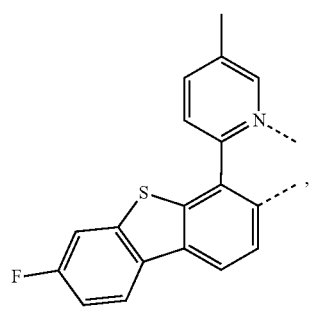
L<sub>a3-73</sub>
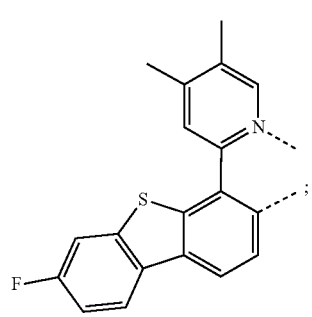
L<sub>a4-47</sub>
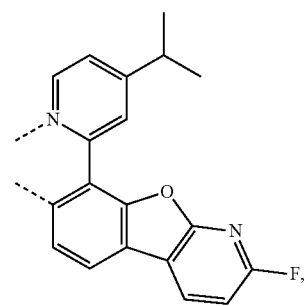

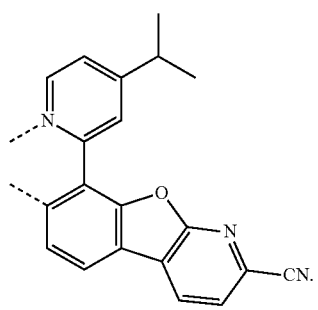
L<sub>a4-48</sub>
17. The organic electroluminescent device according to claim 12, wherein the ligands $L_b$ and $L_c$ are, at each occurrence identically or differently, selected from the group consisting of the following:
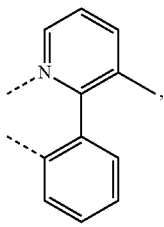
L<sub>b5</sub>
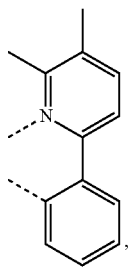
L<sub>b6</sub>
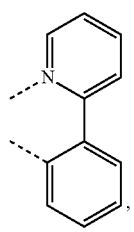
L<sub>b1</sub>
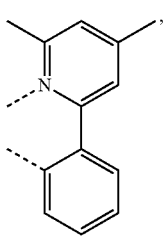
L<sub>b7</sub>
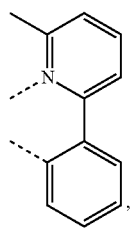
L<sub>b2</sub>
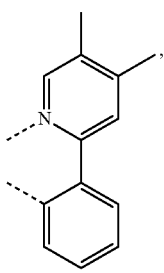
L<sub>b8</sub>
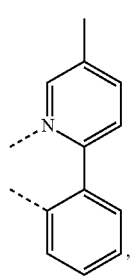
L<sub>b3</sub>
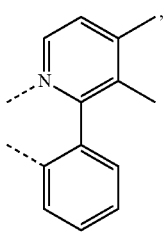
L<sub>b9</sub>
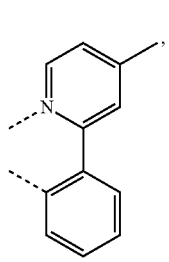
L<sub>b4</sub>
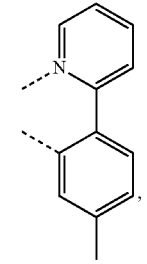
L<sub>b10</sub>

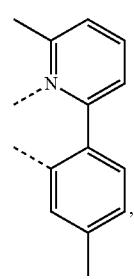, L_{b11}
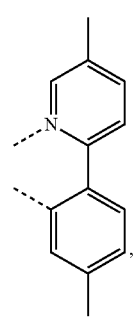, L_{b12}
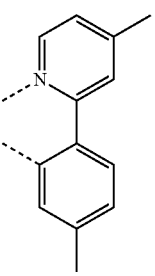, L_{b13}
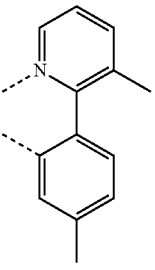, L_{b14}
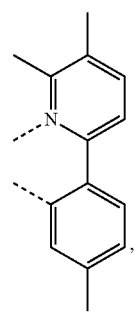, L_{b15}
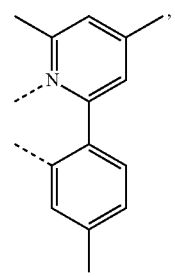, L_{b16}
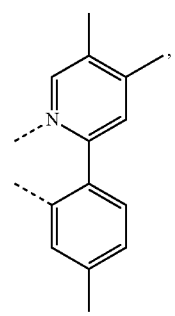, L_{b17}
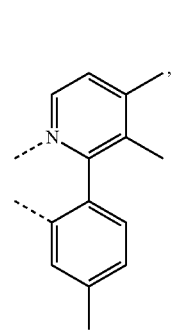, L_{b18}
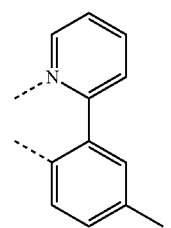, L_{b19}
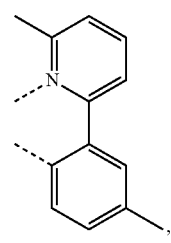, L_{b20}

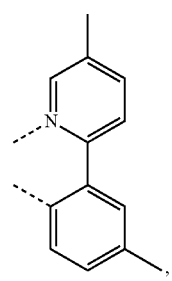 L_{b21}
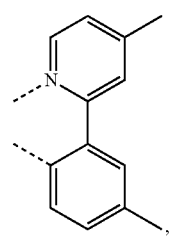 L_{b22}
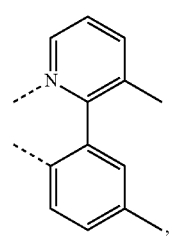 L_{b23}
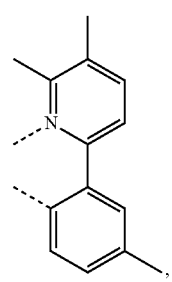 L_{b24}
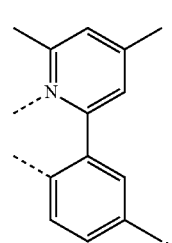 L_{b25}
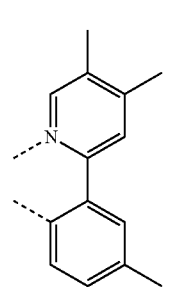 L_{b26}
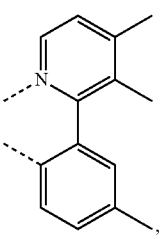 L_{b27}
L_{b28}
L_{b29}
L_{b30}
L_{b31}
L_{b32}

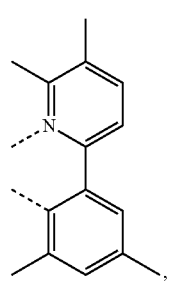 L_{b33},
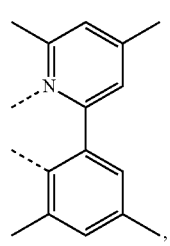 L_{b34},
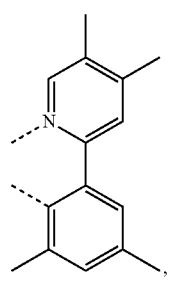 L_{b35},
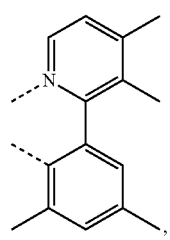 L_{b36},
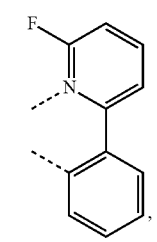 L_{b37},
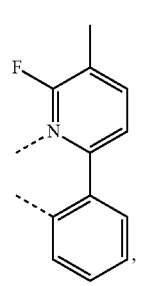 L_{b38},
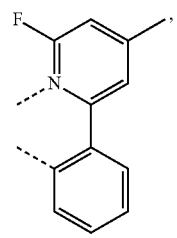 L_{b39},
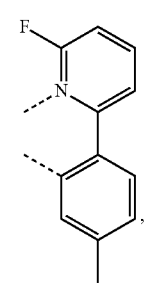 L_{b40},
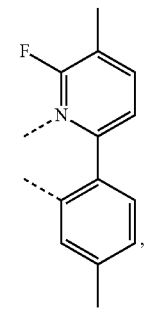 L_{b41},
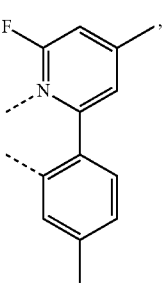 L_{b42},
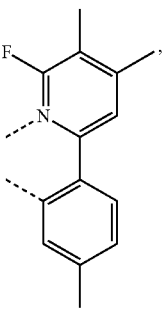 L_{b43}

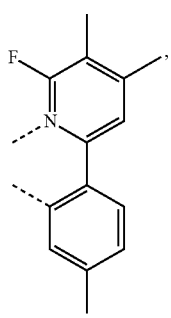 L<sub>b44</sub>
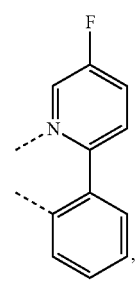 L<sub>b45</sub>
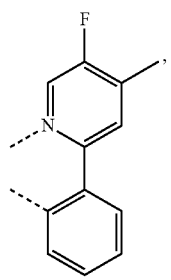 L<sub>b46</sub>
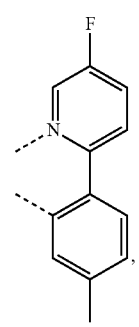 L<sub>b47</sub>
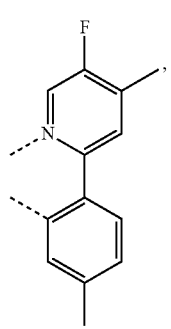 L<sub>b48</sub>
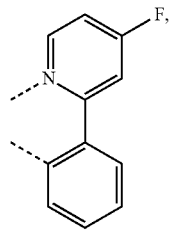 L<sub>b49</sub>
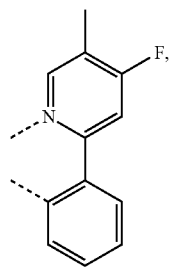 L<sub>b50</sub>
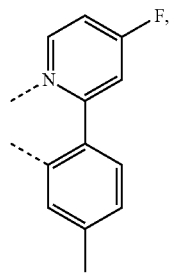 L<sub>b51</sub>
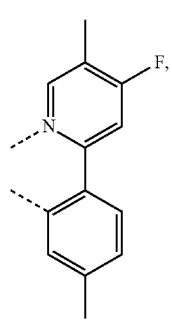 L<sub>b52</sub>
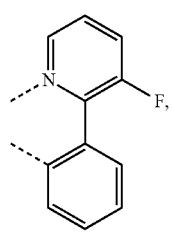 L<sub>b53</sub>
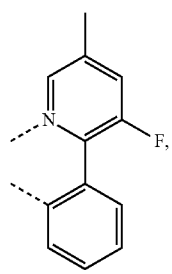 L<sub>b54</sub>

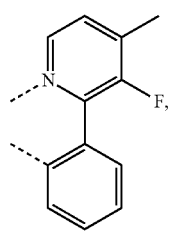 L<sub>b55</sub>
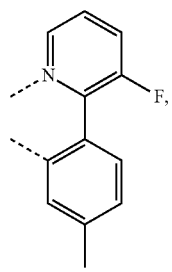 L<sub>b56</sub>
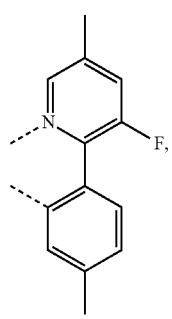 L<sub>b57</sub>
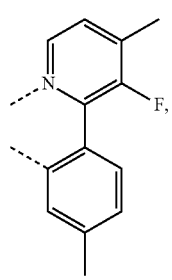 L<sub>b58</sub>
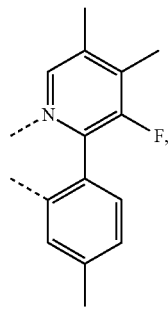 L<sub>b59</sub>
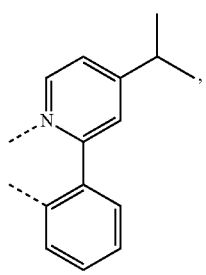 L<sub>b60</sub>
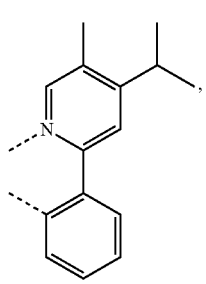 L<sub>b61</sub>
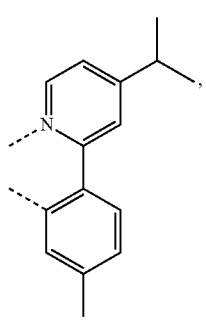 L<sub>b62</sub>
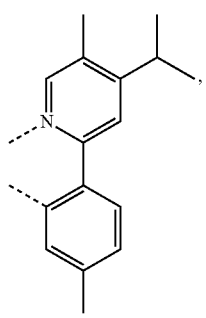 L<sub>b63</sub>
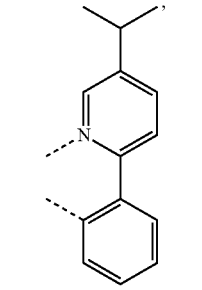 L<sub>b64</sub>

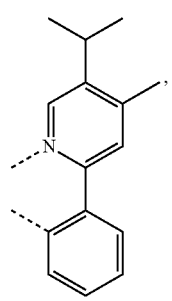 L<sub>b65</sub>
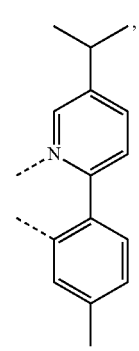 L<sub>b66</sub>
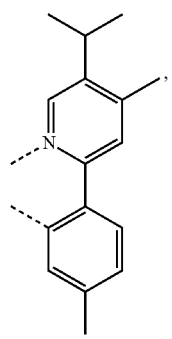 L<sub>b67</sub>
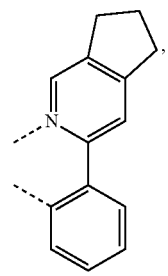 L<sub>b68</sub>
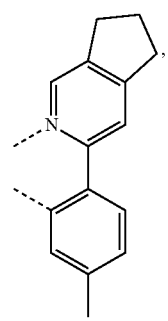 L<sub>b69</sub>
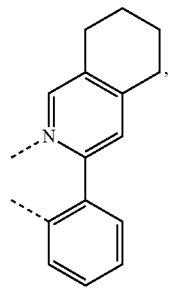 L<sub>b70</sub>
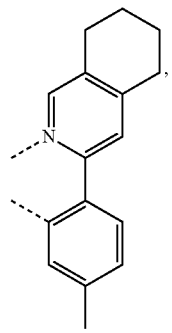 L<sub>b71</sub>
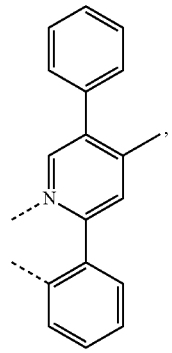 L<sub>b72</sub>
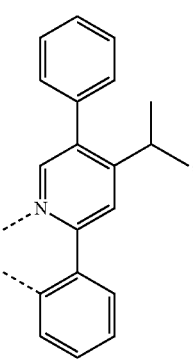 L<sub>b73</sub>

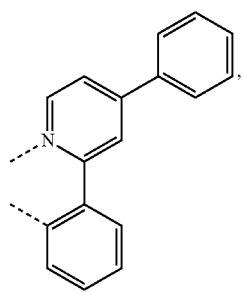 L<sub>b74</sub>
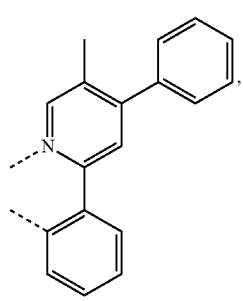 L<sub>b75</sub>
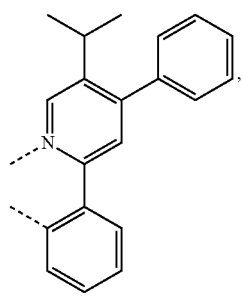 L<sub>b76</sub>
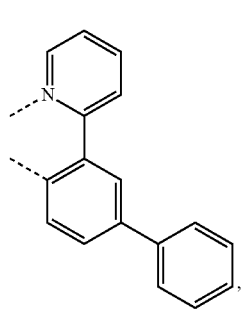 L<sub>b77</sub>
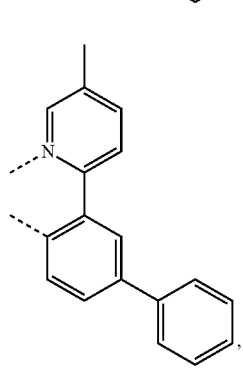 L<sub>b78</sub>
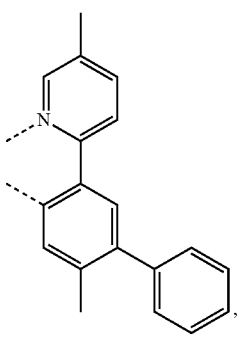 L<sub>b79</sub>
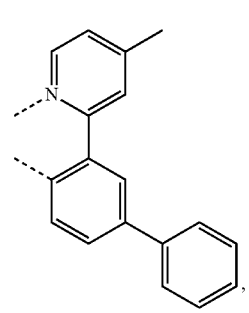 L<sub>b80</sub>
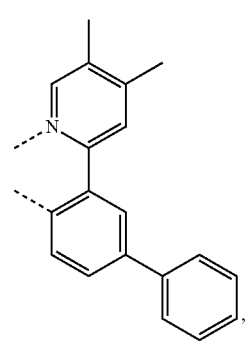 L<sub>b81</sub>
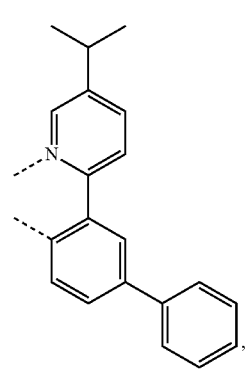 L<sub>b82</sub>

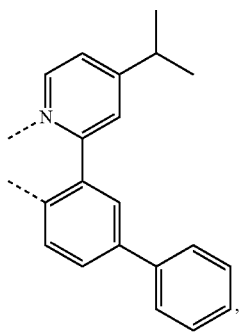
L_{b83}
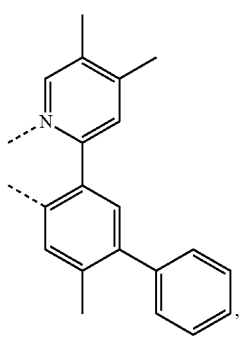
L_{b84}
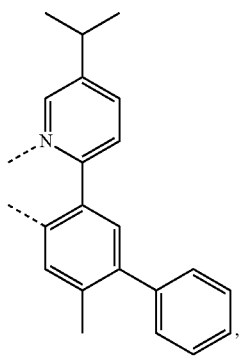
L_{b85}
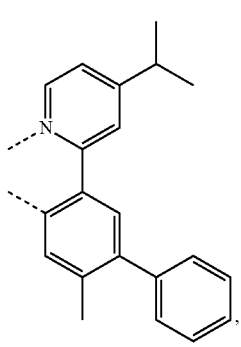
L_{b86}
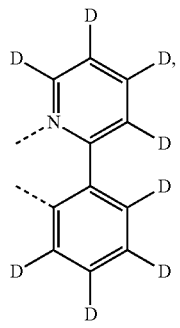
L_{b87}
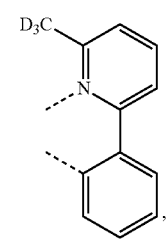
L_{b88}
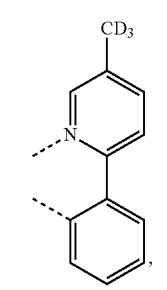
L_{b89}
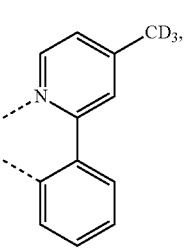
L_{b90}
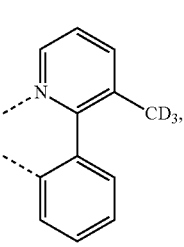
L_{b91}
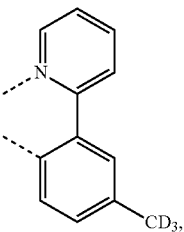
L_{b92}

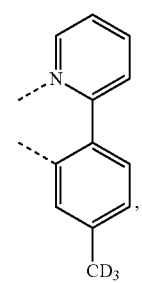 L<sub>b93</sub>
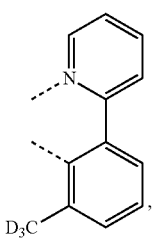 L<sub>b94</sub>
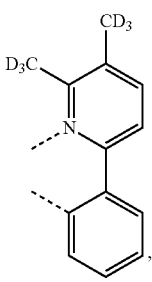 L<sub>b95</sub>
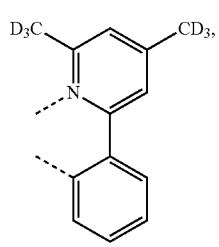 L<sub>b96</sub>
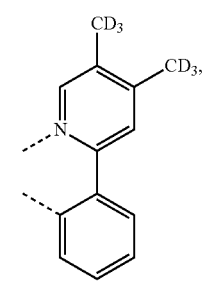 L<sub>b97</sub>
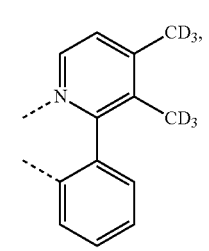 L<sub>b98</sub>
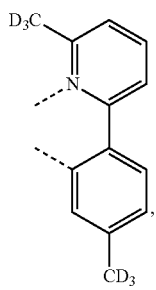 L<sub>b99</sub>
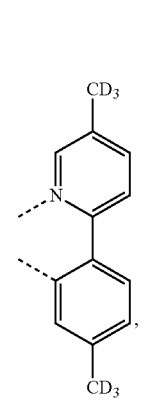 L<sub>b100</sub>
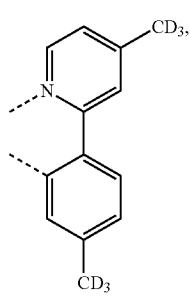 L<sub>b101</sub>
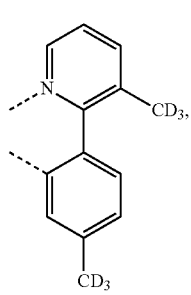 L<sub>b102</sub>
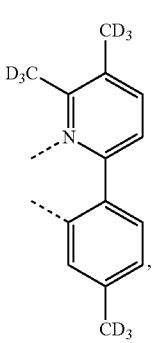 L<sub>b103</sub>

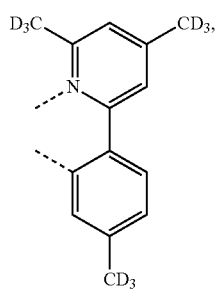
$L_{b104}$
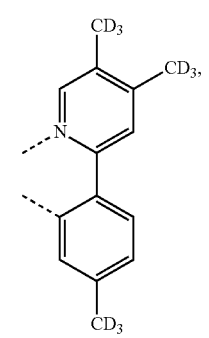
$L_{b105}$
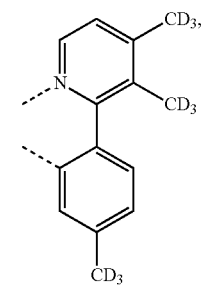
$L_{b106}$
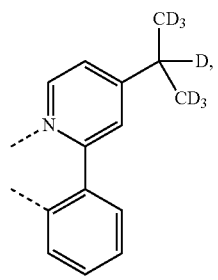
$L_{b107}$
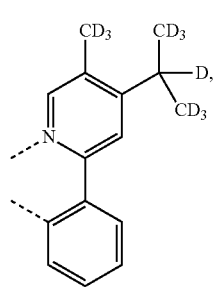
$L_{b108}$
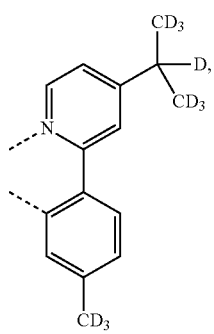
$L_{b109}$
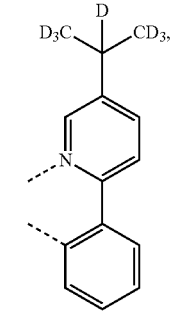
$L_{b110}$
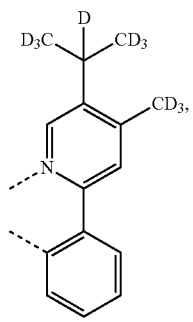
$L_{b111}$
$L_{b112}$

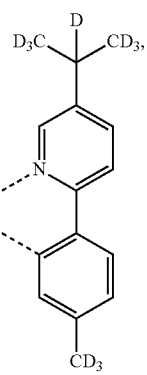 L_{b113}
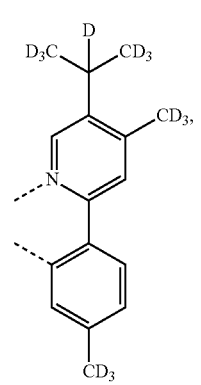 L_{b114}
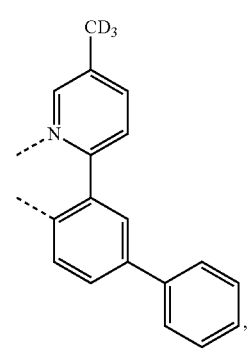 L_{b115}
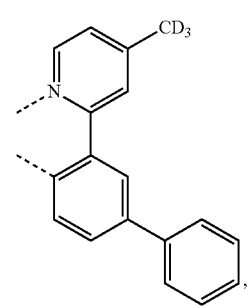 L_{b116}
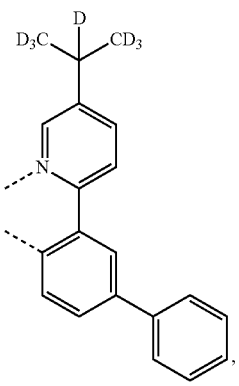 L_{b117}
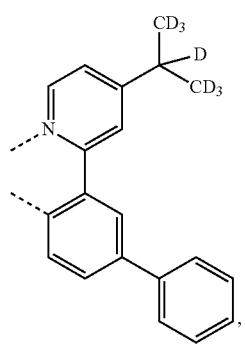 L_{b118}
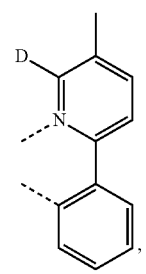 L_{b119}
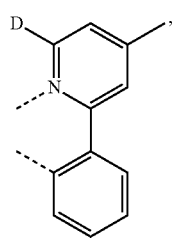 L_{b120}
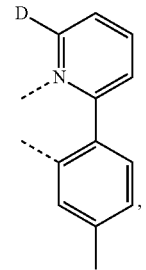 L_{b121}

L_{b122} 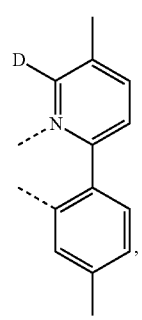
L_{b123} 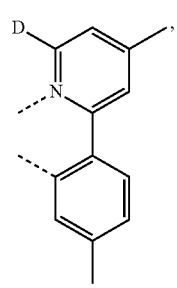
L_{b124} 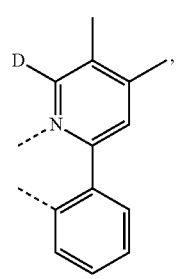
L_{b125} 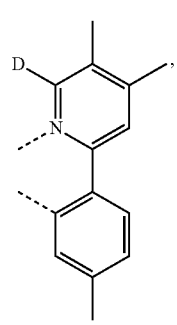
L_{b126} 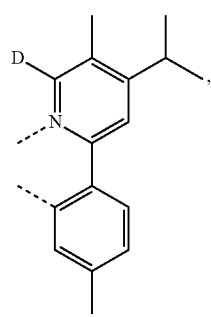
L_{b127} 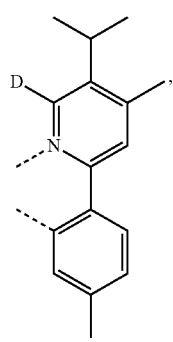
L_{b128} 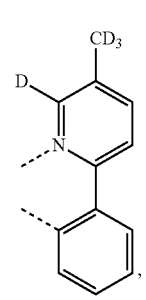
L_{b129} 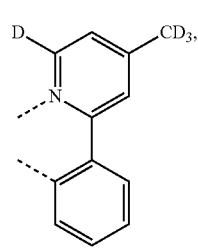
L_{b130} 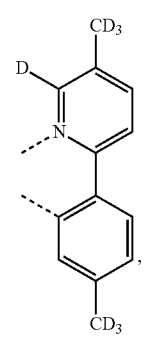
L_{b131} 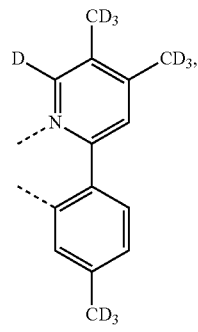

L_{b132} 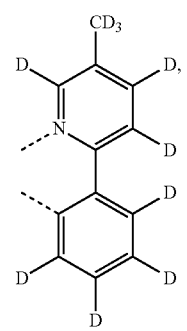
L_{b133} 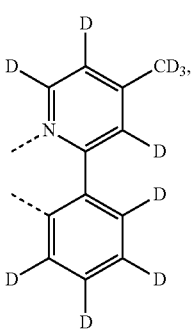
L_{b134} 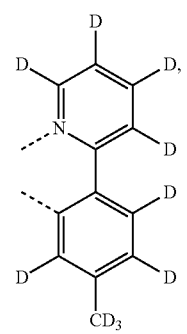
L_{b135} 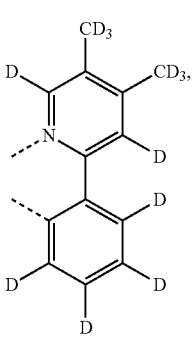
L_{b136} 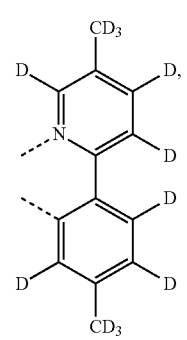
L_{b137} 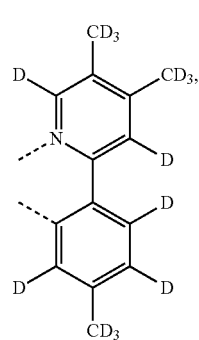
L_{b138} 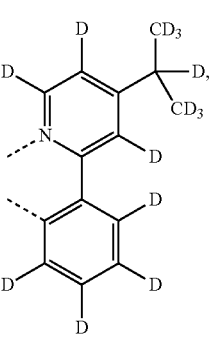
L_{b139} 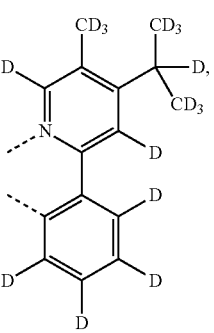
L_{b140} 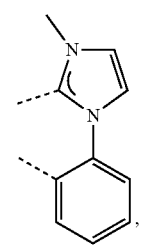
L_{b141} 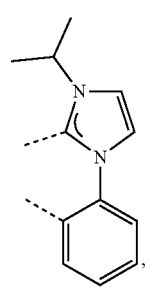

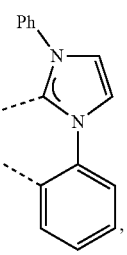 L<sub>b</sub>142
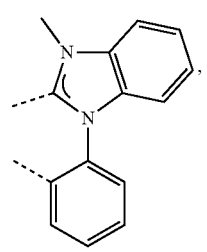 L<sub>b</sub>143
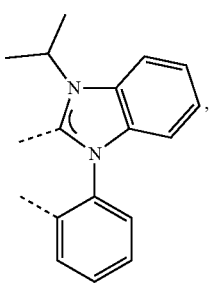 L<sub>b</sub>144
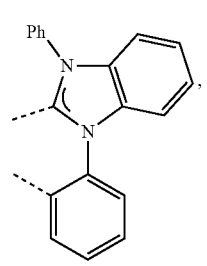 L<sub>b</sub>145
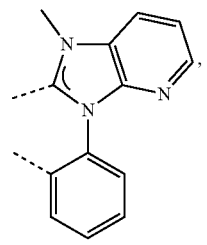 L<sub>b</sub>146
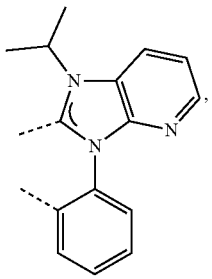 L<sub>b</sub>147
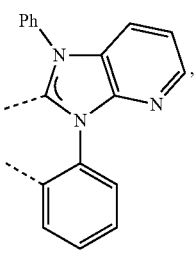 L<sub>b</sub>148
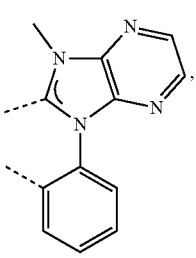 L<sub>b</sub>149
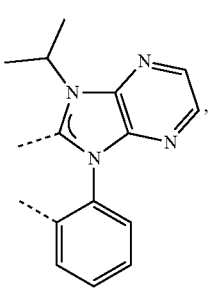 L<sub>b</sub>150
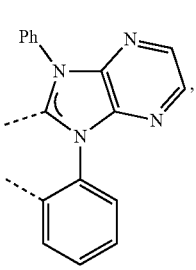 L<sub>b</sub>151
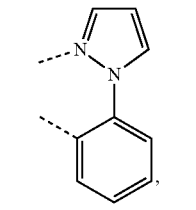 L<sub>b</sub>152
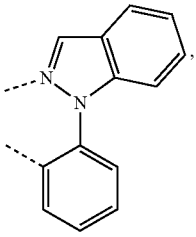 L<sub>b</sub>153

-continued
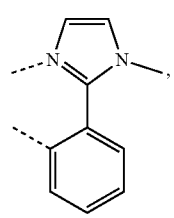 L<sub>b</sub>154
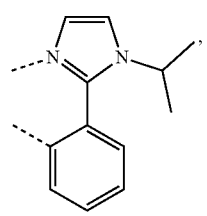 L<sub>b</sub>155
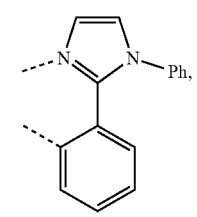 L<sub>b</sub>156
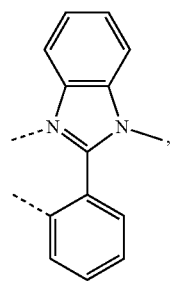 L<sub>b</sub>157
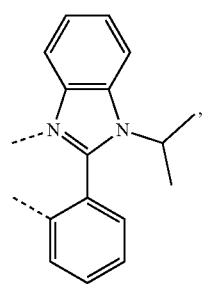 L<sub>b</sub>158
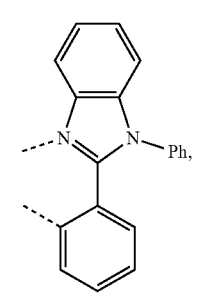 L<sub>b</sub>159
-continued
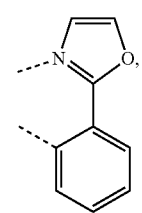 L<sub>b</sub>160
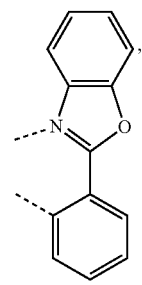 L<sub>b</sub>161
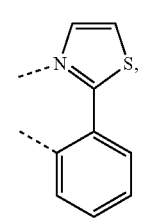 L<sub>b</sub>162
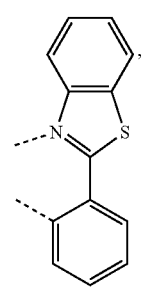 L<sub>b</sub>163
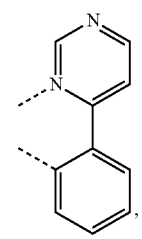 L<sub>b</sub>164
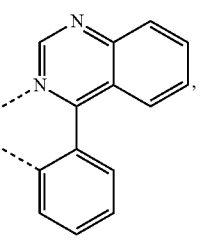 L<sub>b</sub>165

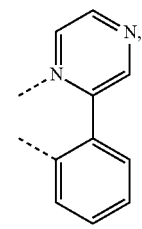
L_{b166}
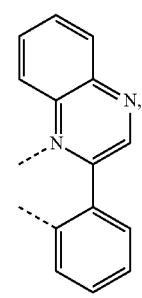
L_{b167}
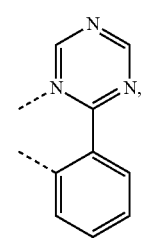
L_{b168}
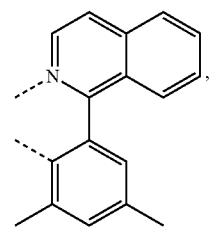
L_{b169}
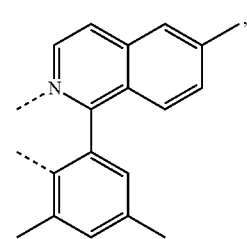
L_{b170}
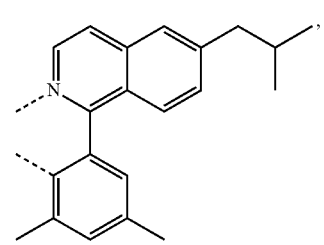
L_{b171}
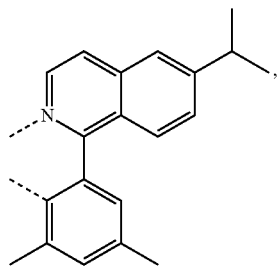
L_{b172}
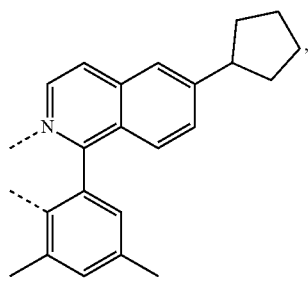
L_{b173}
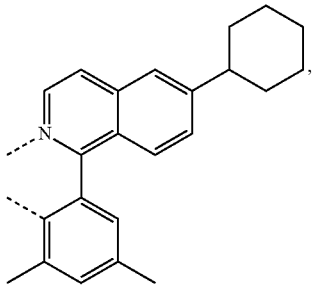
L_{b174}
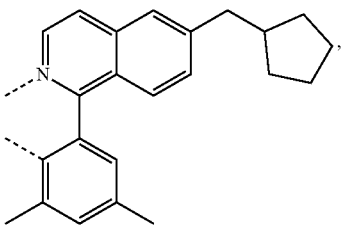
L_{b175}
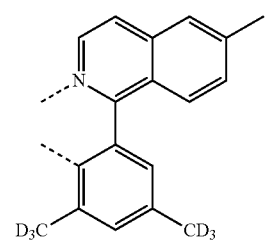
L_{b176}
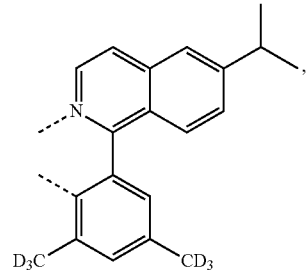
L_{b177}

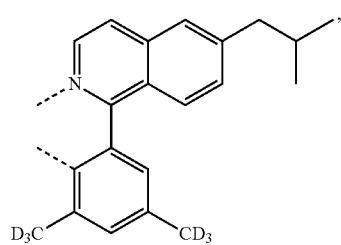 $L_{b178}$
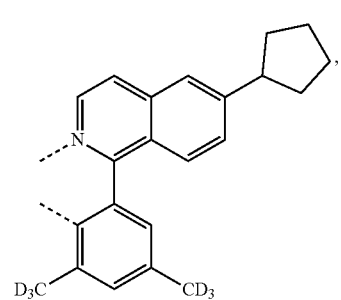 $L_{b179}$
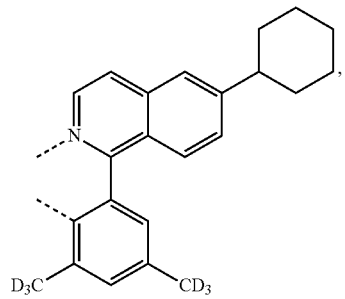 $L_{b180}$
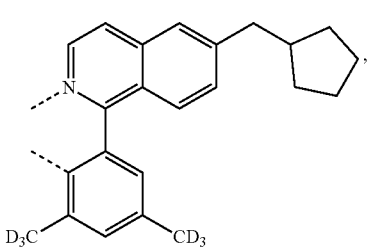 $L_{b181}$
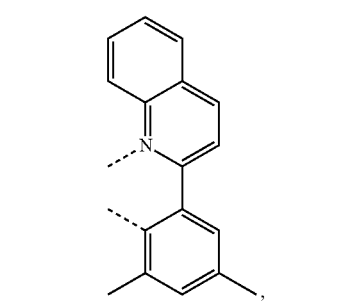 $L_{b182}$
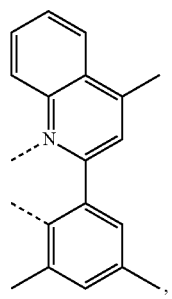 $L_{b183}$
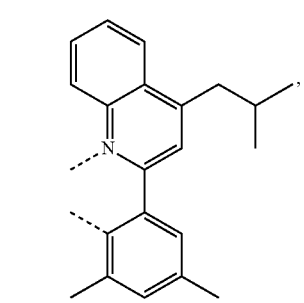 $L_{b184}$
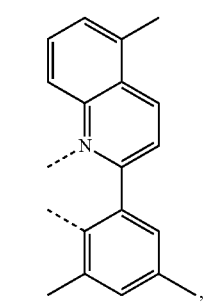 $L_{b185}$
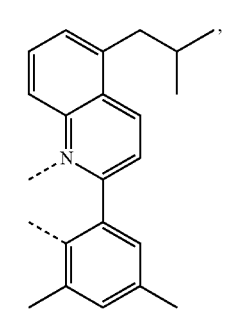 $L_{b186}$
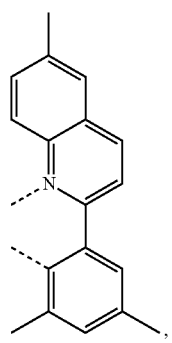 $L_{b187}$ -continued
L<sub>b188</sub> 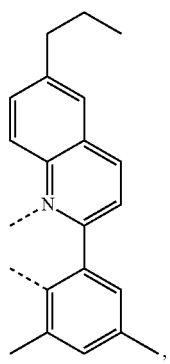
L<sub>b189</sub> 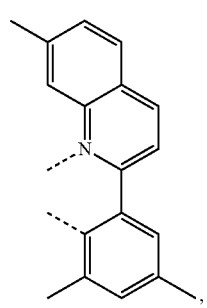
L<sub>b190</sub> 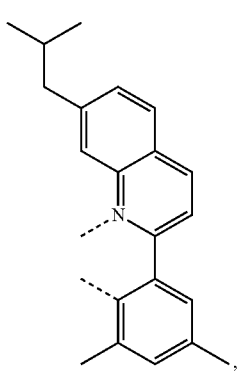
L<sub>b191</sub> 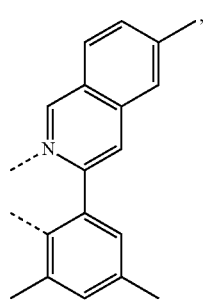
-continued
L<sub>b192</sub> 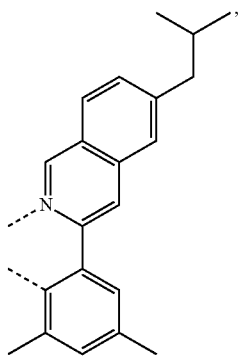
L<sub>b193</sub> 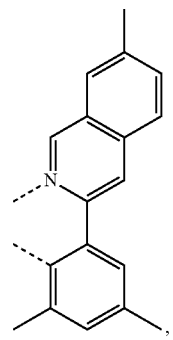
L<sub>b194</sub> 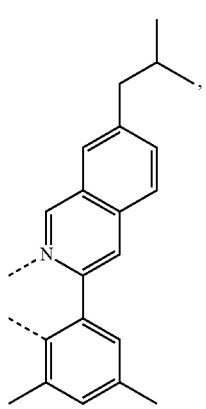
L<sub>b195</sub> 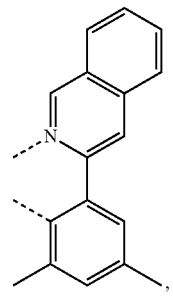

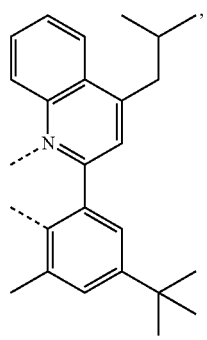
L<sub>b196</sub>
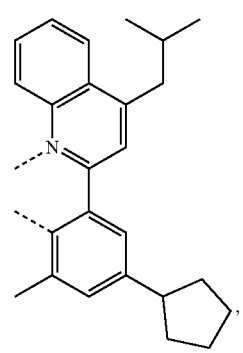
L<sub>b197</sub>
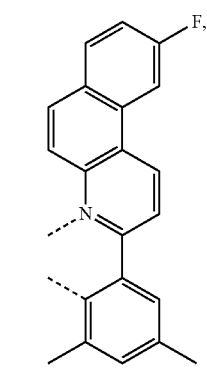
L<sub>b198</sub>
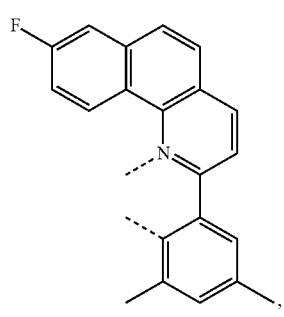
L<sub>b199</sub>
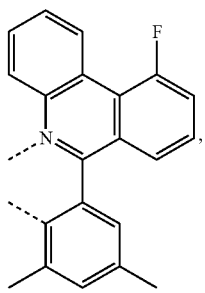
L<sub>b200</sub>
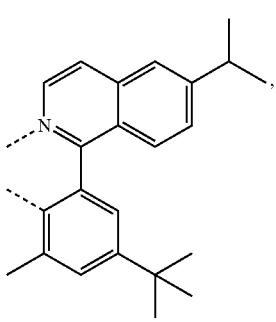
L<sub>b201</sub>
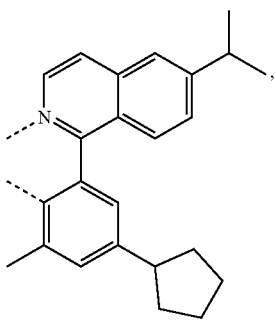
L<sub>b202</sub>
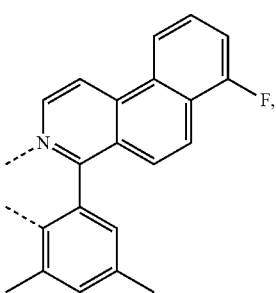
L<sub>b203</sub>
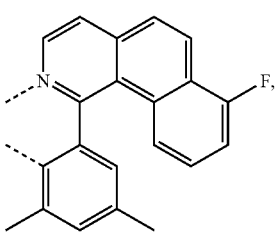
L<sub>b204</sub>

L_{b205}
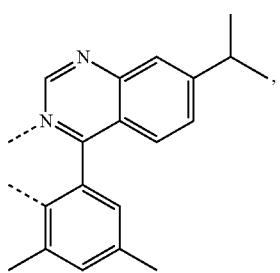
L_{b206}
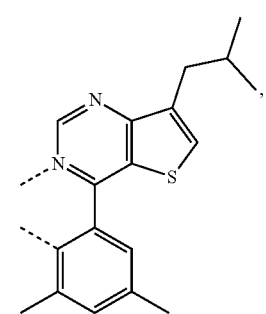
L_{b207}
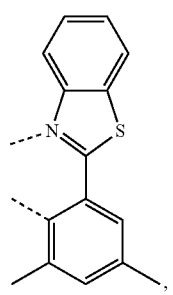
L_{b208}
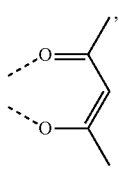
L_{b209}
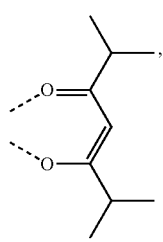
L_{b210}
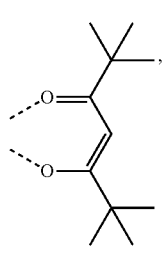
L_{b211}
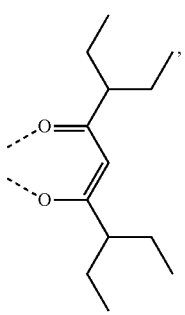
L_{b212}
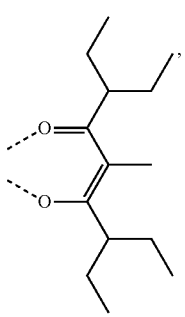
L_{b213}
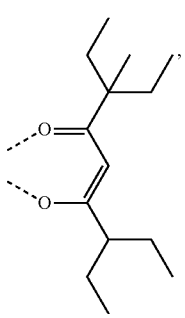
L_{b214}
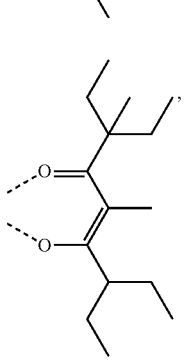
L_{b215}
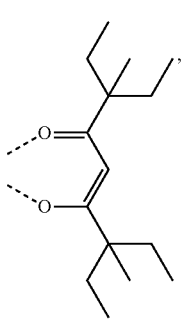

| | |
|---|---|
| 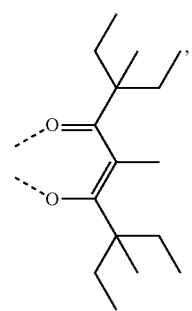 L<sub>b216</sub> | 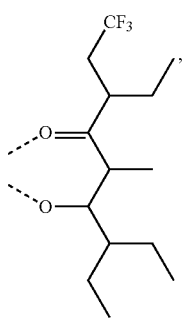 L$_{b221}$ |
| 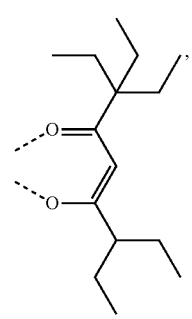 L$_{b217}$ | 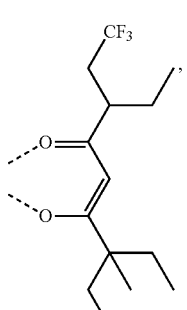 L$_{b222}$ |
| 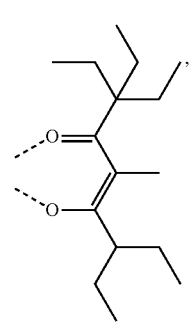 L$_{b218}$ | 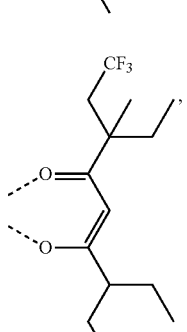 L$_{b223}$ |
| 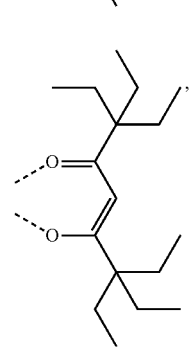 L$_{b219}$ | 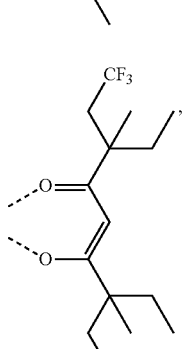 L$_{b224}$ |
| 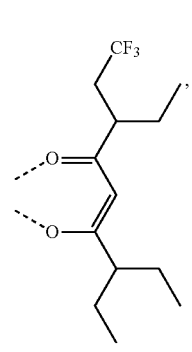 L$_{b220}$ | 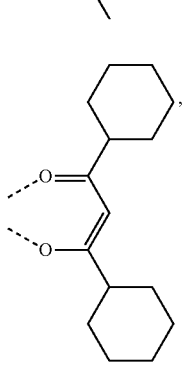 L$_{b225}$ |

L_{b226}
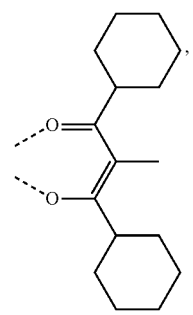
L_{b227}
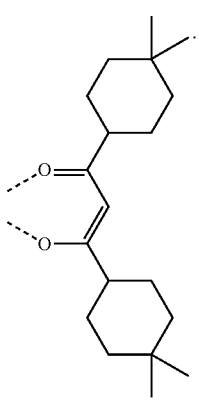
18. The organic electroluminescent device according to claim 12, wherein the first metal complex is selected from the group consisting of the following compounds:
GD2-1
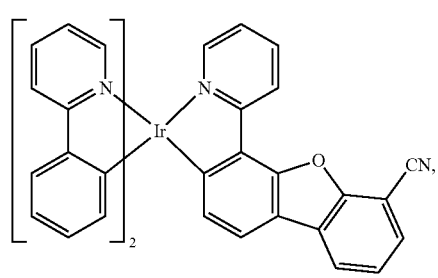
GD2-2
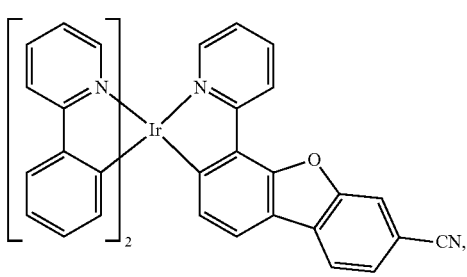
GD2-3
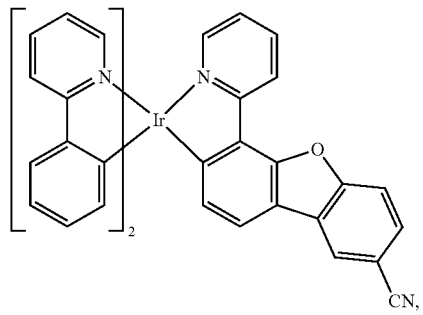
GD2-4
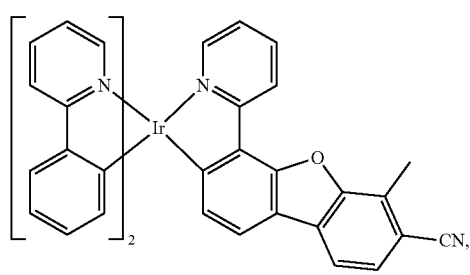
GD2-5
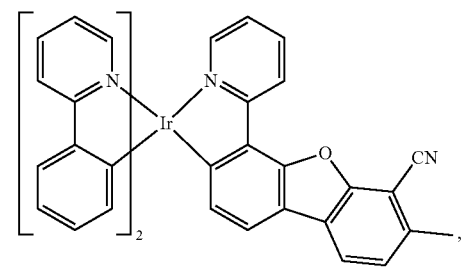
GD2-6
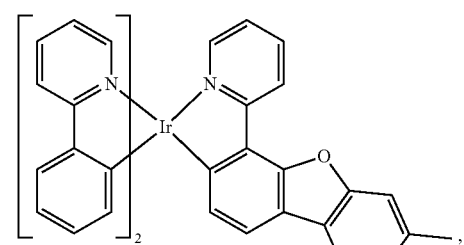
GD2-7
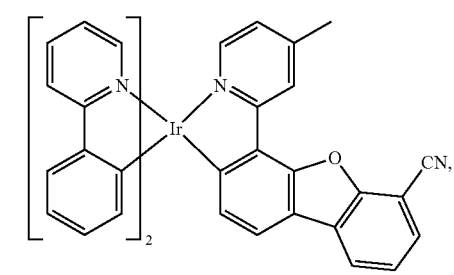

GD2-8
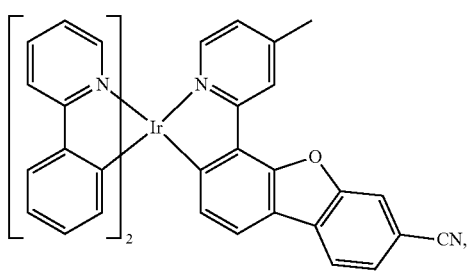
GD2-9
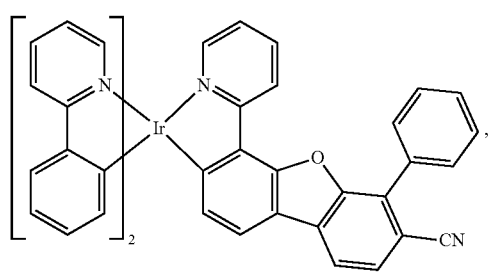
GD2-10
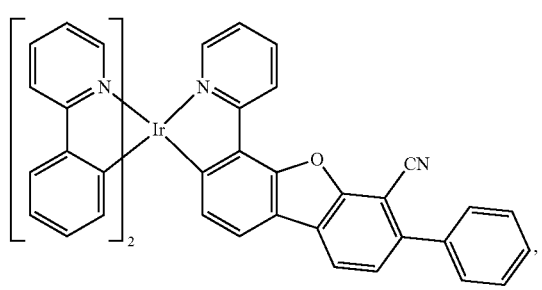
GD2-11
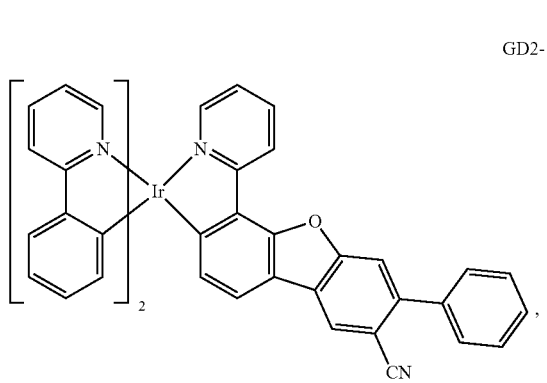
GD2-12
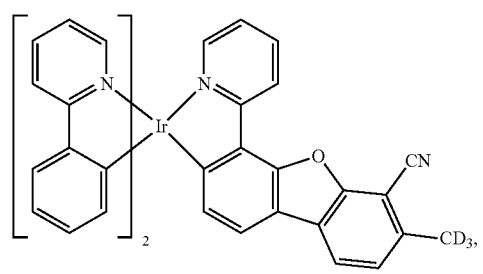
GD2-13
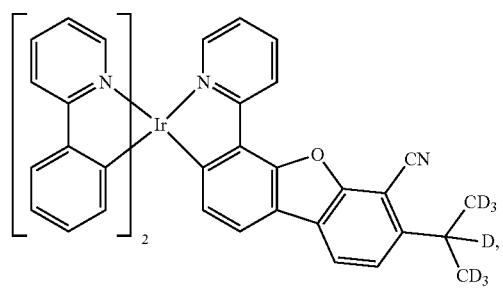
GD2-14
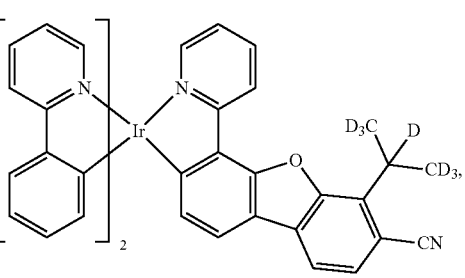
GD2-15
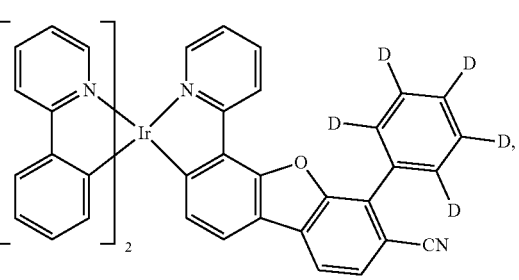
GD2-16
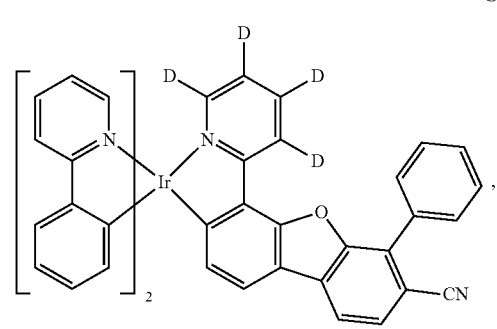
GD2-17
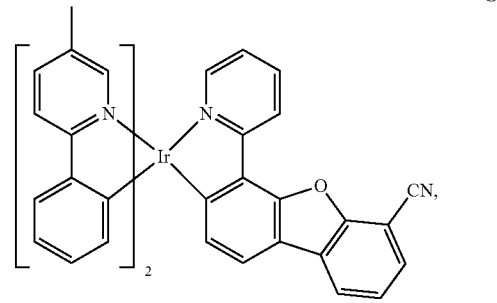

GD2-18
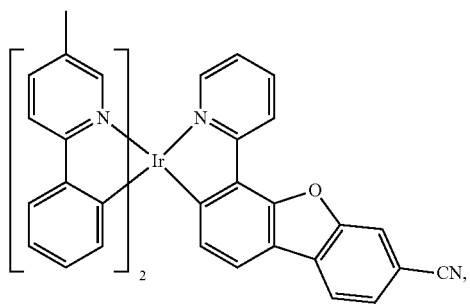
GD2-19
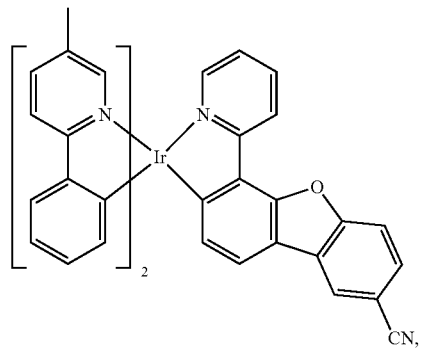
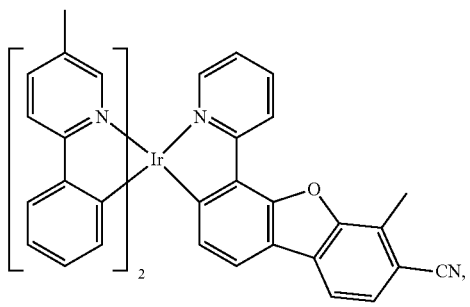
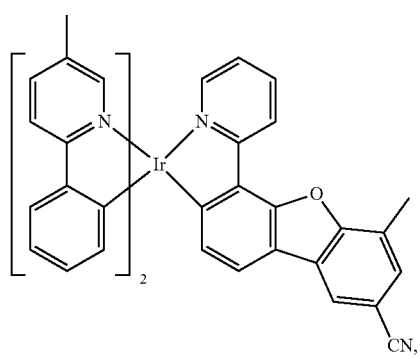
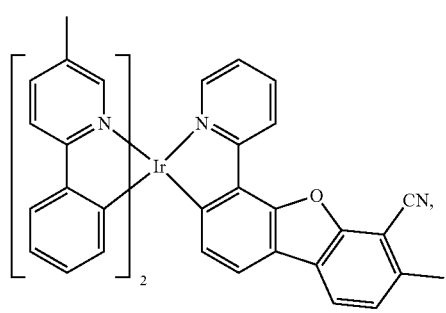
GD2-23
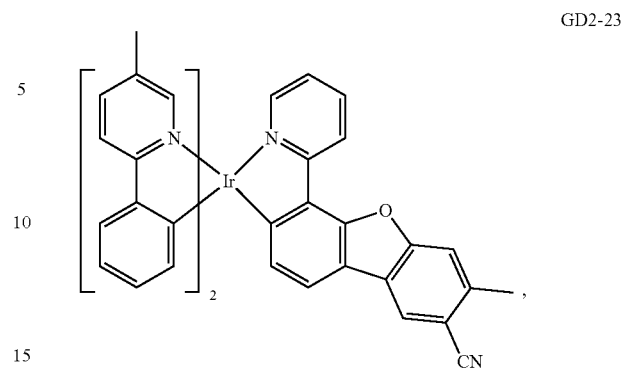
GD2-24
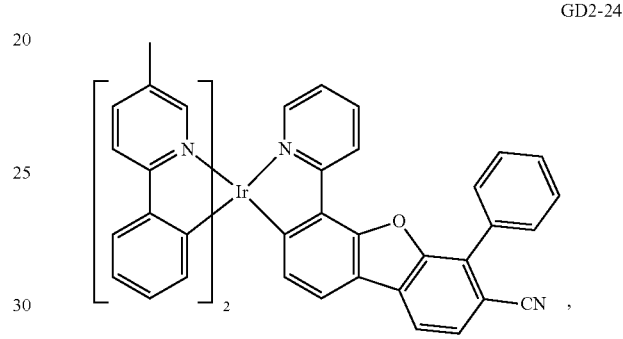
GD2-25
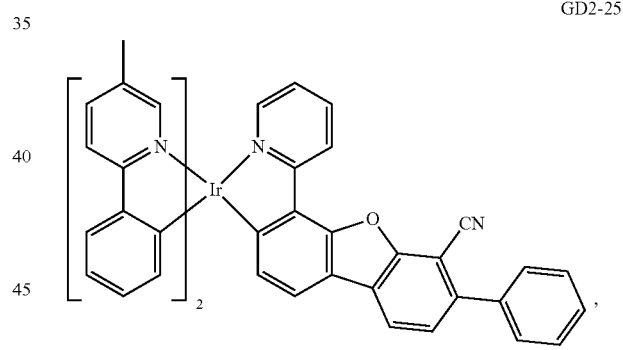
GD2-26
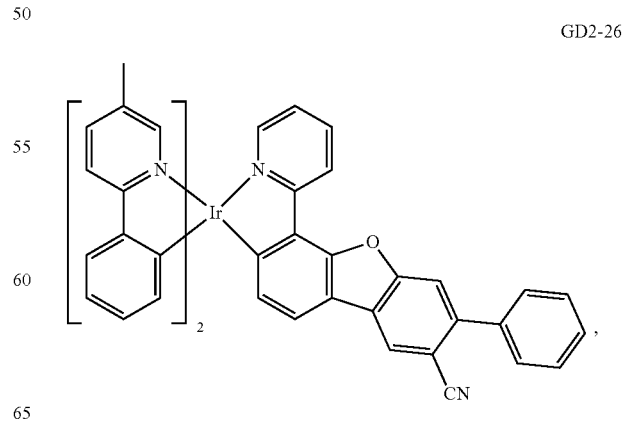

GD2-27
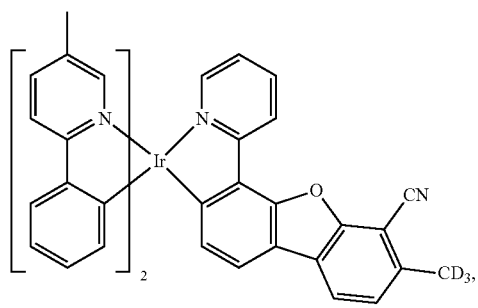
GD2-28
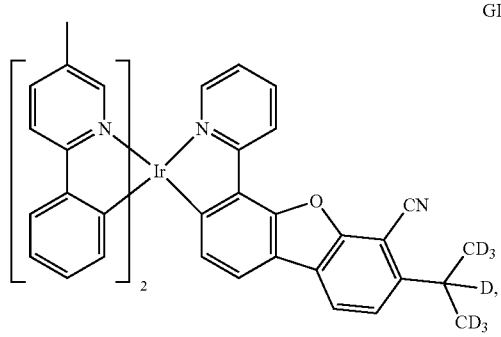
GD2-29
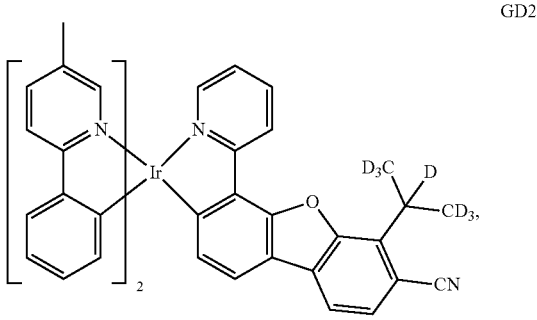
GD2-30
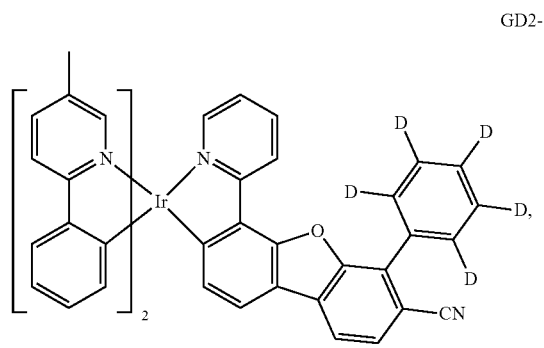
GD2-31
GD-32
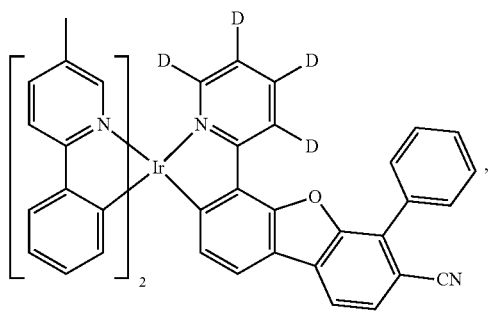
GD2-33
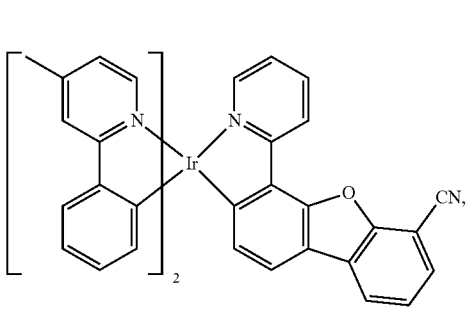
GD2-34
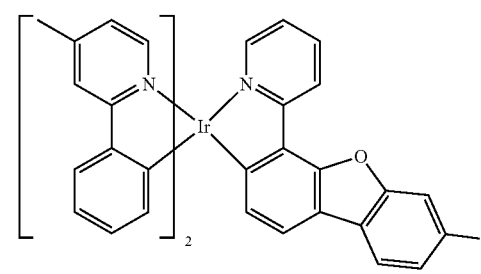
GD2-35
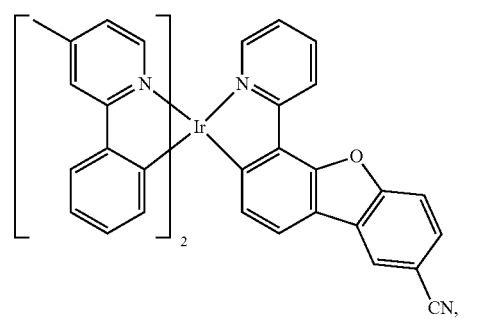
GD2-36
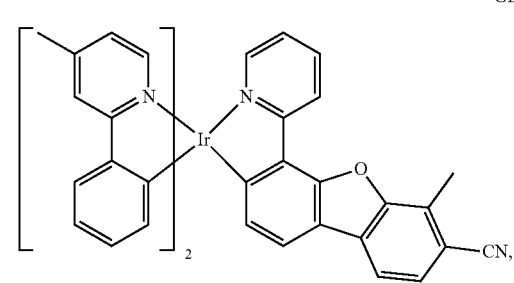

GD2-37
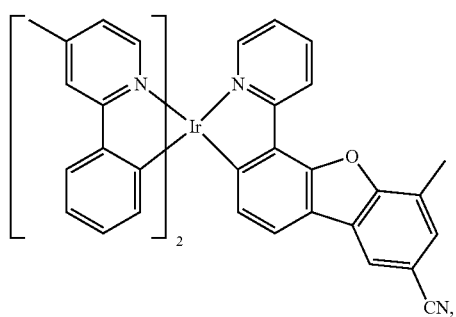
GD2-38
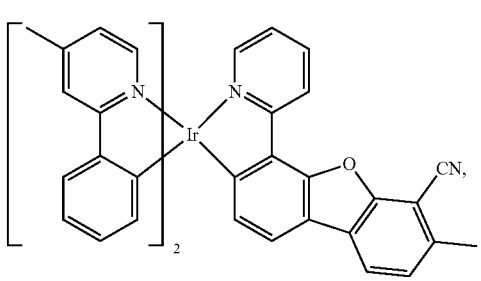
GD2-39
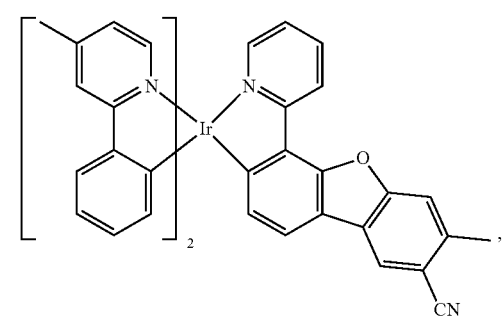
GD2-40
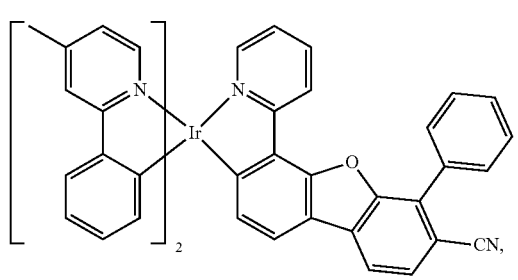
GD2-41
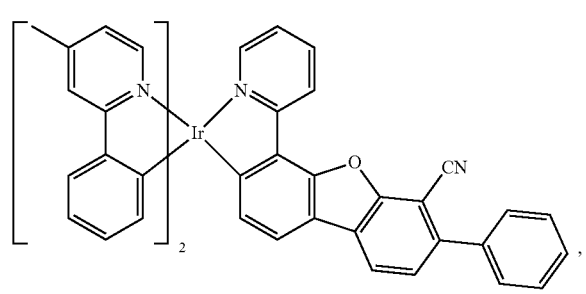
GD2-42
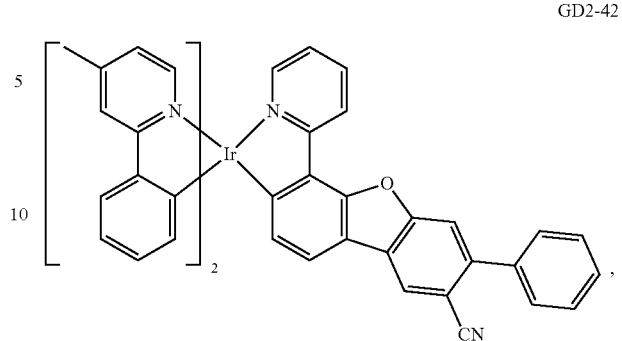
GD2-43
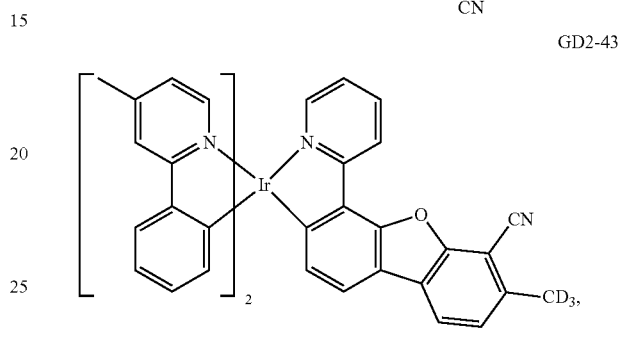
GD2-44
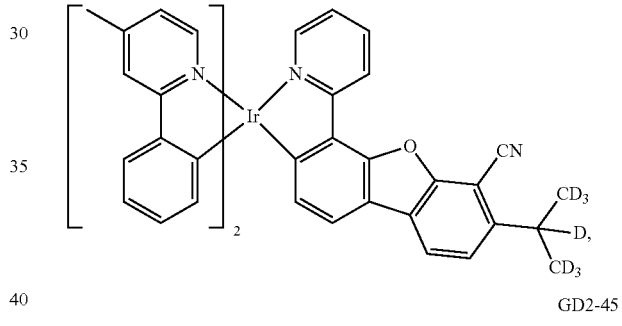
GD2-45
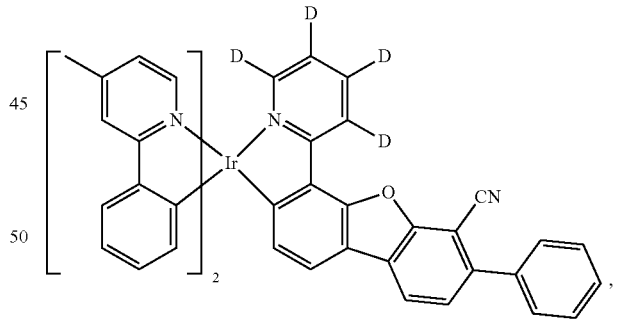
GD2-46
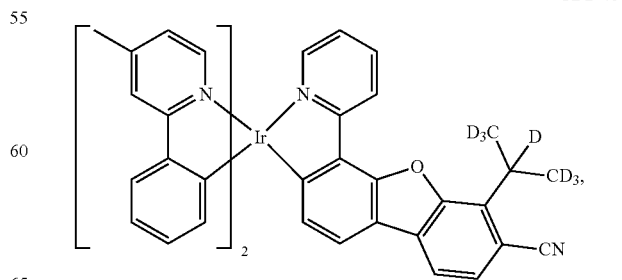

GD2-47
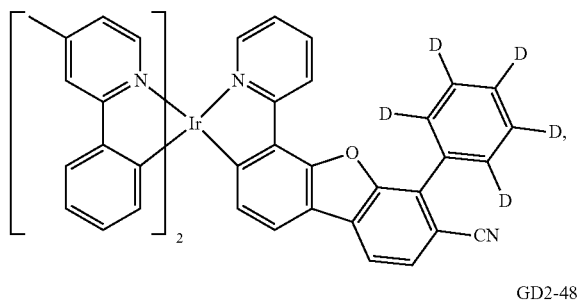
GD2-48
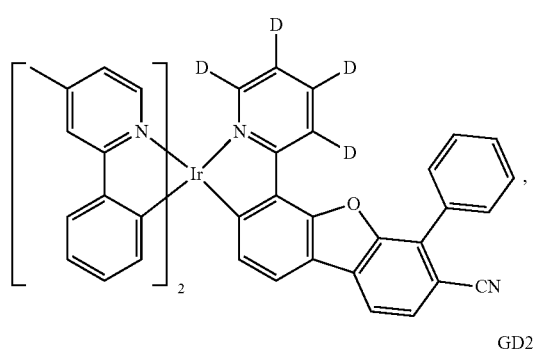
GD2-49
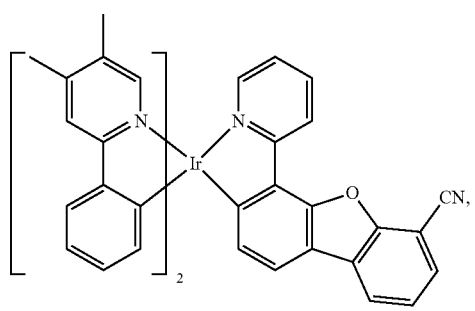
GD2-50
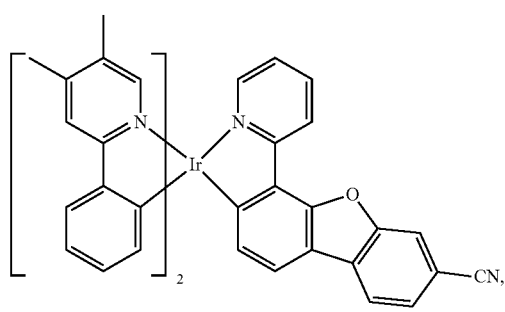
GD2-51
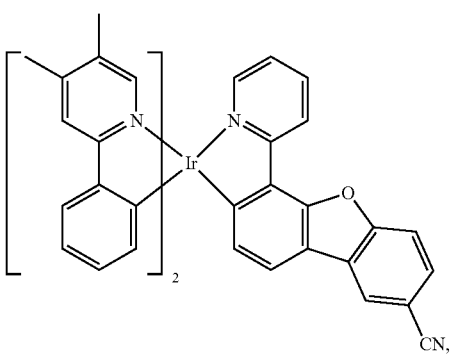
GD2-52
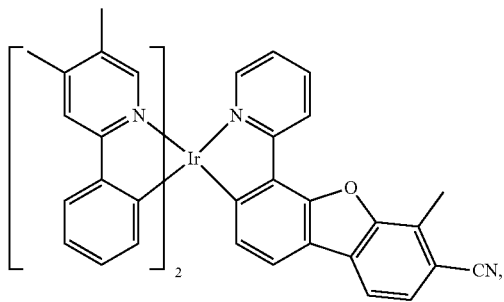
GD2-53
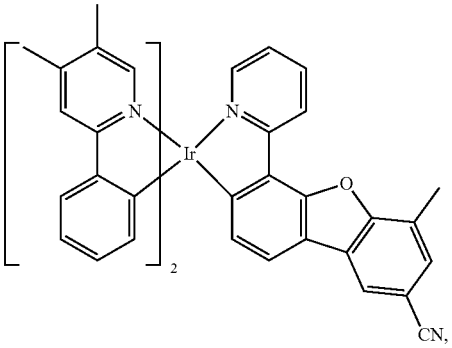
GD2-54
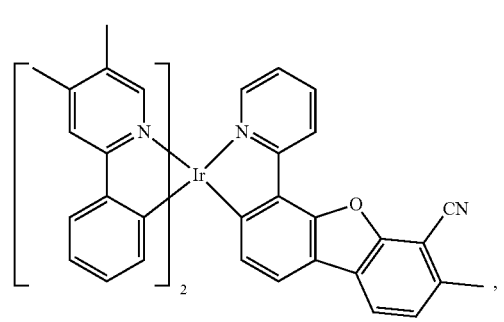
GD2-55
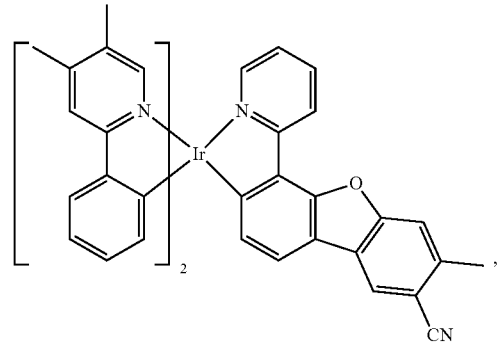

GD2-56
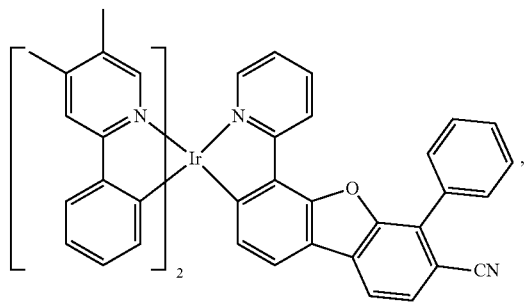
GD2-57
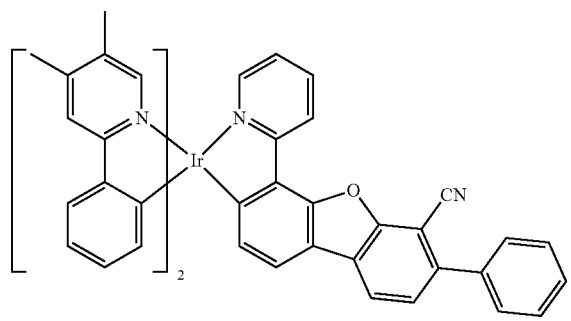
GD2-58
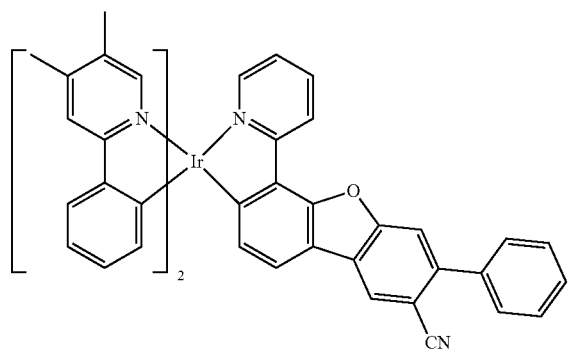
GD2-59
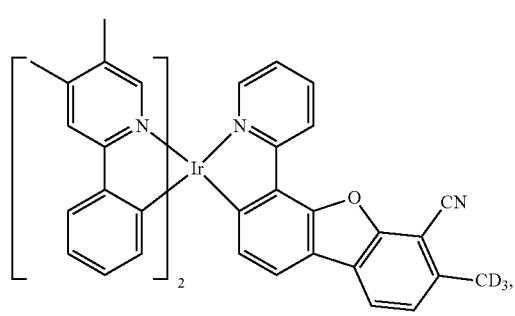
GD2-60
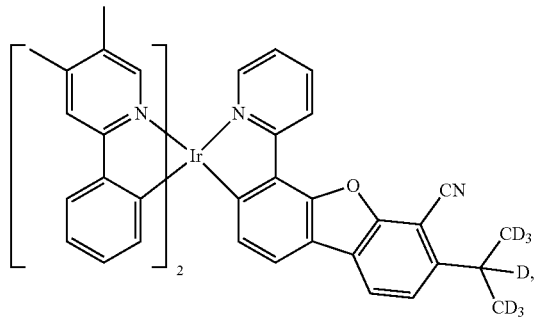
GD2-61
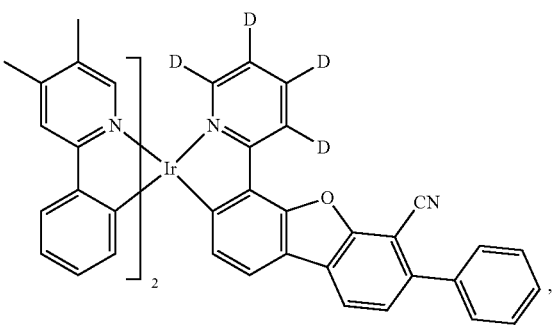
GD2-62
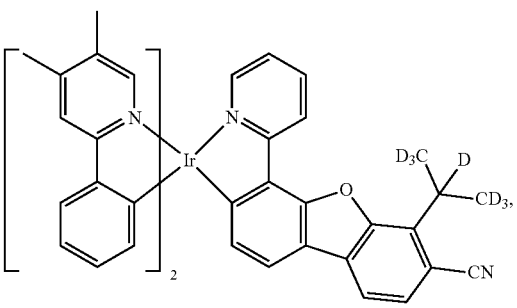
GD2-63
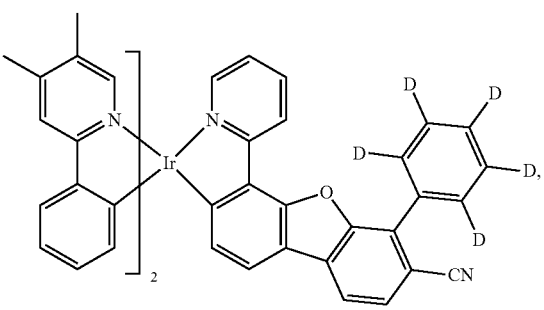

-continued
GD2-64
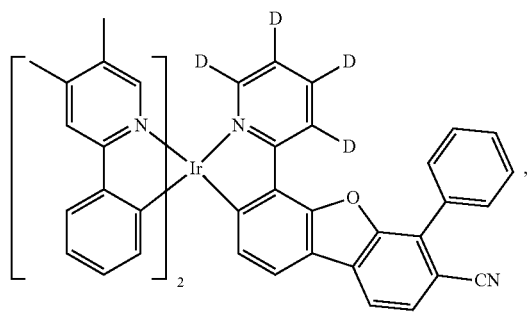
GD2-68
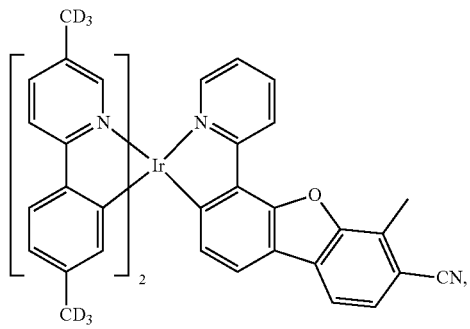
GD2-65
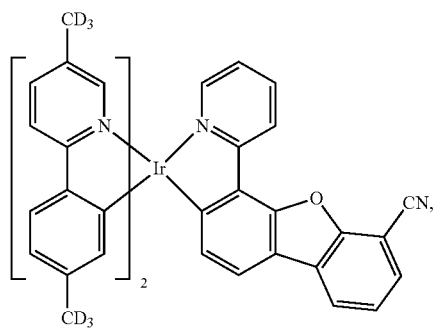
GD2-69
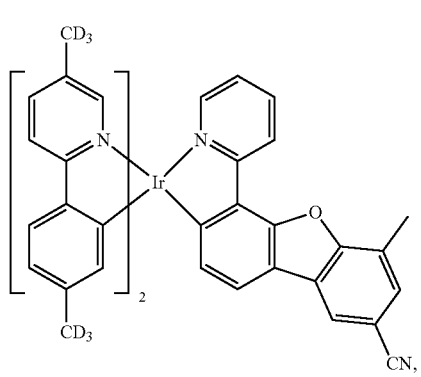
GD2-66
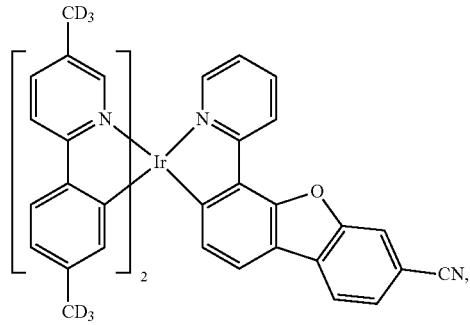
GD2-70
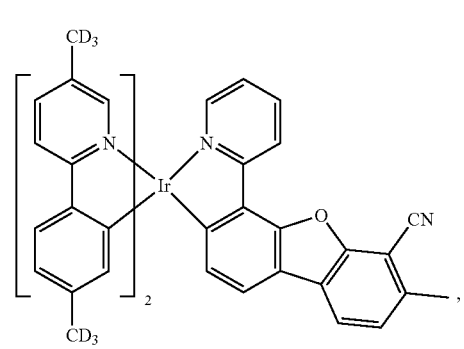
GD2-67
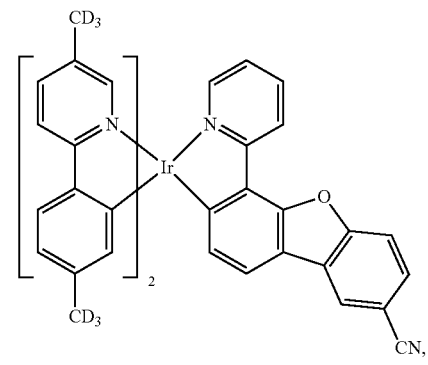
GD2-71
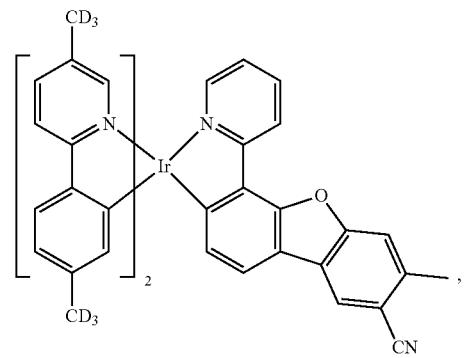

GD2-72 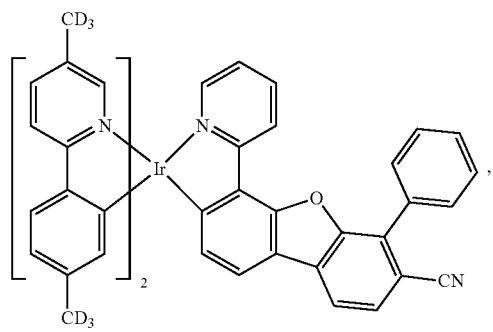
GD2-76 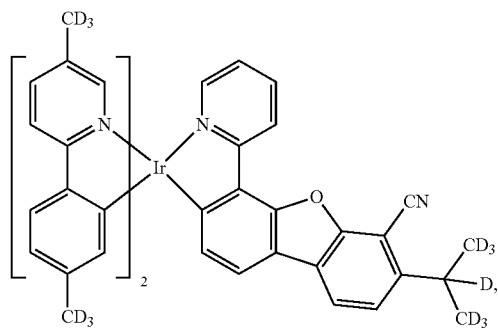
GD2-73 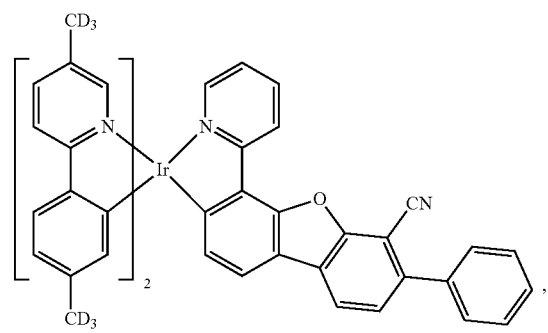
GD2-77 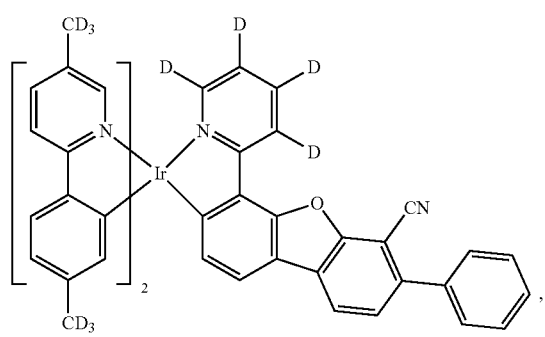
GD2-74 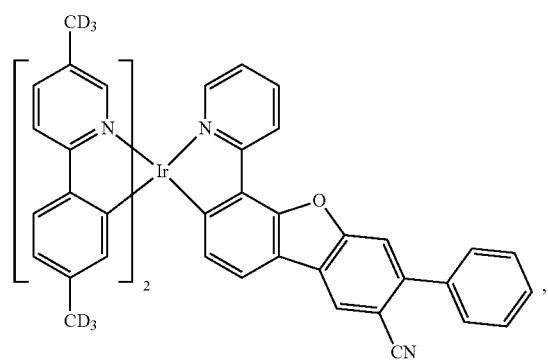
GD2-78 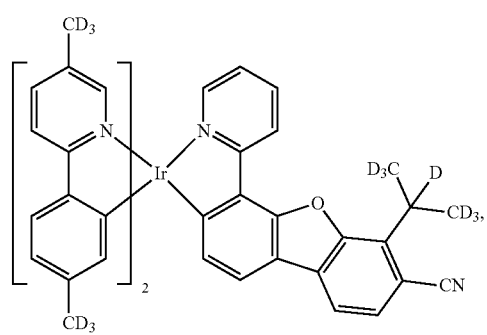
GD2-75 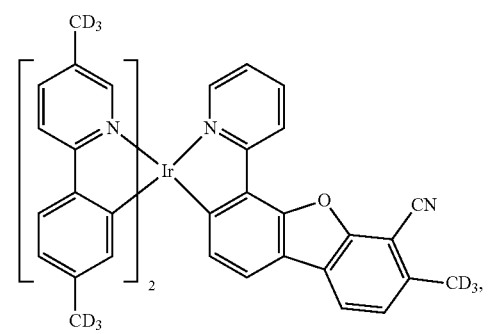
GD2-79 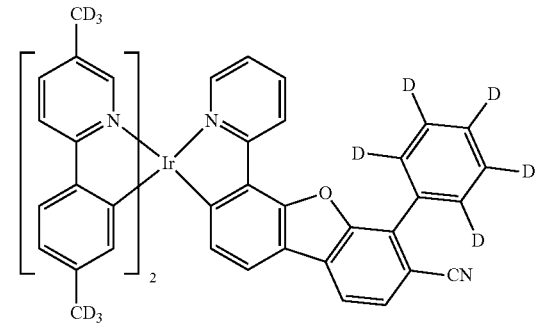

GD2-80
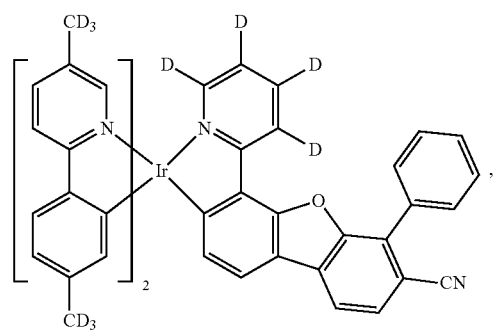
GD3-1
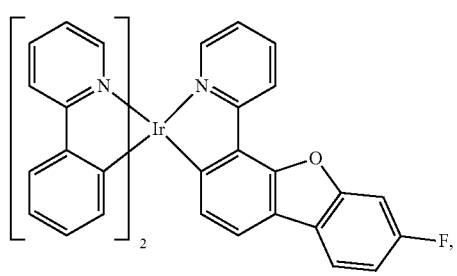
GD3-2
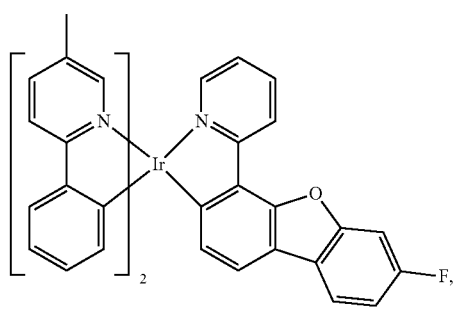
GD3-3
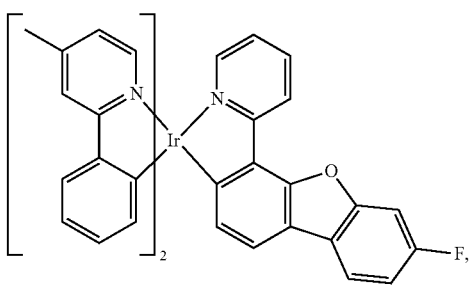
GD3-4
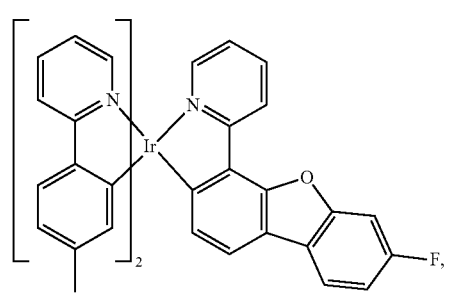
GD3-5
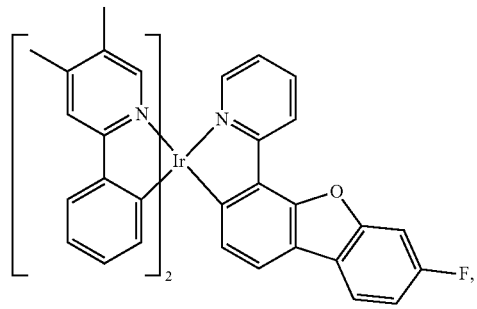
GD3-6
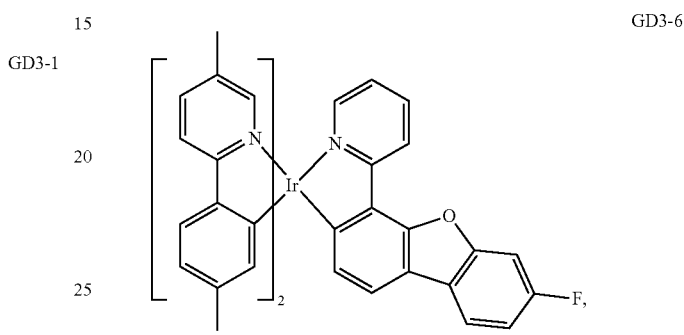
GD3-7
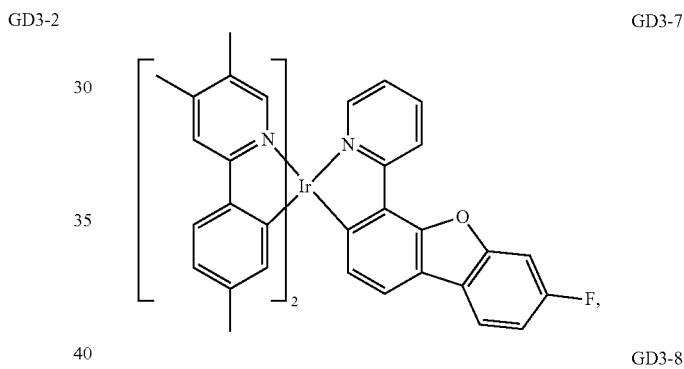
GD3-8
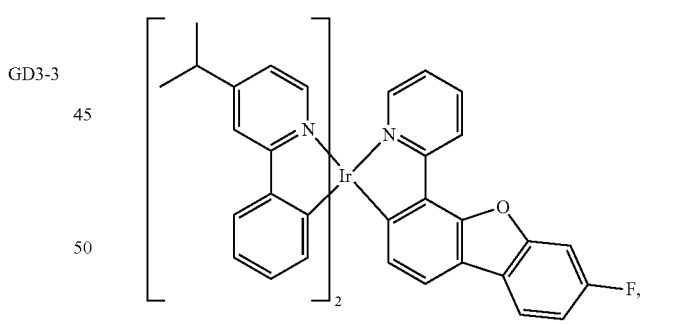
GD3-9
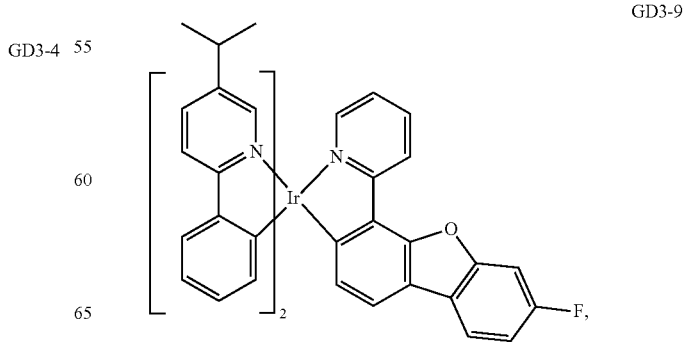

GD3-10
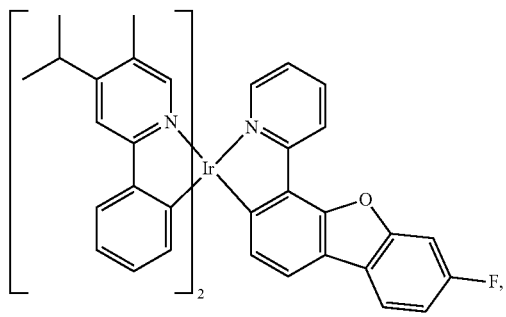
GD3-11
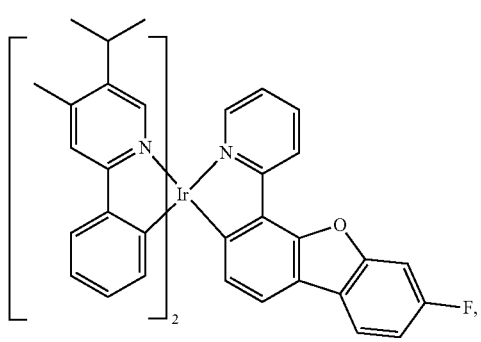
GD3-12
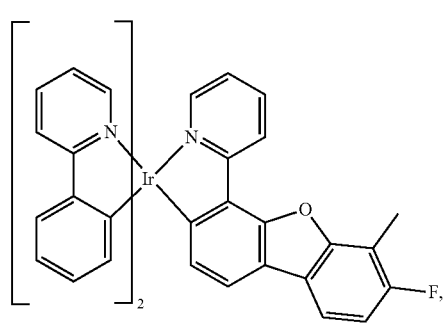
GD3-13
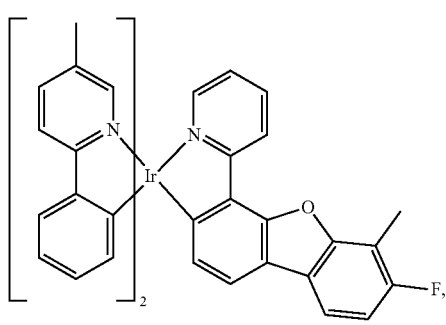
GD3-14
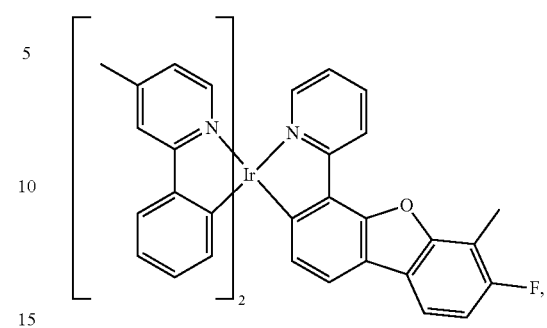
GD3-15
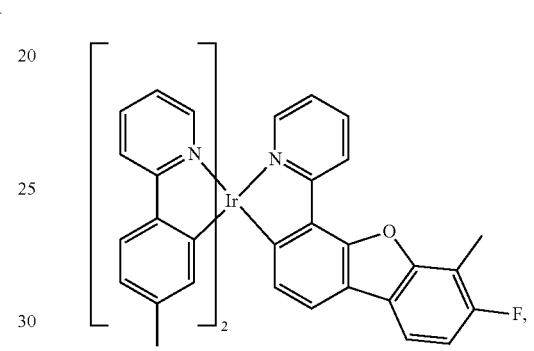
GD3-16
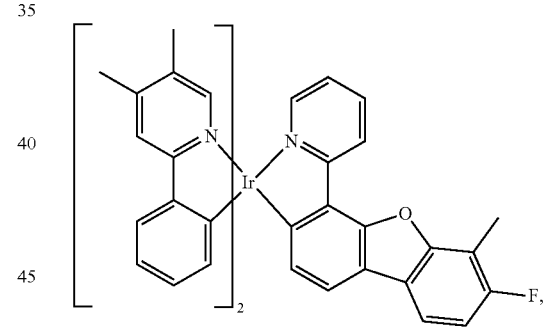
GD3-17
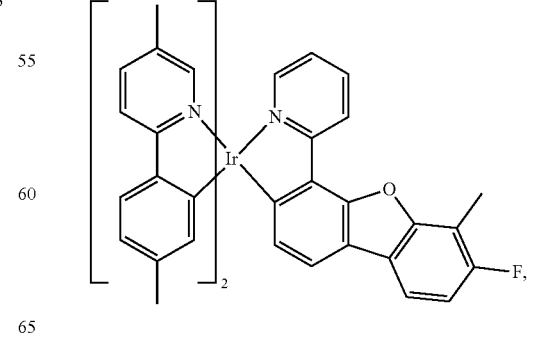

GD3-18
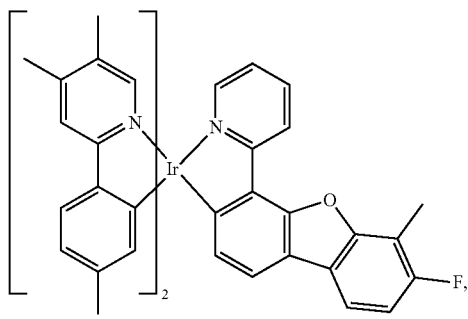
GD3-22
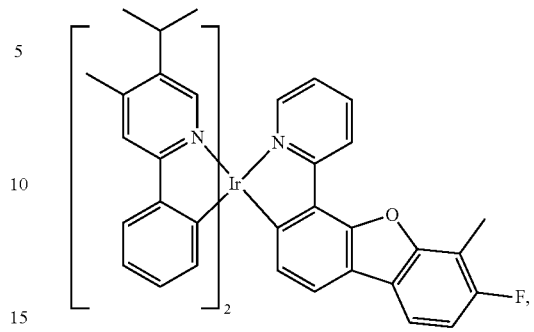
GD3-19
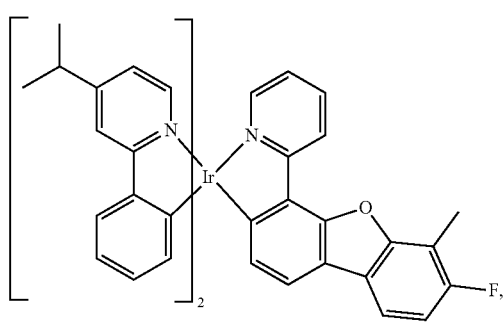
GD3-23
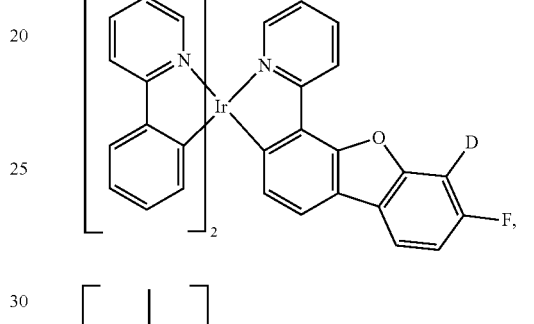
GD3-24
GD3-20
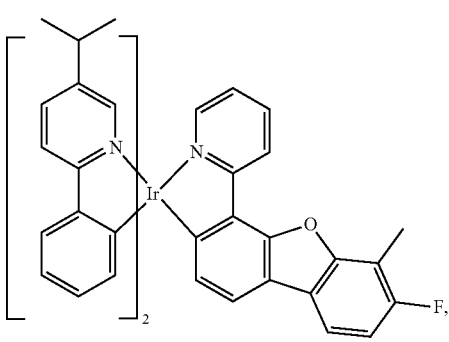
GD3-25
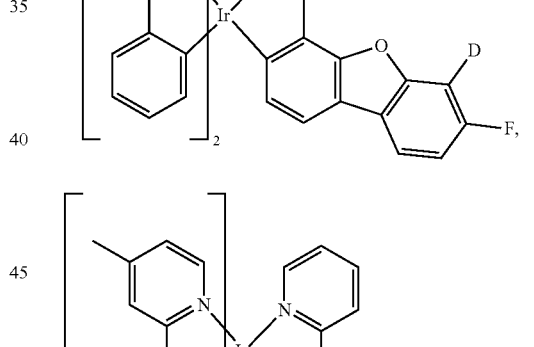
GD3-21
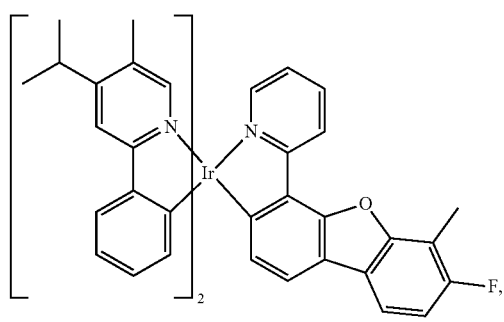
GD3-26
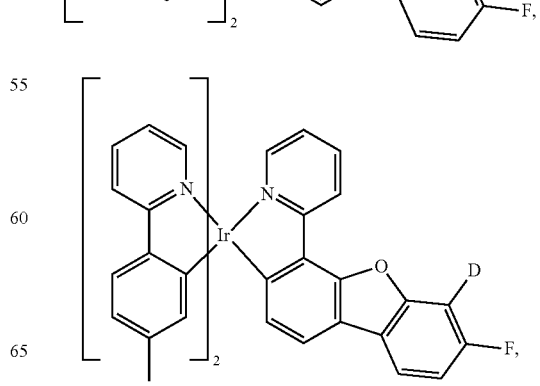

-continued
GD3-27
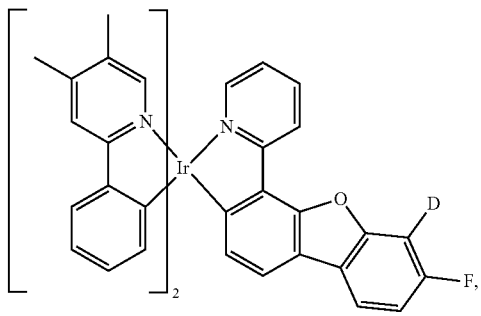
GD3-28
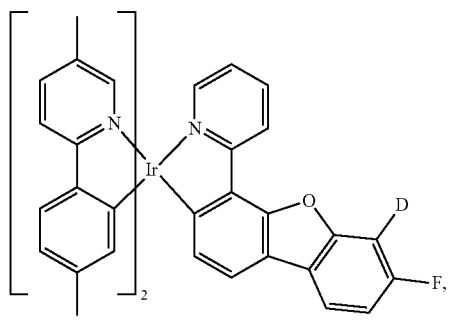
GD3-29
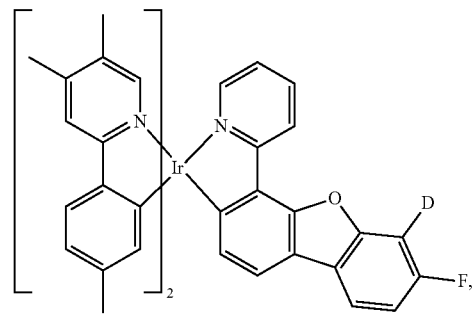
GD3-30
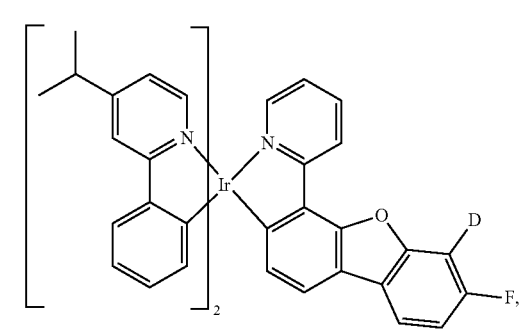
GD3-31
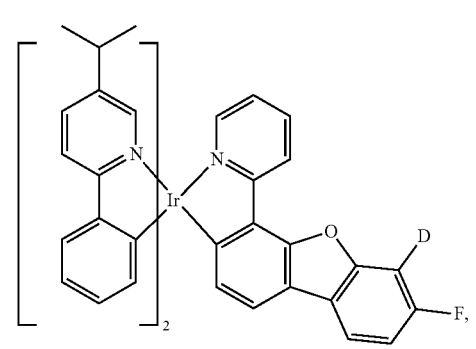
-continued
GD3-32
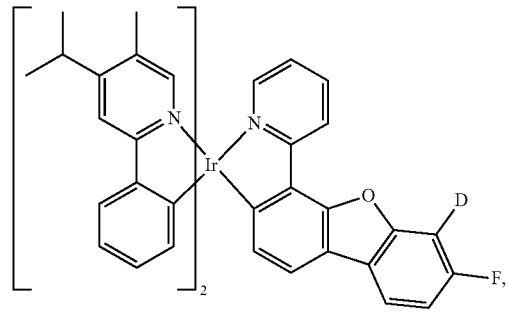
GD3-33
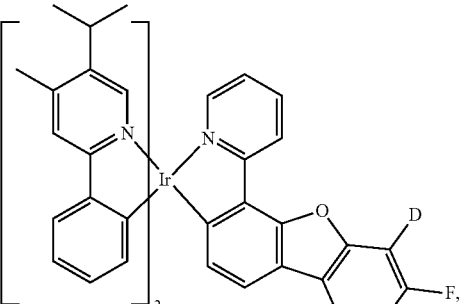
GD3-34
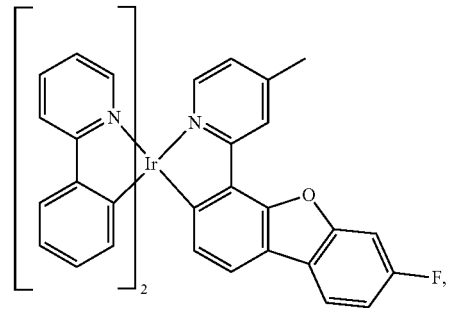
GD3-35
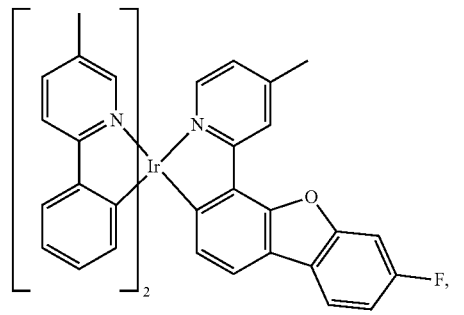
GD3-36
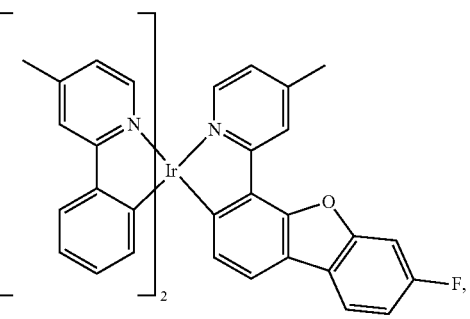

GD3-37
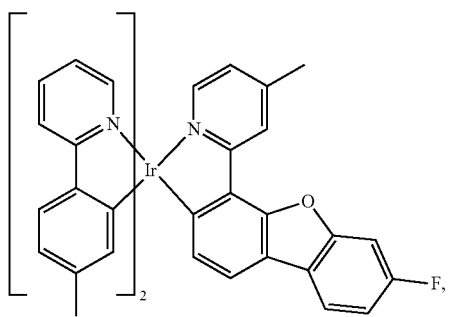
GD3-38
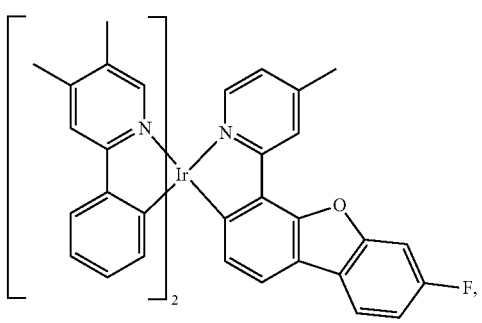
GD3-39
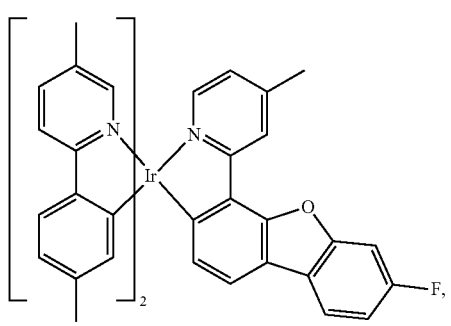
GD3-40
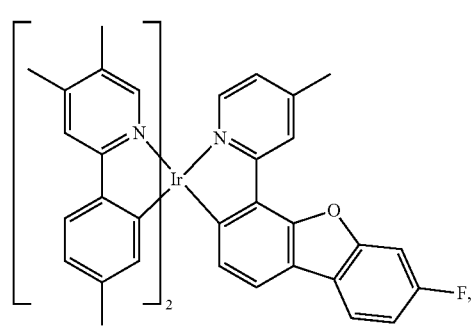
GD3-41
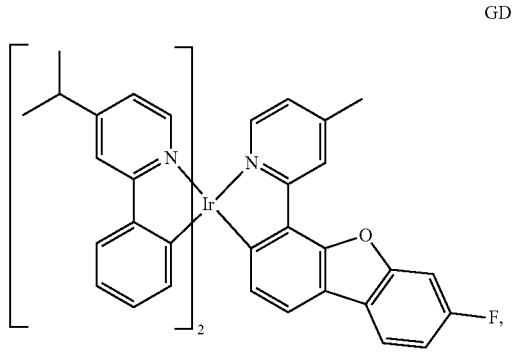
GD3-42
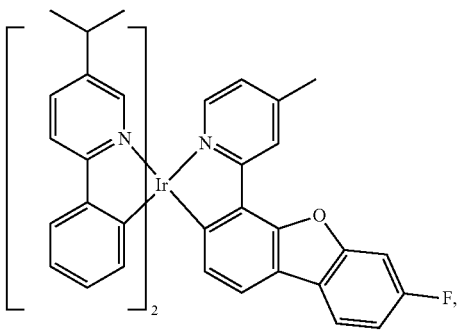
GD3-43
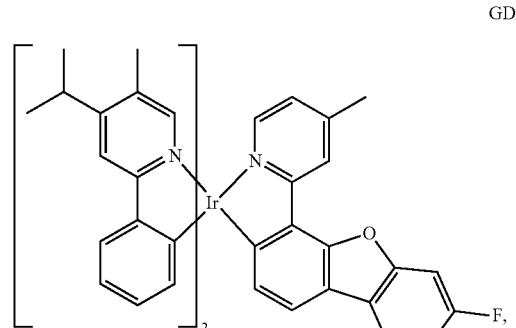
GD3-44
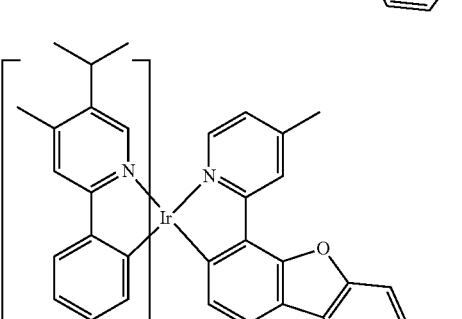
GD3-45
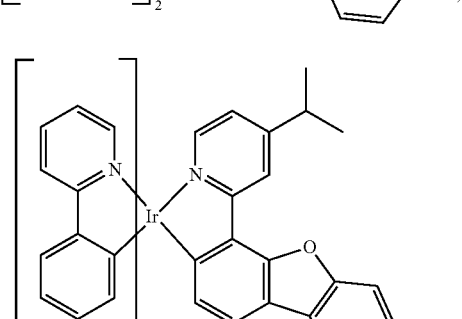
GD3-46
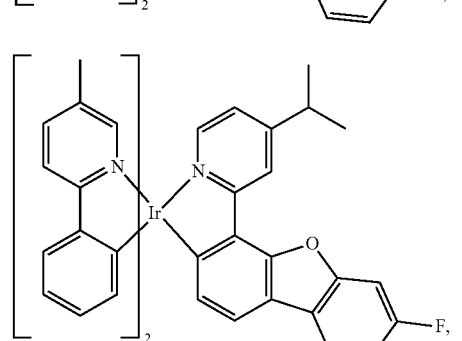

GD3-47
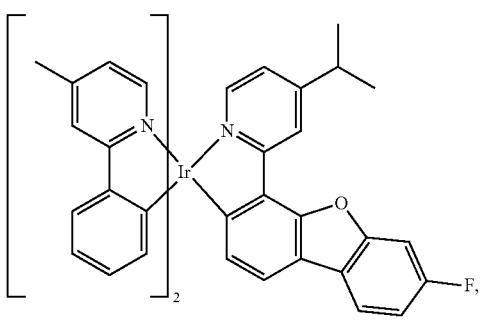
GD3-48
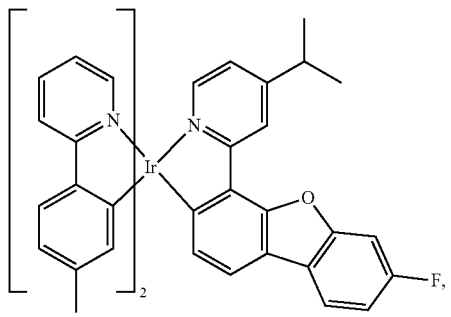
GD3-49
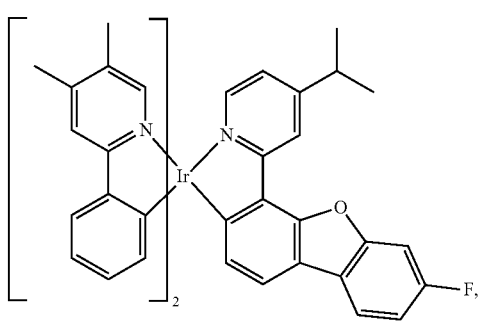
GD3-50
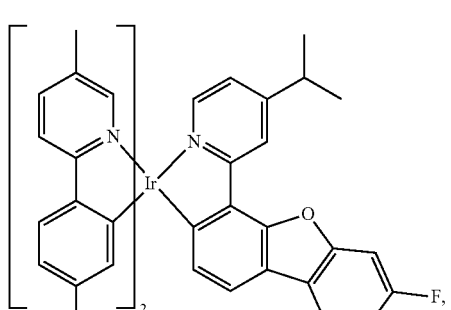
GD3-51
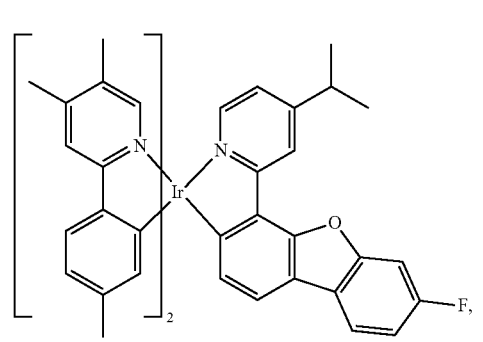
GD3-52
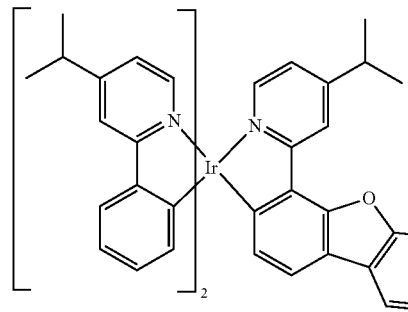
GD3-53
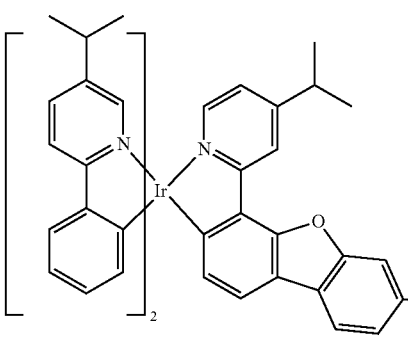
GD3-54
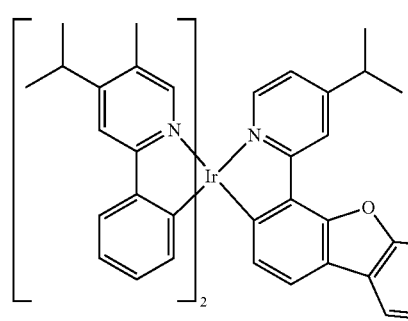
GD3-55
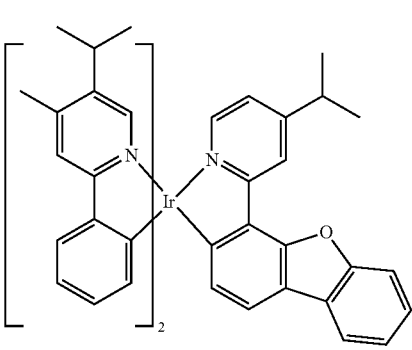

GD3-56
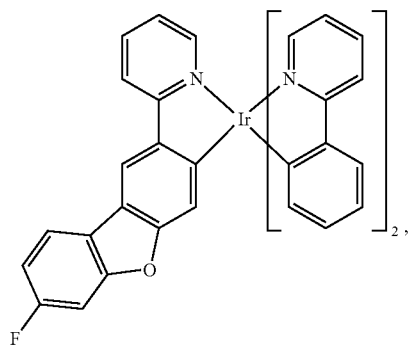
GD3-60
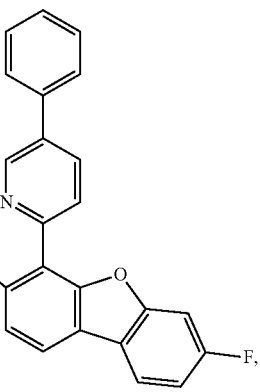
GD3-57
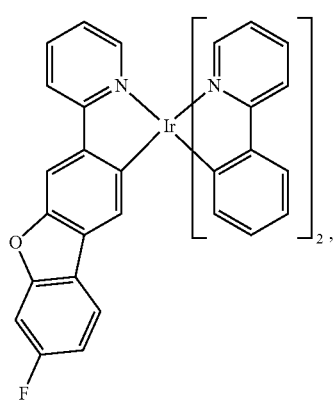
GD3-61
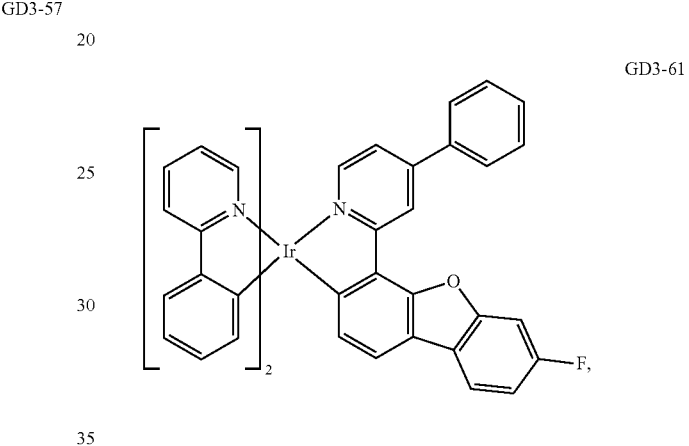
GD3-58
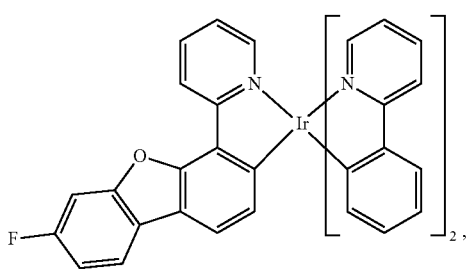
GD3-62
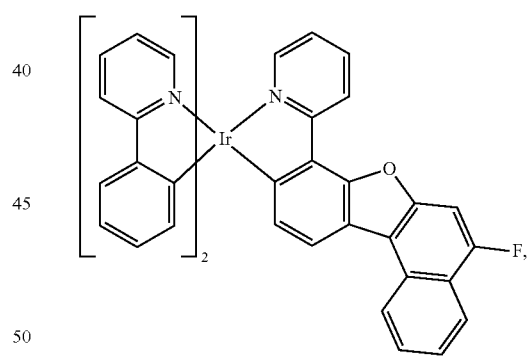
GD3-59
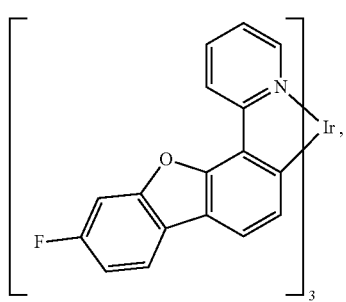
GD3-63
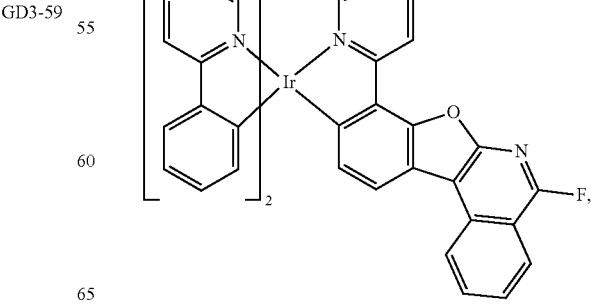

GD3-64
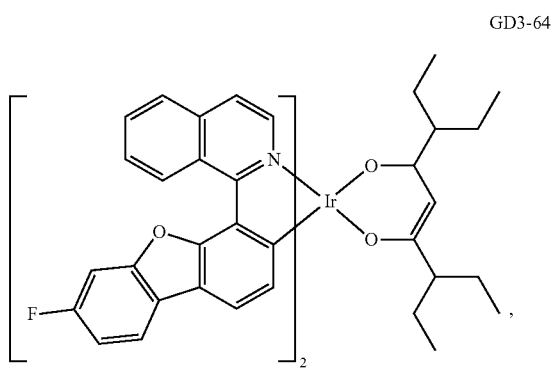
GD3-65
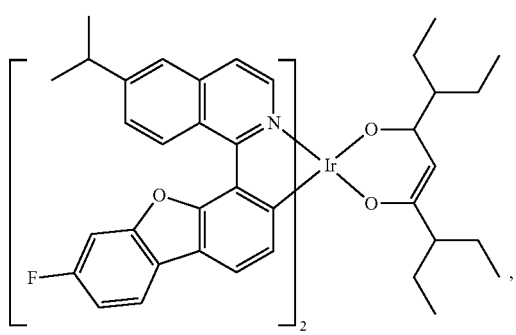
GD3-66
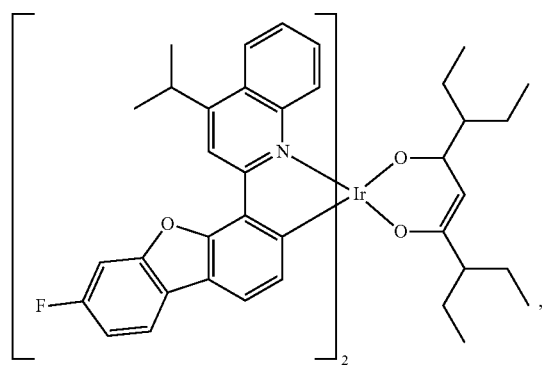
GD3-67
GD3-68
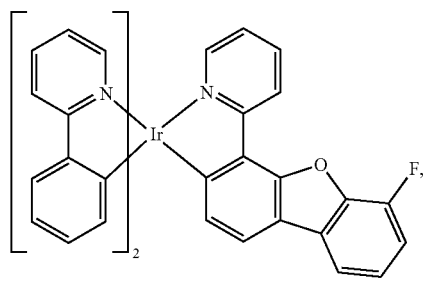
GD3-69
GD3-70
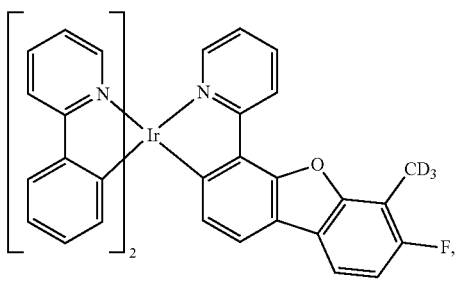
GD3-71
GD3-72
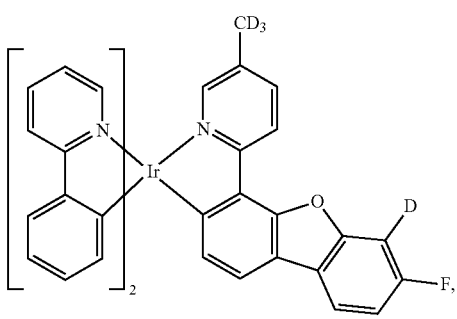

GD3-73
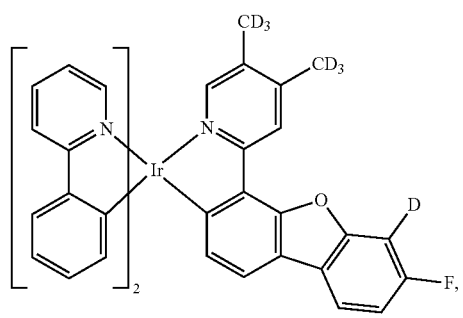
GD3-74
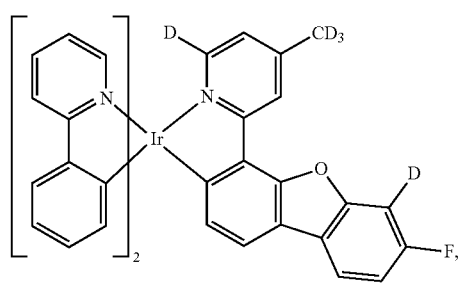
GD3-75
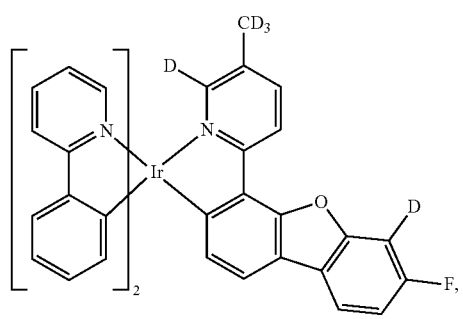
GD4-1
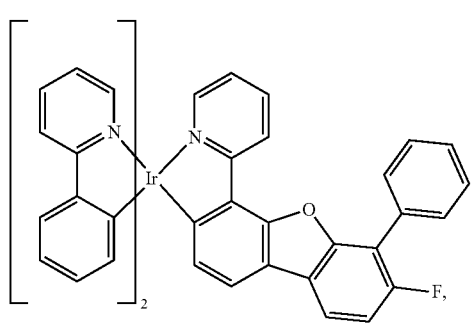
GD4-2
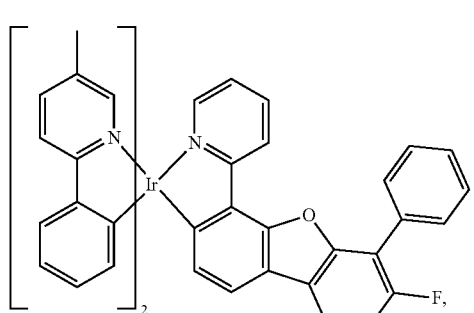
GD4-3
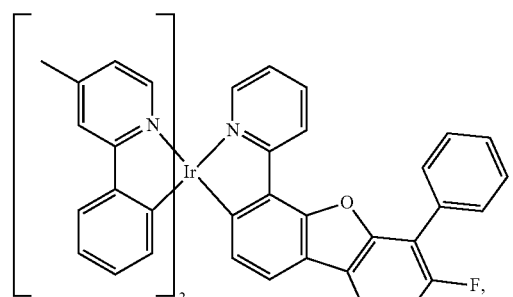
GD4-4
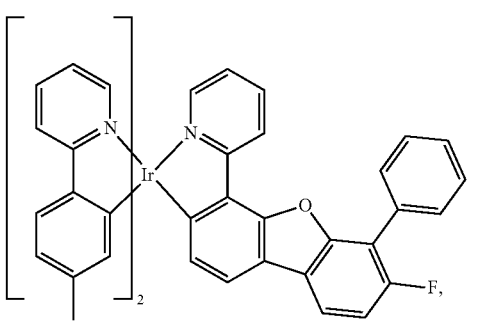
GD4-5
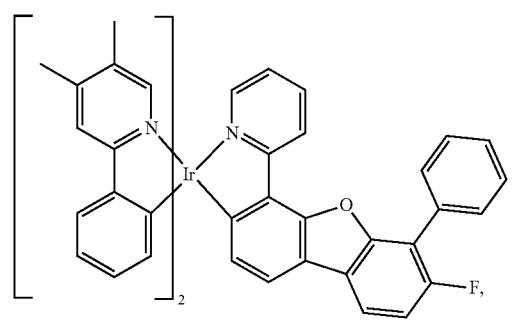
GD4-6
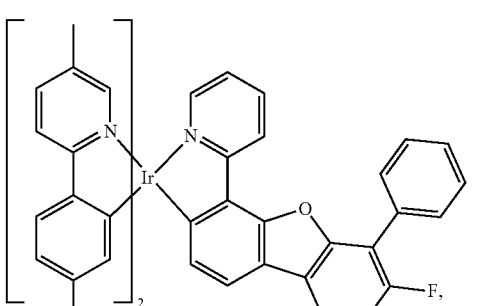
GD4-7
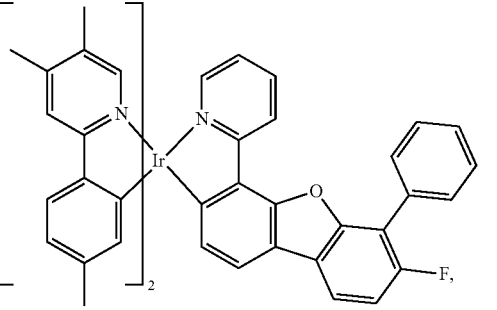

GD4-8
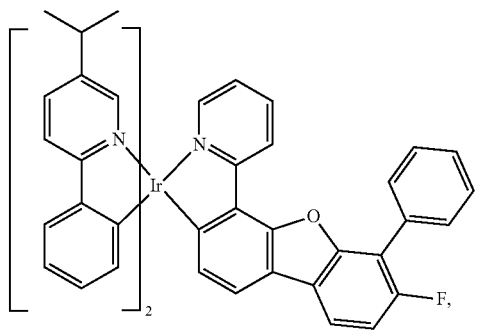
GD4-9
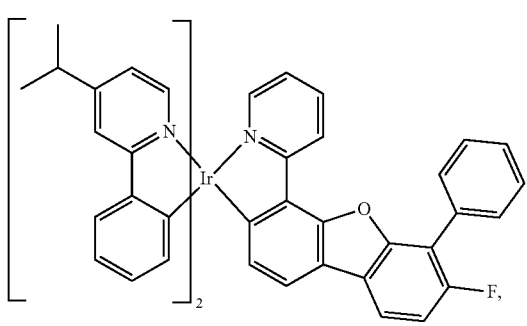
GD4-10
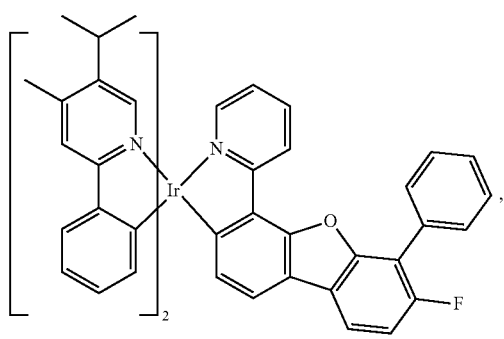
GD4-11
GD4-12
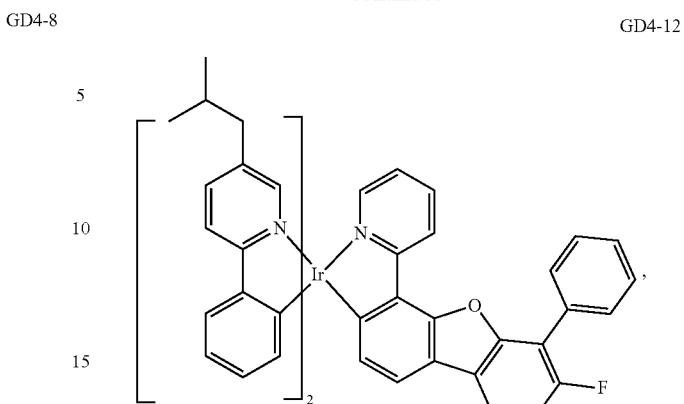
GD4-13
GD4-14
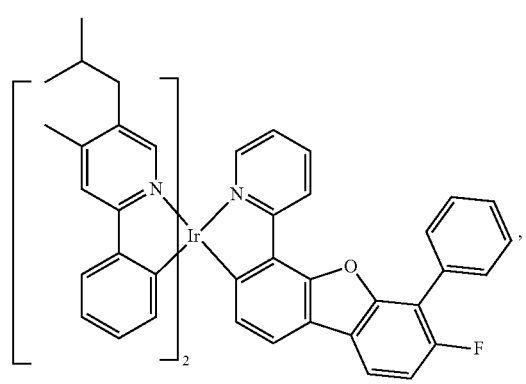
GD4-15
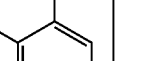

GD4-16
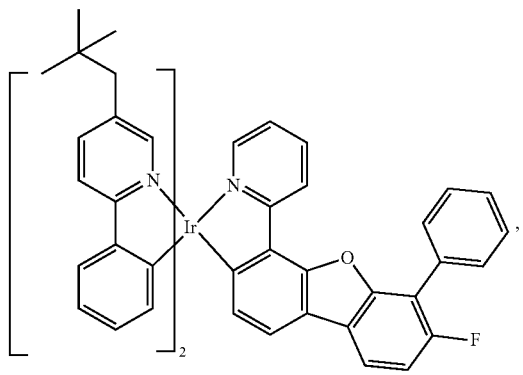
GD4-17
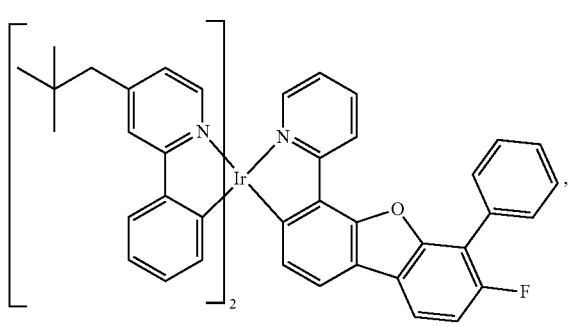
GD4-18
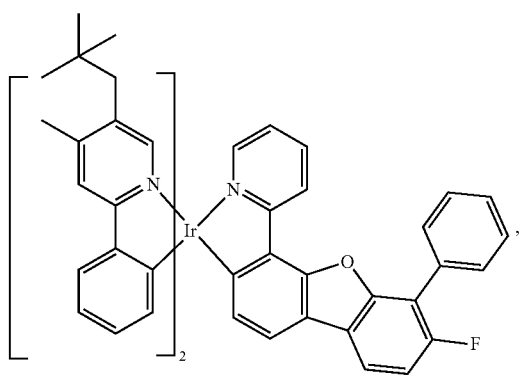
GD4-19
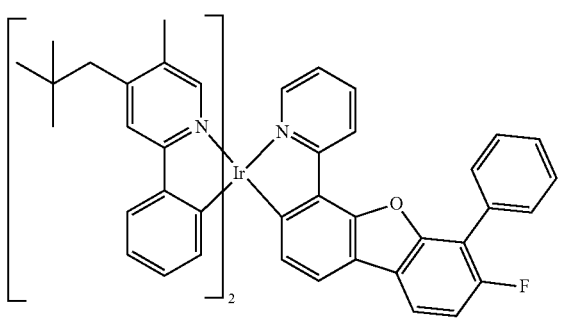
GD4-20
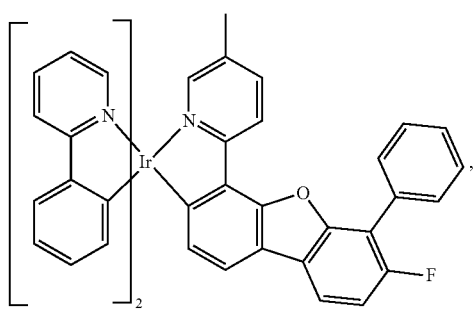
GD4-21
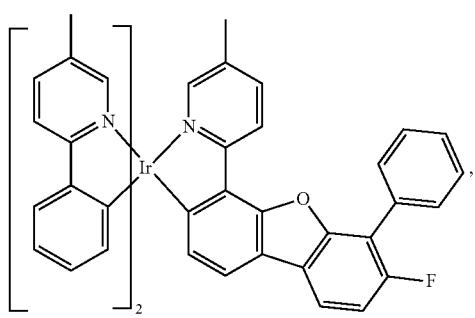
GD4-22
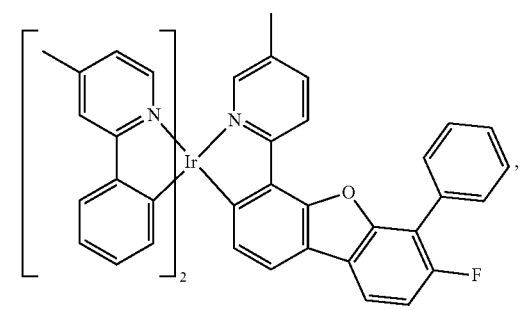
GD4-23
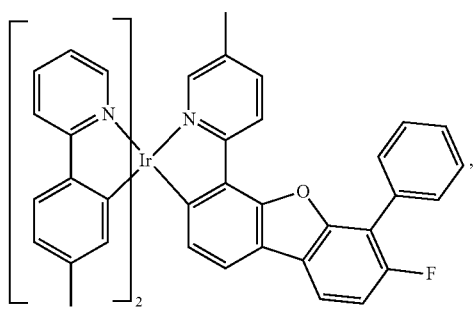

GD4-24
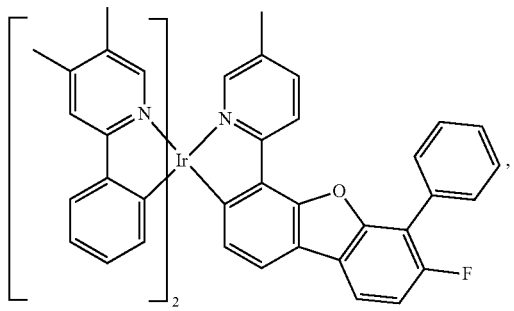
GD4-28
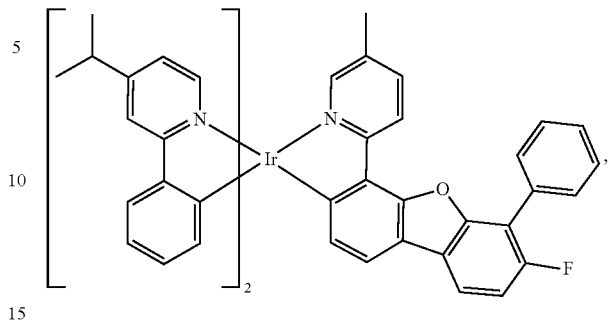
GD4-25
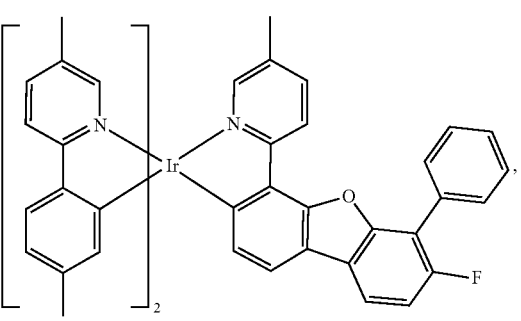
GD4-29
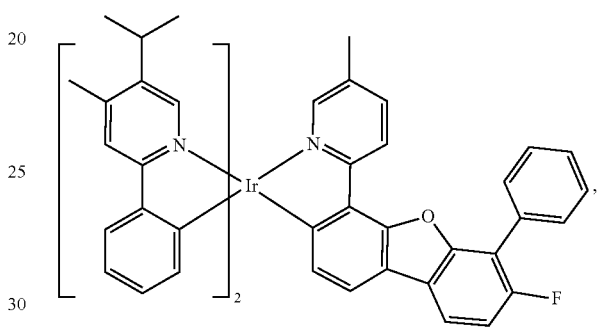
GD4-26
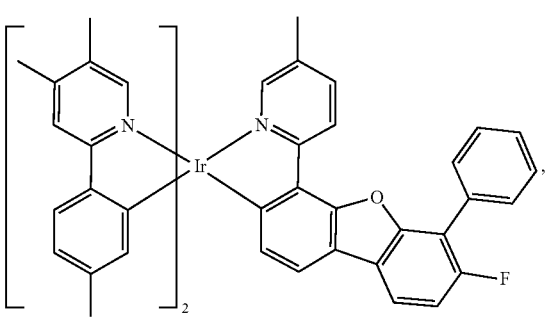
GD4-30
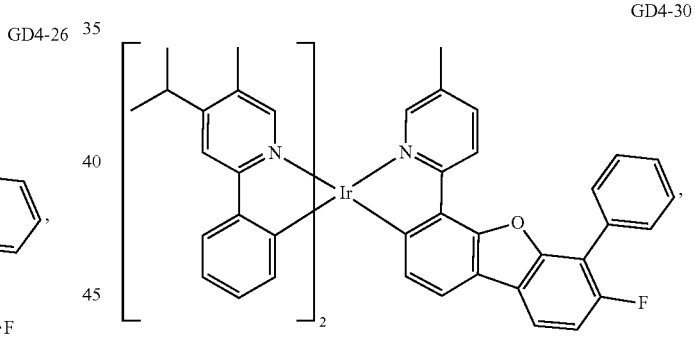
GD4-27
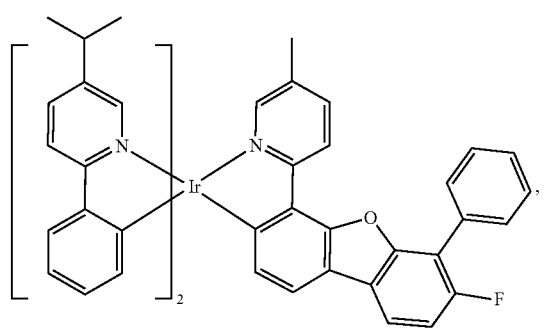
GD4-31
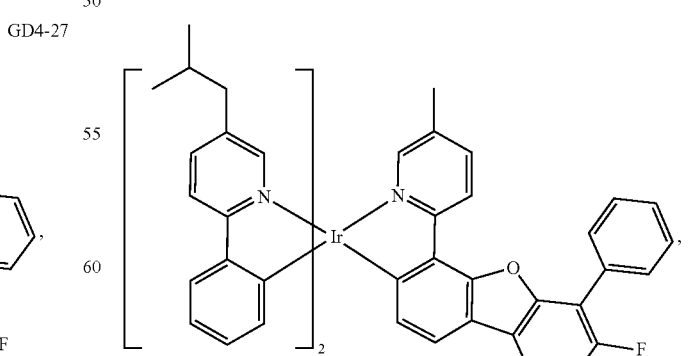

GD4-32
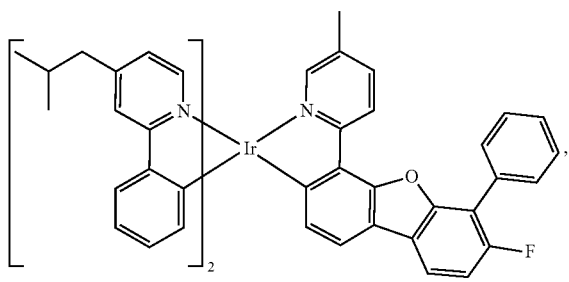
GD4-33
GD4-36
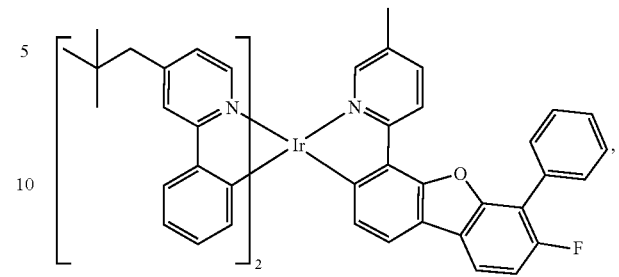
GD4-37
GD4-34
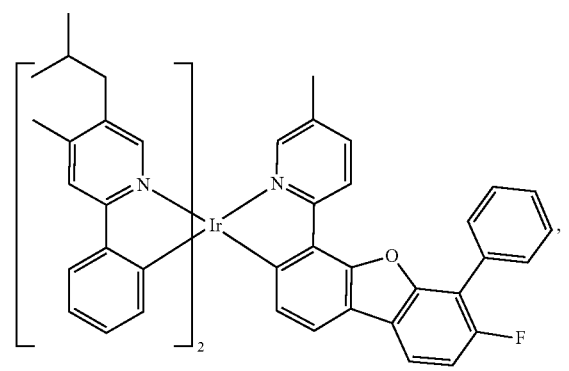
GD4-38
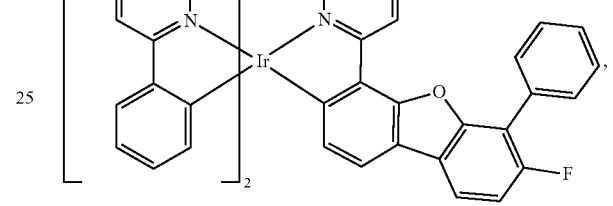
GD4-35
GD4-39
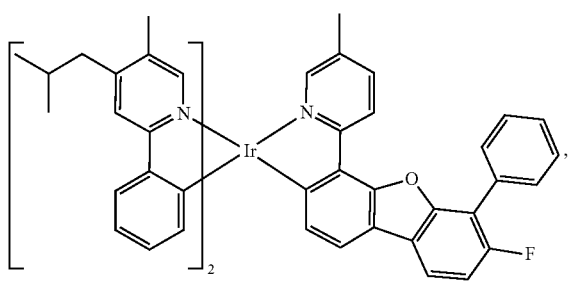
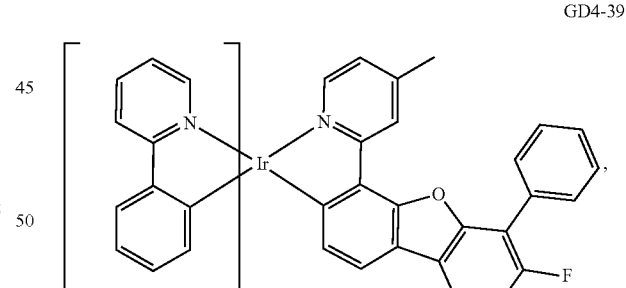
GD4-40
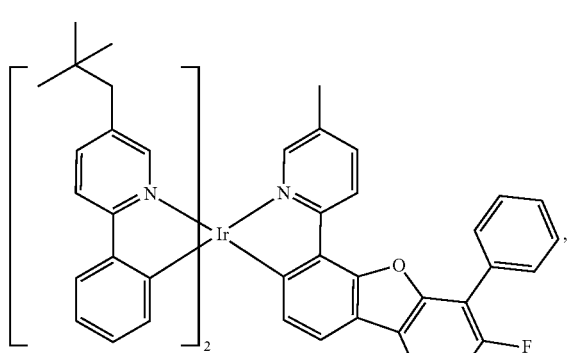
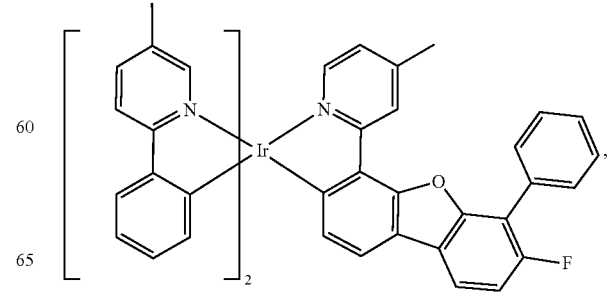

GD4-41
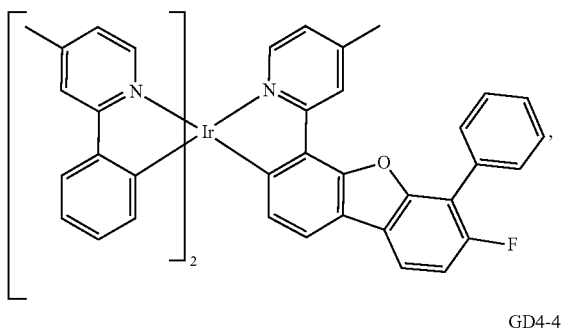
GD4-46
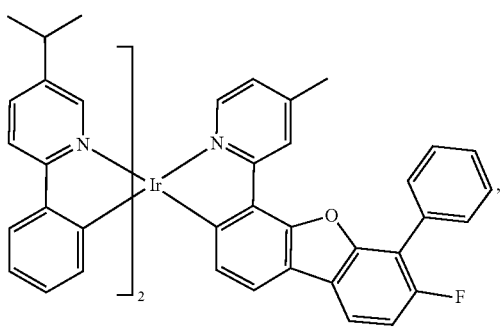
GD4-42
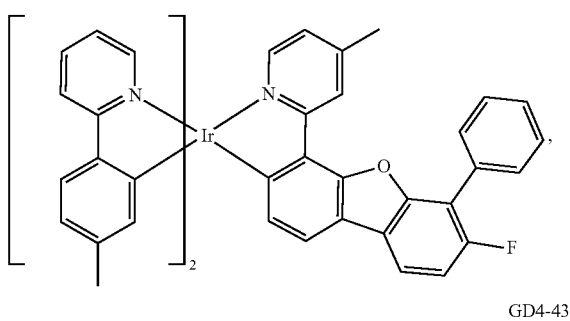
GD4-47
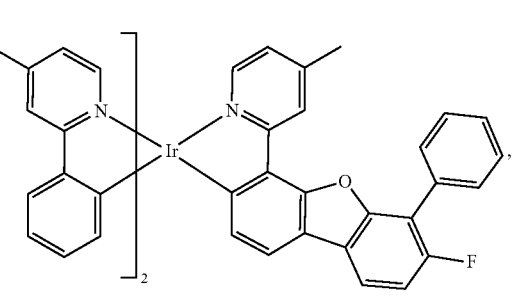
GD4-43
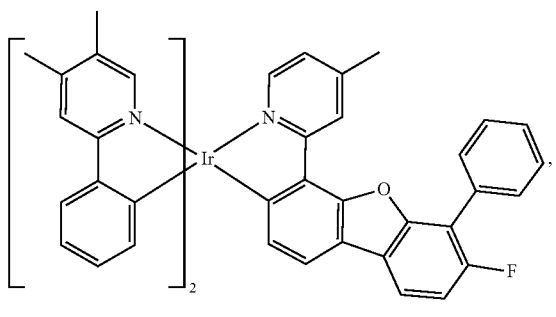
GD4-48
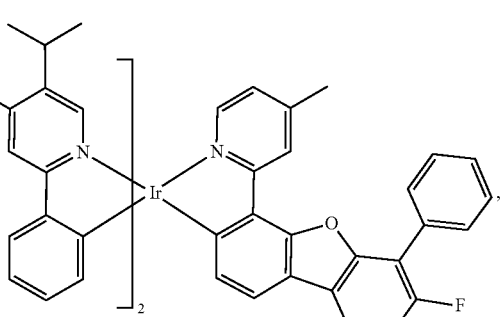
GD4-44
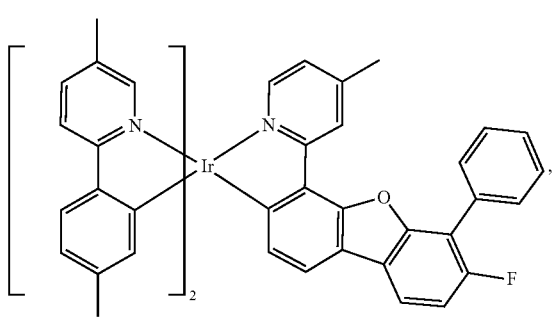
GD4-45
GD4-49
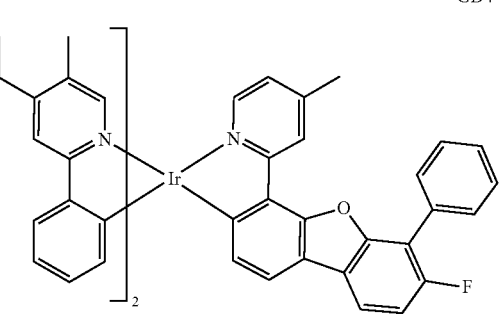

-continued
GD4-50
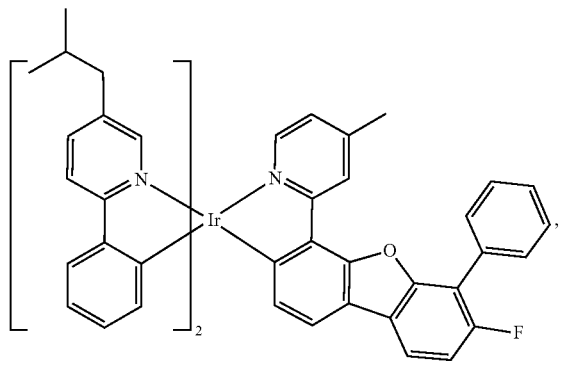
GD4-54
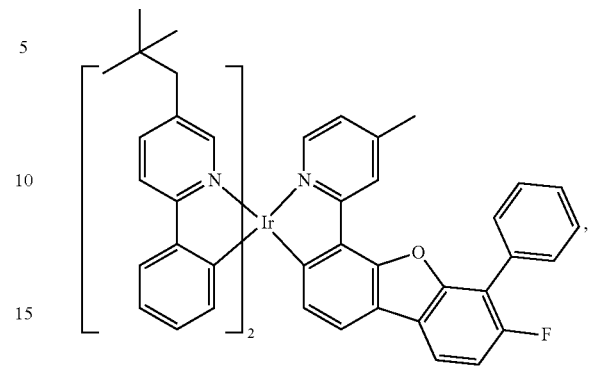
GD4-51
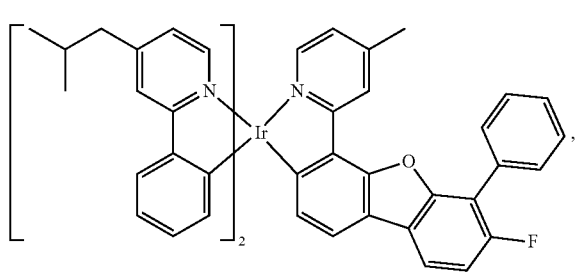
GD4-55
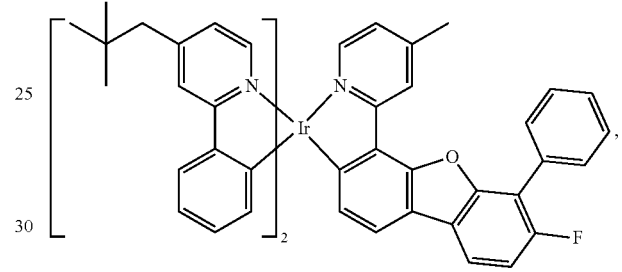
GD4-52
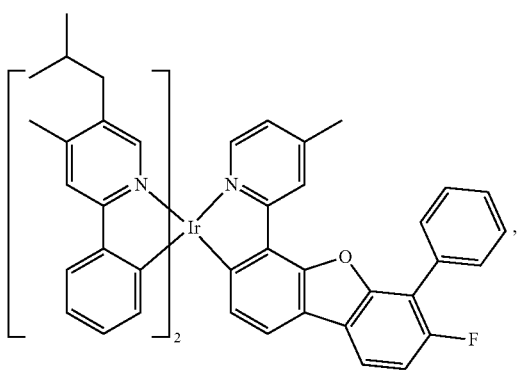
GD4-56
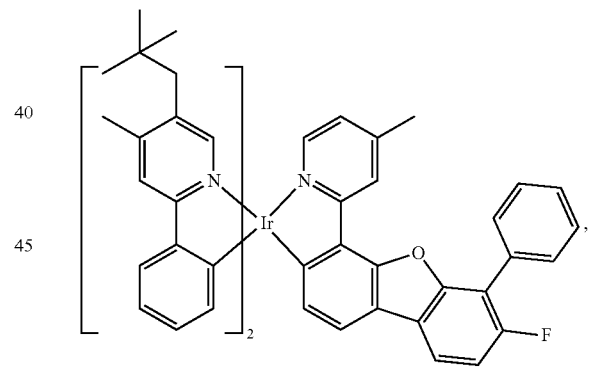
GD4-53
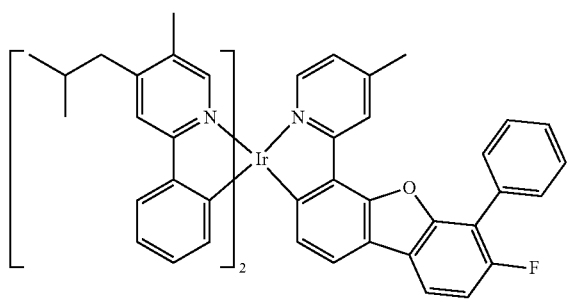
GD4-57
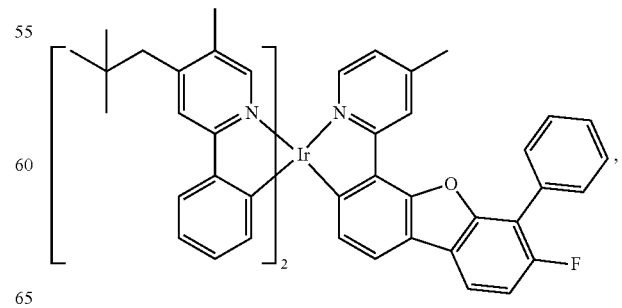

-continued
GD4-58
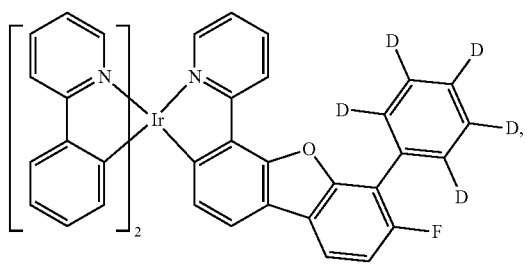
GD4-59
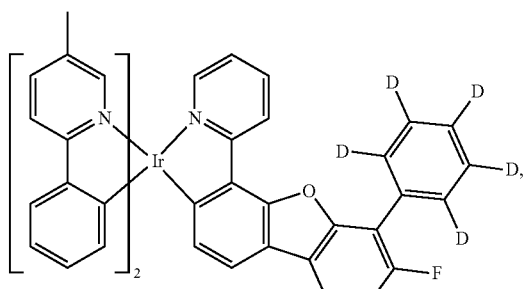
GD4-60
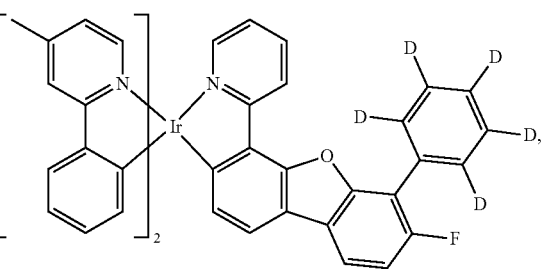
GD4-61
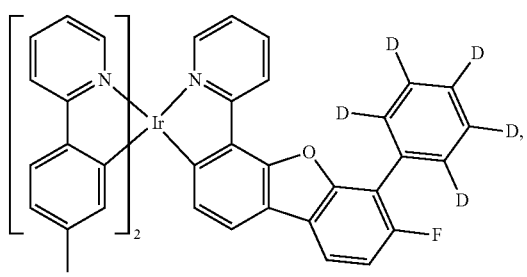
GD4-62
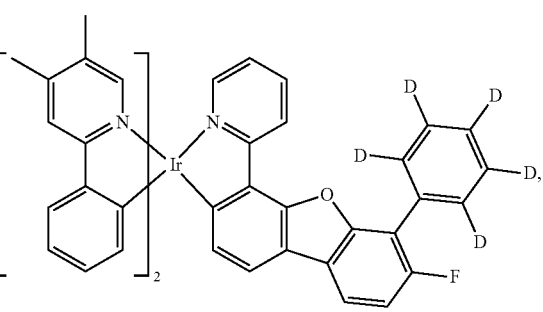
-continued
GD4-63
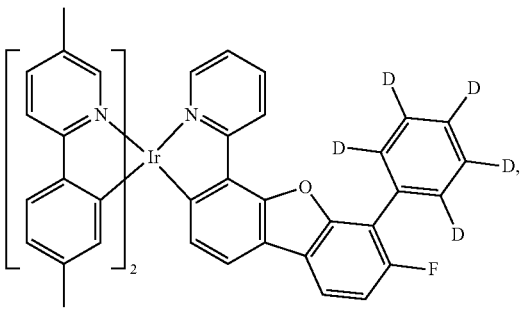
GD4-64
GD4-65
GD4-66

GD4-67
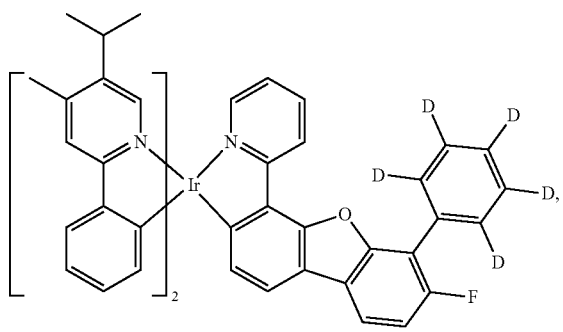
GD4-68
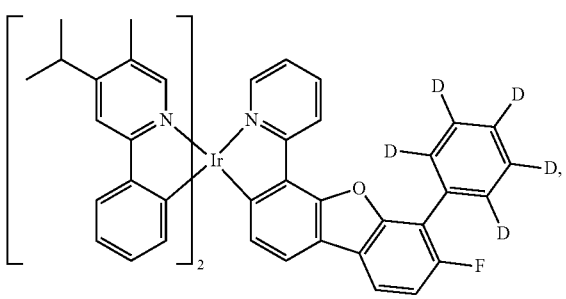
GD4-69
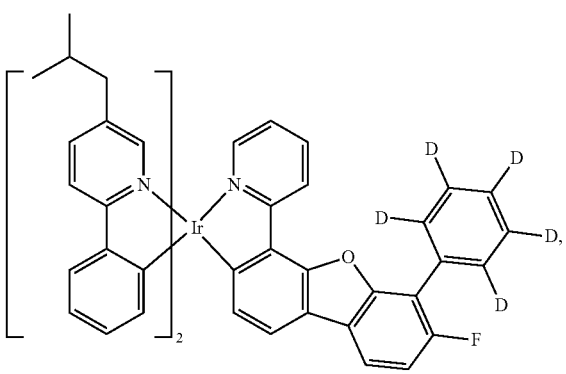
GD4-70
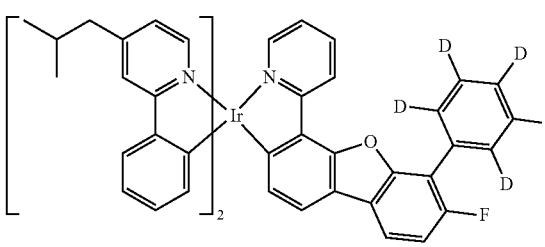
GD4-71
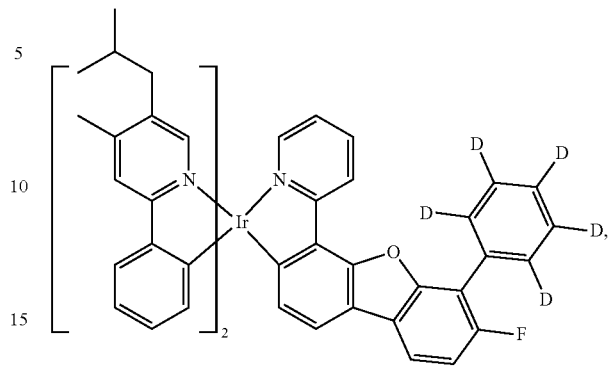
GD4-72
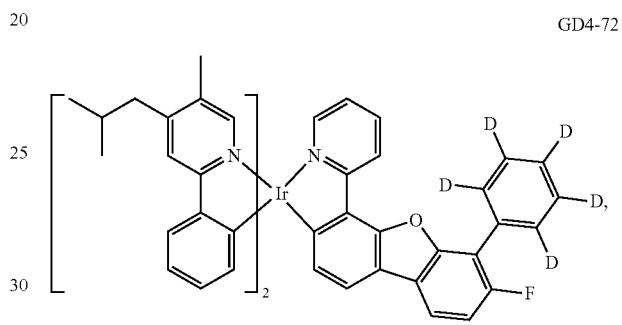
GD4-73
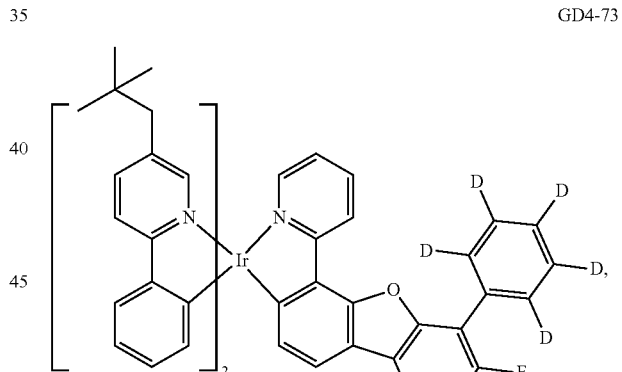
GD4-74
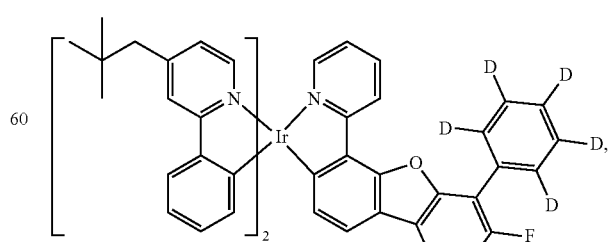

GD4-75
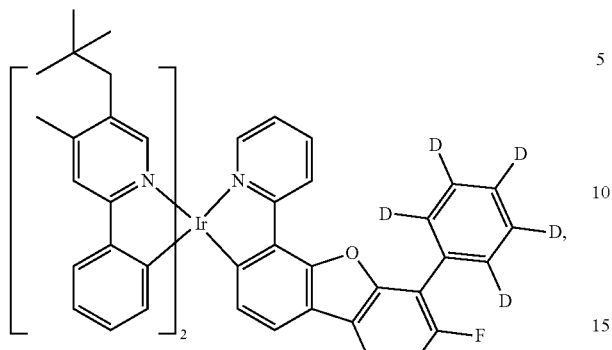
GD4-76
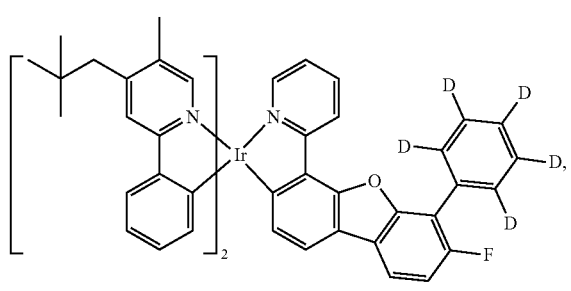
GD4-77
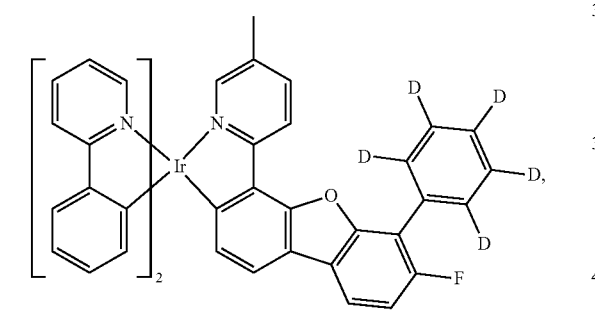
GD4-78
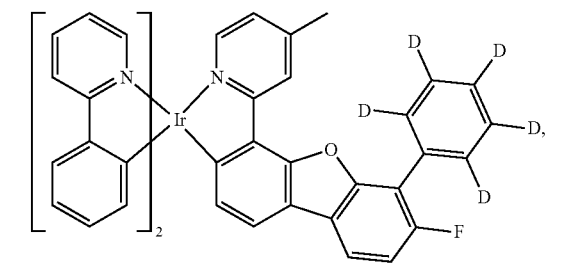
GD4-79
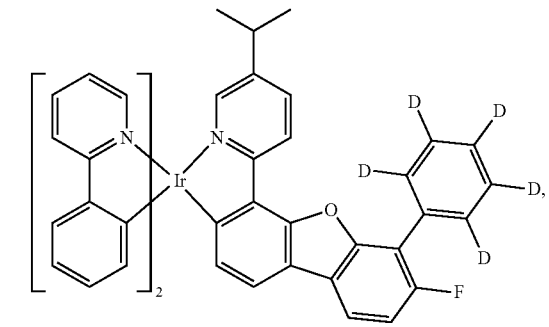
GD4-80
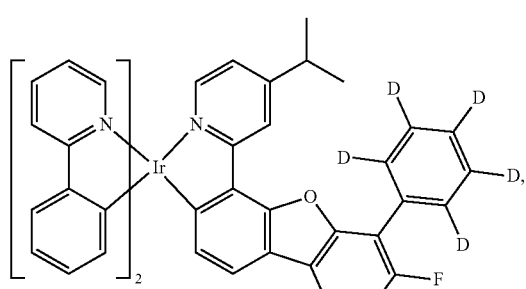
GD4-81
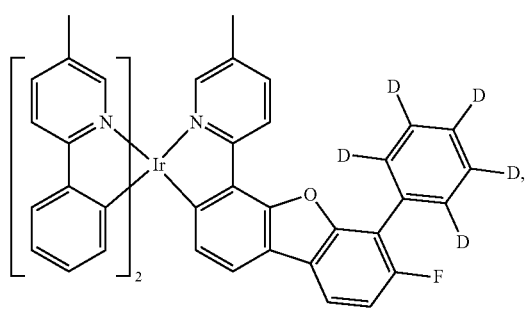
GD4-82
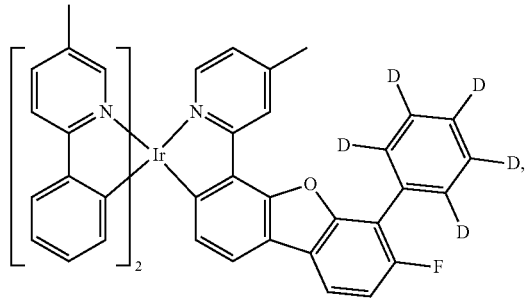
GD4-83
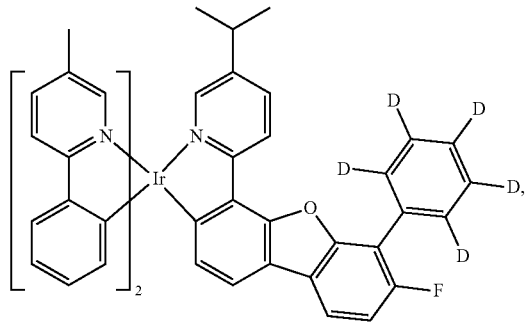

GD4-84
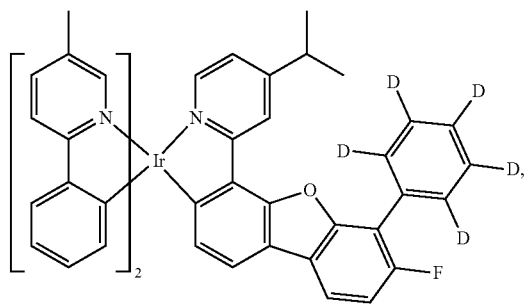
GD4-85
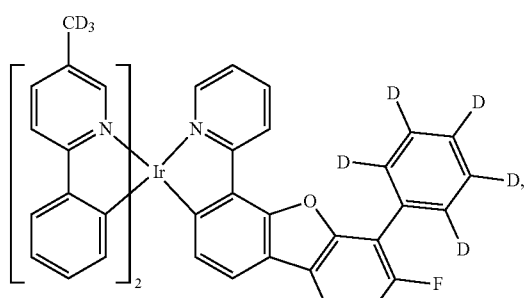
GD4-86
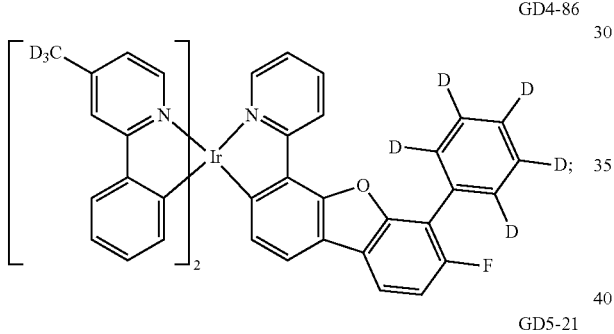
GD5-21
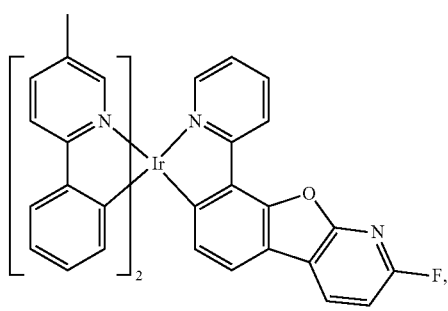
GD5-22
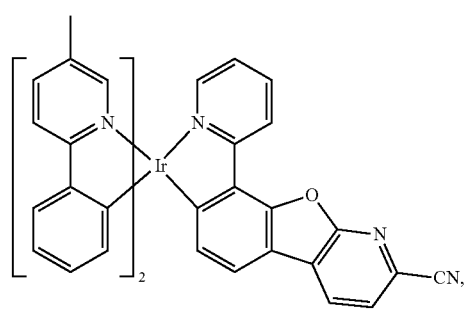
GD5-37
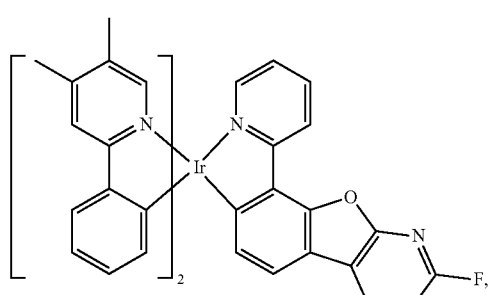
GD5-38
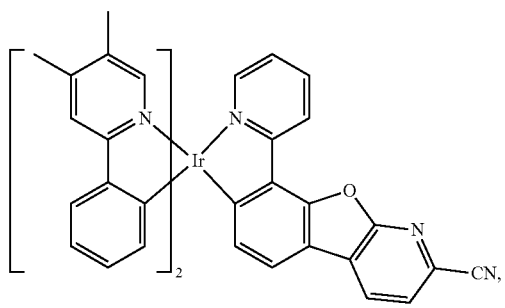
GD5-53
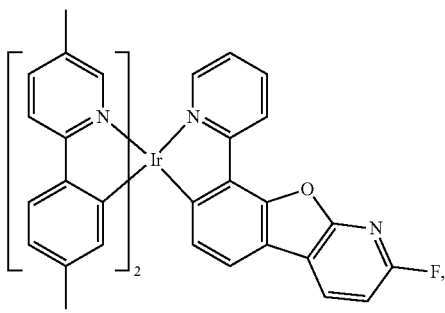
GD5-54
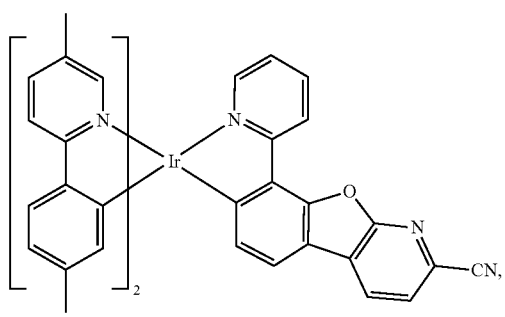

GD5-69

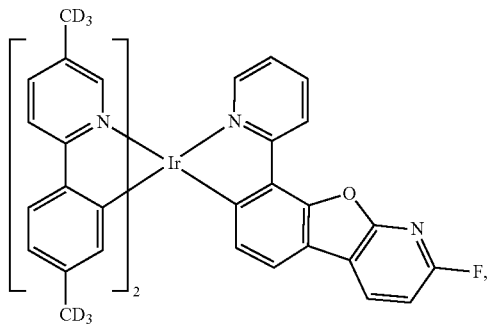

GD5-85

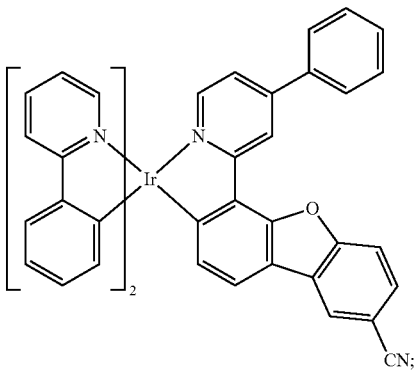

GD5-70

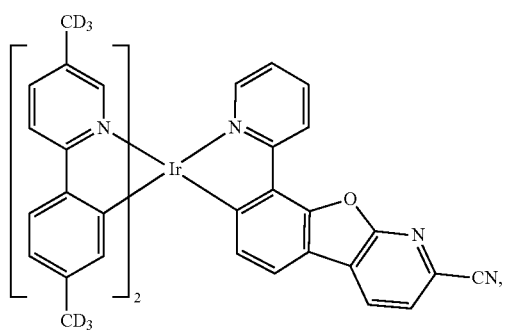

GD5-83

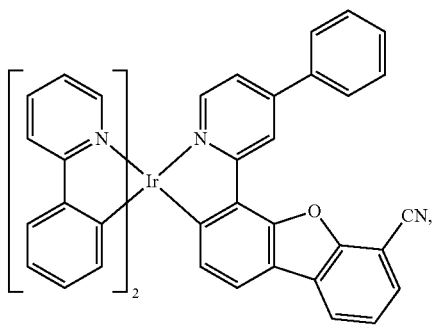

GD5-84

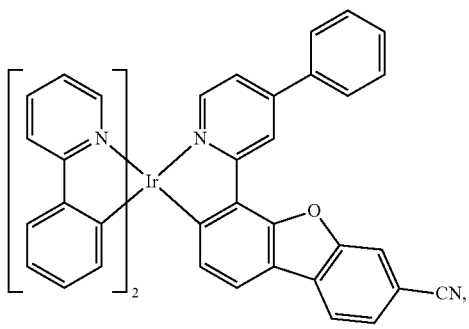

wherein in the above structure, Cy represents cyclohexyl.

19. The organic electroluminescent device according to claim 12, wherein the light-emitting layer further contains a second host compound, wherein the second host compound comprises at least one chemical group selected from the group consisting of: benzene, pyridine, pyrimidine, triazine, carbazole, azacarbazole, indolocarbazole, dibenzothiophene, aza-dibenzothiophene, dibenzofuran, azadibenzofuran, dibenzoselenophene, triphenylene, azatriphenylene, fluorene, silafluorene, naphthalene, quinoline, isoquinoline, quinazoline, quinoxaline, phenanthrene, azaphenanthrene and combinations thereof.

20. The organic electroluminescent device according to claim 19, wherein the second host compound has a structure represented by Formula 5 or Formula 6:

Formula 5

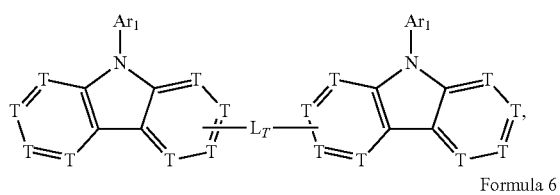

Formula 6

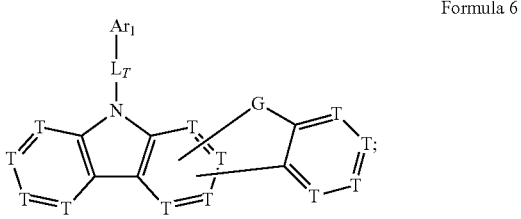

wherein

G is, at each occurrence identically or differently, selected from $C(R_g)_2$, $NR_g$, O or S;

$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;

T is, at each occurrence identically or differently, selected from C, $CR_t$ or N;

$R_t$ and $R_g$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_1$ is, at each occurrence identically or differently, selected from substituted or unsubstituted aryl having 6 to 30 carbon atoms, substituted or unsubstituted heteroaryl having 3 to 30 carbon atoms or a combination thereof;

adjacent substituents $R_t$ can be optionally joined to form a ring;

adjacent substituents $R_f$, $R_g$ can be optionally joined to form a ring.

21. The organic electroluminescent device according to claim 20, wherein the second host compound has a structure represented by one of Formulas 5-a to 5-j and Formulas 6-a to 6-f:

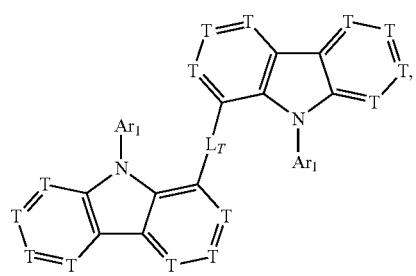

Formula 5-a

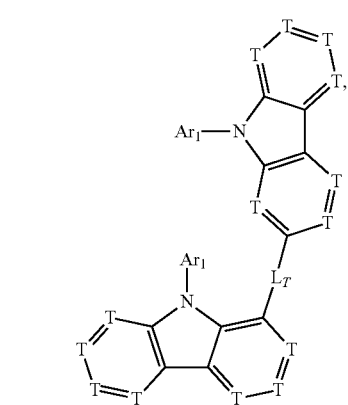

Formula 5-b

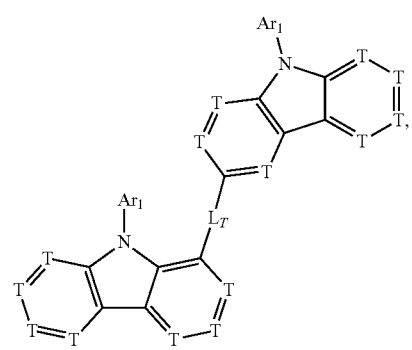

Formula 5-c

Formula 5-d

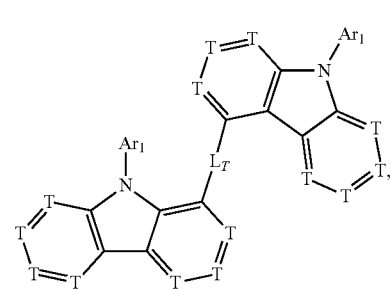

Formula 5-e

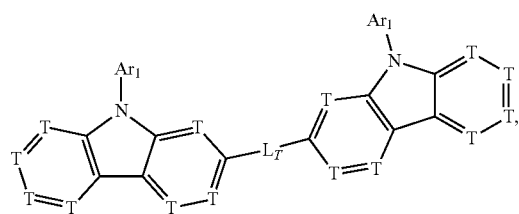

Formula 5-f

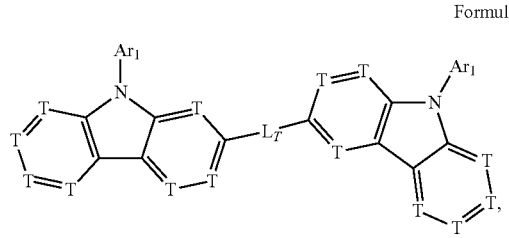

Formula 5-g

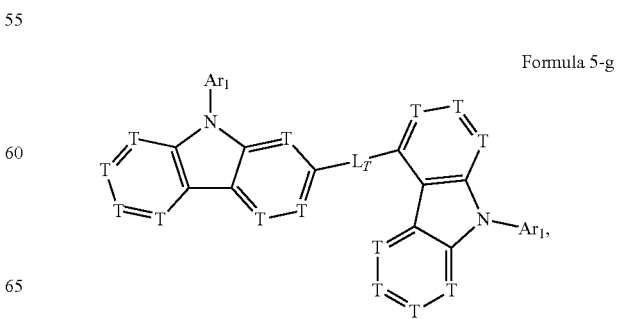

Formula 5-h
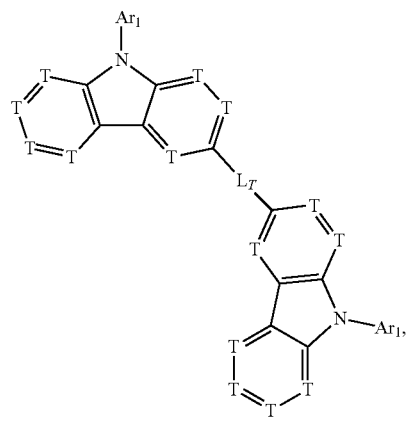

Formula 5-i
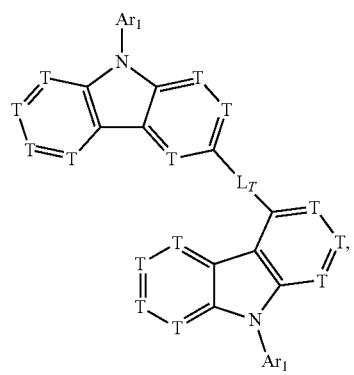

Formula 5-j
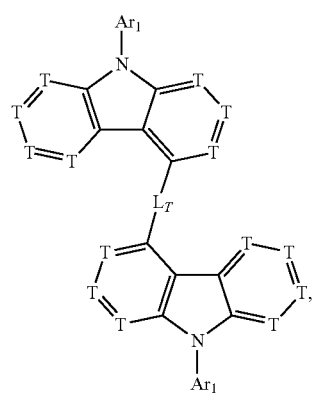

Formula 6-a
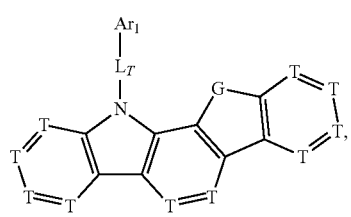

Formula 6-b
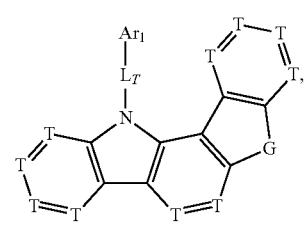

Formula 6-c
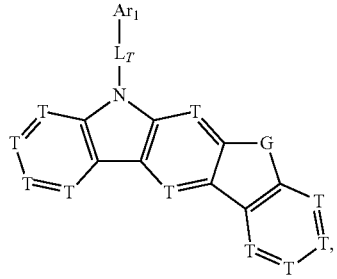

Formula 6-d
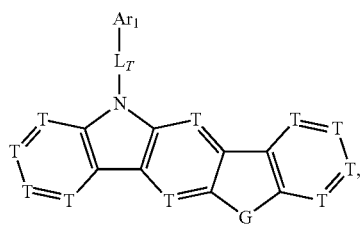

Formula 6-e
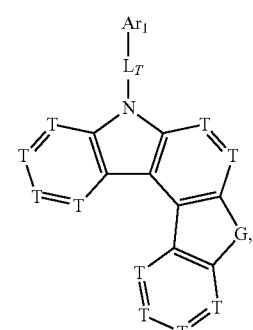

Formula 6-f
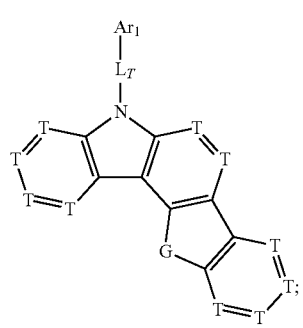

wherein
G is, at each occurrence identically or differently, selected from $C(R_g)_2$, $NR_g$, O or S;
$L_T$ is, at each occurrence identically or differently, selected from a single bond, substituted or unsubstituted alkylene having 1 to 20 carbon atoms, substituted or unsubstituted cycloalkylene having 3 to 20 carbon atoms, substituted or unsubstituted arylene having 6 to 20 carbon atoms, substituted or unsubstituted heteroarylene having 3 to 20 carbon atoms or a combination thereof;
T is, at each occurrence identically or differently, selected from $CR_t$ or N;
$R_t$ and $R_g$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a hydroxyl group, a sulfinyl group, a sulfonyl group, a phosphino group and combinations thereof;

$Ar_1$ is, at each occurrence identically or differently, selected from substituted or unsubstituted aryl having 6 to 30 carbon atoms, substituted or unsubstituted heteroaryl having 3 to 30 carbon atoms or a combination thereof;

adjacent substituents $R_t$ can be optionally joined to form a ring;

adjacent substituents $R_t$, $R_g$ can be optionally joined to form a ring.

* * * * *